United States Patent
Bamdad

(10) Patent No.: US 11,976,132 B2
(45) Date of Patent: May 7, 2024

(54) **DIAGNOSTIC METHODS USING ANTI-MUC1\* ANTIBODIES**

(71) Applicant: MINERVA BIOTECHNOLOGIES CORPORATION, Waltham, MA (US)

(72) Inventor: Cynthia Bamdad, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 926 days.

(21) Appl. No.: 16/975,625

(22) PCT Filed: Feb. 26, 2019

(86) PCT No.: PCT/US2019/019566
§ 371 (c)(1),
(2) Date: Aug. 25, 2020

(87) PCT Pub. No.: WO2019/165421
PCT Pub. Date: Aug. 29, 2019

(65) Prior Publication Data
US 2020/0407462 A1    Dec. 31, 2020

Related U.S. Application Data

(63) Continuation-in-part of application No. PCT/US2018/062569, filed on Nov. 27, 2018.

(60) Provisional application No. 62/791,661, filed on Jan. 11, 2019, provisional application No. 62/640,697, filed on Mar. 9, 2018, provisional application No. 62/635,378, filed on Feb. 26, 2018.

(51) Int. Cl.
*C07K 16/30* (2006.01)
*A61K 35/17* (2015.01)
*A61K 47/68* (2017.01)
*G01N 33/574* (2006.01)

(52) U.S. Cl.
CPC .......... *C07K 16/3092* (2013.01); *A61K 35/17* (2013.01); *A61K 47/6851* (2017.08); *G01N 33/57492* (2013.01); *C07K 2317/34* (2013.01)

(58) Field of Classification Search
None
See application file for complete search history.

(56) References Cited

U.S. PATENT DOCUMENTS

| 10,239,950 | B2 | 3/2019 | Nishimura et al. |
| 2014/0356359 | A1 | 12/2014 | Siebel et al. |

FOREIGN PATENT DOCUMENTS

| CN | 1455680 A | 11/2003 | |
| CN | 106661110 A | 5/2017 | |
| WO | WO-0222685 A2 | 3/2002 | |
| WO | 2008/058127 | 5/2008 | |
| WO | 2016/130726 | 8/2016 | |
| WO | WO-2016130726 A1 * | 8/2016 | ......... A61K 39/0011 |
| WO | WO-2019165421 A1 | 8/2019 | |

OTHER PUBLICATIONS

International Search Report for PCT/US2019/019566 dated Jun. 27, 2019, 5 pages.
Written Opinion of the ISA for PCT/US2019/019566 dated Jun. 27, 2019, 8 pages.
Immunoglobulin, Kappa Chain, Variable Region, Partial [Mus musculus]. GenBank: CAA10057.1, Jul. 26, 2016; downloaded from the internet <https://www.ncbi.nlm.nih.gov/protein/CAA10057.1?report=genbank&log$=protalign&blast_rank=1&RID=D6E6TDK9014> on May 8, 2019, pp. 1-2.
1g Heavy Chain Precursor V Region (mAb H8)—Mouse (Fragment). PIR: PC1213. Jul. 23, 1999; downloaded from the internet <https:///www.ncbi.nlm.nih.gov/protein/PC1213?report=genbank&log$=protalign&blast_rank=1&RID=D6FNSFA6015> on May 8, 2019, 1 page.
Bamdad et al. Abstract 3330: MUC1* targeting CAR T. Cancer Research 77(13):3330 (2017).
Gong et al. Expression of matrix metalloproteinases and the tissue inhibitors of metalloproteinases and their local invasiveness and metastasis in Chinese human pancreatic cancer. J Surg Oncol 73:95-99 (2000).
Mehner et al. Tumor cell-produced matrix metalloproteinase 9 (MMP-9) drives malignant progression and metastasis of basal-like triple negative breast cancer. Oncotarget 5(9):2736-2749 (2014).
Radisky et al. Matrix metalloproteinases as breast cancer drivers and therapeutic targets. Front Biosci (Landmark Ed). 20:1144-1163 (2015).
Schevchenko et al. Mass spectrometric sequencing of proteins silver-stained polyacrylamide gels. Anal. Chem. 68:850-858 (1996).
Sillanpaa et al. Prognostic significance of matrix metalloproteinase-9 (MMP-9) in epithelial ovarian cancer. Gynecologic Oncology 104:296-303 (2007).
Sorensen et al. Chemoenzymatically synthesized multimeric Tn/STn MUC1 glycopeptides elicit cancer-specific anti-MUC1 antibody responses and override tolerance. Glycobiology 16(2):96-107 (2006).
Tadic-Latinovic et al. The prognostic value of MMP-9 expression in lung adenocarcinoma. Arch Oncol 21(3-4):109-14 (2013).
Yousef et al. MMP-9 expression varies according to molecular subtypes of breast cancer. BMC Cancer 14:609 (2014).

\* cited by examiner

*Primary Examiner* — Laura B Goddard
*Assistant Examiner* — Sarah A Alsomairy
(74) *Attorney, Agent, or Firm* — WILSON SONSINI GOODRICH & ROSATI

(57) ABSTRACT

The present application discloses a method of determining suitability of treating a patient suffering from cancer or metastasis of cancer characterized by aberrant expression of MUC1, with a MUC1* targeting therapeutic.

18 Claims, 76 Drawing Sheets
Specification includes a Sequence Listing.

**Serial sections of breast cancer arrays stained with anti-MUC1-full-length, VU4H5 or anti-MUC1*, MNC2**

Array: AGTA-528.HH. Sector 1 -4    MUC1-FL

Array: AGTA-528.HH. Sector 1 -4    MUC1*

Red & orange show breast cancer tissues where MUC1* staining is high; green shows tissues where MUC1* staining is high and there is no MUC1-FL White: no sample
Black: no stain
Yellow: weak stain Fig. 2A
VU4H5 anti-MUC1-FL
mouse monoclonal
Fig. 2B
MNC2 anti-MUC1\*
mouse monoclonal IgG
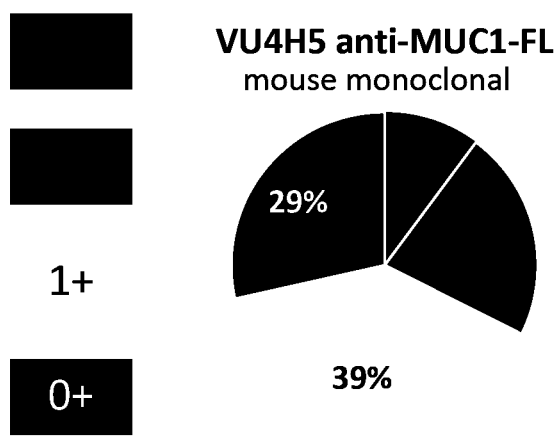
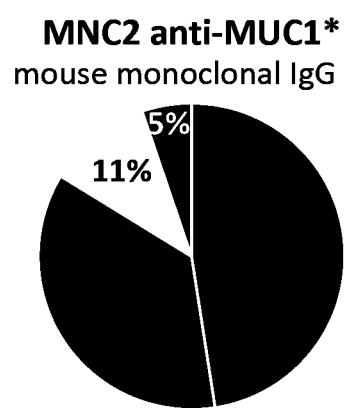

Breast cancer array BR1141
huMNC2-scFv-Fc-biotin

Fig. 4A
Array BC1141
Position: A7
Cell Type: Invasive Ductal Carcinoma
Tumor Grade: 2
TNM: T2N1M0
Pathologist Score: Negative
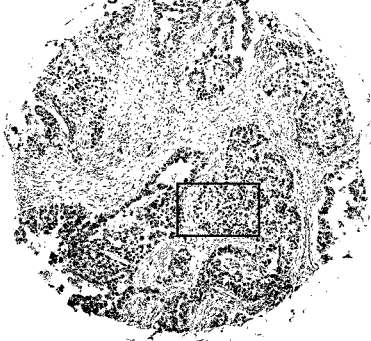
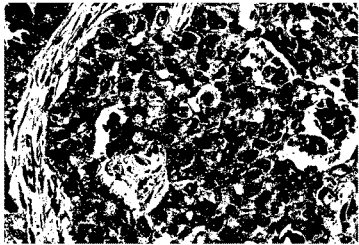
Fig. 4B
Array BC1141
Position: A9
Cell Type: Invasive Ductal Carcinoma
Tumor Grade: 2
TNM: T2N1M0
Pathologist Score: 1
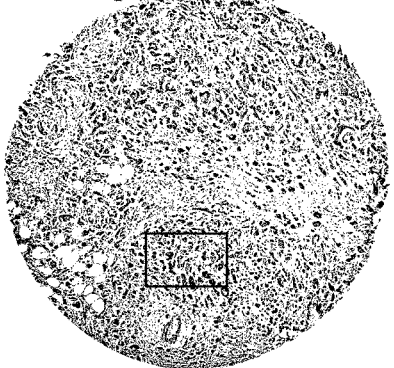
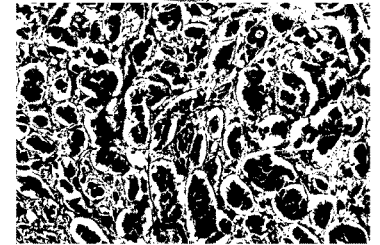
Fig. 4C
Array BC1141
Position: B10
Cell Type: Invasive Ductal Carcinoma
Tumor Grade: 2
TNM: T3N1M0
Pathologist Score: 2
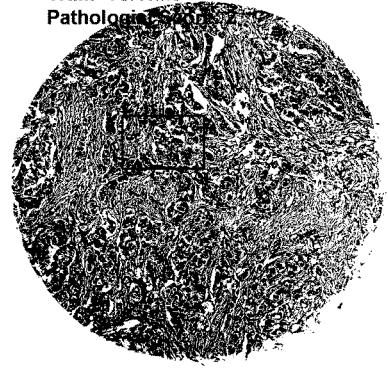

Fig. 5A
Array BC1141
Position: D7
Cell Type: Invasive Ductal Carcinoma
Tumor Grade: 2
TNM: T2N0M0
Pathologist Score: 3
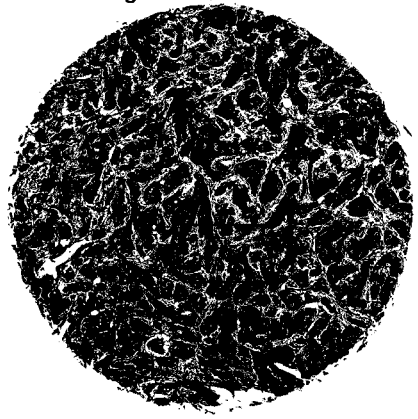
Fig. 5B
Array BC1141
Position: F6
Cell Type: Invasive Ductal Carcinoma
Tumor Grade: 2
TNM: T2N1M0
Pathologist Score: 4
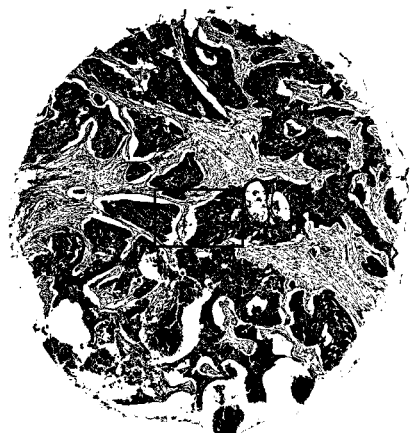

Breast Cancer
BR1141 – G11
Score 4

Grade 2 - T2N0M0

Ovarian cancer
BC11115a – C5
Score 3

Grade 2 – T1cN0M0
Serous Papillary

Pancreatic Cancer
PA805b – F3
Score 3

Grade 3 - T2N1M0

Fig. 8A | Fig. 8B | Fig. 8C | Fig. 8D
breast | ovarian | pancreatic | lung
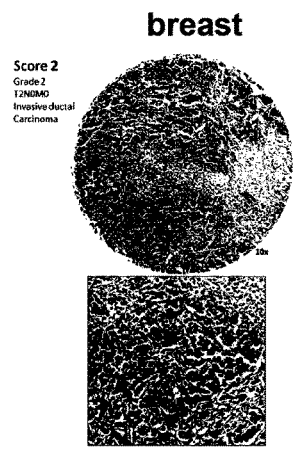
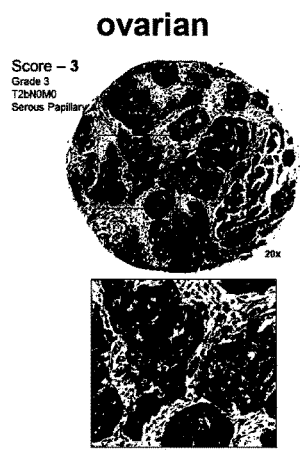
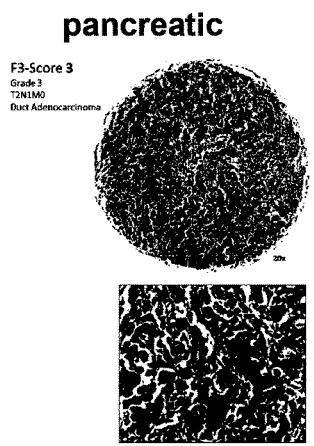
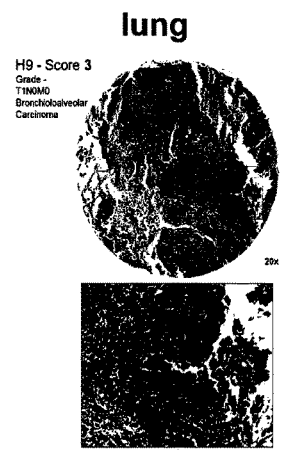

51yo Female - Normal Kidney
Array MNO961; D7
Score 1

39yo Male - Normal Kidney
Array MNO961; D8
Score 0

30yo Male - Normal Kidney
Array MNO961; D9
Score 1 huMNC2-scFv-Fc-Biotin – Normal Human Kidney

Esophageal Cancer Array
Biomax BC001113
Antibody: MN-hC2-scFv-Fc-Biotin

40%

30%

Negative   Trace   ■ Score 1   ■ Score 2   ■ Score 3

Score/Grade
3/2 = Score 3;Grade 2

Esophageal Cancer Array; MN-hC2-scFv-Fc-biotin

D6-Score 2
Grade 4
Adenoca...

D5-Score 3
Grade 3
Adenocar...

Esophageal Cancer Array; huMNC2-scFv-Fc-Biotin

Pancreatic Cancer Array
Biomax PA805b B030
Monoclonal Antibody: huMNC2-scFv-Fc-Biotin

21%

29%

Negative   Trace   ■ Score 1   ■ Score 2   ■ Score 3

Score/Grade
3/2 = Score 3; Grade 2

F3-Score 3
Grade 3
T2N1M0
Duct Adeno

B1-Score 2
Grade 1
T3N0M0
Duct Aden

Pancreatic Cancer Array Antibody: huMNC2-scFv-Fc-Biotin

A2-Score 2
Grade 1
T2N0M0
Duct Adenocarcinoma

C3-Score 2
Grade 2
T3N0M0
Duct Adenocarcinoma

Pancreatic Cancer Array Antibody: huMNC2-scFv-Fc-Biotin

C6-Score 2
Grade 2
T3N0M0
Duct Adenoc

D1-Score 3
Grade 3
T4N1M0
Duct Adenoc

Pancreatic Cancer Array Antibody: huMNC2-scFv-Fc-Biotin

E2-Score 2
Grade 1
T3N0M0
Duct Adenocarcinoma

E10-Score 3
Grade 3
T2N1M0
Duct Adenocarcinoma

Pancreatic Cancer Array Antibody: huMNC2-scFv-Fc-Biotin

Pancreatic Cancer Array
No Primary Antibody
Biomax - PA805b

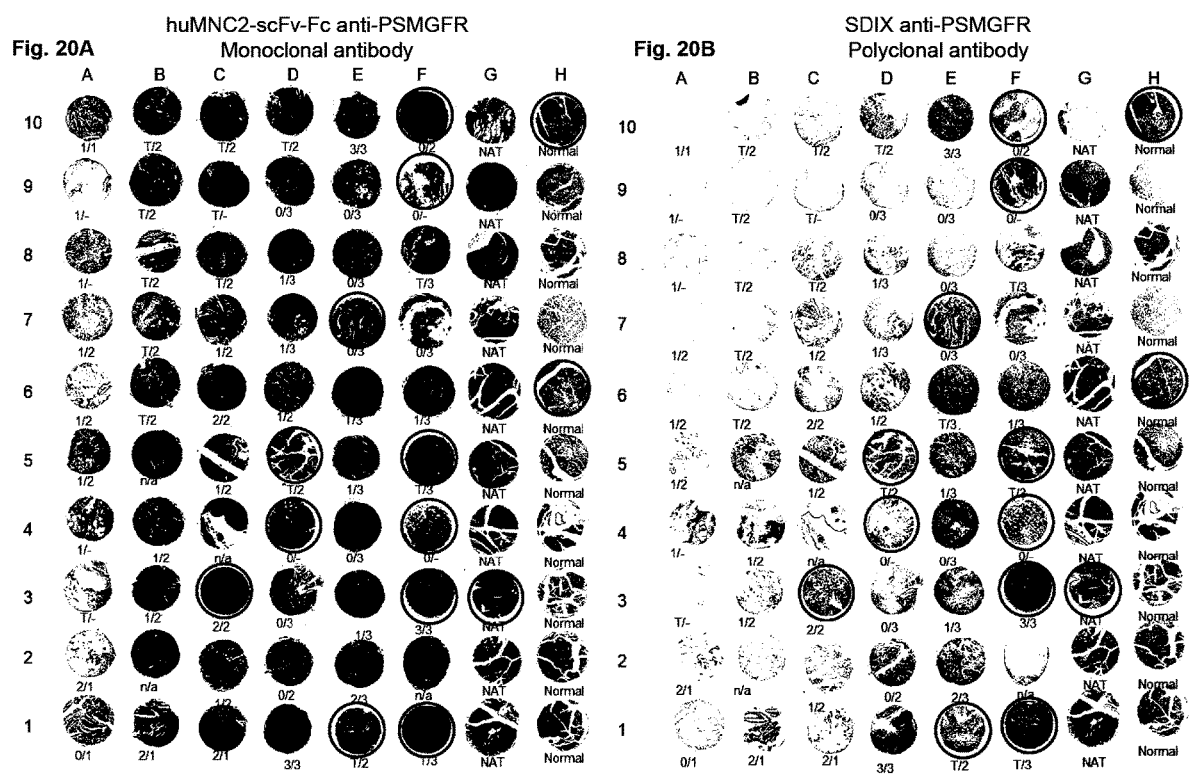

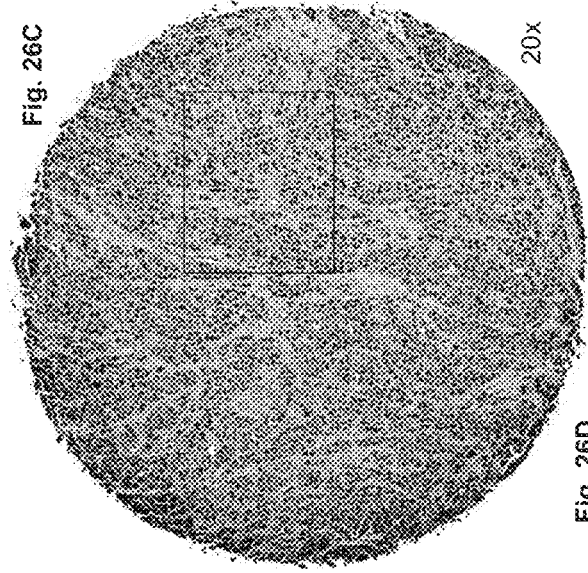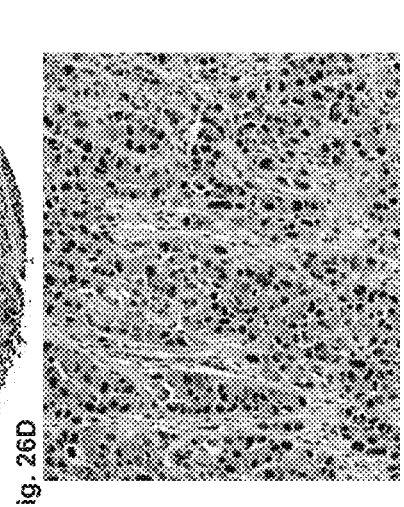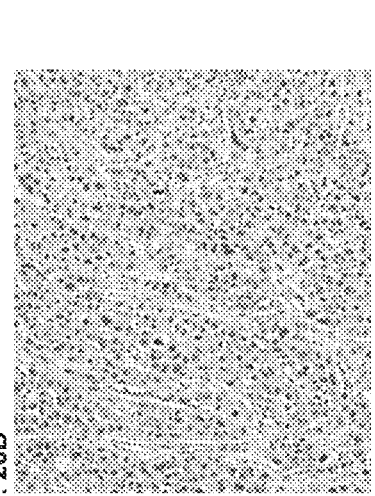
Figure 26A-26D

G7
Normal adjacent pancreas
tissue huMNC2-scFv-Fc
Monoclonal

SDIX
Polyclonal

G8
Normal adjacent pancreas tissue

20x

20x huMNC2-scFv-Fc
Monoclonal

SDIX
Polyclonal

G9
Normal adjacent pancreas
tissue huMNC2-scFv-Fc
Monoclonal

SDIX
Polyclonal

The conformation as well as length of MUC1* extra cellular domain varies according to which cleavage enzyme cleaves MUC1; monoclonal antibodies are identified that are cleavage enzyme dependent, cancer sub-type dependent, patient dependent or tissue/cell type dependent.

Fig. 38A

| PSMGFR clones | [ ] ug/mL |
|---|---|
| 18B4-1 | 17.3 |
| 18B4-2 | 6.8 |
| 18G12-1 | 2.6 |
| 18G12-2 | 5.9 |
| 20A10-1 | 18.3 |
| 20A10-2 | 16.2 |
| 25E6-1 | 3.4 |
| 25E6-2 | 2.1 |
| 28F9-1 | 3.9 |
| 28F9-2 | 8.2 |

Fig. 38B

| N+20/C-27 | [ ] ug/mL |
|---|---|
| 1E4-1 | 13.8 |
| 1E4-2 | 6.3 |
| 29H1-1 | 12.3 |
| 29H1-2 | 11.6 |
| 31A1-1 | 4.3 |
| 31A1-2 | 5.9 |
| 32C1-1 | 3.3 |
| 32C1-2 | 1.8 |
| 45C11-1 | 2.2 |
| 45C11-2 | 1.7 |

Fig. 38C

| N+9/C-9 | [ ] ug/mL |
|---|---|
| 3C5-1 | 2.4 |
| 3C5-2 | 5.5 |
| 8A9-1 | 1.0 |
| 8A9-2 | 1.1 |
| 17H6-1 | 4.2 |
| 17H6-2 | 2.4 |
| 39H5-1 | 1.6 |
| 39H5-2 | 2.6 |

```
N+20/C-27    SNIKFRPGSVVVQLTLAFREGTINVHDVETQFNQYKTE
N+9/C-9               VQLTLAFREGTINVHDVETQFNQYKTEAASRYNLTISDVSVSDVP
PSMGFR                              GTINVHDVETQFNQYKTEAASRYNLTISDVSVSDVPFPFSAQSGA
N-10                                        QFNQYKTEAASRYNLTISDVSVSDVPFPFSAQSGA
C-10                                GTINVHDVETQFNQYKTEAASRYNLTISDVSVSDV
```

FACS: Binding of anti-PSMGFR monoclonal antibodies to T47D breast cancer cells

N+20/C-27    SNIKFRPGSVVVQLTLAFREGTINVHDVETQFNQYKTE
N+9/C-9               VQLTLAFREGTINVHDVETQFNQYKTEAASRYNLTISDVSVSDVP
PSMGFR                        GTINVHDVETQFNQYKTEAASRYNLTISDVSVSDVPFPFSAQSGA
N-10                                  QFNQYKTEAASRYNLTISDVSVSDVPFPFSAQSGA
C-10                          GTINVHDVETQFNQYKTEAASRYNLTISDVSVSDV

FACS: Binding of anti-N+20/C-27 monoclonal antibodies to T47D breast cancer cells

| | |
|---|---|
| N+20/C-27 | SNIKFRPGSVVVQLTLAFREGTINVHDVETQFNQYKTE |
| N+9/C-9 | VQLTLAFREGTINVHDVETQFNQYKTEAASRYNLTISDVSVSDVP |
| PSMGFR | GTINVHDVETQFNQYKTEAASRYNLTISDVSVSDVPFPFSAQSGA |
| N-10 | QFNQYKTEAASRYNLTISDVSVSDVPFPFSAQSGA |
| C-10 | GTINVHDVETQFNQYKTEAASRYNLTISDVSVSDV |

FACS: Binding of N+9/C-9 monoclonal antibodies to T47D breast cancer cells

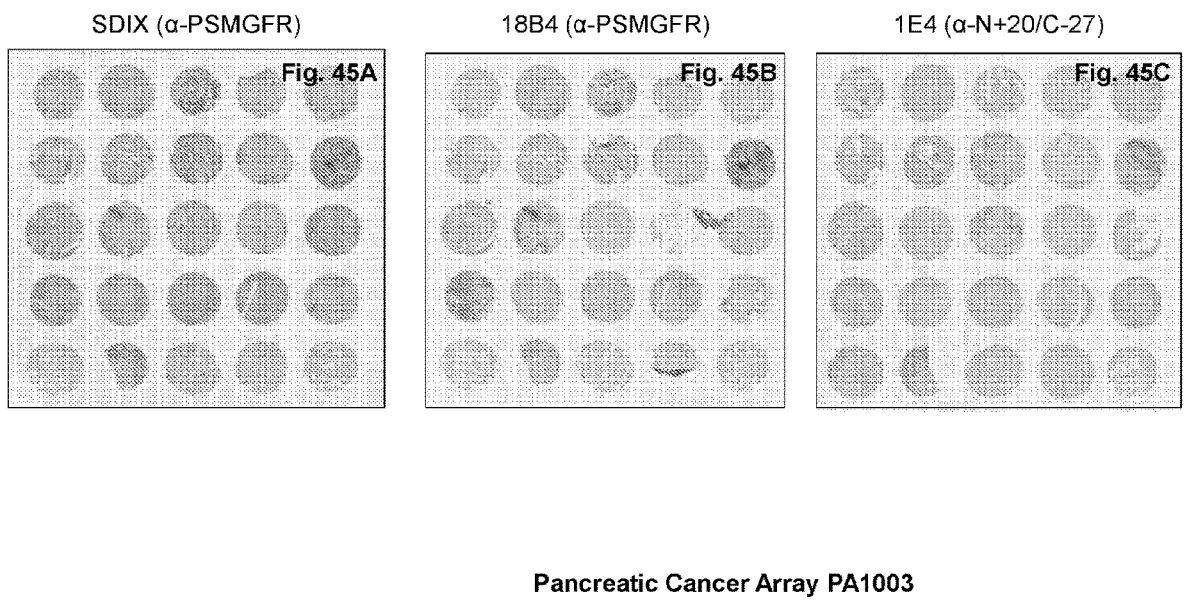
Pancreatic Cancer Array PA1003

SDIX (α-PSMGFR)　　　　18B4 (α-PSMGFR)　　　　1E4 (α-N+20/C-27)

Pancreatic Cancer Array PA1003

SDIX (α-PSMGFR)   18B4 (α-PSMGFR)

Pancreatic Cancer Array PA1003

SDIX (α-PSMGFR)   18B4 (α-PSMGFR)
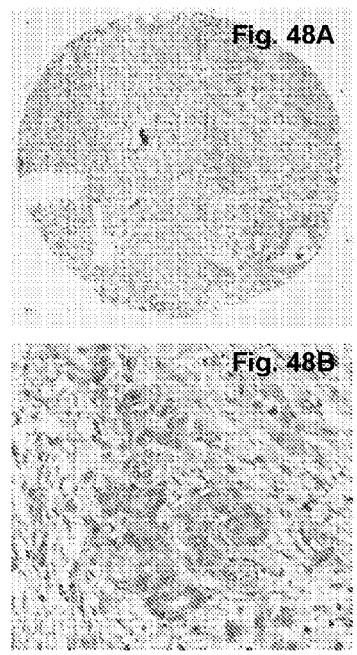
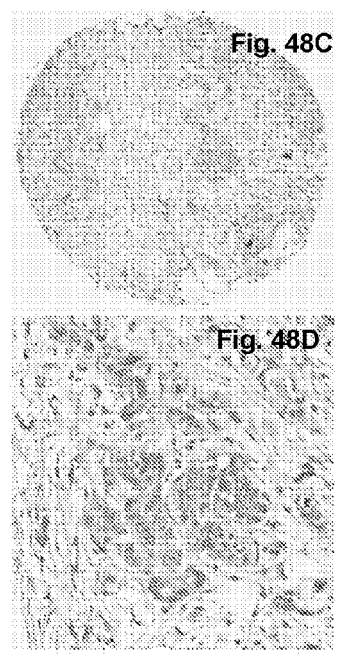
Pancreatic Cancer Array PA1003

SDIX (α-PSMGFR)                    1E4 (α-N+20/C-27)

Pancreatic Cancer Array PA1003

SDIX (α-PSMGFR)  1E4 (α-N+20/C-27)
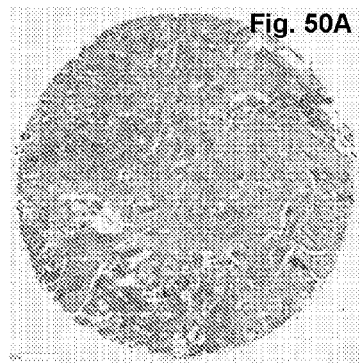 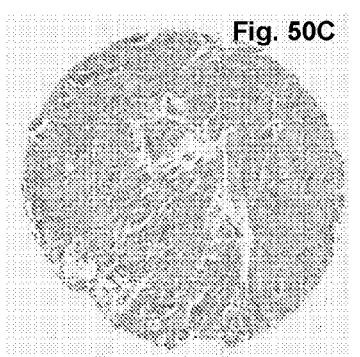
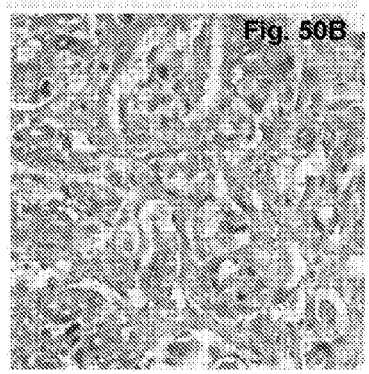 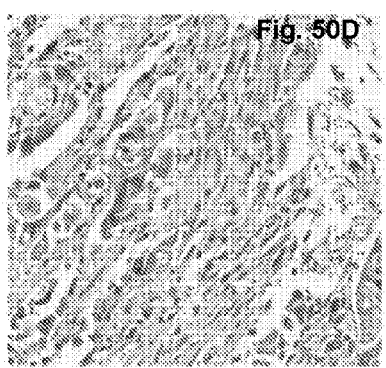
Pancreatic Cancer Array PA1003

SDIX (α-PSMGFR)   20A10 (α-PSMGFR)   29H1-1 (α-N+20/C-27)

Pancreatic Cancer Array PA1003

Pancreatic Cancer Array PA1003

17H6 (α- N+9/C-9)

32C1 (α-N+20/C-27)

45C11 (α-N+20/C-27)

31A1 (α-N+20/C-27)

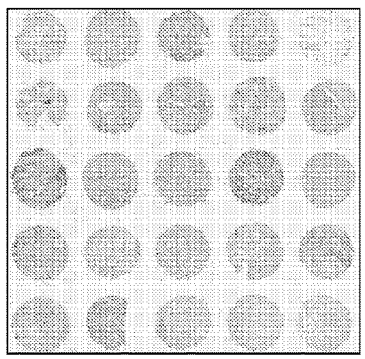
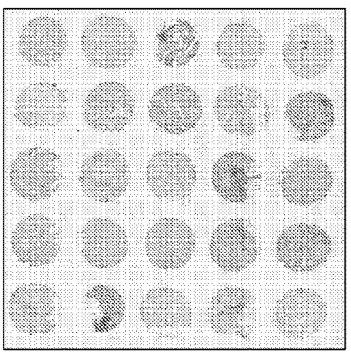
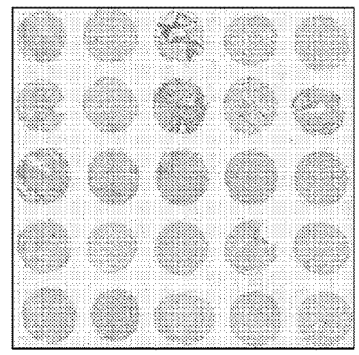
Pancreatic Cancer Array PA1003

SDIX (α-PSMGFR)

20A10 (α-PSMGFR)

29H1 (α-N+20/C-27)

31A1 (α-N+20/C-27)

Esophageal Cancer Array ES1001

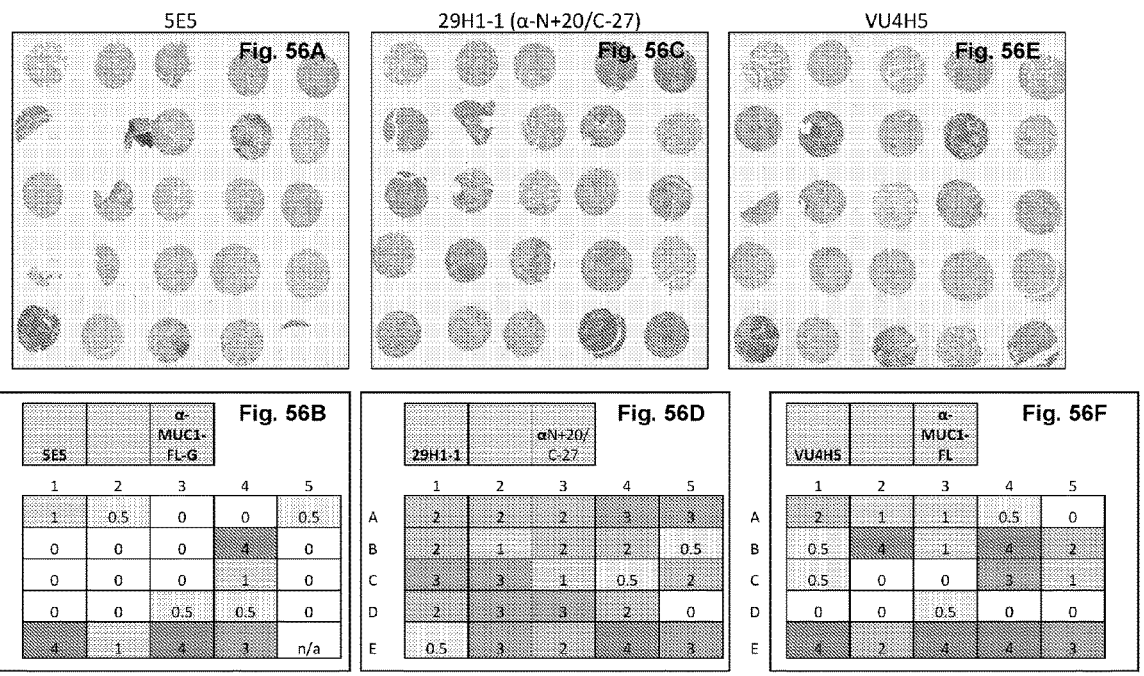

Fig. 57A 5E5 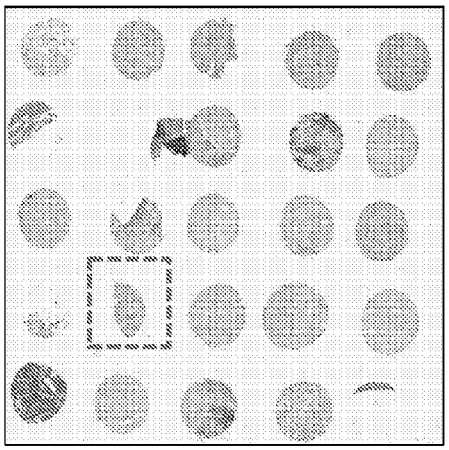
Fig. 57B 29H1 (α-N+20/C-27) 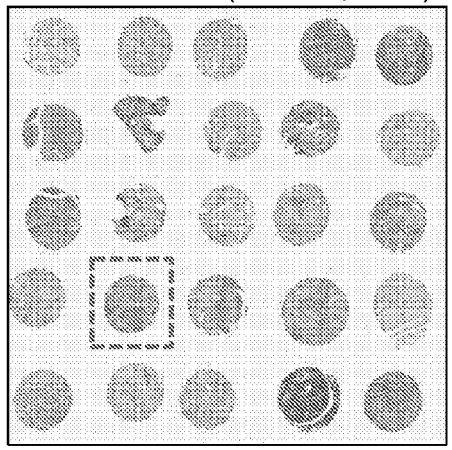
Fig. 57C VU4H5 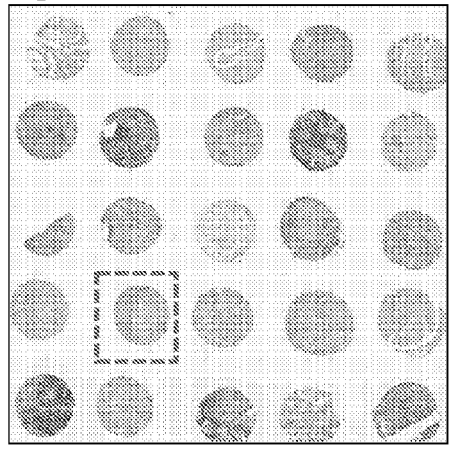
Fig. 57D No primary antibody control 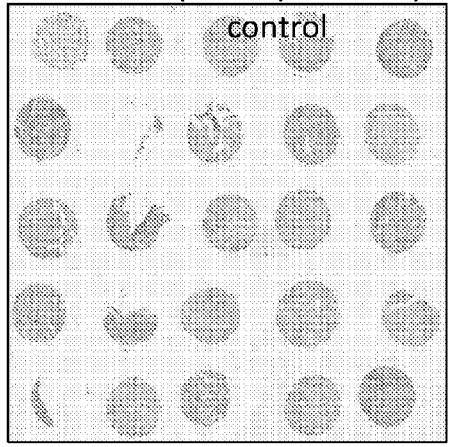
Esophageal Cancer Array ES1001

Esophageal Cancer Array ES1001

5E5

VU4H5

29H1 (α-N+20/C-27)

Fig. 58A  
SDIX (α-PSMGFR)
Fig. 58B  
20A10 (α-PSMGFR)
Fig. 58C  
29H1 (α-N+20/C-27)
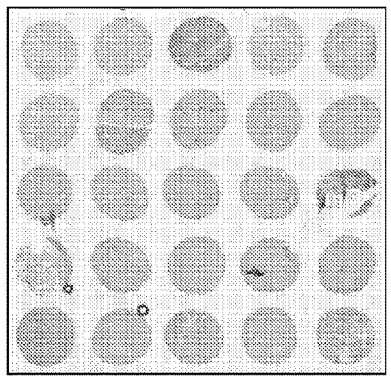
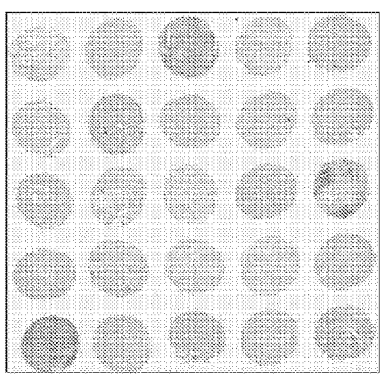
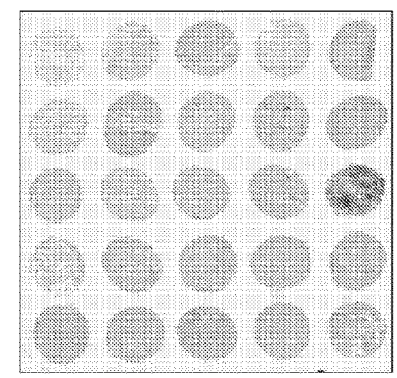
Prostate Cancer Array PR1001

MNC2 (α-PSMGFR)

18B4 (α-PSMGFR)

32C1-1 (α-N+20/C-27)

SDIX (α-PSMGFR)

31A1-2 (α-N+20/C-27)

Prostate Cancer Array PR1001

Fig. 60A
5E5
Fig. 60C
29H1-1 (α-N+20/C-27)
Fig. 60E
VU4H5
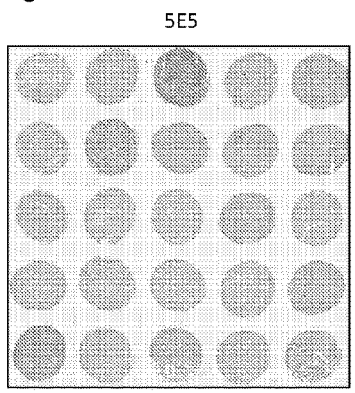
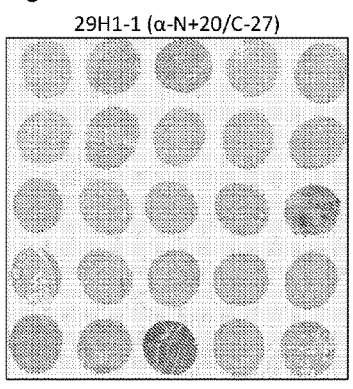
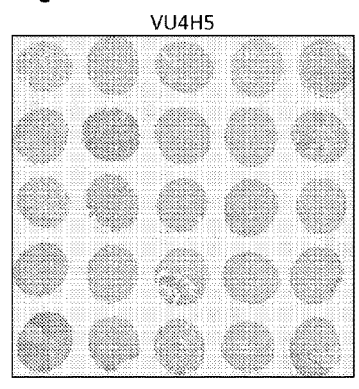
Fig. 60B
|   | 5E5 |   | α-MUC1-FL-G |   |   |
|---|---|---|---|---|---|
|   | 1 | 2 | 3 | 4 | 5 |
| A | 0 | 0 | 0 | 0 | 0 |
| B | 0 | 0 | 0 | 0 | 0 |
| C | 0 | 0 | 0 | 0 | 1 |
| D | 0 | 0 | 0 | 0 | 0 |
| E | 2 | 0 | 0 | 0 | 0 |
Fig. 60D
|   | 29H1-1 |   | α-(N+20/C-27) |   |   |
|---|---|---|---|---|---|
|   | 1 | 2 | 3 | 4 | 5 |
| A | 0.5 | 2 | 0 | 0.5 | 0.5 |
| B | 0 | 0.5 | 0 | 0.5 | 1 |
| C | 2 | 0 | 0 | 1 | 4 |
| D | 1 | 0 | 2 | 1 | 0.5 |
| E | 2 | 3 | 4 | 2 | 1 |
Fig. 60F
|   | VU4H5 |   | α-MUC1-FL |   |   |
|---|---|---|---|---|---|
|   | 1 | 2 | 3 | 4 | 5 |
| A | 0 | 0 | 0 | 0 | 0 |
| B | 0 | 0 | 0 | 0 | 0 |
| C | 0 | 0 | 0 | 0 | 1 |
| D | 0 | 0 | 0 | 0 | 0 |
| E | 2 | 0 | 0 | 0 | 0 |
Prostate Cancer Array PR1001

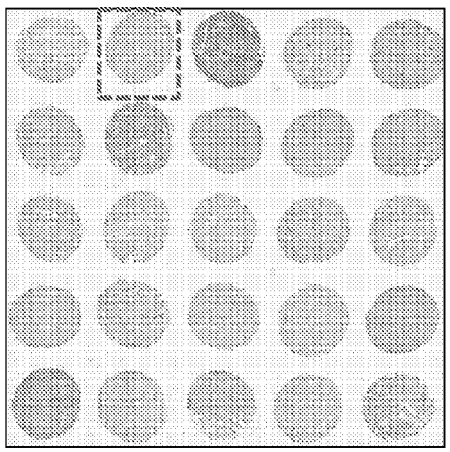
Fig. 61A  5E5
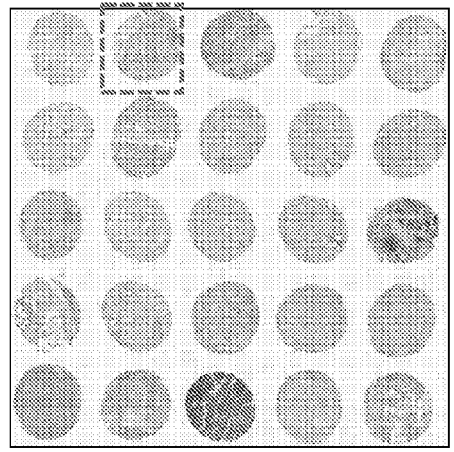
Fig. 61B  29H1 (α-N+20/C-27)
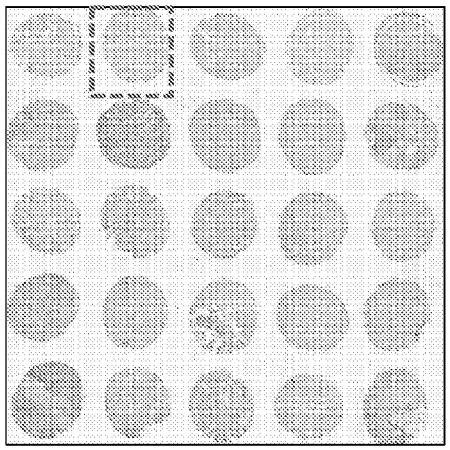
Fig. 61C  VU4H5
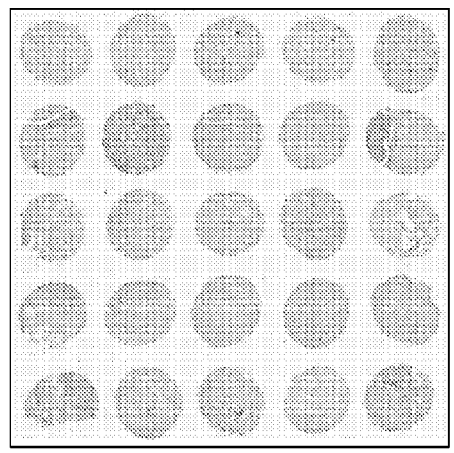
Fig. 61D
No primary antibody control
Prostate Cancer Array PR1001

Fig. 61E
5E5
Fig. 61F
29H1 (α-N+20/C-27)
Fig. 61G
VU4H5
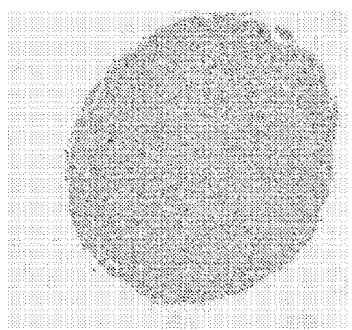
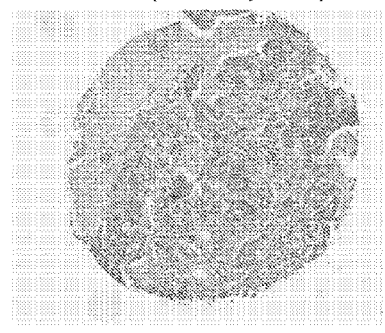
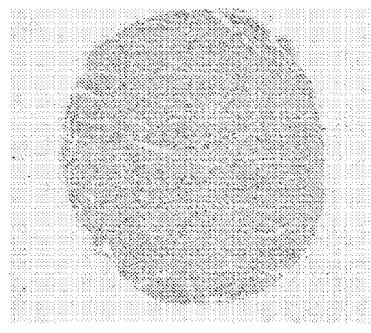
Prostate Cancer Array PR1001

MNC2 (α-PSMGFR)

20A10 (α-PSMGFR)

Breast Cancer Array BR1141

Fig. 63A
MNC2 (α-PSMGFR)
Fig. 63B
25E6 (α-PSMGFR)
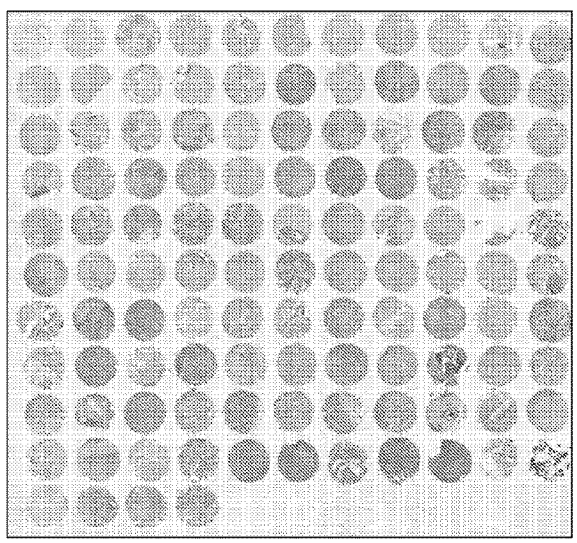
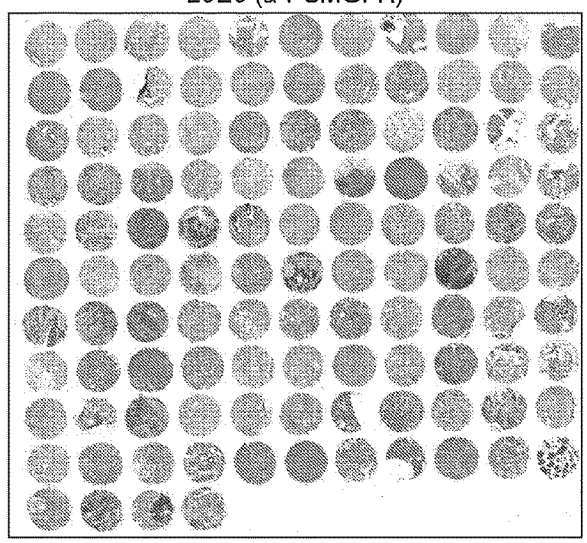
Breast Cancer Array BR1141

Fig. 64A
MNC2 (α-PSMGFR)
Fig. 64B
18B4 (α-PSMGFR)
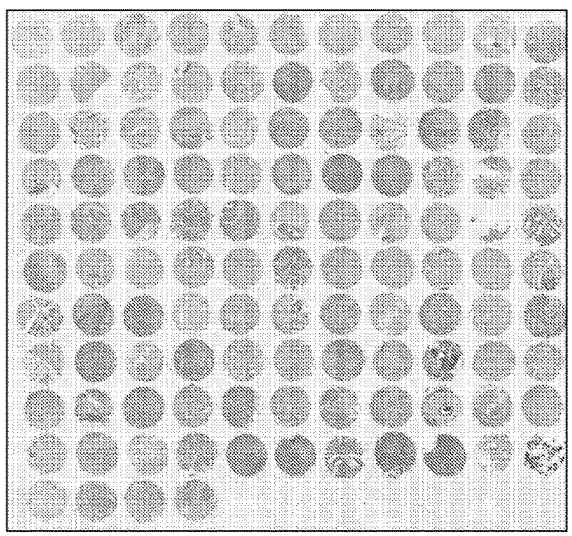
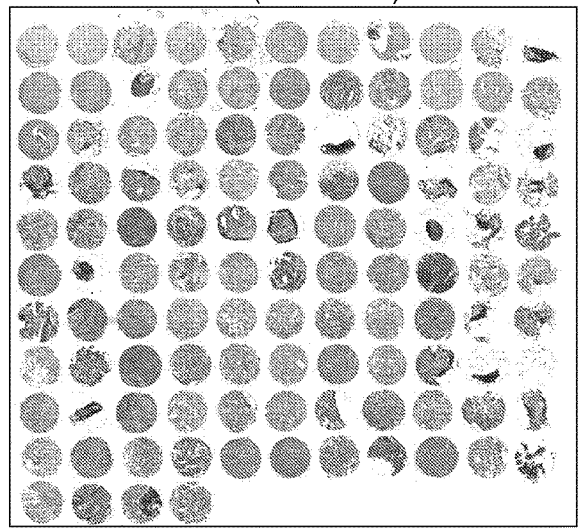
Breast Cancer Array BR1141

MNC2 (α-PSMGFR)

18G12 (α-PSMGFR)

Breast Cancer Array BR1141

Fig. 66A
MNC2 (α-PSMGFR)
Fig. 66B
8A9 (α-N+9/C-9)
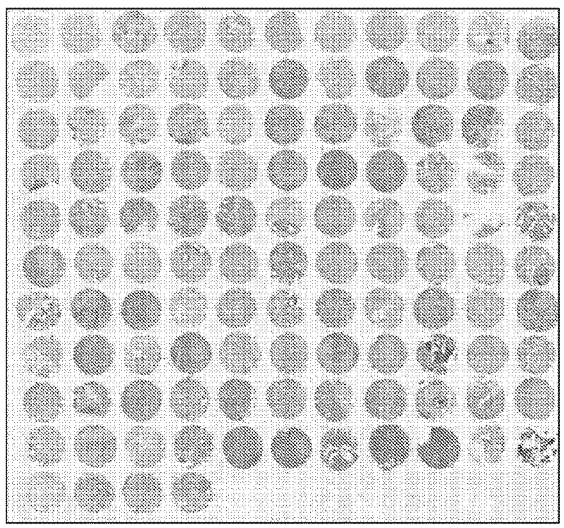
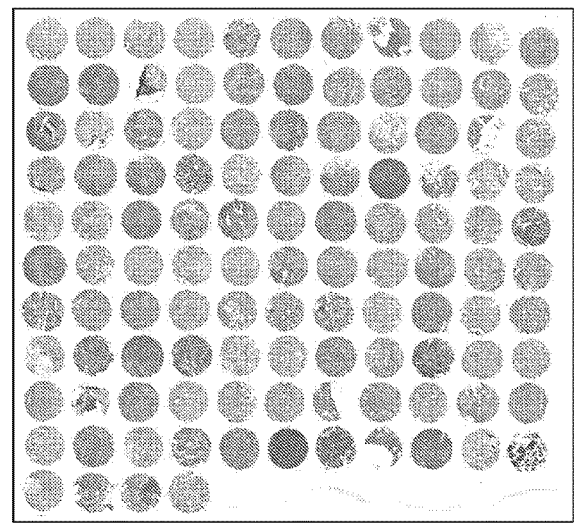
Breast Cancer Array BR1141

Fig. 67A
Fig. 67B
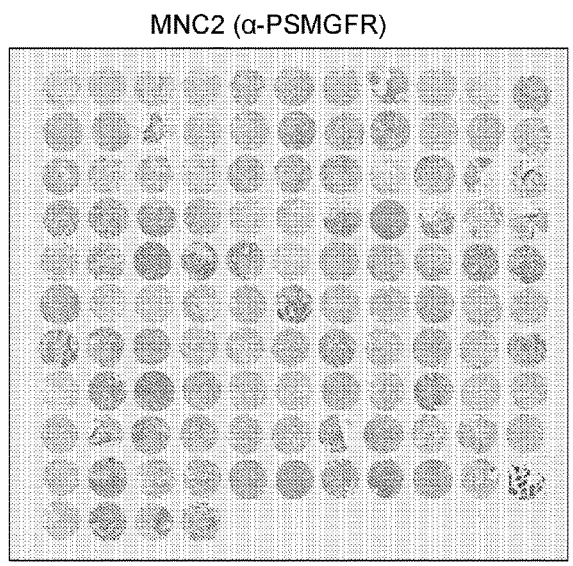
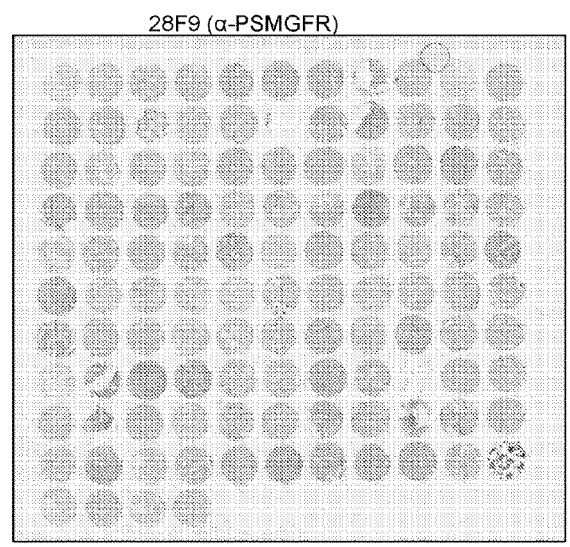
Breast Cancer Array Br1141

Fig. 68A
Fig. 68B
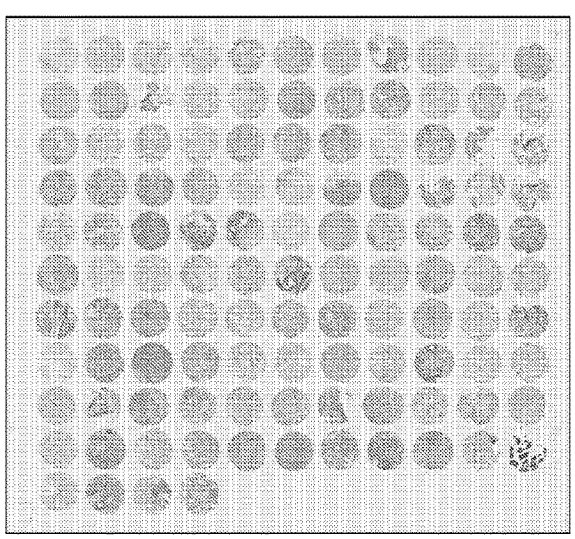
MNC2 (α-PSMGFR)
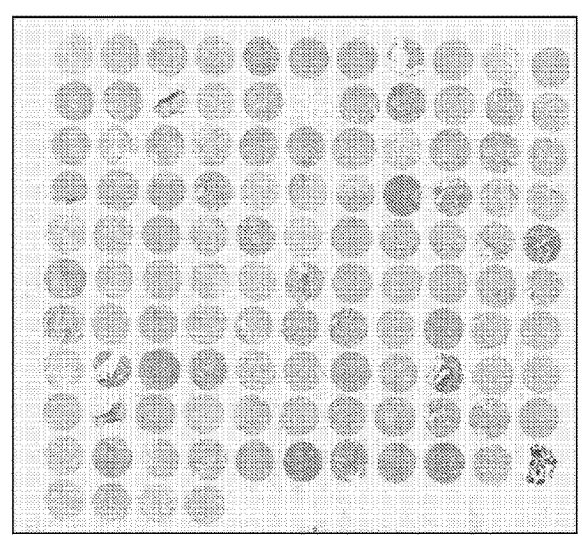
17H6 (α-N+9/C-9)
Breast Cancer Array Br1141

Fig. 69A
Fig. 69B
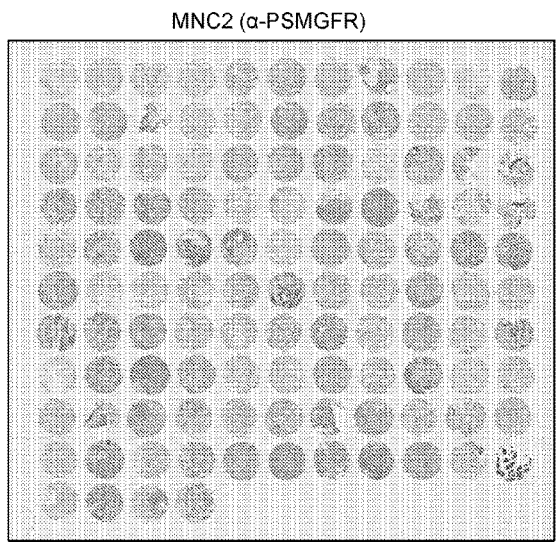
MNC2 (α-PSMGFR)
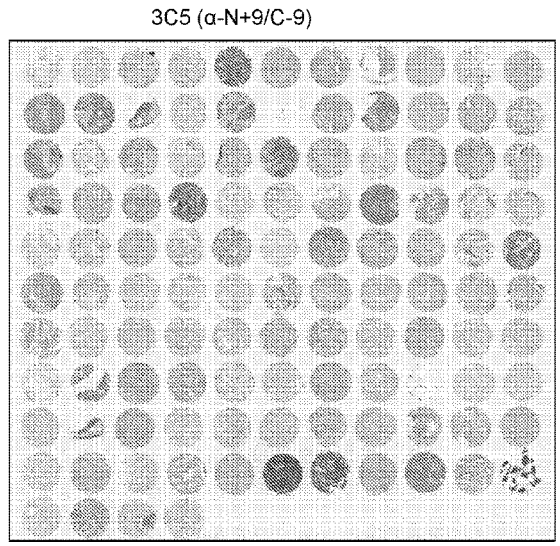
3C5 (α-N+9/C-9)
Breast Cancer Array Br1141

20A10 (α-PSMGFR)

29H1 (α-N+20/C-27)

45C11 (α-N+20/C-27)

32C1 (α-N+20/C-27)

Breast Cancer Array BR1007

Fig. 70E        Fig. 70F        Fig. 70G
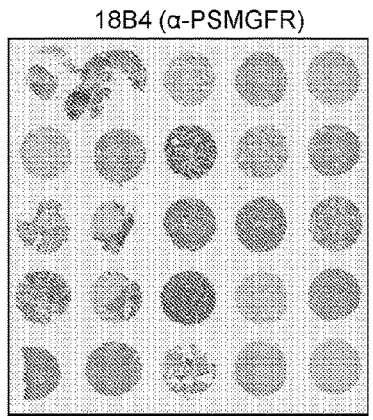
18B4 (α-PSMGFR)
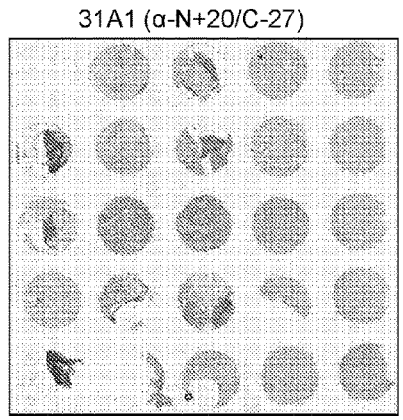
31A1 (α-N+20/C-27)
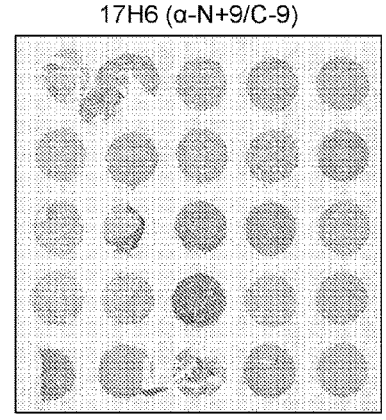
17H6 (α-N+9/C-9)
Breast Cancer Array BR1007

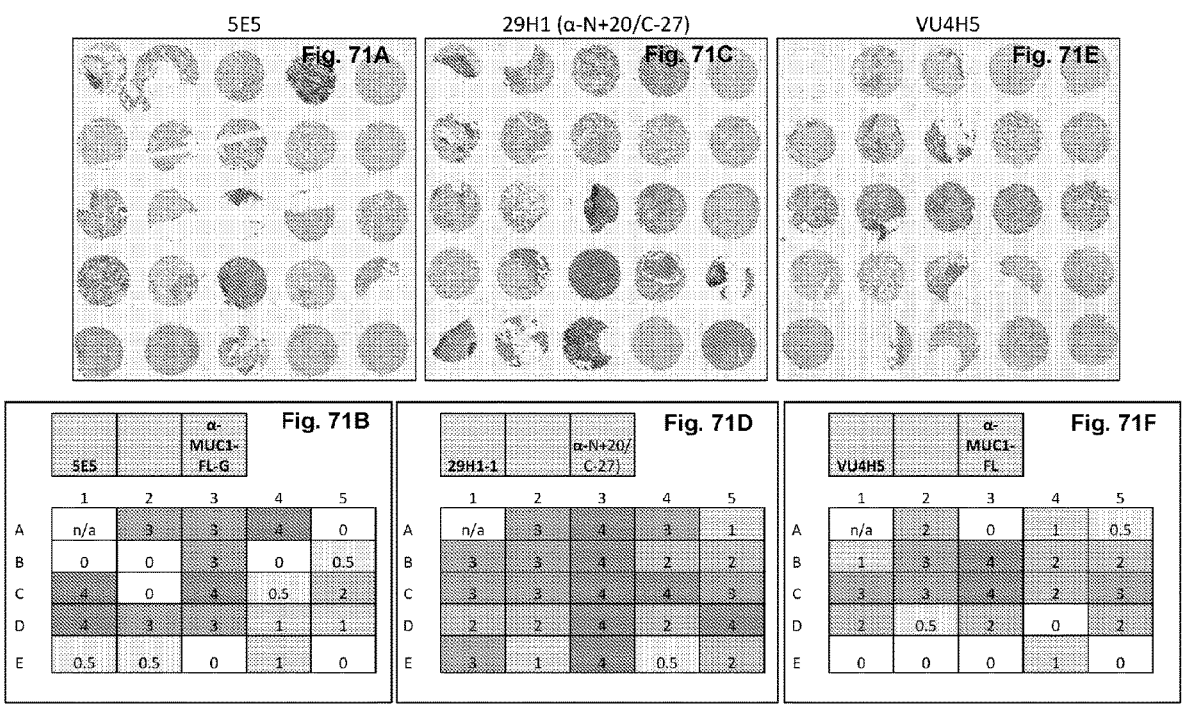
Breast Cancer Array BR1007

Fig. 72A MNC2 IgG (α-PSMGFR) 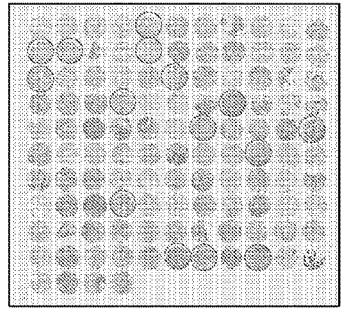
Fig. 72B 20A10 (α-PSMGFR) 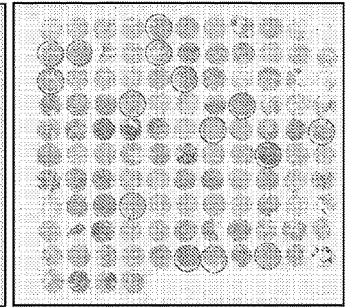
Fig. 72C 25E6 (α-PSMGFR) 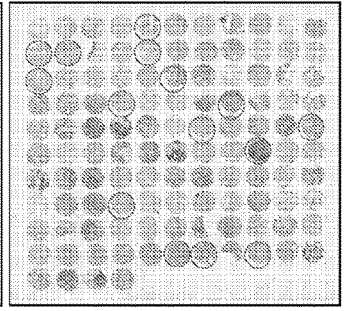
Fig. 72D 28F9 (α-PSMGFR) 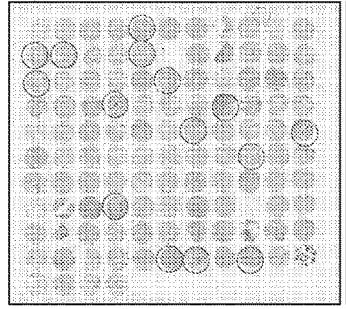
Fig. 72E 18G12 (α-PSMGFR) 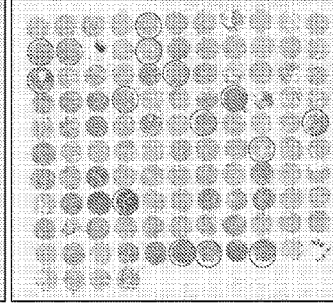
Fig. 72F 18B4 (α-PSMGFR) 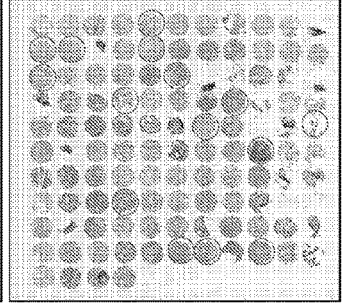
Breast Cancer Array BR1141

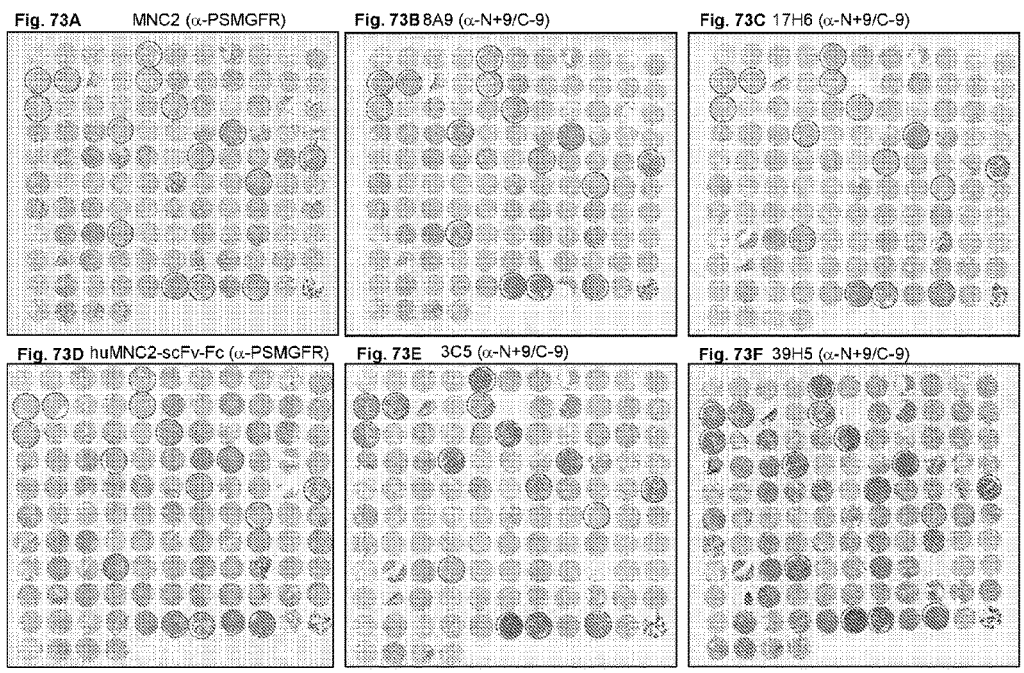

DIAGNOSTIC METHODS USING ANTI-MUC1* ANTIBODIES

This application is the U.S. national phase of International Application No. PCT/US2019/019566 filed Feb. 26, 2019 which designated the U.S. and claims priority to U.S. Provisional Patent Application No. 62/635,378 filed Feb. 26, 2018, IB Application No. PCT/US2018/062569 filed Nov. 27, 2018, U.S. Provisional Patent Application No. 62/640,697 filed Mar. 9, 2018, and U.S. Provisional Patent Application No. 62/791,661 filed Jan. 11, 2019, the entire contents of each of which are hereby incorporated by reference.

SUMMARY OF THE INVENTION

The present invention is directed to a method of diagnosing cancer and determining suitability of treating a patient suffering from cancer or metastasis of cancer characterized by aberrant expression of MUC1, with a MUC1* targeting therapeutic, comprising contacting cells or tissue of a patient diagnosed with or suspected of having cancer, with an antibody that binds to a form of MUC1 that is devoid of the tandem repeat domain, wherein the presence of specific binding of the antibody to the cleaved or truncated form of MUC1, and wherein such binding is in an abnormal pattern, indicates that a MUC1* targeting therapeutic is suitable to be used to treat the patient.

Here, we define MUC1* as a transmembrane cleavage product of MUC1 that functions as a growth factor receptor and is devoid of the tandem repeat sequences. However, MUC1 can be cleaved by different enzymes, which cleave at different sites. Which cleavage enzyme clips MUC1 may be tissue specific or patient specific. The conformation of the extra cellular domain of MUC1* may change depending on which cleavage enzyme cleaves it. Anti-MUC1* antibodies may bind to the extra cellular domain of the transmembrane receptor that remains after cleavage.

In one aspect, the antibody may bind to a peptide of Primary Sequence of MUC1 Growth Factor (PSMGFR), PSMGFR N−10, PSMGFR C−10, or may bind to PSMGFR N−10 but not to PSMGFR C−10, or may bind to PSMGFR C−10 but not to PSMGFR N−10, or may bind to the PSMGFR N+20 peptides such as N+20/C−22, N+20/C−41, or N+20/C−27 peptide, or a N+9/C−9 peptide. The antibody may bind to a peptide having a sequence that is extended N-terminally beyond the PSMGFR sequence. The antibody may bind to a peptide of sequence N+20-PSMGFR or N+9-PSMGFR. In one aspect of the invention, diagnostic assays employing anti-MUC1* antibodies or fragments thereof are used to screen patients to determine their potential benefit from a MUC1* targeting therapeutic. In one aspect of the invention, the antibody used in the diagnostic and the antibody or fragment thereof that is incorporated into the therapeutic are derived from the same antibody. The species of the diagnostic antibody and the therapeutic antibody do not need to be the same.

In one example, (i) a suspect cellular or tissue specimen, which may be a biopsy, from a patient diagnosed with cancer or suspected of developing cancer is contacted with an anti-MUC1* antibody; (ii) a normal cellular or tissue specimen from the patient or from a healthy donor is contacted with the same anti-MUC1* antibody, which may be an archived reference specimen; (iii) antibody binding is detected; (iv) the extent and pattern of antibody binding to the suspect specimen is compared to that of the normal specimen; (v) a determination that the suspect specimen overexpresses MUC1*, or expresses MUC1* in a uniform pattern as opposed to expression that is restricted to the apical border, indicates that the patient is suffering from a MUC1* positive cancer; (vi) a therapeutic agent that incorporates an anti-MUC1* antibody, or fragment thereof, is administered to the patient.

In another aspect of the invention, anti-MUC1* antibodies can be attached to an imaging agent for use in a patient as a whole body diagnostic to determine if the patient has a MUC1* positive tumor or, depending on the specific antibody used, if the patient would benefit from a therapeutic comprising all or a fragment of the antibody that is attached to the imaging agent. The species of the diagnostic antibody and the therapeutic antibody do not need to be the same. Antibodies generated in camelid species are particularly useful for in vivo diagnostic assays because camelids generated small monovalent antibodies that have a short half-life in humans.

In another aspect of the invention, anti-MUC1* antibodies, which may be attached to an imaging agent are used intra-surgically to detect or mark cancerous tissues so they can be excised during the surgery.

In another aspect of the invention, anti-MUC1* antibodies or fragments thereof that bind to a peptide having some or all of the sequence of the PSMGFR peptide are used for the diagnosis and/or treatment of breast cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of pancreatic cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of esophageal cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of prostate cancers.

In one aspect, the MUC1* targeting therapeutic may be a cancer immunotherapy. The MUC1* targeting therapeutic may be a CAR T, a BiTE, an ADC (antibody drug conjugate), a bispecific antibody or an antibody mimic.

The MUC1* targeting therapeutic may be an antibody that binds to a cleaved form of MUC1 wherein the cleaved form is the extra cellular domain of the transmembrane receptor that remains after cleavage. The antibody may bind to a peptide known as Primary Sequence of MUC1 Growth Factor (PSMGFR) or to a peptide that is N-terminally extended for up to 20 amino acids beyond the PSMGFR sequence. The antibody used in the therapeutic may be derived from the antibody used in the diagnostic assay, but need not be generated in the same species animal.

The inventive method may be an in vitro assay. The assay may be carried out on a tissue specimen, bodily fluid sample, or a blood sample.

In another aspect, the assay may be an in vivo assay. An imaging agent may be attached to the antibody.

In another aspect, the invention may comprise a second antibody, and the steps may comprise determining the ratio of the amount of a first antibody to a second antibody. The first antibody may bind to an extra cellular domain of the transmembrane receptor that remains after cleavage and the second antibody may bind to a portion of the MUC1 extra cellular domain that is N-terminal of the cleavage site, such as the tandem repeat sequences.

In another aspect, in reference to all of the above methods, the non-human, human or humanized anti-MUC1* antibody or antibody fragment or antibody-like protein may specifically bind to
  (i) PSMGFR region of MUC1;
  (ii) PSMGFR peptide as set forth in SEQ ID NO:4;
  (iii) PSMGFR N+20/C−22, a peptide having amino acid sequence of (SEQ ID NO: 5)
  SNIKFRPGSVVVQLTLAFREGTINVHDVETQFNQYKTEAASRY;

(iv) PSMGFR N+12/C−22, a peptide having amino acid sequence of (SEQ ID NO: 6)
  SVVVQLTLAFREGTINVHDVETQFNQYKTEAASRY;

(v) PSMGFR N+9/C−30, a peptide having amino acid sequence of (SEQ ID NO: 7)
  VQLTLAFREGTINVHDVETQFNQY;

(vi) PSMGFR N+20/C−41, a peptide having amino acid sequence of (SEQ ID NO: 8)
  SNIKFRPGSVVVQLTLAFREGTIN (vii) PSMGFR N+20/C−27, a peptide having amino acid sequence of (SEQ ID NO: 9)
  SNIKFRPGSVVVQLTLAFREGTINVHDVETQFNQYKTE;

or
  (viii) PSMGFR N+9/C−9, a peptide having amino acid sequence of (SEQ ID NO: 10)
  VQLTLAFREGTINVHDVETQFNQYKTEAASRYNLTISDVSVSDVP.

The antibody that binds to the extra cellular domain of the transmembrane receptor that remains after cleavage may be SDIX SRY polyclonal antibody, MNC2 monoclonal antibody, MNE6 monoclonal antibody, or monoclonal antibodies 1E4, 29H1, 31A1, 32C1, and 45C11 reactive with PSMGFR N+20/C−27; 17H6, 39H5, 3C5, 8A9 reactive with PSMGFR N+9/C−9; 18G12, 20A10, 25E6, 28F9, and 18B4 reactive with PSMGFR, as well as MNC2 and MNE6, which are also reactive with PSMGFR. These antibodies may be human, humanized, mouse, camelid, llama, alpaca, camel, rabbit, goat, hamster or other non-human species.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1A shows photographs of the breast cancer tissue arrays after they were stained with VU4H5, which is an antibody that binds to the tandem repeat domains of full-length MUC1. FIG. 1B shows graphs of the pathologist scores for the tissues pictured in FIG. 1A. FIG. 1C shows photographs of the breast cancer tissue arrays after they were stained with MNC2, which is an antibody that binds to an epitope within the PSMGFR region of MUC1*. FIG. 1D shows graphs of the pathologist scores for the tissues pictured in FIG. 1C.

FIG. 2A-2B shows pie chart graphs of the pathologist scores of the arrays shown in FIG. 1A and FIG. 1C. FIG. 2A shows that the antibody that binds to tandem repeats of full-length MUC1 misses 30% of breast cancers. FIG. 2B shows that the anti-MUC1* antibody MNC2 recognizes 95% of breast cancers. Anti-MUC1-full-length only binds strongly to 10% of the breast tumors, while anti-MUC1* antibody MNC2 binds strongly to about 50% of breast tumors.

FIG. 4A-4C shows photographs, at two different magnifications, of individual breast cancer specimens from breast cancer array BR1141 after staining with anti-MUC1* antibody huMNC2-scFv-Fc. The position in the array, cancer sub-type, tumor grade, TNM (Tumor stage, Node involvement, and Metastasis) and pathologist score are indicated in figures. Standard immunohistochemistry methods were used. Antibody concentration was titered using the highest concentration at which the antibody showed expected staining of normal tissues without staining stroma. The antibody was conjugated to a biotin through its Fc region, to avoid false positive due to anti-human secondary antibodies staining host antibodies as well as B cell follicules. FIG. 4A shows the specimen at position A7 which was negative for huMNC2 reactive cells. FIG. 4B shows the specimen at position A9 which is a Grade 2 cancer, with lymph node involvement that scored +1 for huMNC2 reactivity. FIG. 4C shows the specimen at position B10 which is a larger Grade 2 tumor, with lymph node involvement that scored +2 for huMNC2 reactivity.

FIG. 5A-5B shows photographs, at two different magnifications, of individual breast cancer specimens from breast cancer array BR1141 after staining with anti-MUC1* antibody huMNC2-scFv-Fc. FIG. 5A shows the specimen at position D7 which is a Grade 2 cancer, without lymph node involvement that scored +3 for huMNC2 reactivity. FIG. 5B shows the specimen at position F6 which is a Grade 2 tumor, with lymph node involvement that scored +4 for huMNC2 reactivity.

FIG. 7A shows a photograph of a Grade 2 breast tumor that pathologist scored +4. FIG. 7B shows a photograph of a Grade 2 ovarian tumor that pathologist scored +3. FIG. 7C shows a photograph of a Grade 3 pancreatic tumor that pathologist scored +3. IHC studies of over 1,000 tumor specimens showed that huMNC2-scFv recognized 95% of Breast Cancers (90% triple negative), 83% Ovarian, 78% Pancreatic & 71% Lung Cancers.

FIG. 8A-8D shows magnified photographs of different cancer sub-types after staining with anti-MUC1* antibody huMNC2-scFv-Fc. FIG. 8A shows a photograph of a Grade 2 breast tumor that pathologist scored +2. FIG. 8B shows a photograph of a Grade 3 ovarian tumor that pathologist scored +3. FIG. 8C shows a photograph of a Grade 3 pancreatic tumor, with lymph node involvement that pathologist scored +3. FIG. 8D shows a photograph of a lung cancer that pathologist scored +3.

FIG. 9A shows normal adrenal gland tissue. FIG. 9B shows normal brain tissue. FIG. 9C shows normal breast tissue. FIG. 9D shows normal stomach tissue. FIG. 9E shows normal heart tissue. FIG. 9F shows normal kidney tissue. FIG. 9G shows normal testis tissue. FIG. 9H shows normal intestine tissue. FIG. 9I shows normal liver tissue.

FIG. 10A shows normal kidney tissue with huMNC2 reactivity limited to the apical border, which is normal expression. FIG. 10B is the same tissue at greater magnification. FIG. 10C shows another example of normal kidney tissue with undetectable huMNC2 reactivity. FIG. 10D is the same tissue at greater magnification. FIG. 10E shows another example of normal kidney tissue with huMNC2 reactivity limited to the apical border, which is normal expression. FIG. 10F is the same tissue at greater magnification. Further studies showed that less than 10% of normal kidney tissue showed huMNC2 reactivity at distal collecting tubules wherein such reactivity was strictly limited to the apical border, which is a normal expression pattern.

FIG. 12A shows the specimen at position A4 which was negative for huMNC2 reactive cells. FIG. 12B shows the same specimen at greater magnification. FIG. 12C shows the specimen at position D2 which the pathologist scored as trace reactivity to huMNC2. FIG. 12D shows the same specimen at greater magnification. FIG. 12E shows the specimen at position B8 which the pathologist scored as +1 reactivity to huMNC2. FIG. 12F shows the same specimen at greater magnification.

FIG. 13A shows the specimen at position D6, a Grade 4 tumor, which the pathologist scored +2. FIG. 13B shows the same specimen at greater magnification. FIG. 13C shows the specimen at position D5, a Grade 3 tumor, which the pathologist scored +3. FIG. 12D shows the same specimen at greater magnification.

FIG. 15A shows the specimen at position F3, a Grade 3 tumor, which the pathologist scored +3. FIG. 15B shows the same specimen at greater magnification. FIG. 15C shows the specimen at position B1, a Grade 1 tumor, which the pathologist scored +2. FIG. 15D shows the same specimen at greater magnification.

FIG. 16A shows the specimen at position A2, a Grade 1 tumor, which the pathologist scored +2. FIG. 16B shows the same specimen at greater magnification. FIG. 16C shows the specimen at position C3, a Grade 2 tumor, which the pathologist scored +2. FIG. 16D shows the same specimen at greater magnification.

FIG. 17A shows the specimen at position C6, a Grade 2 tumor, which the pathologist scored +2. FIG. 17B shows the same specimen at greater magnification. FIG. 17C shows the specimen at position D1, a larger Grade 3 tumor, with lymph node involvement that the pathologist scored +3. FIG. 17D shows the same specimen at greater magnification.

FIG. 18A shows the specimen at position E2, a Grade 1 tumor, which the pathologist scored +2. FIG. 18B shows the same specimen at greater magnification. FIG. 18C shows the specimen at position E10, a smaller Grade 3 tumor, with lymph node involvement that the pathologist scored +3. FIG. 18D shows the same specimen at greater magnification.

FIG. 20A-20B shows photographs of pancreatic cancer array PA805b that were stained with an anti-MUC1* monoclonal antibody or an anti-MUC1* polyclonal antibody. FIG. 20A shows a photograph of the pancreatic cancer array that was stained with anti-MUC1* monoclonal antibody huMNC2-scFv. FIG. 20B shows a photograph of the pancreatic cancer array that was stained with anti-MUC1* polyclonal antibody SDIX. Both polyclonal and monoclonal antibodies were generated by immunizing the animals with the PSMGFR peptide. The circled specimens are indicated because they show different staining when probed with the monoclonal versus the polyclonal antibody. The numbers beneath each specimen indicate the pathologist score, when probed with huMNC2-scFv, followed by a slash mark, then the tumor grade.

FIGS. 26A-26D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.

35A depicts MUC1* on a cancer cell being probed by anti-MUC1* monoclonal antibody, MNC2. FIG. 35B depicts MUC1* on normal hematopoietic stem cells being probed by anti-MUC1* monoclonal antibody, MNC3. Both antibodies were generated by immunizing the animal with a PSMGFR peptide. MNC2 does not bind to normal hematopoietic stem cells but MNC3 does.

FIG. 36A shows a graph of FACS results showing that the SDIX polyclonal antibody and the MNC3 monoclonal antibody recognize nearly 100% of the hematopoietic stem cells but MNC2 monoclonal antibody does not bind to them. FIG. 36B shows an overlay of the FACs scans, which shows that MNC2 binding is no different than the control antibody, while MNC3 produces a clear shift in the cell populations. All three antibodies were generated by immunizing with the PSMGFR peptide.

FIG. 38A-38C lists new anti-MUC1* monoclonal antibodies that were generated by immunizing animals with one of three different peptides derived from the MUC1* extra cellular domain sequence. FIG. 38A lists monoclonal antibodies that were generated when animals were immunized with the PSMGFR peptide. FIG. 38B lists monoclonal antibodies that were generated when animals were immunized with the PSMGFR N+20/C-27 peptide. FIG. 38C lists monoclonal antibodies that were generated when animals were immunized with the PSMGFR N+9/C-9 peptide. The -1 or -2 designation refers to sister clones from the same well. Concentrations of stock antibody solutions are given.

FIG. 40A shows the Mean Fluorescence Intensity. FIG. 40B shows the percent of cells that stained positive with the respective antibody.

FIG. 42A shows the Mean Fluorescence Intensity. FIG. 42B shows the percent of cells that stained positive with the respective antibody.

FIG. 44A shows the Mean Fluorescence Intensity. FIG. 44B shows the percent of cells that stained positive with the respective antibody.

FIG. 45A-45C shows photographs of adjacent serial sections from a pancreatic cancer array, which was stained by standard IHC methods with various anti-MUC1* antibodies. FIG. 45A shows the array stained with the SDIX polyclonal anti-MUC1* antibody, wherein the immunogen for the antibody was the PSMGFR peptide. FIG. 45B shows the array stained with the 18B4 monoclonal anti-MUC1* antibody, wherein the immunogen for the antibody was the PSMGFR peptide. FIG. 45C shows the array stained with the 1E4 monoclonal anti-MUC1* antibody, wherein the immunogen for the antibody was the PSMGFR N+20/C-27 peptide.

FIG. 46A shows a specimen stained with the SDIX polyclonal antibody. FIG. 46B shows the same tissue specimen at a greater magnification. FIG. 46C shows the adjacent tissue section stained with the 18B4 monoclonal antibody. FIG. 46D shows the same tissue specimen at a greater magnification. FIG. 46E shows the adjacent tissue section stained with the 1E4 monoclonal antibody. FIG. 46F shows the same tissue specimen at a greater magnification.

FIG. 47A shows a specimen stained with the SDIX polyclonal antibody. FIG. 47B shows the same tissue specimen at a greater magnification. FIG. 47C shows the adjacent tissue section stained with the 18B4 monoclonal antibody. FIG. 47D shows the same tissue specimen at a greater magnification.

FIG. 48A-48D shows photographs of individual specimens from the pancreatic cancer array shown in FIG. 45. FIG. 48A shows a specimen stained with the SDIX polyclonal antibody. FIG. 48B shows the same tissue specimen at a greater magnification. FIG. 48C shows the adjacent tissue section stained with the 18B4 monoclonal antibody. FIG. 48D shows the same tissue specimen at a greater magnification.

FIG. 49A shows a specimen stained with the SDIX polyclonal antibody. FIG. 49B shows the same tissue specimen at a greater magnification. FIG. 49C shows the adjacent tissue section stained with the 1E4 monoclonal antibody. FIG. 49D shows the same tissue specimen at a greater magnification. Comparing FIG. 49A to FIG. 49C, it is clear that the monoclonal antibody generated by immunizing with the PSMGFR N+20/C-27 peptide recognizes a different cell population within the tumor than that recognized by the polyclonal antibody, SDIX, that was generated by immunizing with the PSMGFR peptide.

FIG. 50A-50D shows photographs of individual specimens from the pancreatic cancer array shown in FIG. 45. FIG. 50A shows a specimen stained with the SDIX polyclonal antibody. FIG. 50B shows the same tissue specimen at a greater magnification. FIG. 50C shows the adjacent tissue section stained with the 1E4 monoclonal antibody. FIG. 50D shows the same tissue specimen at a greater magnification. Comparing FIG. 50A to FIG. 50C, it is clear that the monoclonal antibody generated by immunizing with the PSMGFR N+20/C−27 peptide recognizes a different cell population within the tumor than that recognized by the polyclonal antibody, SDIX, that was generated by immunizing with the PSMGFR peptide.

FIG. 51A shows the array stained with the SDIX polyclonal anti-MUC1* antibody, wherein the immunogen for the antibody was the PSMGFR peptide. FIG. 51B shows the array stained with the 20A10 monoclonal anti-MUC1* antibody, wherein the immunogen for the antibody was the PSMGFR peptide. FIG. 51C shows the array stained with the 29H1 monoclonal anti-MUC1* antibody, wherein the immunogen for the antibody was the PSMGFR N+20/C−27 peptide.

FIG. 52A shows the array stained with the 17H6 monoclonal anti-MUC1* antibody, wherein the immunogen for the antibody was the PSMGFR N+9/C−9 peptide. FIG. 52B shows the array stained with the 32C1 monoclonal anti-MUC1* antibody, wherein the immunogen for the antibody was the PSMGFR N+20/C−27 peptide. FIG. 52C shows the array stained with the 45C11 monoclonal anti-MUC1* antibody, wherein the immunogen for the antibody was the PSMGFR N+20/C−27 peptide. FIG. 52D shows the array stained with the 31A1 monoclonal anti-MUC1* antibody, wherein the immunogen for the antibody was the PSMGFR N+20/C−27 peptide.

FIG. 53A-53F shows photographs and graphical representations of pathologist staining scores of adjacent serial sections from a pancreatic cancer array, which was stained by standard IHC methods with either antibodies that recognize full-length MUC1 or an antibody that only recognizes MUC1*. FIG. 53A shows the pancreatic cancer array stained with antibody 5E5, which is an antibody that binds to a trapped O-linked glycan in the tandem repeat domain of full-length MUC1. FIG. 53B shows the pathologist's score for each specimen in the array. FIG. 53C shows the pancreatic cancer array stained with anti-MUC1* antibody 29H1, which is an antibody that binds to the PSMGFR N+20/C−27 peptide of MUC1*. FIG. 53D shows the pathologist's score for each specimen in the array. FIG. 53E shows the pancreatic cancer array stained with antibody VU4H5, which is an antibody that binds to an epitope in the tandem repeat domain of full-length MUC1. FIG. 53F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C−27 peptide recognize epitopes that are prevalent on pancreatic cancers.

FIG. 54A shows the array stained with the SDIX polyclonal anti-MUC1* antibody, wherein the immunogen for the antibody was the PSMGFR peptide. FIG. 54B shows the array stained with the 20A10 monoclonal anti-MUC1* antibody, wherein the immunogen for the antibody was the PSMGFR peptide. FIG. 54C shows the array stained with the 29H1 monoclonal anti-MUC1* antibody, wherein the immunogen for the antibody was the PSMGFR N+20/C−27 peptide.

FIG. 55A shows the array stained with the SDIX polyclonal anti-MUC1* antibody, wherein the immunogen for the antibody was the PSMGFR peptide. FIG. 55B shows the array stained with the 17H6 monoclonal anti-MUC1* antibody, wherein the antibody binds to the PSMGFR N+9/C−9 peptide.

FIG. 55C shows the array stained with the MNC2 monoclonal anti-MUC1* antibody, wherein the antibody binds to the PSMGFR peptide.

FIG. 56A-56F shows photographs and graphical representations of pathologist staining scores of adjacent serial sections from a esophageal cancer array, which was stained by standard IHC methods with either antibodies that recognize full-length MUC1 or an antibody that only recognizes MUC1*. FIG. 56A shows the esophageal cancer array stained with antibody 5E5, which is an antibody that binds to a trapped O-linked glycan in the tandem repeat domain of full-length MUC1. FIG. 56B shows the pathologist's score for each specimen in the array. FIG. 56C shows the esophageal cancer array stained with anti-MUC1* antibody 29H1, which is an antibody that binds to the PSMGFR N+20/C−27 peptide of MUC1*. FIG. 56D shows the pathologist's score for each specimen in the array. FIG. 56E shows the esophageal cancer array stained with antibody VU4H5, which is an antibody that binds to an epitope in the tandem repeat domain of full-length MUC1. FIG. 56F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C−27 peptide recognize epitopes that are prevalent on esophageal cancers.

FIG. 57A-57G shows photographs of the prostate cancer array, which was stained with either antibody 5E5 or VU4H5, which both recognize full-length MUC1 or 29H1 that only recognizes MUC1* and binds to the PSMGFR N+20/C−27 peptide. FIG. 57A shows the esophageal cancer array stained with antibody 5E5. FIG. 57B shows the esophageal cancer array stained with antibody 29H1. FIG. 57B shows the esophageal cancer array stained with antibody 29H1. FIG. 57C shows the esophageal cancer array stained with antibody VU4H5. FIG. 57D shows the esophageal cancer array stained with the secondary antibody only, as a control. FIG. 57E shows the tissue marked by red box in FIG. 57A at greater magnification, wherein staining was done with 5E5. FIG. 57F shows the tissue marked by red box in FIG. 57B at greater magnification, wherein staining was done with 29H1. FIG. 57G shows the tissue marked by red box in FIG. 57C at greater magnification, wherein staining was done with VU4H5. The dashed red boxes indicate just one patient's specimen of many esophageal tumor specimens that stain negative for antibodies that recognize full-length MUC1, but highly positive when probed with anti-MUC1* antibodies, and particularly those antibodies that bind to the PSMGFR N+20/C−27 peptide.

FIG. 58A-58C shows photographs of adjacent serial sections from a prostate cancer array, which was stained by standard IHC methods with various anti-MUC1* antibodies. FIG. 58A shows the array stained with the SDIX polyclonal anti-MUC1* antibody, wherein the immunogen for the antibody was the PSMGFR peptide. FIG. 58B shows the array stained with the 18B4 monoclonal anti-MUC1* antibody, wherein the antibody binds to the PSMGFR peptide. FIG. 58C shows the array stained with the 1E4 monoclonal anti-MUC1* antibody, wherein the antibody binds to the PSMGFR N+20/C−27 peptide.

FIG. 59A shows the array stained with the MNC2 monoclonal antibody that binds to the PSMGFR peptide but not the C−10 peptide. FIG. 59B shows the array stained with the 18B4 antibody that binds to the PSMGFR peptide. FIG. 59C shows the array stained with the 32C1 antibody that binds to the PSMGFR N+20/C−27 peptide. FIG. 59D shows the array stained with the SDIX polyclonal anti-MUC1* antibody, wherein the immunogen for the antibody was the PSMGFR peptide. FIG. 59E shows the array stained with the 31A1 monoclonal anti-MUC1* antibody that binds to the PSMGFR N+20/C−27 peptide.

FIG. 60A-60F shows photographs and graphical representations of pathologist staining scores of adjacent serial sections from a prostate cancer array, which was stained by standard IHC methods with either antibodies that recognize full-length MUC1 or an antibody that only recognizes MUC1*. FIG. 60A shows the prostate cancer array stained with antibody 5E5, which is an antibody that binds to a trapped O-linked glycan in the tandem repeat domain of full-length MUC1. FIG. 60B shows the pathologist's score for each specimen in the array. FIG. 60C shows the prostate cancer array stained with anti-MUC1* antibody 29H1, which is an antibody that binds to the PSMGFR N+20/C−27 peptide of MUC1*. FIG. 60D shows the pathologist's score for each specimen in the array. FIG. 60E shows the prostate cancer array stained with antibody VU4H5, which is an antibody that binds to an epitope in the tandem repeat domain of full-length MUC1. FIG. 60F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C−27 peptide recognize epitopes that are prevalent on prostate cancers.

FIG. 61A-61G shows photographs of the prostate cancer array, which was stained with either antibody 5E5 or VU4H5, which both recognize full-length MUC1 or 29H1 that only recognizes MUC1* and binds to the PSMGFR N+20/C−27 peptide. FIG. 61A shows the prostate cancer array stained with antibody 5E5. FIG. 61B shows the prostate cancer array stained with antibody 29H1. FIG. 61B shows the prostate cancer array stained with antibody 29H1. FIG. 61C shows the prostate cancer array stained with antibody VU4H5. FIG. 61D shows the prostate cancer array stained with the secondary antibody only, as a control. FIG. 61E shows the tissue marked by red box in FIG. 61A at greater magnification, wherein staining was done with 5E5. FIG. 61F shows the tissue marked by red box in FIG. 61B at greater magnification, wherein staining was done with 29H1. FIG. 61G shows the tissue marked by red box in FIG. 61C at greater magnification, wherein staining was done with VU4H5. The dashed red boxes indicate just one patient's specimen of many prostate tumor specimens that stain negative for antibodies that recognize full-length MUC1, but highly positive when probed with anti-MUC1* antibodies, and particularly those antibodies that bind to the PSMGFR N+20/C−27 peptide.

FIG. 62A shows a photograph of the breast cancer array that was stained with anti-MUC1* monoclonal antibody MNC2. FIG. 62B shows a photograph of the breast cancer array that was stained with anti-MUC1* monoclonal antibody 20A10. Both monoclonal antibodies bind to the PSMGFR peptide, the N−10 peptide but not to the C10 peptide.

FIG. 63A-63B shows photographs of adjacent serial sections of breast cancer array BR1141 that were stained with two different anti-MUC1* monoclonal antibodies. FIG. 63A shows a photograph of the breast cancer array that was stained with anti-MUC1* monoclonal antibody MNC2. FIG. 63B shows a photograph of the breast cancer array that was stained with anti-MUC1* monoclonal antibody 25E6. Both monoclonal antibodies bind to the PSMGFR peptide and to the N−10 peptide. Whereas MNC2 cannot bind to the C−10 peptide, 25E6 shows some low level of binding to the C−10 peptide, indicating that they bind to different epitopes.

FIG. 64A-64B shows photographs of adjacent serial sections of breast cancer array BR1141 that were stained with two different anti-MUC1* monoclonal antibodies. FIG. 64A shows a photograph of the breast cancer array that was stained with anti-MUC1* monoclonal antibody MNC2. FIG. 64B shows a photograph of the breast cancer array that was stained with anti-MUC1* monoclonal antibody 18B4. Both monoclonal antibodies bind to the PSMGFR peptide. However, unlike MNC2, 18B4 cannot bind to the N−10 epitope, indicating that they bind to different epitopes and that 18B4 may require the 10 N-terminal amino acids of the PSMGFR peptide for binding.

FIG. 65A shows a photograph of the breast cancer array that was stained with anti-MUC1* monoclonal antibody MNC2. FIG. 65B shows a photograph of the breast cancer array that was stained with anti-MUC1* monoclonal antibody 18G12. Both monoclonal antibodies bind to the PSMGFR peptide. However, unlike MNC2, 18G12 binds to the C–10 epitope to some degree, indicating they bind to different epitope within PSMGFR peptide.

FIG. 66A-66B shows photographs of adjacent serial sections of breast cancer array BR1141 that were stained with two different anti-MUC1* monoclonal antibodies. FIG. 66A shows a photograph of the breast cancer array that was stained with anti-MUC1* monoclonal antibody MNC2. FIG. 66B shows a photograph of the breast cancer array that was stained with anti-MUC1* monoclonal antibody 8A9. Monoclonal antibody MNC2 binds to the PSMGFR peptide, whereas 8A9 binds to the PSMGFR N+9/C–9 peptide. The peptides to which they bind, combined with the very different staining patterns indicates that they bind to different MUC1* epitopes.

FIG. 67A-67B shows photographs of adjacent serial sections of breast cancer array BR1141 that were stained with two different anti-MUC1* monoclonal antibodies. FIG. 67A shows a photograph of the breast cancer array that was stained with anti-MUC1* monoclonal antibody MNC2. FIG. 67B shows a photograph of the breast cancer array that was stained with anti-MUC1* monoclonal antibody 28F9. Both monoclonal antibodies bind to the PSMGFR peptide.

FIG. 68A-68B shows photographs of adjacent serial sections of breast cancer array BR1141 that were stained with two different anti-MUC1* monoclonal antibodies. FIG. 68A shows a photograph of the breast cancer array that was stained with anti-MUC1* monoclonal antibody MNC2. FIG. 68B shows a photograph of the breast cancer array that was stained with anti-MUC1* monoclonal antibody 17H6. Monoclonal antibody MNC2 binds to the PSMGFR peptide, whereas 17H6 binds to the PSMGFR N+9/C–9 peptide. The peptides to which they bind, combined with the very different staining patterns indicates that they bind to different MUC1* epitopes.

FIG. 69A-69B shows photographs of adjacent serial sections of breast cancer array BR1141 that were stained with two different anti-MUC1* monoclonal antibodies. FIG. 69A shows a photograph of the breast cancer array that was stained with anti-MUC1* monoclonal antibody MNC2. FIG. 69B shows a photograph of the breast cancer array that was stained with anti-MUC1* monoclonal antibody 3C5. Monoclonal antibody MNC2 binds to the PSMGFR peptide, whereas 3C5 binds to the PSMGFR N+9/C–9 peptide. The peptides to which they bind, combined with the very different staining patterns indicates that they bind to different MUC1* epitopes.

FIG. 70A-70G shows photographs of adjacent serial sections of breast cancer array BR1007 that were stained with four different anti-MUC1* monoclonal antibodies. FIG. 70A shows a photograph of the breast cancer array that was stained with anti-MUC1* monoclonal antibody 20A10, which binds to the PSMGFR peptide. FIG. 70B shows a photograph of the breast cancer array that was stained with anti-MUC1* monoclonal antibody 29H1, which binds to the PSMGFR N+20/C–27 peptide. FIG. 70C shows a photograph of the breast cancer array that was stained with anti-MUC1* monoclonal antibody 45C11, which binds to the PSMGFR N+20/C–27 peptide. FIG. 70D shows a photograph of the breast cancer array that was stained with anti-MUC1* monoclonal antibody 32C1, which binds to the PSMGFR N+20/C–27 peptide.

FIG. 70E shows a photograph of the breast cancer array that was stained with anti-MUC1* monoclonal antibody 18B4, which binds to the PSMGFR peptide. FIG. 70F shows a photograph of the breast cancer array that was stained with anti-MUC1* monoclonal antibody 31A1, which binds to the PSMGFR N+20/C–27 peptide. FIG. 70G shows a photograph of the breast cancer array that was stained with anti-MUC1* monoclonal antibody 17H6, which binds to the PSMGFR N+9/C–9 peptide.

FIG. 71A-71F shows photographs and graphical representations of pathologist staining scores of adjacent serial sections from a breast cancer array, which was stained by standard IHC methods with either antibodies that recognize full-length MUC1 or an antibody that only recognizes MUC1*. FIG. 71A shows the breast cancer array stained with antibody 5E5, which is an antibody that binds to a trapped O-linked glycan in the tandem repeat domain of full-length MUC1. FIG. 71B shows the pathologist's score for each specimen in the array. FIG. 71C shows the breast cancer array stained with anti-MUC1* antibody 29H1, which is an antibody that binds to the PSMGFR N+20/C–27 peptide of MUC1*. FIG. 71D shows the pathologist's score for each specimen in the array. FIG. 71E shows the breast cancer array stained with antibody VU4H5, which is an antibody that binds to an epitope in the tandem repeat domain of full-length MUC1. FIG. 71F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1.

FIG. 72A-72F shows photographs of adjacent serial sections of breast cancer tissue array BR1141 that have been stained with various anti-MUC1* monoclonal antibodies, wherein all antibodies bind to the PSMGFR peptide. FIG. 72A shows breast cancer specimens that were stained with MNC2. FIG. 72B shows breast cancer specimens that were stained with 20A10. FIG. 72C shows breast cancer specimens that were stained with 25E6. FIG. 72D shows breast cancer specimens that were stained with 28F9. FIG. 72E shows breast cancer specimens that were stained with 18G12. FIG. 72F shows breast cancer specimens that were stained with 18B4. All these antibodies bind to the PSMGFR peptide and roughly produce the same staining pattern of this breast cancer array. However, there are some differences in how these antibodies recognize individual specimens within the array, which could represent MUC1 to MUC1* cleavage by different enzymes. Referring to FIG. 39, MNC2 and 20A10 bind to the N–10 peptide but not to the C–10 peptide, indicating the 10 membrane proximal amino acids are important for their binding. Antibodies 18B4, 18G12 and 25E6 show some binding to the C–10 peptide and 28F9 shows even more binding to C–10 peptide. Notably, 18B4 does not bind to the N–10 peptide, indicating that it binds to an epitope that is more N-terminal within PSMGFR than the others. Red circles indicate specimens of interest for comparison.

FIG. 73A-73F shows photographs of adjacent serial sections of breast cancer tissue array BR1141 that have been stained with various anti-MUC1* monoclonal antibodies, wherein antibodies that bind to the PSMGFR N+9/C−9 peptide are compared to MNC2 and its humanized single chain form, huMNC2-scFv-Fc, which both bind to PSMGFR, N−10 but not to C−10 peptides. FIG. 73A shows breast cancer specimens that were stained with MNC2. FIG. 73B shows breast cancer specimens that were stained with 8A9. FIG. 73C shows breast cancer specimens that were stained with 17H6. FIG. 73D shows breast cancer specimens that were stained with huMNC2-scFv-Fc. FIG. 73E shows breast cancer specimen that was stained with 3C5. FIG. 73F shows breast cancer specimens that were stained with 39H5. Referring now to the patient specimens that are marked by red circles, it is plain to see that antibodies that bind to the PSMGFR N+9/C−9 peptide recognize a population of breast cancer cells that MNC2 anti-PSMGFR antibodies miss or bind weakly to.

Figure 1A:
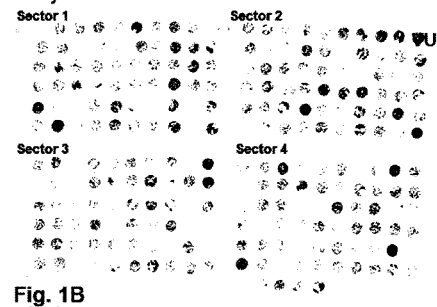
FIG. 1A-1D shows photographs of adjacent serial sections of breast cancer tissue arrays and graphical representations of the pathologist scores, according to Allred scoring system. Pathologist score is 0-3, where 0 showed no staining and 3 is the greatest staining. The graphs are also color coded, where a pathologist score zero is black, 1 is yellow, 2 is orange, and 3 is red; tissues that scored zero when probed with an antibody that recognizes full-length MUC1 but positive when probed with an antibody that recognizes MUC1* were colored green; and missing or uninterpretable tissues were scored −1.

In addition to monoclonal antibodies MNC2, MNE6, MNC3, MNC8, and 18B4, 18G12, 20A10, 25E6, 1E4, 29H1, 31A1, 32C1, 45C11, 3C5, 8A9, 17H6, and 39H5 disclosed in the present application, other monoclonal antibody sequences are recited in SEQ ID NOS:237-349 that are made from inoculation with the PSMGFR peptide.

DETAILED DESCRIPTION OF THE PREFERRED EMBODIMENTS

In the present application, "a" and "an" are used to refer to both single and a plurality of objects.

As used herein, occasionally, in short hand, a polypeptide is indicated as being "transduced or transfected" into a cell. In these occurrences, it is understood that the nucleic acid encoding the polypeptide sequence is transduced or transfected into the cell, as it is an impossibility that a polypeptide could be transduced or transfected into a cell.

As used herein, occasionally when referring to number of cells injected into an animal or otherwise contextually wherein the number of cells is referred to, "M" refers to millions, and "K" refers to thousands.

As used herein, interchangeable designations for various monoclonal antibodies are used, such as, "MN-C2", which is interchangeable with "C2", "Min-C2" and "MNC2"; "MN-E6", which is interchangeable with "E6", "Min-E6" and "MNE6"; "MN-C3", which is interchangeable with "C3", "Min-C3" and "MNC3"; and "MN-C8", which is interchangeable with "C8", "Min-C8" and "MNC8".

As used herein, "h" or "hu" placed before an antibody construct is short-hand for human or humanized.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human Fabs that are then screened for binding to peptide epitopes from target proteins. The selected Fab regions can then be engineered into a scaffold or framework so that they resemble antibodies.

As used herein, "PSMGFR" is abbreviation for Primary Sequence of the MUC1 Growth Factor Receptor which is identified by SEQ ID NO:4, and thus is not to be confused with a six amino acid sequence. "PSMGFR peptide" or "PSMGFR region" refers to a peptide or region that incorporates the Primary Sequence of the MUC1 Growth Factor Receptor (SEQ ID NO:4).

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:4). In this regard, the "N-number" as in "N−10 PSMGFR", "N−15 PSMGFR", or "N−20 PSMGFR" refers to the number of amino acid residues that have been deleted at the N-terminal end of PSMGFR, likewise "N+10 PSMGFR", "N+15 PSMGFR", or "N+20 PSMGFR" refers to the number of amino acid residues that have been added at the N-terminal end of PSMGFR. Likewise "C-number" as in "C−10 PSMGFR", "C−15 PSMGFR", or "C−20 PSMGFR" refers to the number of amino acid residues that have been deleted at the C-terminal end of PSMGFR, and "C+10 PSMGFR", "C+15 PSMGFR", or "C+20 PSMGFR" refers to the number of amino acid residues that have been added at the C-terminal end of PSMGFR. Moreover, combinations are possible, such as, "N+20/C−27 PSMGFR", "PSMGFR N+20/C−27" or "N+20/C−27" which refer to the same peptide, in which the N terminus of PSMGFR includes 20 additional amino acids of MUC1 peptide, and is deleted 27 amino acids at the C-terminus of PSMGFR.

As used herein, when it is desired to refer to a genus of PSMGFR peptides, they are referred to as "PSMGFR group". For example, "N+20 PSMGFR group" refers to peptides that have additional 20 amino acids at the N-terminus, without regard to how the C-terminus is modified, whether amino acids have been deleted, or added and so on.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, the "MUC1*" extra cellular domain is defined primarily by the PSMGFR sequence (GTINVHDVETQFNQYKTEAAS-RYNLTISDVSVSDVPFPFSAQSGA (SEQ ID NO:4)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

Other clipped amino acid sequences may include

```
                                              (SEQ ID NO: 5)
SNIKFRPGSVVVQLTLAFREGTINVHDVETQFNQYKTEAASRY;
or (SEQ ID NO: 6)
SVVVQLTLAFREGTINVHDVETQFNQYKTEAASRY.
```

As used herein "sequence identity" means homology in sequence of a particular polypeptide or nucleic acid to a reference sequence of nucleic acid or amino acid such that the function of the homologous peptide is the same as the reference peptide or nucleic acid. Such homology can be so close with the reference peptide such that at times the two sequences may be 90%, 95% or 98% identical yet possess the same function in binding or other biological activities.

As used herein, "MUC1 positive" cell refers to a cell that expresses a gene for MUC1, MUC1-Y or MUC1-Z or other MUC1 variant.

As used herein, "MUC1 negative" cell refers to a cell that does not express a gene for MUC1.

As used herein, "MUC1* positive" cell refers to a cell that expresses a gene for MUC1, wherein that gene's expressed protein is a transmembrane protein that is devoid of tandem repeats, which may be a consequence of post-translational modification, cleavage, alternative splicing, or transfecting or transducing a cell with a MUC1 protein that is devoid of tandem repeats.

As used herein, "MUC1* negative" cell refers to a cell that may or may not express a gene for MUC1 but does not express a MUC1 transmembrane protein that is devoid of tandem repeats.

As used herein, "MUC1 positive" cancer cell refers to a cancer cell that overexpresses the gene for MUC1, expresses MUC1 in an aberrant pattern, wherein its expression is not restricted to the apical border and/or expresses a MUC1 that is devoid of tandem repeats.

As used herein, "MUC1 negative" cancer cell refers to a cancer cell that may or may not express a gene for MUC1 but does not overexpress MUC1 or does not overexpress a MUC1 transmembrane protein that is devoid of tandem repeats.

As used herein, "MUC1* positive" cancer cell refers to a cancer cell that overexpresses a MUC1 transmembrane protein that is devoid of tandem repeats.

As used herein, "MUC1* negative" cancer cell refers to a cancer cell that may or may not express a gene for MUC1 but does not overexpress a MUC1 transmembrane protein that is devoid of tandem repeats.

The present invention involves, generally, diagnostic assays related to cancers that are characterized by the aberrant expression of a class of cell surface receptors characterized by interchain binding regions or increased cleavage of extra cellular domain in cancerous tissues. One such set of cancers are those characterized by the aberrant expression of mucin family proteins, such as MUC1, MUC2, MUC3, MUC4, up to and including MUC16. Much of the description of the invention herein is directed to cells and tissues that aberrantly express MUC1, as an example of the larger class of proteins involved in cancers which have extra cellular domains that are increasingly cleaved in cancers and/or have an inter-chain binding region (IBR). It is to be understood that in these instances the description is to be considered exemplary, and that the principles of the invention apply to other transmembrane proteins that function by a similar mechanism. With the disclosure herein, those of ordinary skill in the art will readily be able to identify other transmembrane proteins that function by this or a similar mechanism, and to apply the invention to those cancers characterized by aberrant expression of receptors. The invention is based on a novel mechanism involving transmembrane proteins that have regions of their extra cellular domain that self-aggregate and/or are increasingly cleaved, exemplified by MUC1, which was elucidated by the inventors.

MUC1 comprises several regions termed herein as follows. From the C-terminus inside the cell to the N-terminus outside the cell, the MUC1 protein is comprised of the following domains: 1) cytoplasmic tail; 2) transmembrane section; 3) MGFR; 4) IBR (interchain binding region) 5) UR (unique region); and 6) the tandem repeats.

One aspect of our previous invention featured the discovery that a specific region of the MUC1 receptor, i.e., the IBR, binds strongly to identical regions of other MUC1 molecules. That is, the MUC1 receptor has the ability to aggregate (i.e. self-aggregate) with other MUC1 receptors via the IBR of the respective receptors. A gold nanoparticle experiment was performed that showed that the IBR aggregates with itself which can occlude the binding of ligands to MUC1 or its cleavage product MUC1*. The boundary between the IBR and MGFR varies depending on where MUC1 is cleaved, which is determined by which cleavage enzyme cleaves it.

This self-aggregation may contribute to MUC1 receptor clustering, observed in healthy cells. The discovery that the IBR portion of the MUC1 receptor self-aggregates is consistent with the following mechanistic model for which the inventors present supporting evidence. (1) receptor clustering is associated with the healthy state because the aggregated IBR portions block access of ligands, such as growth factors, modifying enzymes and the like to the neighboring extracellular portions of the MUC1 receptor that act as the functional receptor; clustering also blocks access of intracellular tails to intracellular modifying enzymes and signaling ligands; (2) when the MUC1 receptor is cleaved at a position that releases some or all of the self-aggregating portions, the critical force that keeps the receptors clustered is lost and receptors are free to migrate within the cell membrane or interact with modifying enzymes, secreted ligands such as activating ligands or growth factors or other cell surface receptors. These interactions involve a new, inductive multimerization state, such as dimerization, that triggers a cell proliferation signaling cascade.

Cleavage of MUC1 releases the bulk of the extra cellular domain, including the tandem repeat domain and leaves a transmembrane protein with a truncated extra cellular domain comprising at least the PSMGFR region. Cleavage and release of the bulk of the tandem repeat domain, exposes binding sites of ligands that bind to and dimerize the truncated extra cellular domain, leading to activation of growth and survival pathways. We call the MUC1 cleavage product "MUC1*".

MUC1* is a growth factor receptor that is activated by ligand induced dimerization of its truncated extra cellular domain. Bivalent antibodies that bind to PSMGFR peptide, which is the 45 amino acid sequence of the membrane proximal portion of MUC1 dimerize MUC1* and stimulate growth. The anti-PSMGFR antibody stimulated growth of T47D MUC1 positive cancer cells in a concentration dependent manner. In a similar experiment, a concentration of the anti-PSMGFR antibody, identified to maximize cancer cell proliferation, was added to a first group of T47D tumor cells, grown as described above. The same amount of the anti-PSMGFR antibody was added to a set of control cells, K293 cells. The addition of the anti-PSMGFR antibody to MUC1 tumor cells (T47D) enhanced proliferation by 180% 24 hours, but had no effect on the control cells.

Ligands that dimerize the extra cellular domain of MUC1* induce growth and survival of cells. Ligands of MUC1* that we identified are NME1, NME2, NME6, NME7-AB and alternative splice variant NME7-X1.

MUC1* is the growth factor receptor that drives the growth of cancer cells, whereas full-length MUC1 does not. Therefore, detection of an amount of MUC1* that is above normal levels is an indicator of cancer and the higher the amount of MUC1*, the worse the cancer. Cleavage of MUC1 may occur at more than one site, depending on which cleavage enzyme the tumor expresses. Cleavage of MUC1 releases the portion of the extracellular domain that contains the tandem repeats and could, depending on cleavage site, contain portions of the unique region or portions of the IBR. The amount of MUC1 that has been cleaved can be inferred by measuring the amount of full-length MUC1 that remains on cells or tissues. This can be accomplished by contacting the cells or tissues with an antibody that binds to the tandem repeats, or the unique region or the IBR. An antibody that binds to the tandem repeat domain is an antibody that is able to bind to a peptide having the sequence PDTRPAPGSTAP-PAHGVTSA (SEQ ID NO:235). Commonly used antibodies that bind to the tandem repeat domain include but are not limited to VU4H5 (Santa Cruz Biotechnology, Dallas Tex. Cat. No. SC-7313), HMPV, 5E5 (Sorensen et al., Glycobiology, Vol. 16, no. 2, pp. 96-107, 2006), PR81, and LDQ10. In these cases, it is most effective to measure an amount of full-length MUC1 compared to an amount of MUC1* expressed on the same cells or tissues. The ratio of MUC1*: MUC1 full-length is an indicator of cancer and cancer aggressiveness, wherein the more MUC1*, the more aggressive the cancer. Detection of an amount of MUC1* or the ratio of MUC1* to MUC1 full-length can also be used to determine the suitability of a cancer treatment where the therapeutic drug targets MUC1* or MUC1. Similarly, the effectiveness of such a therapy can be evaluated by detecting an amount of MUC1* or the ratio of MUC1* to MUC1 full-length before and after treatment, wherein a reduction in the amount of MUC1* expressed or a shift in the ratio of MUC1* to MUC1 full-length would be an indicator of efficacy.

There may be alternative splice isoforms of MUC1 that do not contain an IBR or tandem repeats. For example, MUC1-Y or MUC1-X. These alternative splice isoforms still have an extra cellular domain that is comprised of the sequence of the PSMGFR peptide, as this is the portion that interacts with growth factors to promote cancer and survival. Therefore, detection of an amount of MUC1* expressed by cells or tissues would still be a valid indicator of cancer and cancer aggressiveness.

The dominant MUC1 species on breast cancer tissue is the transmembrane cleavage product MUC1* not full-length MUC1. Breast tumor micro arrays were probed with either VU4H5 or MNC2. VU4H5 is a monoclonal antibody that only binds to full-length MUC1 because it recognizes an epitope (PDTRPAPGSTAPPAHGVTSA (SEQ ID NO:235) in the tandem repeat domain of full-length MUC1. This epitope is repeated hundreds of times within the tandem repeat domain of full-length MUC1. Therefore, antibody VU4H5 should give a stronger signal that an antibody that binds to a single epitope on the molecule. MNC2 is a monoclonal antibody that we produced by immunizing animals with the PSMGFR peptide (SEQ ID NO:4). Transfection experiments show that MNC2 does not bind to full-length MUC1. MNC2 binds to a cryptic epitope that is exposed after MUC1 is cleaved to a form of MUC1* that comprises at least the first 35 membrane proximal amino acids of the MUC1* extra cellular domain, as it binds to the PSMGFR peptide (45 amino acids), the N-10 peptide (35 amino acids) but not to the C-10 peptide, indicating that its cognate epitope is encompassed at least in part within the 10 membrane proximal amino acids of the MUC1* extra cellular domain. Importantly, MNC2 competitively inhibits the binding of MUC1* activating growth factors NME1 and NME7-AB.

Figure 1C:
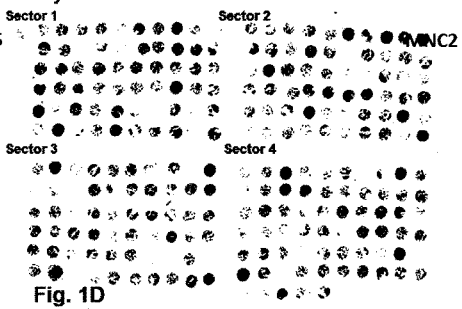
Figure 1B:
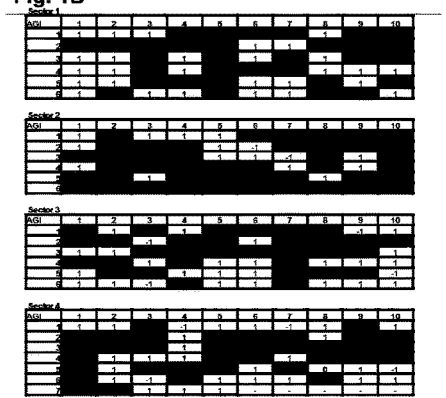
Figure 1D:
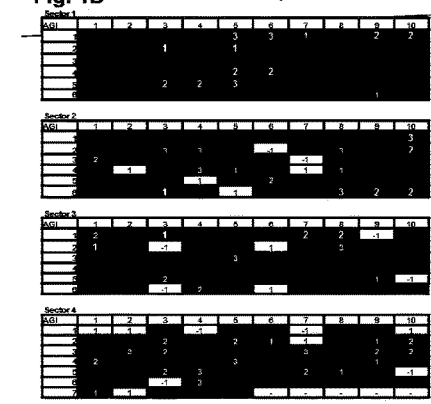

FIG. 1A-1D shows photographs of adjacent serial sections of breast cancer tissue arrays and graphical representations of the pathologist scores, according to Allred scoring system. Pathologist score is 0-3, where 0 showed no staining and 3 is the greatest staining. The graphs are also color coded, where a pathologist score zero is black, 1 is yellow, 2 is orange, and 3 is red; tissues that scored zero when probed with an antibody that recognizes full-length MUC1 but positive when probed with an antibody that recognizes MUC1* were colored green; and missing or uninterpretable tissues were scored -1. FIG. 1A shows photographs of the breast cancer tissue arrays after they were stained with VU4H5, which is an antibody that binds to the tandem repeat domains of full-length MUC1. FIG. 1B shows graphs of the pathologist scores for the tissues pictured in FIG. 1A. FIG. 1C shows photographs of the breast cancer tissue arrays after they were stained with MNC2, which is an antibody that binds to an epitope within the PSMGFR region of MUC1*. FIG. 1D shows graphs of the pathologist scores for the tissues pictured in FIG. 1C. FIG. 2A-2B shows pie chart graphs of the pathologist scores of the arrays shown in FIG. 1A and FIG. 1C. FIG. 2A shows that the antibody that binds to tandem repeats of full-length MUC1 misses 30% of breast cancers. FIG. 2B shows that the anti-MUC1* antibody MNC2 recognizes 95% of breast cancers. Anti-MUC1-full-length only binds strongly to 10% of the breast tumors, while anti-MUC1* antibody MNC2 binds strongly to about 50% of breast tumors. Together these data demonstrate that MUC1*, not full-length MUC1, is the predominant MUC1 species on cancerous tissues. Anti-MUC1* antibodies would detect or diagnose nearly all breast cancers, whereas antibodies that bind to full-length MUC1 would fail to detect about 30% of breast cancers. Further, because MUC1* is a growth factor receptor driving cancer growth, the degree of anti-MUC1* staining of a tissue or cellular specimen would be proportional to the degree or stage of cancer, whereas the expression of full-length MUC1 appears to be inversely proportional to the stage of cancer.

A wide range of cancer cells and tumor specimens were probed with anti-MUC1* antibody MNC2. MNC2 was used to detect MUC1* positive cancers in a wide range of assays, including fluorescence activated cell sorting (FACS), immunofluorescence (IF), immunohistochemistry (IHC). FACS and IF are generally used to study a cell line which is a single immortalized cell that has been propagated in a lab for decades. After decades of propagation in unnatural growth solutions, these cell lines likely show little resemblance to even a single cell within the patient's original tumor and in no way represent the tumor of a recently diagnosed patient seeking treatment. For these reasons, we analyzed thousands of tumor micro arrays, wherein each dot within the array is tumor specimen from a single patient's biopsy. In most cases, the biopsies are from recently diagnosed patients, but the accompanying anonymized patient data gives the age of the patient, cancer sub-type and cancer stage or grade. In some cases we analyzed tissue micro arrays wherein the breast cancers were all HER2+, or all ER+/PR+. In other cases. We analyzed tumor micro arrays that compared the original biopsy specimen to a later metastasis. In these studies, the recognition of tumors by MNC2 was also compared to staining using anti-full-length-MUC1 antibody VU4H5 or a new antibody 5E5 that binds to a trapped O-linked glycan in the tandem repeat domain of full-length MUC1. MNC2 and other anti-MUC1* antibodies consistently recognized tumor tissue better than VU4H5 or 5E5. Normal tissues and normal tissue micro arrays were also extensively studied to determine binding of MNC2 or its humanized singly chain form huMNC2-scFv or huMNC2-scFv-Fc to normal tissues. On normal tissues, expression of MNC2 reactive MUC1* was restricted to the apical border of ducts and glands in a small percentage of only a few tissues. In all cases, MNC2 reactive MUC1* was expressed to a much higher degree in cancerous tissues than in normal tissues and expressed over 50-100% of the cancerous tissues compared to expression of 0.2%-5% of the normal tissue that did express MNC2 reactive MUC1*.

Figure 3A:
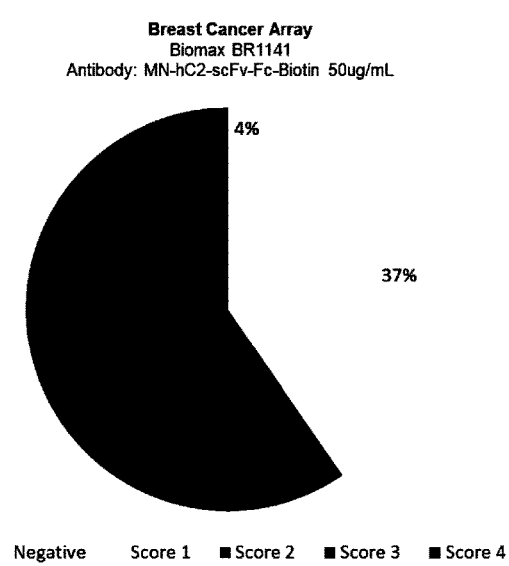
FIG. 3A-3B shows pie chart graphs of the pathologist scores and a photograph of breast cancer array BR1141 after staining with anti-MUC1* antibody huMNC2-scFv-Fc.
Figure 3B:
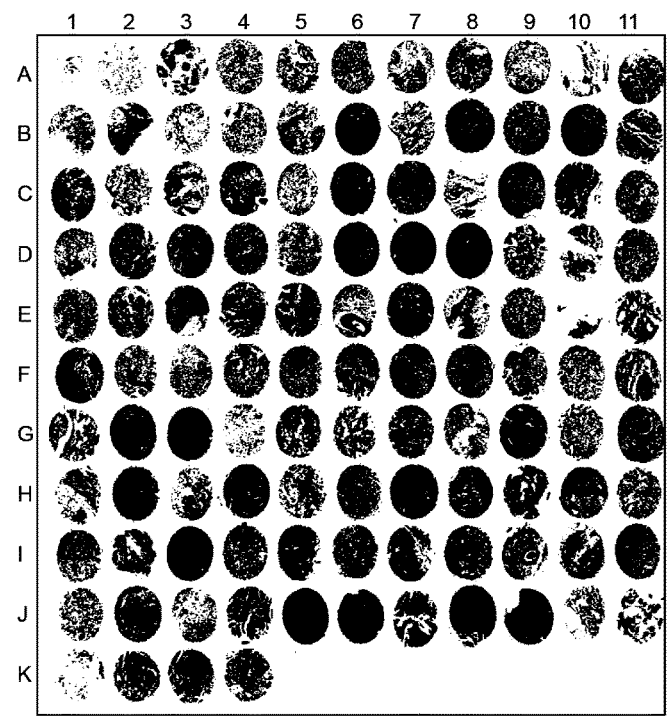
Figure 6A:
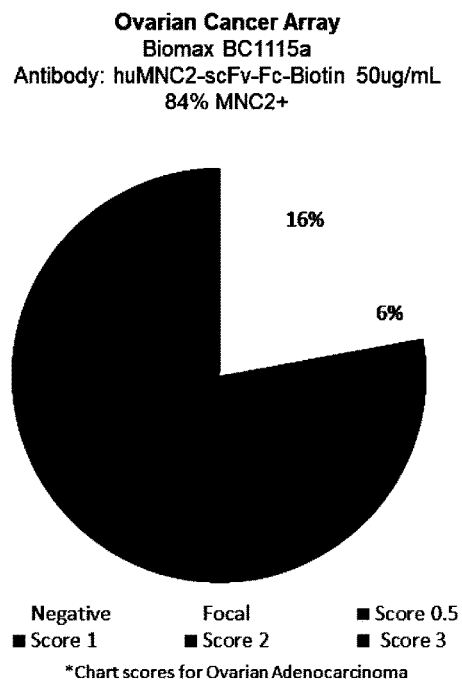
FIG. 6A-6B shows pie chart graphs of the pathologist scores and a photograph of ovarian cancer array BC1115a after staining with anti-MUC1* antibody huMNC2-scFv-Fc.
Figure 6B:
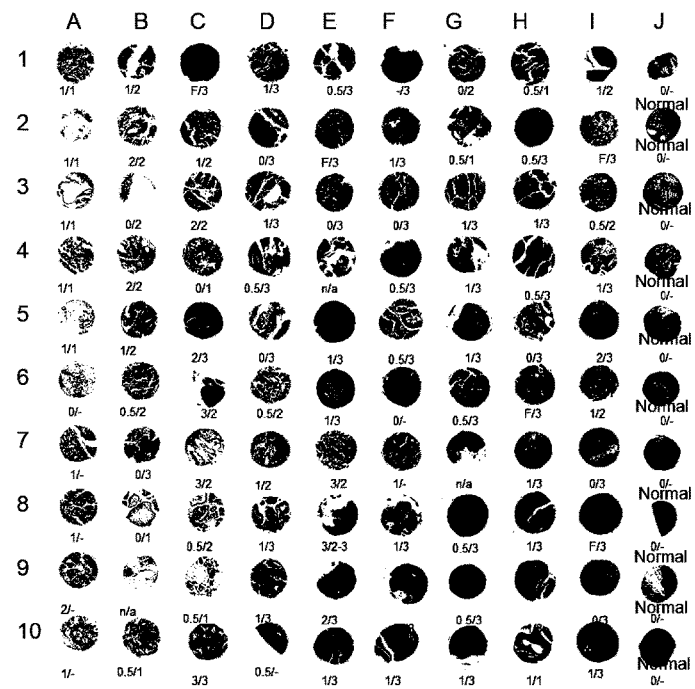
Figure 7A:
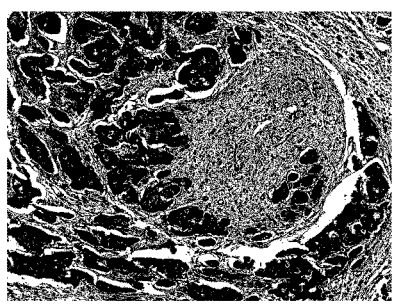
FIG. 7A-7C shows magnified photographs of different cancer sub-types after staining with anti-MUC1* antibody huMNC2-scFv-Fc.
Figure 7B:
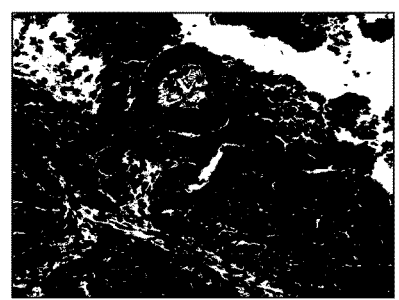
Figure 7C:
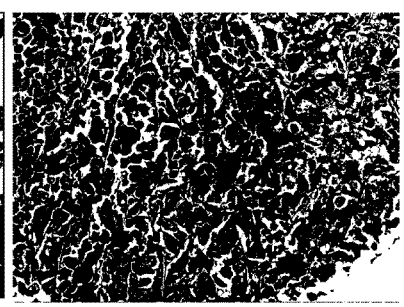
Figures 9A, 9B, 9C, 9D, 9E, 9F, 9G, 9H, 9I:
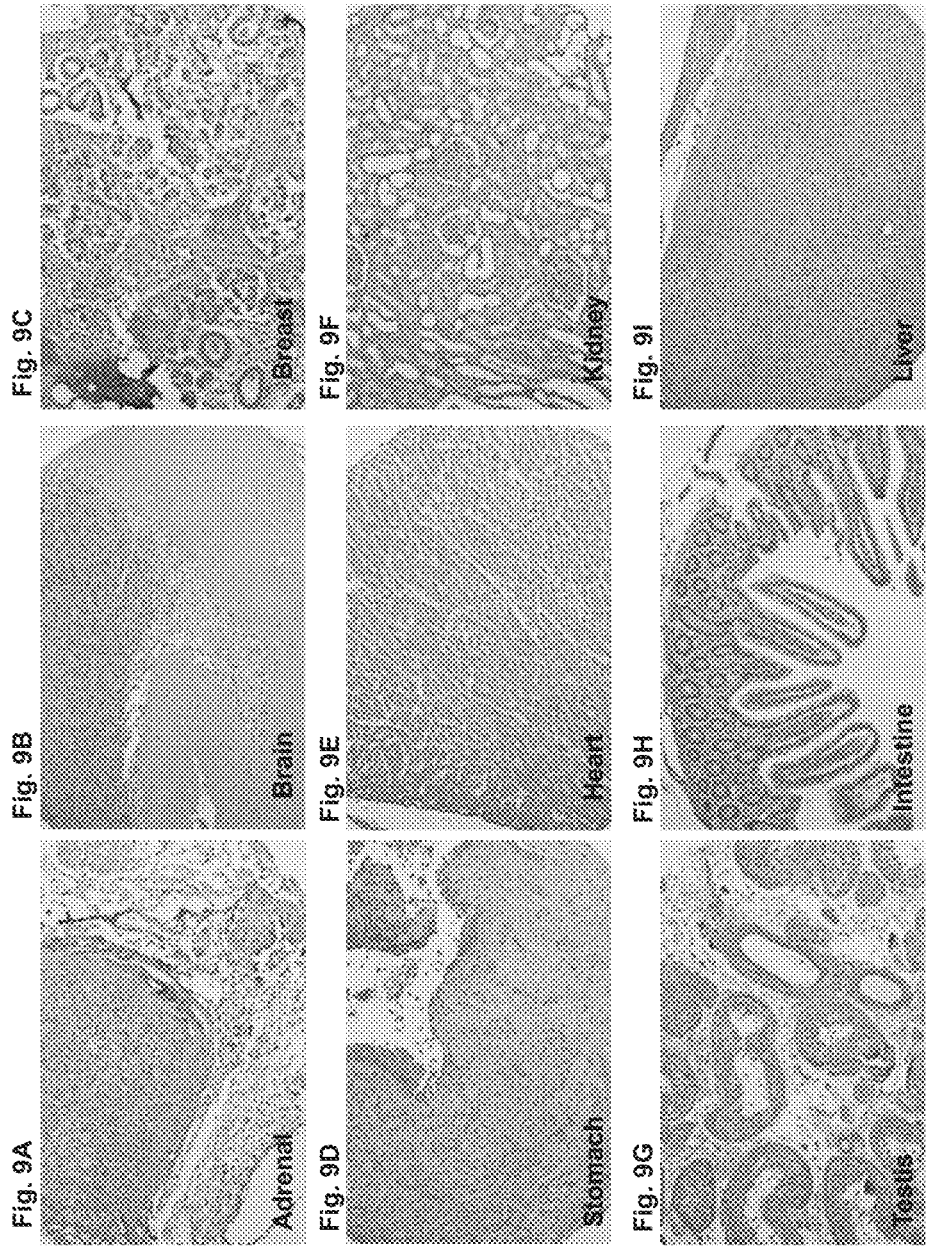
FIG. 9A-9I shows magnified photographs of various normal tissues after staining with anti-MUC1* antibody huMNC2-scFv-Fc. Conditions and concentrations used were identical to those used for studying cancerous tissues.
Figure 10A:
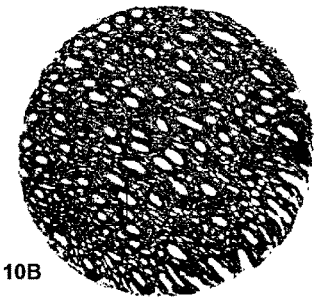
FIG. 10A-10F shows photographs of normal kidney tissues after staining with anti-MUC1* antibody huMNC2-scFv-Fc. Conditions and concentrations used were identical to those used for studying cancerous tissues.
Figure 10C:
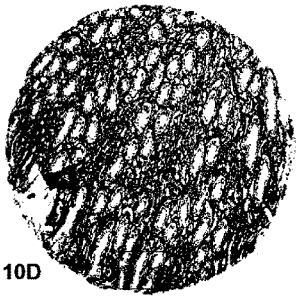
Figure 10E:
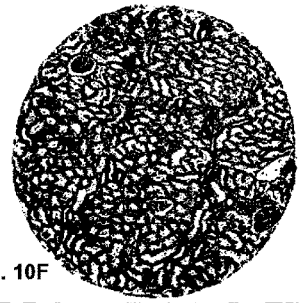
Figure 10B:
Figure 10D:
Figure 10F:
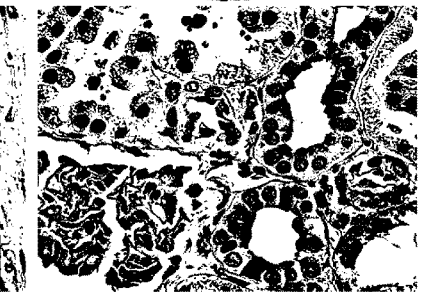
Figure 11A:
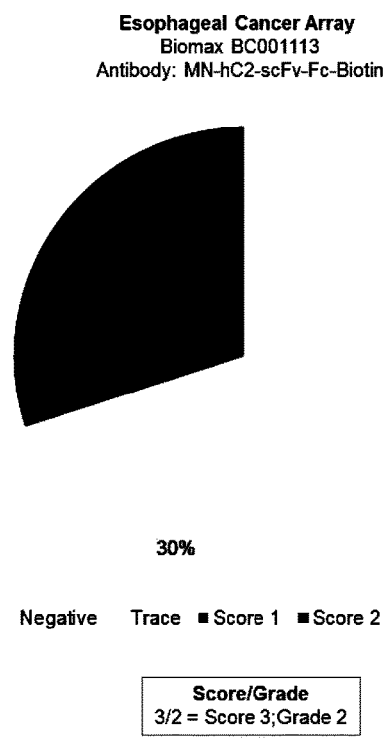
FIG. 11A-11B shows pie chart graphs of the pathologist scores and a photograph of esophageal cancer array BC001113 after staining with anti-MUC1* antibody huMNC2-scFv-Fc.
Figure 11B:
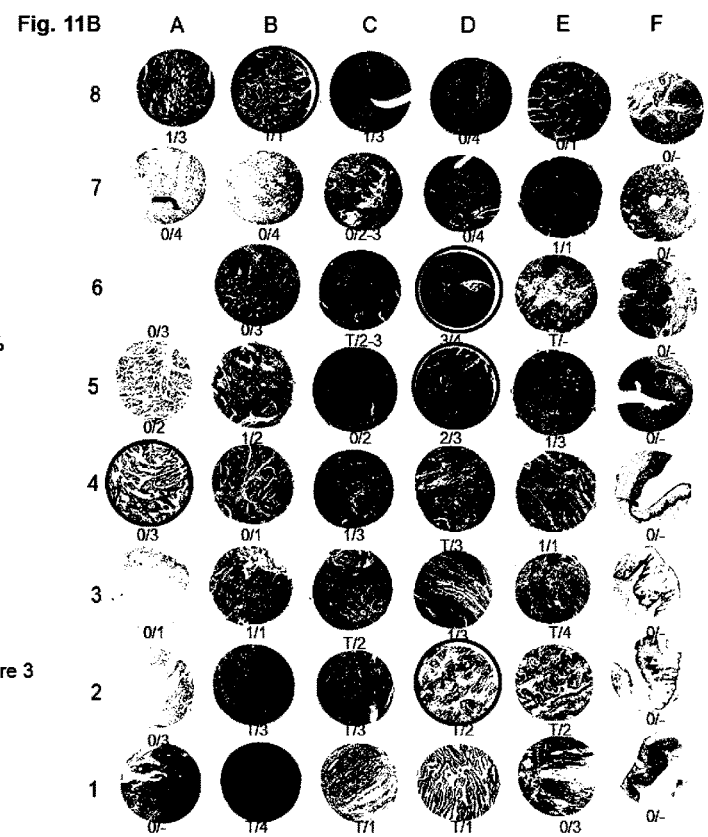
Figure 12A:
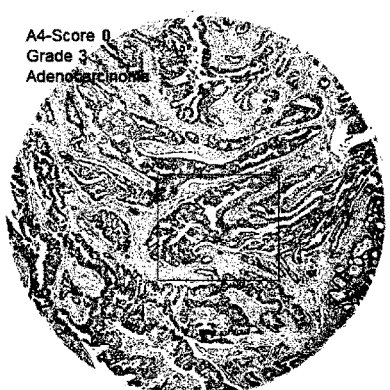
FIG. 12A-12F shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures.
Figure 12B:
Figure 12C:
Figure 12D:
Figure 12E:
Figure 12F:
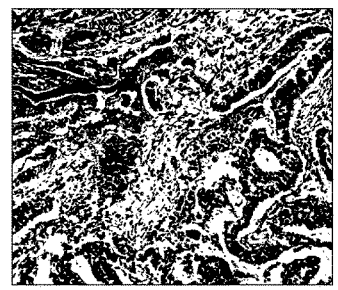
Figure 13A:
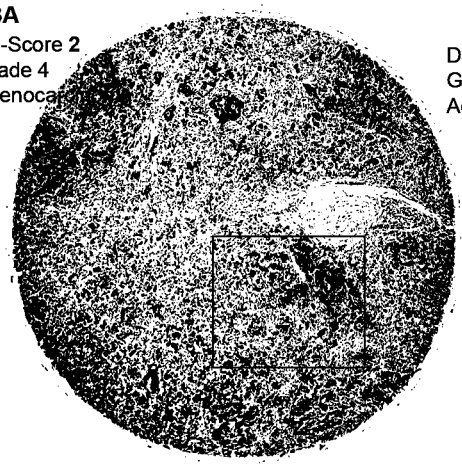
FIG. 13A-13D shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures.
Figure 13C:
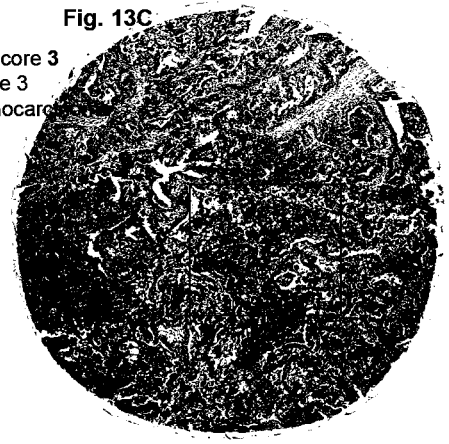
Figure 13B:
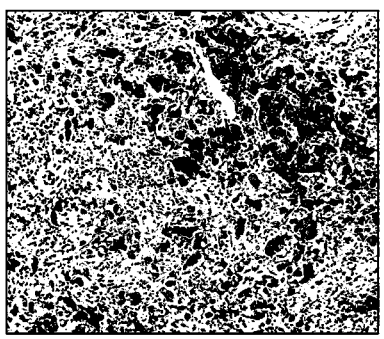
Figure 13D:
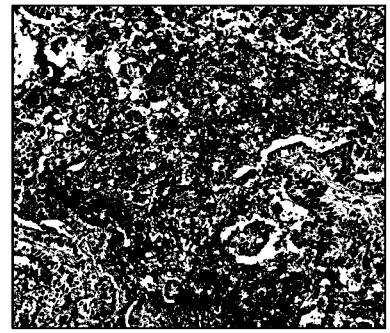
Figure 14A:
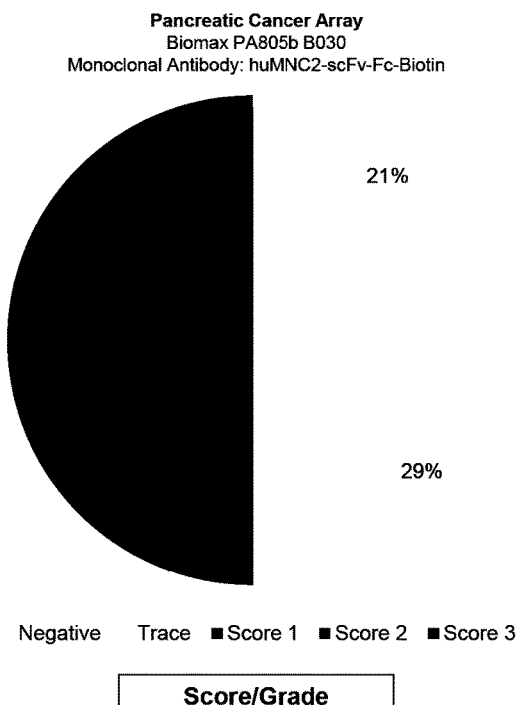
FIG. 14A-14B shows pie chart graphs of the pathologist scores and a photograph of pancreatic cancer array PA805b after staining with anti-MUC1* antibody huMNC2-scFv-Fc.
Figure 14B:
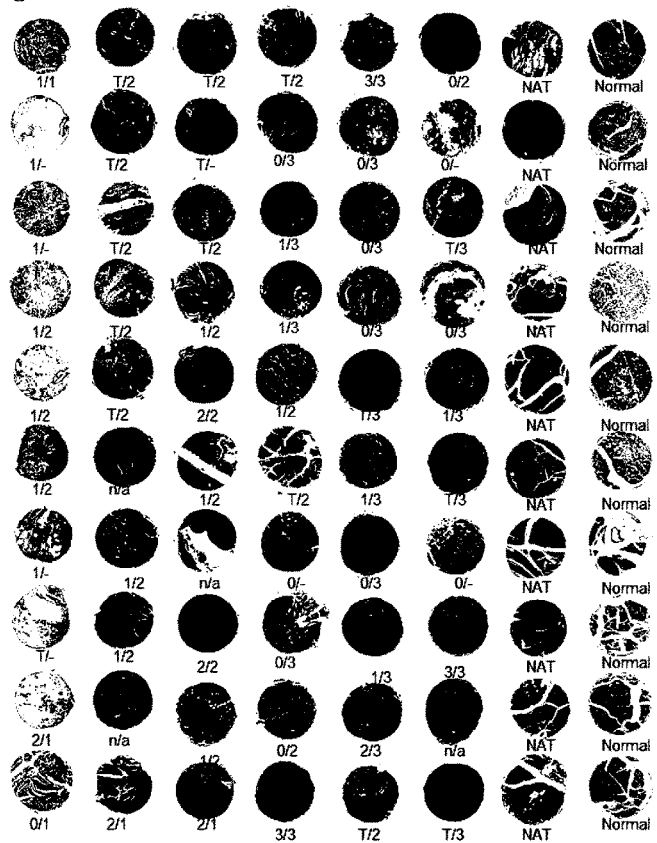
Figure 15A:
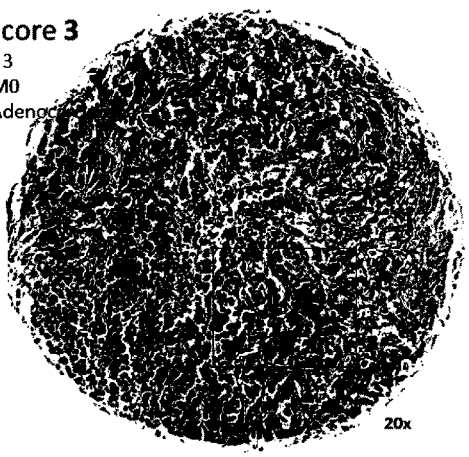
FIG. 15A-15D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 15B:
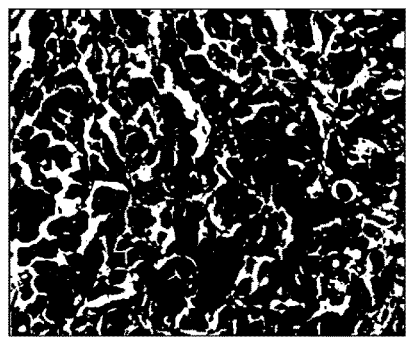
Figure 15C:
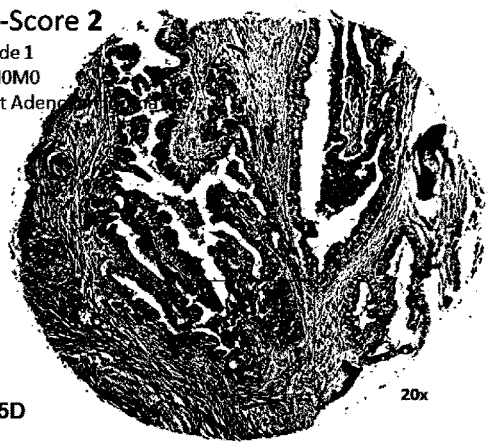
Figure 15D:
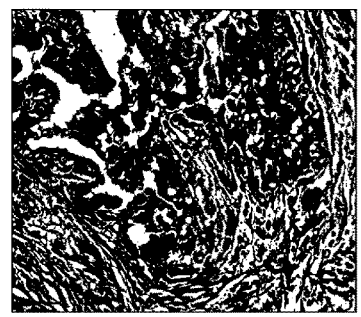
Figure 16A:
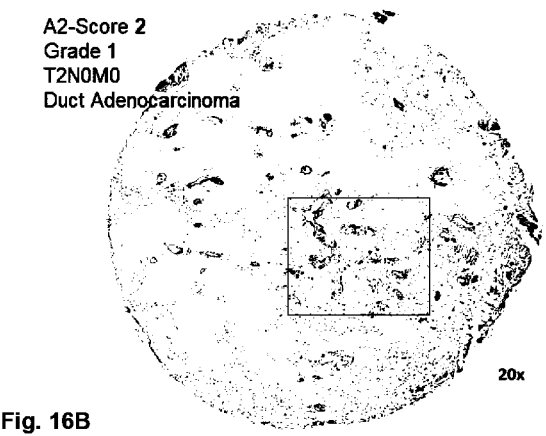
FIG. 16A-16D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 16C:
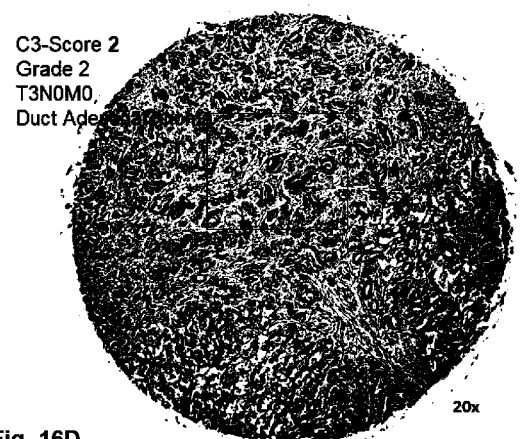
Figure 16B:
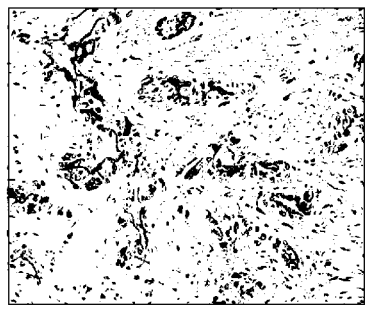
Figure 16D:
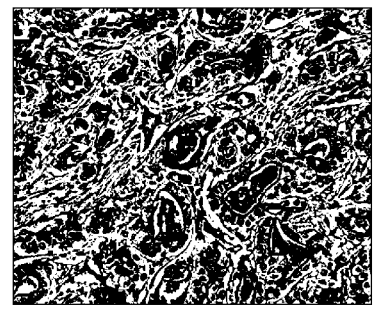
Figure 17A:
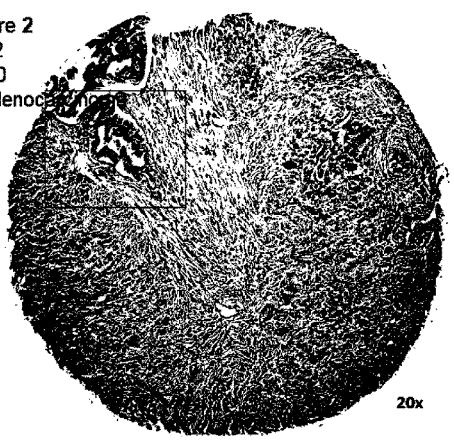
FIG. 17A-17D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 17C:
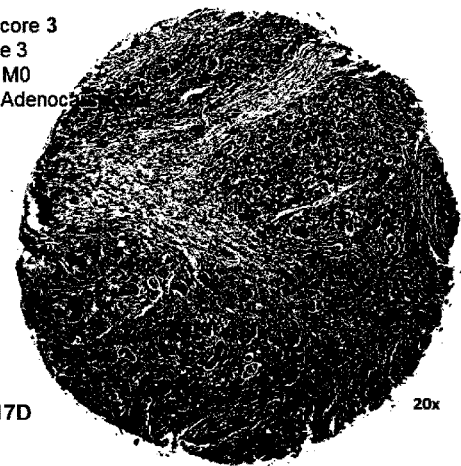
Figure 17B:
Figure 17D:
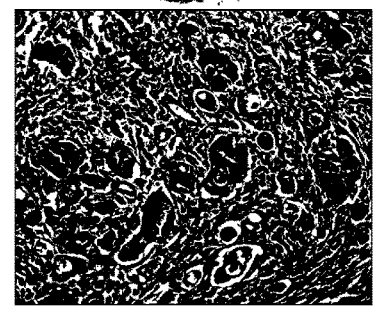
Figure 18A:
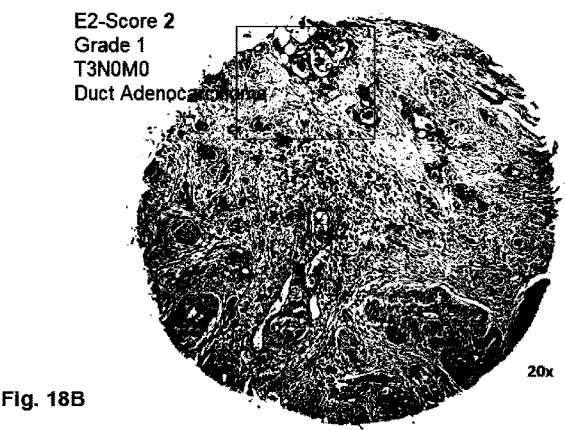
FIG. 18A-18D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 18C:
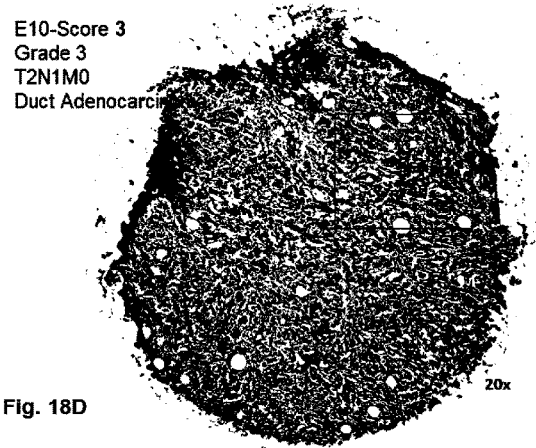
Figure 18B:
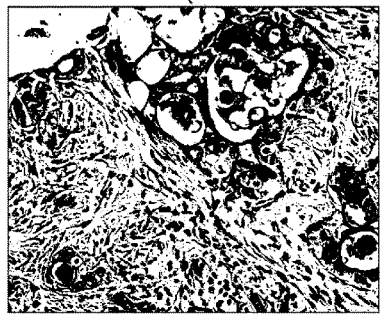
Figure 18D:
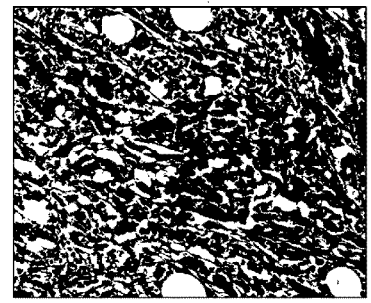
Figure 19:
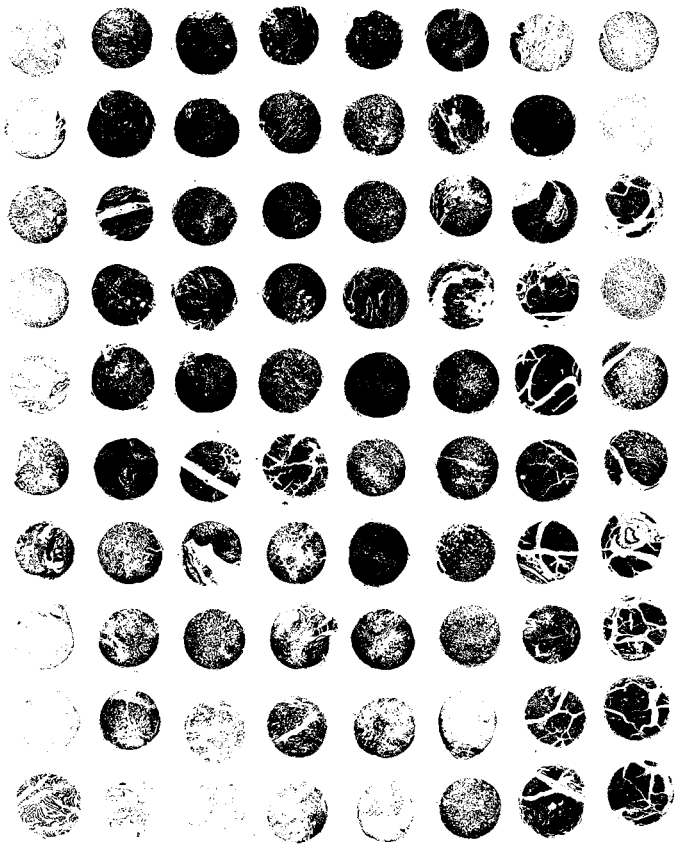
FIG. 19 shows a photograph of pancreatic cancer array PA805b that was stained with the secondary antibody alone, as a control.
Figures 21A, 21B, 21C, 21D:
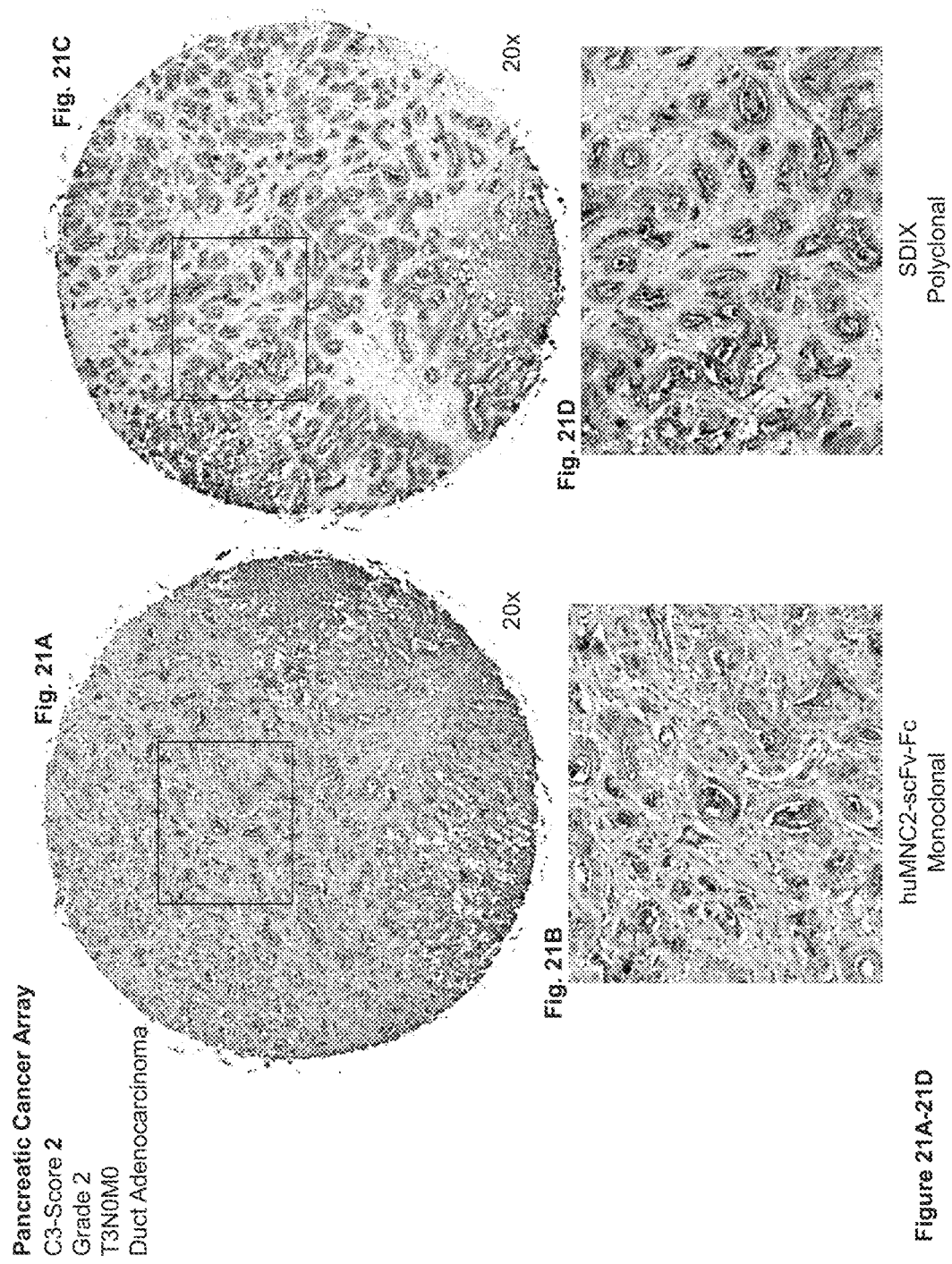
FIGS. 21A-21D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 22A, 22B, 22C, 22D:
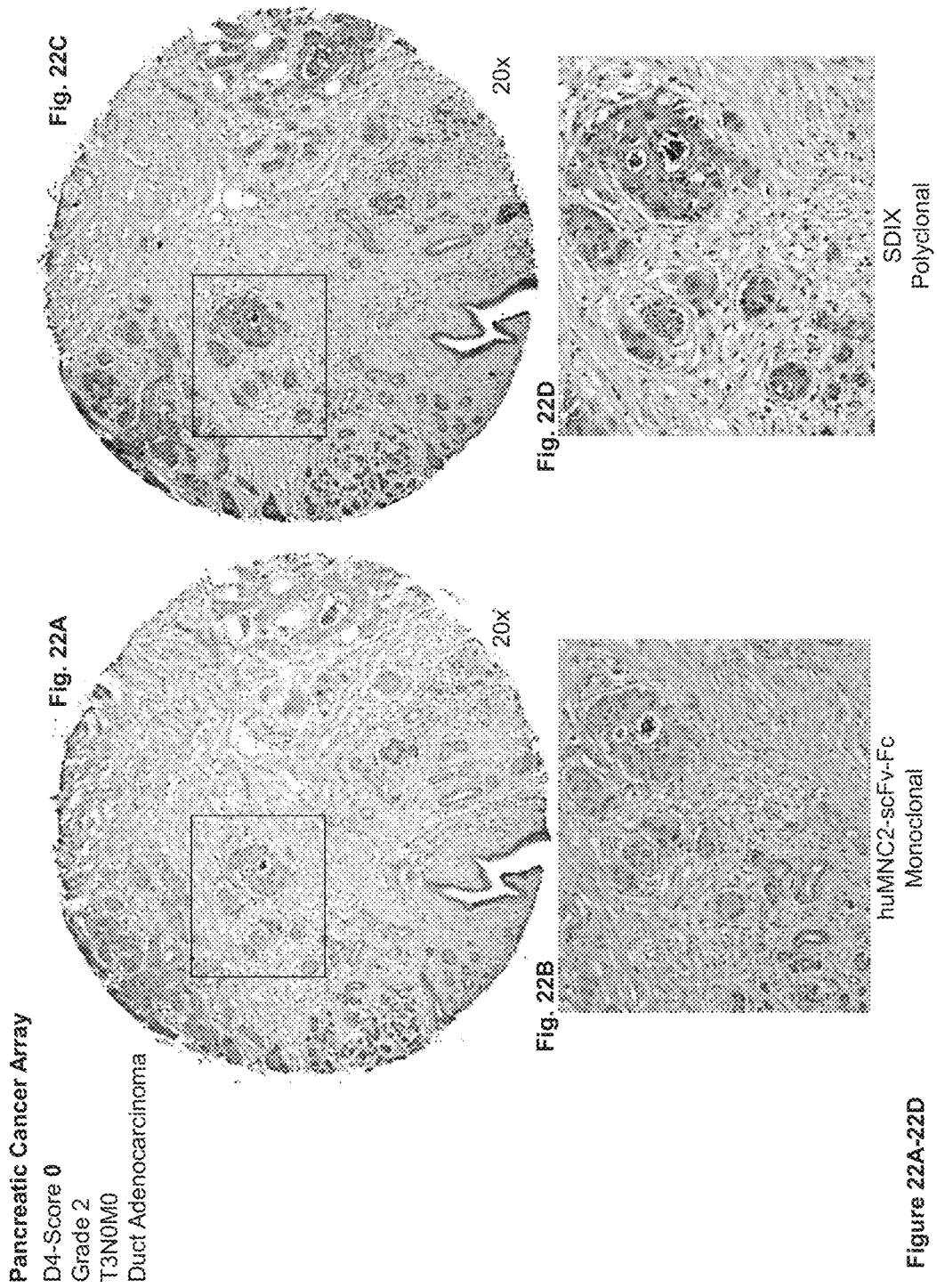
FIGS. 22A-22D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 23A, 23B, 23C, 23D:
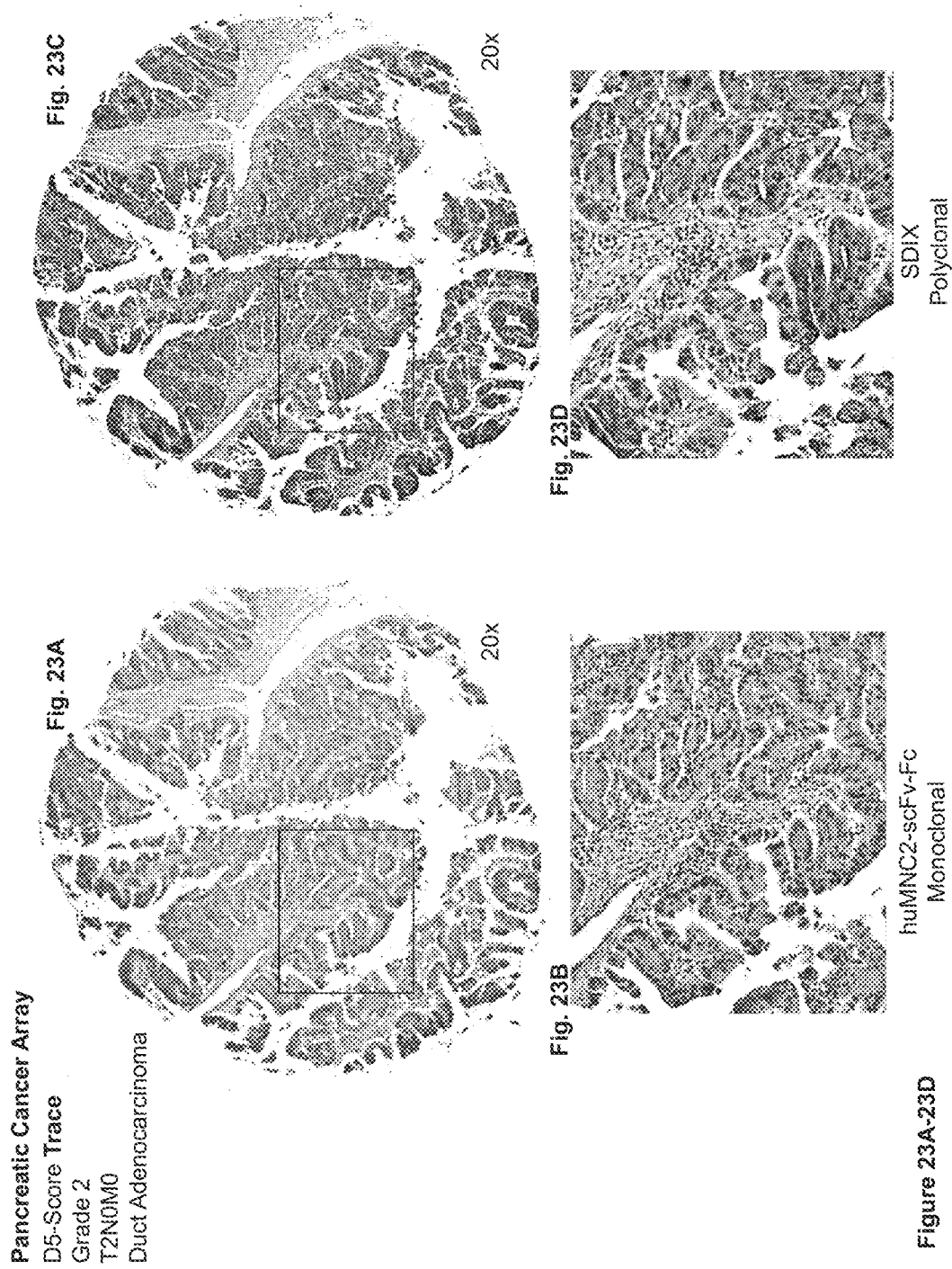
FIGS. 23A-23D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 24A, 24B, 24C, 24D:
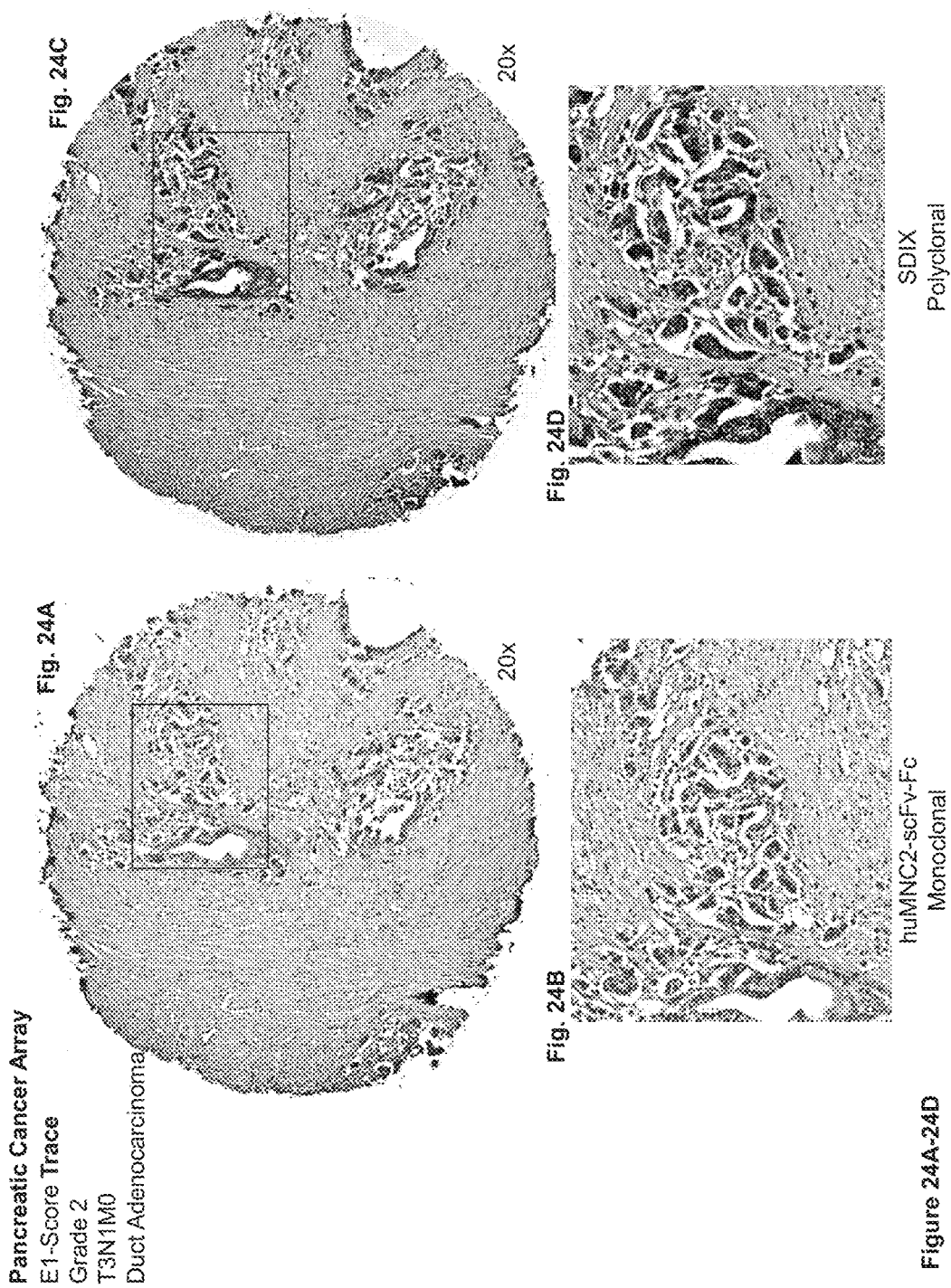
FIGS. 24A-24D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 25A, 25B, 25C, 25D:
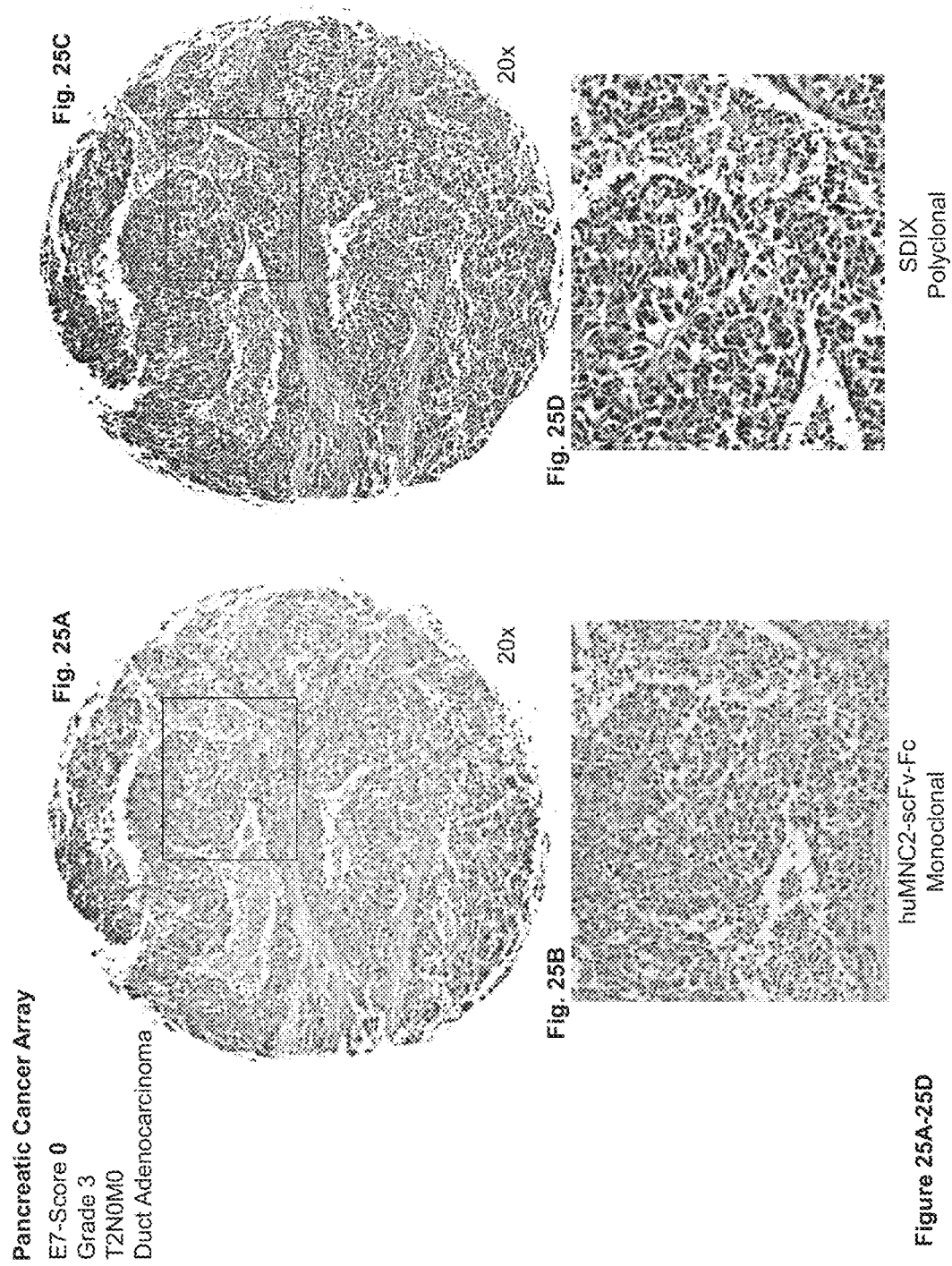
FIGS. 25A-25D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 27A, 27B, 27C, 27D:
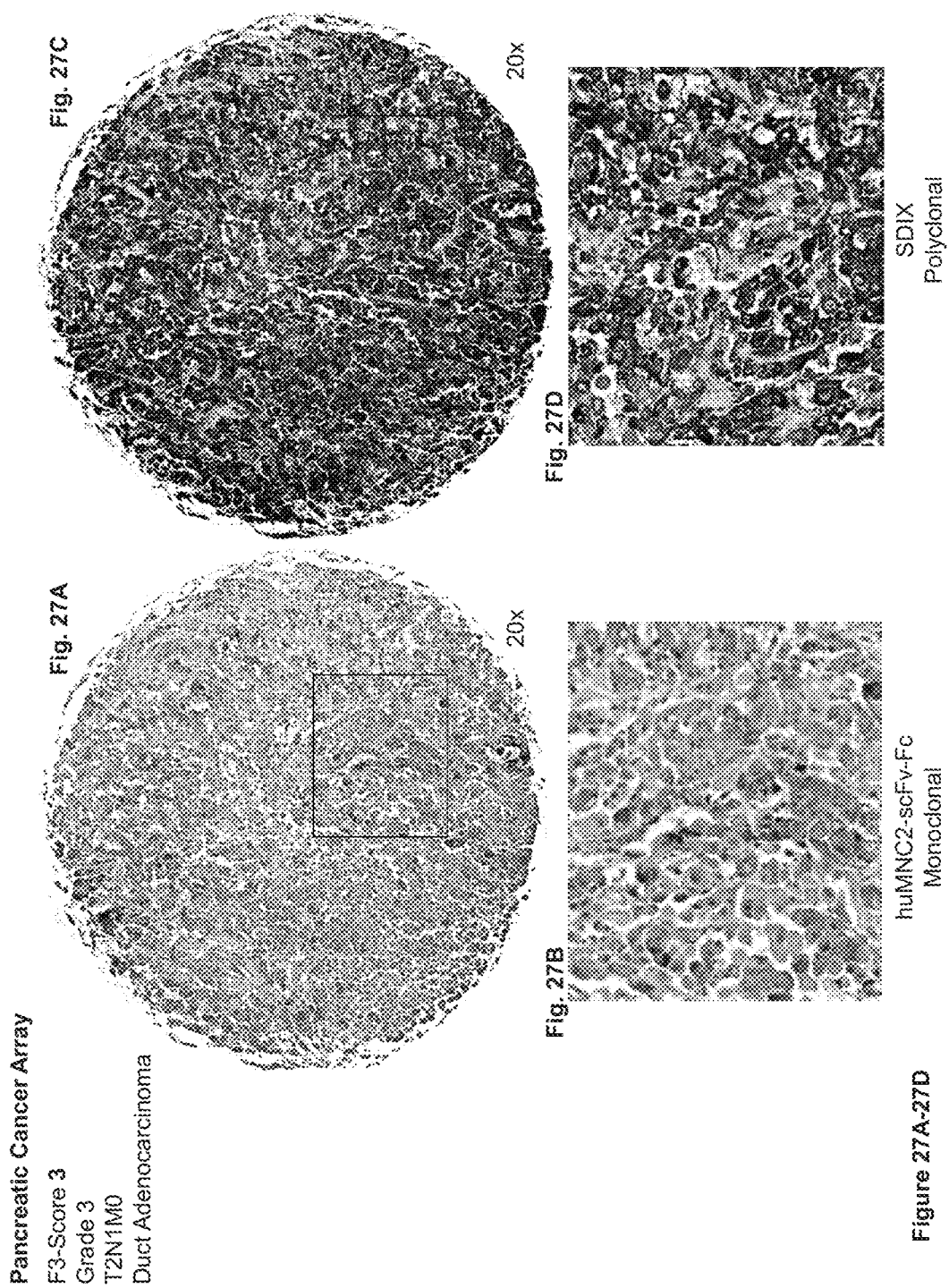
FIGS. 27A-27D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 28A, 28B, 28C, 28D:
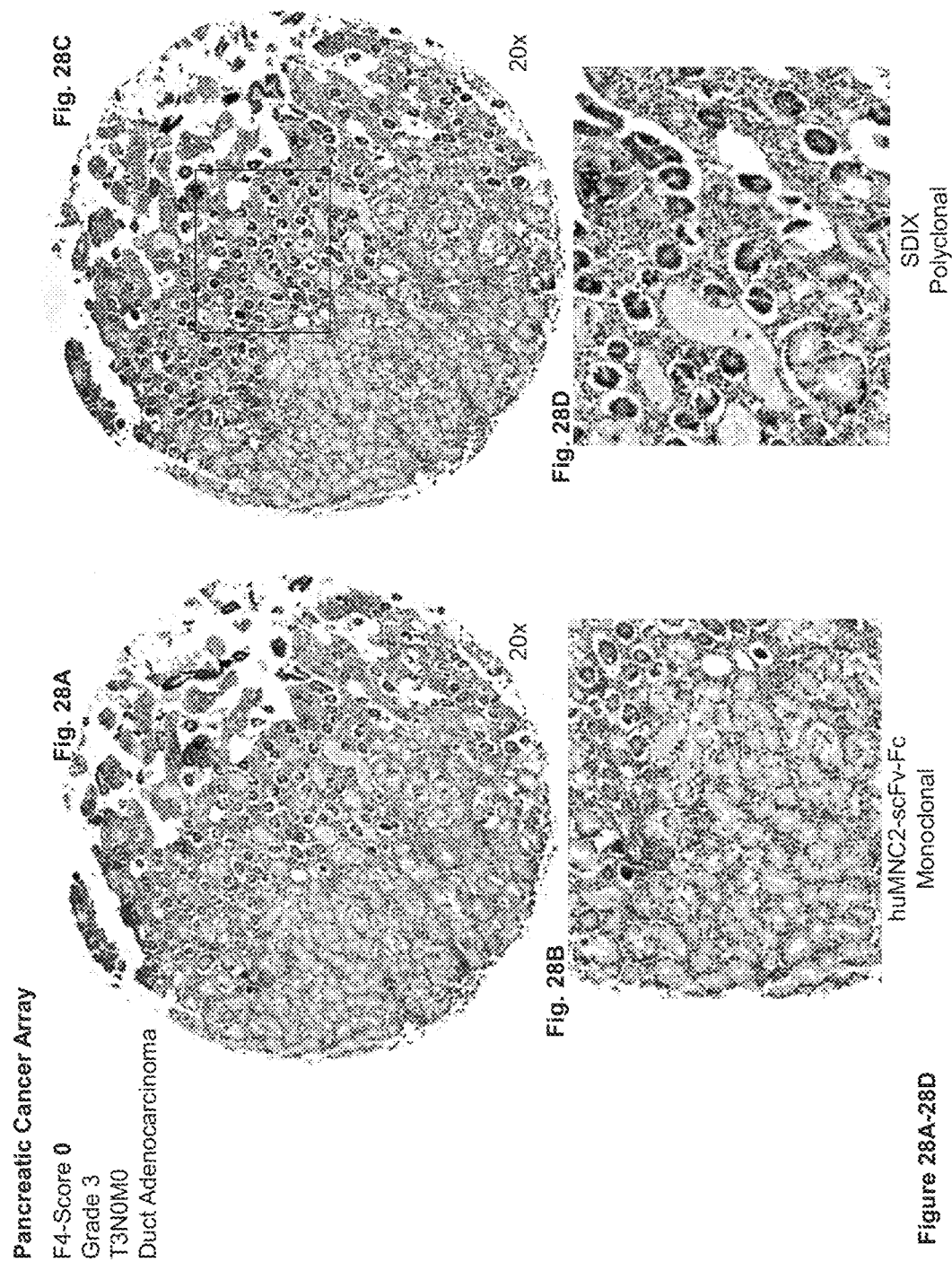
FIGS. 28A-28D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 29A, 29B, 29C, 29D:
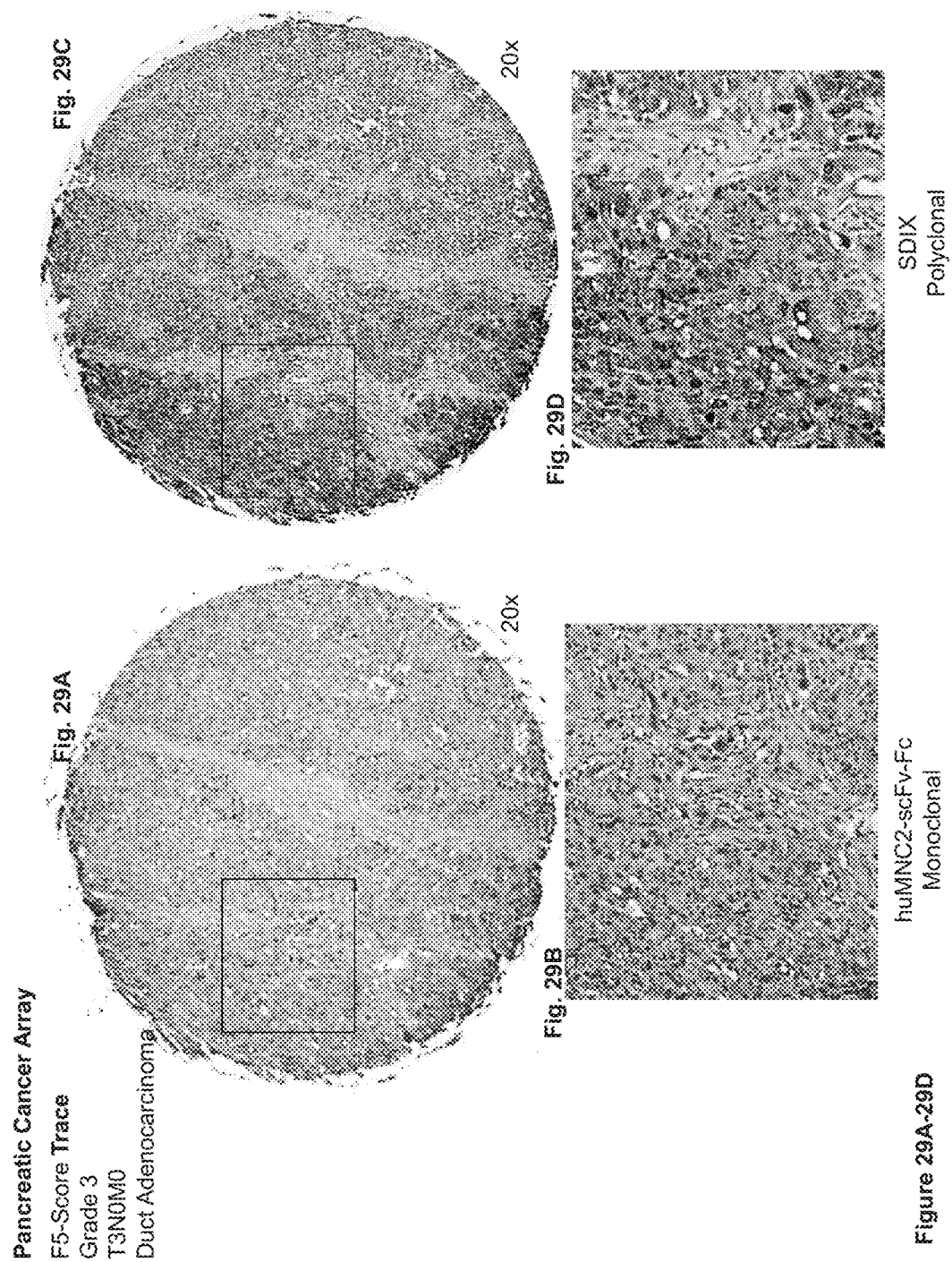
FIGS. 29A-29D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figure 30A:
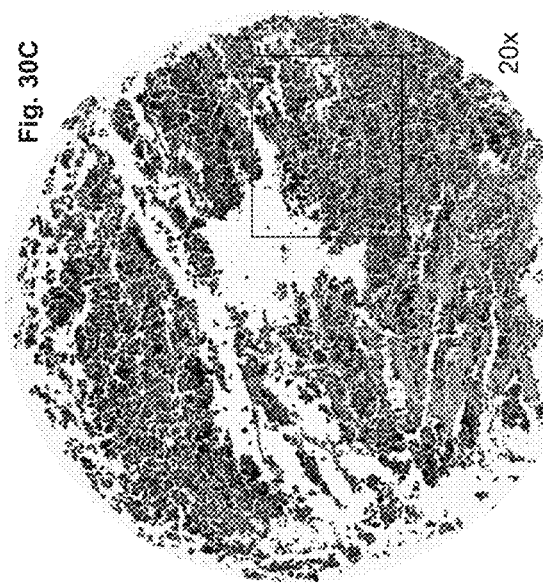
FIGS. 30A-30D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figure 30B:
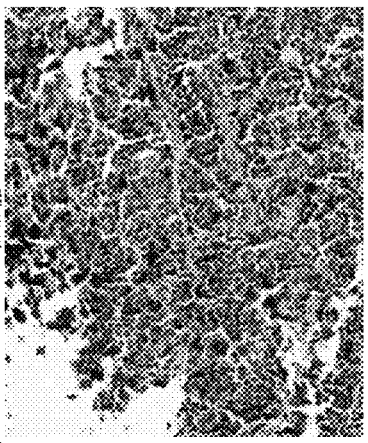
Figure 30C:
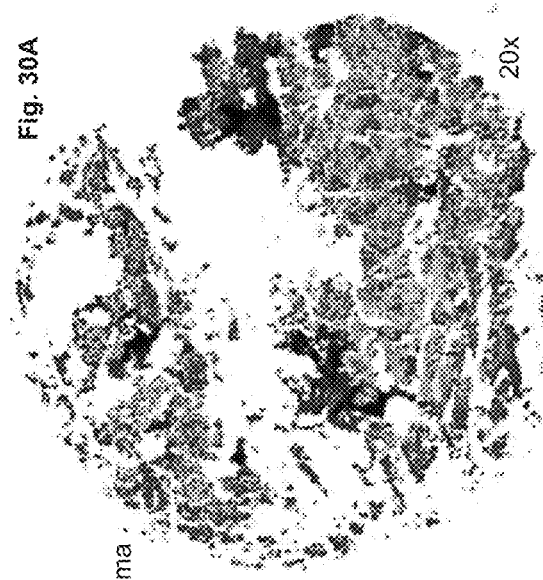
Figure 30D:
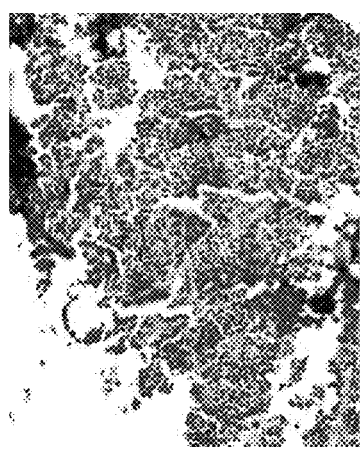
Figure 31A:
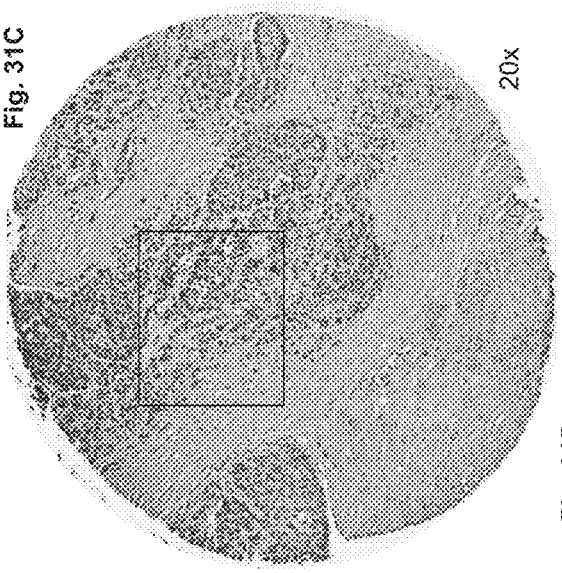
FIGS. 31A-31D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figure 31B:
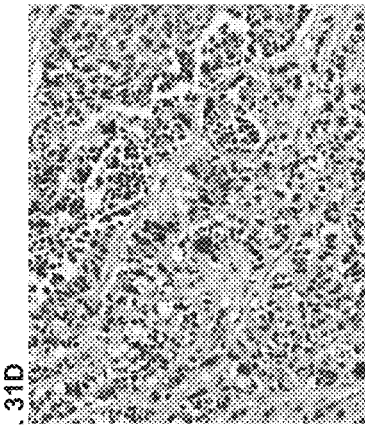
Figure 31C:
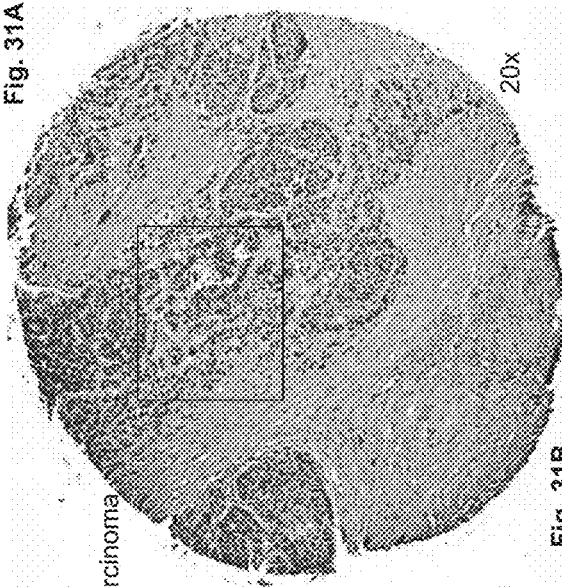
Figure 31D:
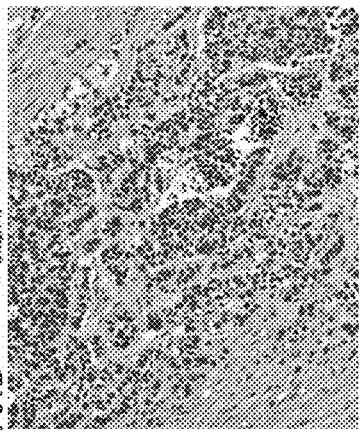
Figure 32A:
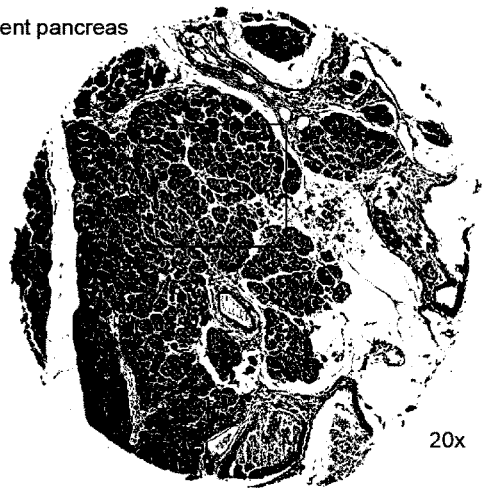
FIGS. 32A-32D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.
Figure 32C:
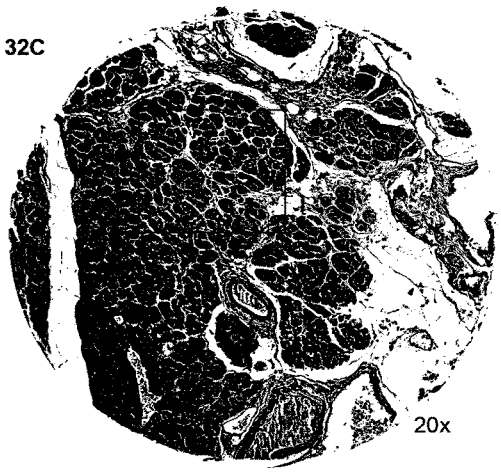
Figure 32B:
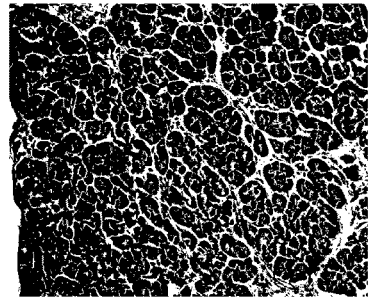
Figure 32D:
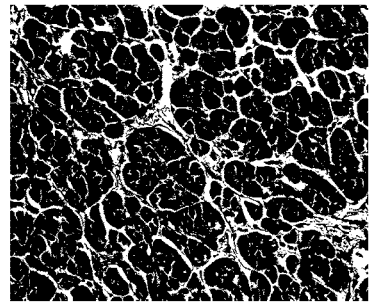
Figure 33A:
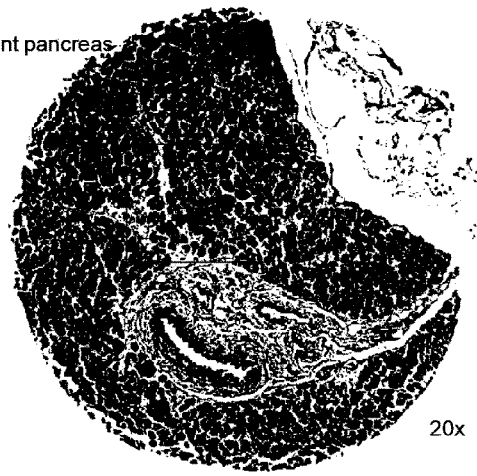
FIGS. 33A-33D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.
Figure 33C:
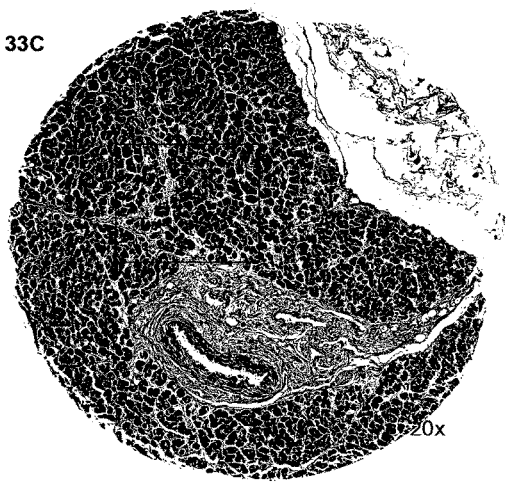
Figure 33B:
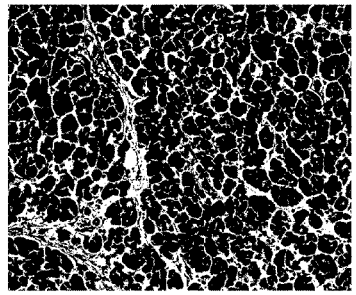
Figure 33D:
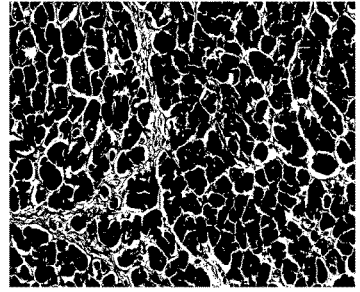
Figure 34A:
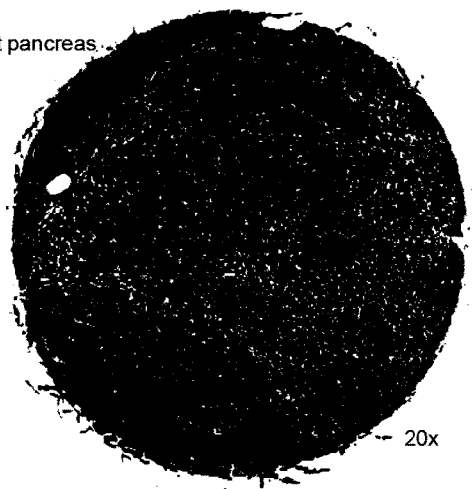
FIGS. 34A-34D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.
Figure 34C:
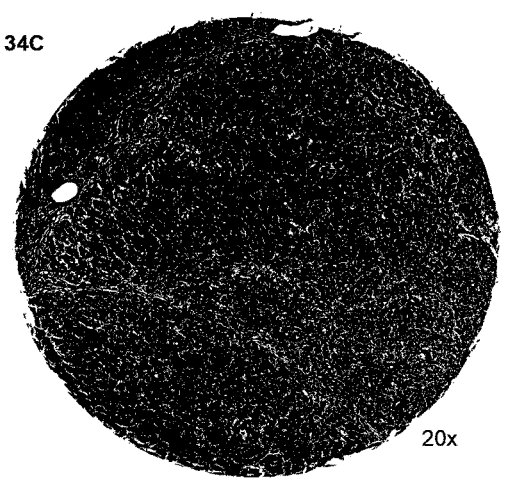
Figure 34B:
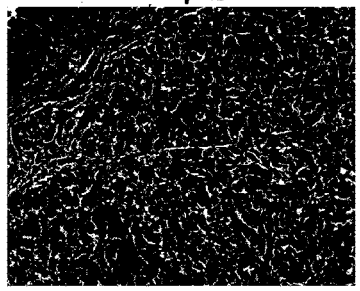
Figure 34D:
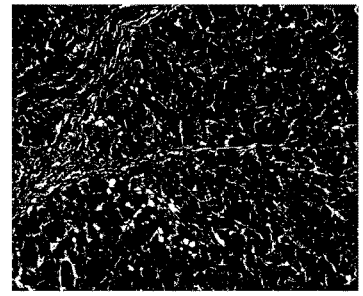

FIG. 3 to FIG. 19 show that monoclonal anti-MUC1* antibody MNC2 binds to high percentages of breast, ovarian, pancreatic, lung and esophageal tumors, while having very little if any binding to normal tissues. FIG. 3A-3B shows pie chart graphs of the pathologist scores and a photograph of breast cancer array BR1141 after staining with anti-MUC1* antibody huMNC2-scFv-Fc. FIG. 4A-4C shows photographs, at two different magnifications, of individual breast cancer specimens from breast cancer array BR1141 after staining with anti-MUC1* antibody huMNC2-scFv-Fc. The position in the array, cancer sub-type, tumor grade, TNM (Tumor stage, Node involvement, and Metastasis) and pathologist score are indicated in figures. Standard immunohistochemistry methods were used. Antibody concentration was titered using the highest concentration at which the antibody showed expected staining of normal tissues without staining stroma. The antibody was conjugated to a biotin through its Fc region, to avoid false positive due to anti-human secondary antibodies staining host antibodies as well as B cell follicules. FIG. 4A shows the specimen at position A7 which was negative for huMNC2 reactive cells. FIG. 4B shows the specimen at position A9 which is a Grade 2 cancer, with lymph node involvement that scored +1 for huMNC2 reactivity. FIG. 4C shows the specimen at position B10 which is a larger Grade 2 tumor, with lymph node involvement that scored +2 for huMNC2 reactivity. FIG. 5A-5B shows photographs, at two different magnifications, of individual breast cancer specimens from breast cancer array BR1141 after staining with anti-MUC1* antibody huMNC2-scFv-Fc. FIG. 5A shows the specimen at position D7 which is a Grade 2 cancer, without lymph node involvement that scored +3 for huMNC2 reactivity. FIG. 5B shows the specimen at position F6 which is a Grade 2 tumor, with lymph node involvement that scored +4 for huMNC2 reactivity. FIG. 6A-6B shows pie chart graphs of the pathologist scores and a photograph of ovarian cancer array BC1115a after staining with anti-MUC1* antibody huMNC2-scFv-Fc. FIG. 7A-7C shows magnified photographs of different cancer sub-types after staining with anti-MUC1* antibody huMNC2-scFv-Fc. FIG. 7A shows a photograph of a Grade 2 breast tumor that pathologist scored +4. FIG. 7B shows a photograph of a Grade 2 ovarian tumor that pathologist scored +3. FIG. 7C shows a photograph of a Grade 3 pancreatic tumor that pathologist scored +3. IHC studies of over 1,000 tumor specimens showed that huMNC2-scFv recognized 95% of Breast Cancers (90% triple negative), 83% Ovarian, 78% Pancreatic and 71% Lung Cancers. FIG. 8A-8D shows magnified photographs of different cancer sub-types after staining with anti-MUC1* antibody huMNC2-scFv-Fc. FIG. 8A shows a photograph of a Grade 2 breast tumor that pathologist scored +2. FIG. 8B shows a photograph of a Grade 3 ovarian tumor that pathologist scored +3. FIG. 8C shows a photograph of a Grade 3 pancreatic tumor, with lymph node involvement that pathologist scored +3. FIG. 8D shows a photograph of a lung cancer that pathologist scored +3. FIG. 9A-9I shows magnified photographs of various normal tissues after staining with anti-MUC1* antibody huMNC2-scFv-Fc. Conditions and concentrations used were identical to those used for studying cancerous tissues. FIG. 9A shows normal adrenal gland tissue. FIG. 9B shows normal brain tissue. FIG. 9C shows normal breast tissue. FIG. 9D shows normal stomach tissue. FIG. 9E shows normal heart tissue. FIG. 9F shows normal kidney tissue. FIG. 9G shows normal testis tissue. FIG. 9H shows normal intestine tissue. FIG. 9I shows normal liver tissue. FIG. 10A-10F shows photographs of normal kidney tissues after staining with anti-MUC1* antibody huMNC2-scFv-Fc. Conditions and concentrations used were identical to those used for studying cancerous tissues. FIG. 10A shows normal kidney tissue with huMNC2 reactivity limited to the apical border, which is normal expression. FIG. 10B is the same tissue at greater magnification. FIG. 10C shows another example of normal kidney tissue with undetectable huMNC2 reactivity. FIG. 10D is the same tissue at greater magnification. FIG. 10E shows another example of normal kidney tissue with huMNC2 reactivity limited to the apical border, which is normal expression. FIG. 10F is the same tissue at greater magnification. Further studies showed that less than 10% of normal kidney tissue showed huMNC2 reactivity at distal collecting tubules wherein such reactivity was strictly limited to the apical border, which is a normal expression pattern. FIG. 11A-11B shows pie chart graphs of the pathologist scores and a photograph of esophageal cancer array BC001113 after staining with anti-MUC1* antibody huMNC2-scFv-Fc. FIG. 12A-12F shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 12A shows the specimen at position A4 which was negative for huMNC2 reactive cells. FIG. 12B shows the same specimen at greater magnification. FIG. 12C shows the specimen at position D2 which the pathologist scored as trace reactivity to huMNC2. FIG. 12D shows the same specimen at greater magnification. FIG. 12E shows the specimen at position B8 which the pathologist scored as +1 reactivity to huMNC2. FIG. 12F shows the same specimen at greater magnification. FIG. 13A-13D shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 13A shows the specimen at position D6, a Grade 4 tumor, which the pathologist scored +2. FIG. 13B shows the same specimen at greater magnification. FIG. 13C shows the specimen at position D5, a Grade 3 tumor, which the pathologist scored +3. FIG. 12D shows the same specimen at greater magnification. FIG. 14A-14B shows pie chart graphs of the pathologist scores and a photograph of pancreatic cancer array PA805b after staining with anti-MUC1* antibody huMNC2-scFv-Fc. FIG. 15A-15D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 15A shows the specimen at position F3, a Grade 3 tumor, which the pathologist scored +3. FIG. 15B shows the same specimen at greater magnification. FIG. 15C shows the specimen at position B1, a Grade 1 tumor, which the pathologist scored +2. FIG. 15D shows the same specimen at greater magnification. FIG. 16A-16D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 16A shows the specimen at position A2, a Grade 1 tumor, which the pathologist scored +2. FIG. 16B shows the same specimen at greater magnification. FIG. 16C shows the specimen at position C3, a Grade 2 tumor, which the pathologist scored +2. FIG. 16D shows the same specimen at greater magnification. FIG. 17A-17D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 17A shows the specimen at position C6, a Grade 2 tumor, which the pathologist scored +2. FIG. 17B shows the same specimen at greater magnification. FIG. 17C shows the specimen at position D1, a larger Grade 3 tumor, with lymph node involvement that the pathologist scored +3. FIG. 17D shows the same specimen at greater magnification. FIG. 18A-18D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 18A shows the specimen at position E2, a Grade 1 tumor, which the pathologist scored +2. FIG. 18B shows the same specimen at greater magnification. FIG. 18C shows the specimen at position E10, a smaller Grade 3 tumor, with lymph node involvement that the pathologist scored +3. FIG. 18D shows the same specimen at greater magnification. FIG. 19 shows a photograph of pancreatic cancer array PA805b that was stained with the secondary antibody alone, as a control.

Although MNC2 recognized about 95% of breast tumors across all breast cancer sub-types, we noticed that some cancer sub-types did not express as much MNC2 reactive MUC1* as breast cancers. In particular, pancreatic, esophageal and prostate cancers expressed lower levels of MNC2 reactive MUC1*. Pancreatic cancer arrays showed that 78% of the tumors were MNC2 reactive but the strength of staining, which is proportional to the tumor's expression levels, was relative weak. The pie chart of FIG. 14A shows that 65% of the pancreatic tumors scored +1 or +2, only 5% scored +3 and none scored +4. The pie chart of FIG. 3A shows that more than half of the breast tumors scored +2 to +3, 6% were +4 and only 4% were negative for MNC2 MUC1* reactivity. Both arrays were stained with the same MNC2 anti-MUC1* antibody and scored by the same board-certified pathologist. We reasoned that the difference between MNC2 staining of MUC1* in breast cancer and pancreatic cancer could be due to differences in cleavage enzymes that cleave MUC1 to MUC1* at different positions that induce conformational or linear changes in the MUC1* extra cellular domain. To investigate, we stained the same pancreatic cancer array with the anti-MUC1* polyclonal antibody SDIX. Although both MNC2 and SDIX were generated by immunizing animals with the PSMGFR peptide, they showed different binding characteristics to tumor tissue. In general, SDIX recognized more pancreatic tissues and stained more robustly than MNC2, although there were cases where MNC2 recognized a tumor that SDIX did not.

On cancerous tissues, MUC1* is expressed over most of the tissue and is characteristic of cancer, all anatomical barriers have broken down in cancerous tissues. In contrast, on normal tissues, expression of MUC1* is restricted to the apical border of ducts and glands. Expression of MNC2 reactive MUC1* is even further restricted. For example, FIG. 6B shows a photograph of an ovarian cancer micro array. However, Column J is made up of normal ovarian tissues. As can be seen, there is no expression of MNC2 reactive MUC1*. Normal kidney does express some MNC2 reactive MUC1*. As can be seen in FIG. 10A-10F, normal MUC1* expression is weak and restricted to the apical border of about 10% of the distal collecting tubules of normal kidney. Normal pancreas expresses MUC1* that is again tightly restricted to the apical border of acinar cells (FIG. 20). Those skilled in the art can readily identify cancerous tissues and can differentiate between MUC1* expression on normal tissue and on cancerous tissues. In general, MUC1* is grossly overexpressed on cancerous tissues and its expression is not restricted to an apical pattern of expression.

In this FIG. 20 through FIG. 34, we show that a series of pancreatic tumors showed no or minimal staining with monoclonal antibody MNC2, but staining the same tissue with the SDIX polyclonal antibody produced robust staining. Both MNC2 and SDIX were generated by immunizing animal with the same peptide: PSMGFR. However, MNC2 only recognizes a subset of those recognized by SDIX. These results strongly argue that MNC2 recognizes an epitope that is only created in a subset of the tumor. The data suggest that the MNC2 reactive subset of MUC1* can be cancer sub-type specific or patient specific, likely due to cleavage by different cleavage enzymes.

Figure 35A:
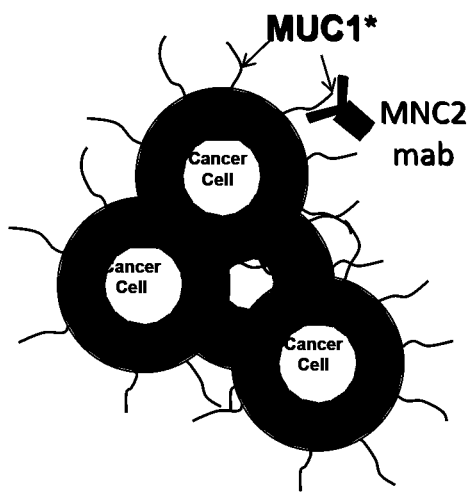
FIG. 35A-35B shows cartoons of MUC1* expression on cancer cells and on normal hematopoietic stem cells. FIG.
Figure 35B:
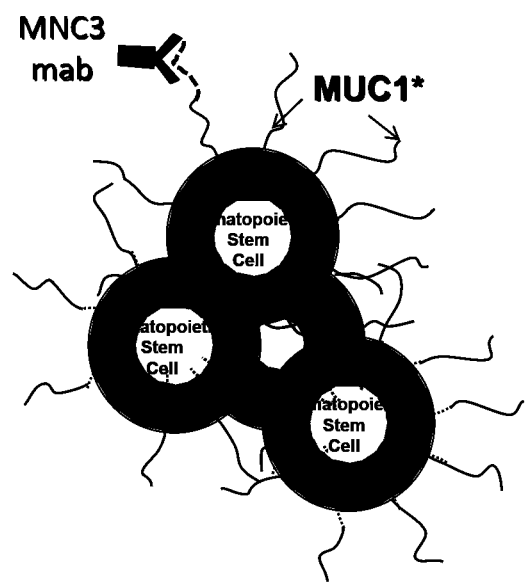
Figure 36A:
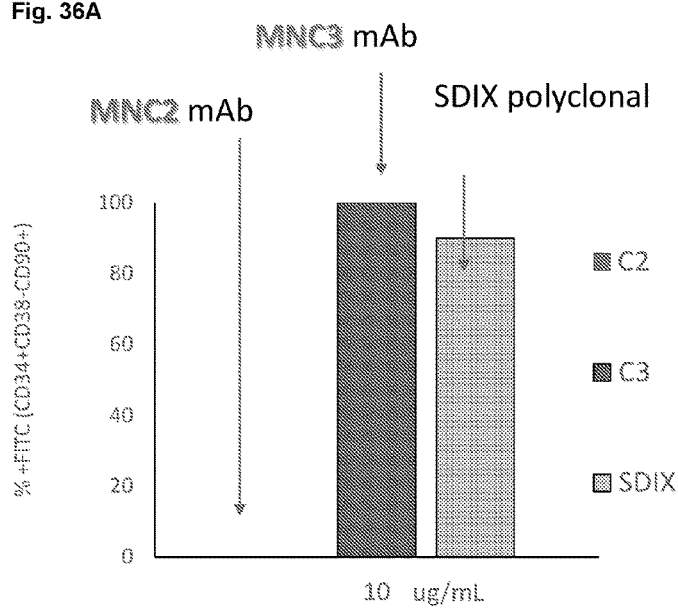
FIG. 36A-36B shows FACS analysis of human hematopoietic stem cells stained with anti-PSMGFR antibodies.
Figure 36B:
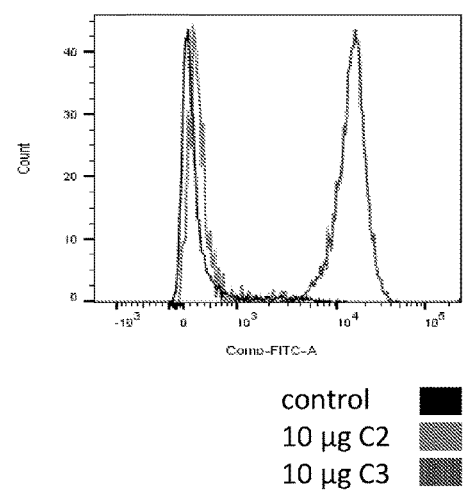
Figure 37:
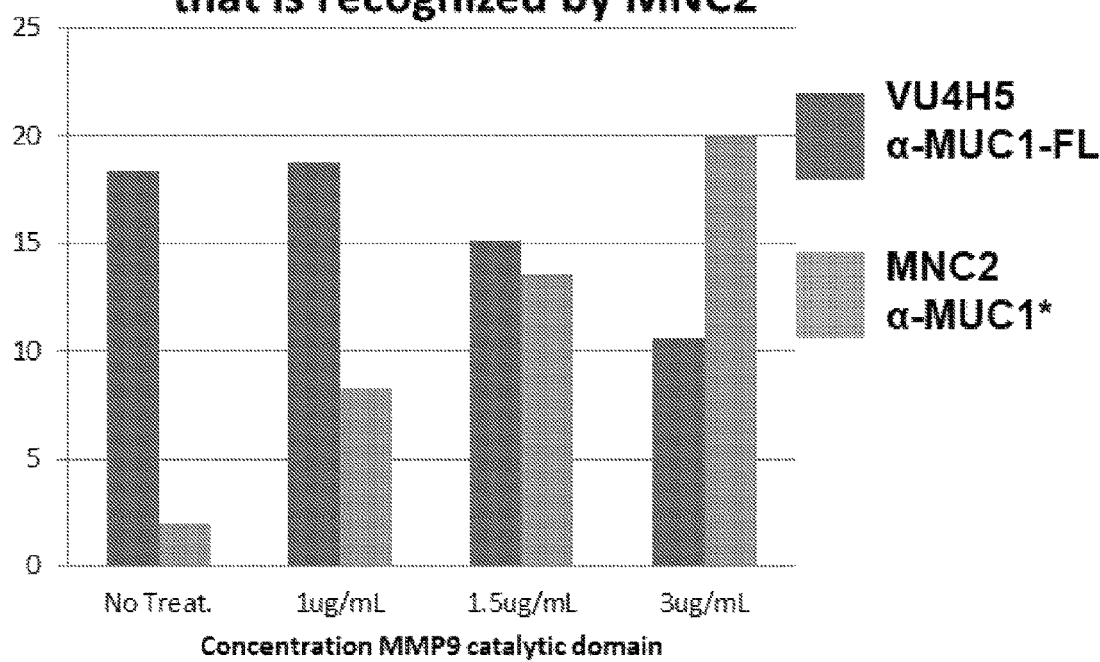
FIG. 37 shows a graph of FACS analysis of cells that express 90% full-length MUC1 after addition of a catalytic domain of cleavage enzyme MMP9, then probing with anti-full-length MUC1 antibody VU4H5 or anti-MUC1* antibody MNC2.

The hypothesis that anti-MUC1* antibody specificity is dependent on the cleavage enzyme that cleaves MUC1 to a MUC1* is supported by data shown in FIG. 35 through FIG. 37. MNC2, MNC3 and SDIX were all generated by immunizing an animal with the PSMGFR peptide. However, monoclonal antibody MNC3 recognizes nearly 100% of hematopoietic stem cells, as does the polyclonal antibody SDIX, while monoclonal antibody MNC2 does not. Conversely, MNC2 binds to nearly 95% of breast tumors, but MNC3 does not. Importantly, we demonstrated that MNC2 recognizes MUC1* after MUC1 is cleaved by cleavage enzyme MMP9, which is overexpressed in most breast cancers, but not in hematopoietic stem cells. Expression of MMP9 is predictor of poor prognosis for most solid tumor cancers (Yousef et al. BMC Cancer 2014, 14:609; Mehner et al, Oncotarget, Vol. 5, No. 9, pp 2736-2749, 2014; Radisky et al., Front Biosci (Landmark Ed).; 20: 1144-1163, 2015; Gong et al., Journal of Surgical Oncology 2000; 73:95-99; Latinovic et al., Arch Oncol 2013; 21(3-4):109-14; Sillanpaa et al., Gynecologic Oncology 104 (2007) 296-303).

In order to generate new anti-MUC1* monoclonal antibodies that were capable of recognizing a wide range of MUC1*'s that can be cancer sub-type specific, patient specific or to better address tumor heterogeneity, we immunized animals with one of the following peptides derived from the sequence of the MUC1* extra cellular domain:

(i) PSMGFR peptide (SEQ ID NO: 4)
GTINVHDVETQFNQYKTEAASRYNLTISDVSVSDVPFPFSAQSGA;

(ii) PSMGFR N+20/C-27

(SEQ ID NO: 9)
SNIKFRPGSVVVQLTLAFREGTINVHDVETQFNQYKTE;

or (iii) PSMGFR N+9/C-9

(SEQ ID NO: 10)
VQLTLAFREGTINVHDVETQFNQYKTEAASRYNLTISDVSVSDVP.

Antibody clones were isolated and a subset from each immunization was selected, first based on their ability to bind to the immunizing peptide, then secondly for their ability to recognize cancerous tissues above normal tissues. FIG. 38A to FIG. 38C shows tables of the selected antibodies, organized according to immunizing peptide. In the tables, designation of −1 or −2 indicates that these are sister clones, which after sequencing showed these were in fact the same antibody. Throughout the rest of the disclosure, antibodies are referred to without the −1 or −2 designation.

FIG. 39 through FIG. 44 show the binding characteristics of new anti-MUC1* antibodies. All antibodies were first selected by virtue of the fact that they bound to the immunizing peptide. For comparison to MNC2 and MNC3, new antibodies were tested for their ability to bind to PSMGFR, the N−10 peptide and the C−10 peptide. New anti-MUC1* antibodies were also tested by FACS to determine their ability to bind to the T47D breast cancer cell line. Because analysis of antibody binding to a single cell line that was generated from a patient decades ago, we expanded the analysis of the new antibodies to hundreds of tumor tissues across multiple cancer sub-types. The number of patients represented in each array varied. Normal tissues were also probed with the antibodies.

FIG. 45 through FIG. 52 compares the binding of the new anti-MUC1* antibodies to the SDIX polyclonal to investigate antibodies that bind to regions that are N-terminal to the PSMGFR sequence. We started with pancreatic cancer arrays because out previous work showed that although MNC2 recognized about 78% of pancreatic cancers, the binding was not so robust and some very nasty tumors were not recognized at all by MNC2 or the SDIX polyclonal.

Figure 51A:
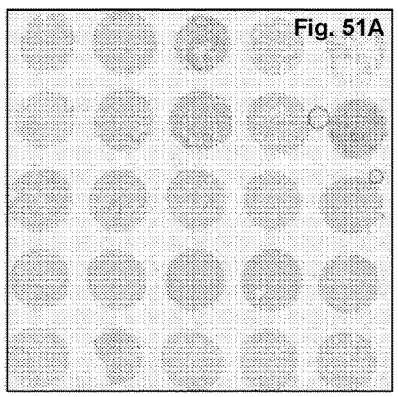
FIG. 51A-51C shows photographs of adjacent serial sections from a pancreatic cancer array, which was stained by standard IHC methods with various anti-MUC1* antibodies.
Figure 51B:
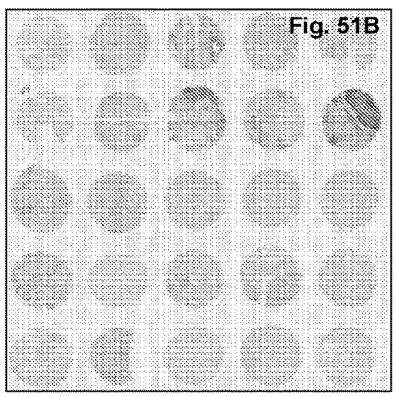
Figure 51C:
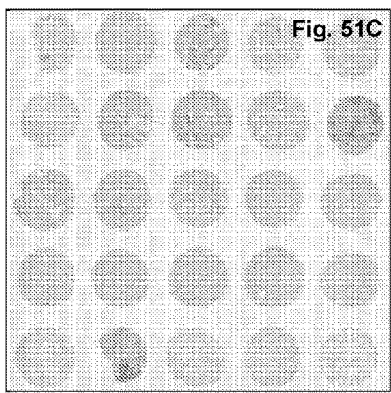
Figure 52A:
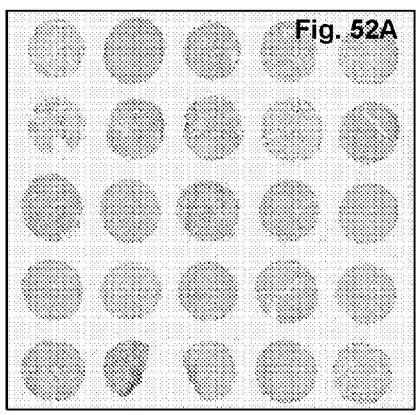
FIG. 52A-52D shows photographs of adjacent serial sections from a pancreatic cancer array, which was stained by standard IHC methods with various anti-MUC1* antibodies.
Figure 52B:
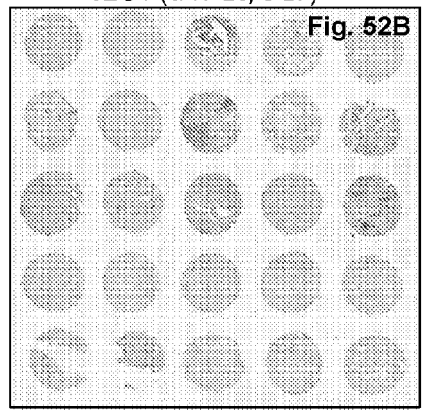
Figure 52C:
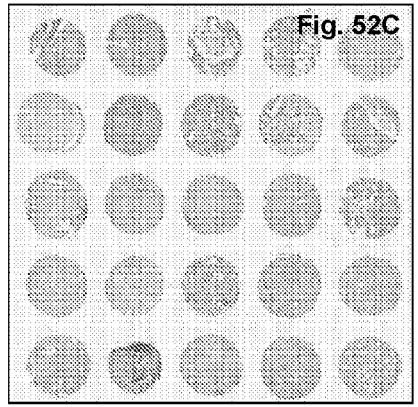
Figure 52D:
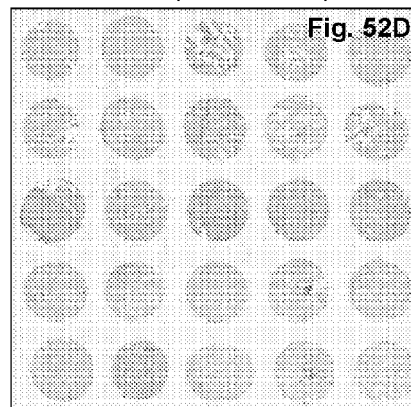

Some anti-PSMGFR antibodies, such as 18B4, appear to recognize the same pancreatic tumor tissues as the polyclonal anti-PSMGFR antibody SDIX (FIG. 45A-45BC). In this small pancreatic cancer array, anti-PSMGFR N+20/C−27 antibody 1E4 appears to recognize the same tumors as SDIX and 18B4, however, the magnified view of these tumor specimens shows that antibody 1E4 recognizes a different population of cancer cells within the tumor than the anti-PSMGFR antibodies (FIG. 46A-46F), Some of the tumors were not recognized well by SDIX but were recognized by monoclonal antibody 18B4 (FIG. 47A-48D). Other pancreatic tumors were recognized better by anti-PSMGFR N+20/C−27 antibody 1E4 (FIG. 49A-49D). Similarly, anti-PSMGFR N+20/C−27 antibody 29H1 recognizes some pancreatic tumors that are missed by anti-PSMGFR antibodies SDIX and 20A10 (FIG. 51A-51C).

These studies showed that, in general, antibodies that bind to the MUC1* extra cellular domain that is extended beyond PSMGFR at the N-terminus recognize pancreatic cancers better than SDIX polyclonal. However, antibody specificity of pancreatic tumors appears to also be patient specific. Some patient specimens stained much better with the SDIX anti-PSMGFR antibody than the new antibodies that bind to PSMGFR N+20/C−27 or PSMGFR N+9/C−9. This supports the idea that patient tumors must be probed with a panel of MUC1* antibodies to determine which treatment is best suited for elimination of their tumor. In one aspect of the invention, the therapeutic agent incorporates some or all of the antibody that is the diagnostic agent or some or all of an antibody that is derived from the antibody that is the diagnostic antibody.

FIG. 53 demonstrates that these new antibodies that are extended at the N-terminus are recognize more pancreatic tumors than antibodies that bind to full-length MUC1. This figure compares the binding of 29H1 to a standard antibody, VU4H5, that binds to the tandem repeats of full-length MUC1, and to a new antibody, 5E5 that binds to a trapped O-linked glycan that is present on some cancer cells.

We next looked at esophageal tumors and prostate tumors. These studies were motivated by our previous findings that monoclonal antibody MNC2 as well as polyclonal antibody SDIX, which both bind to the PSMGFR peptide, showed poor recognition of esophageal tumors and prostate tumors. In fact, those tumors that showed some MNC2 reactivity in the well differentiated portions of a tumor specimen, lost that reactivity in the less well differentiated portion of the same specimen. These results argued that a cleavage enzyme other than MMP9 is dominant in most esophageal and prostate cancers. These studies support that idea.

The new anti-MUC1* antibodies, which bind to peptides PSMGFR N+20/C−27 and/or PSMGFR N+9/C−9, showed markedly better recognition of esophageal and prostate tumors when compared to MNC2, SDIX, and full-length MUC1 antibodies 5E5 and VU4H5.

Figure 54A:
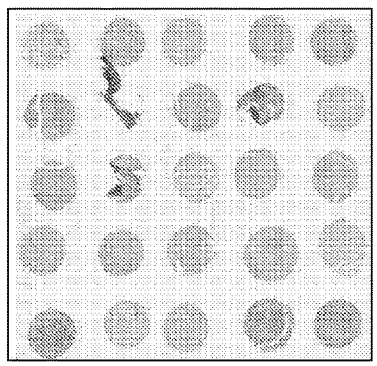
FIG. 54A-54C shows photographs of adjacent serial sections from an esophageal cancer array, which was stained by standard IHC methods with various anti-MUC1* antibodies.
Figure 54B:
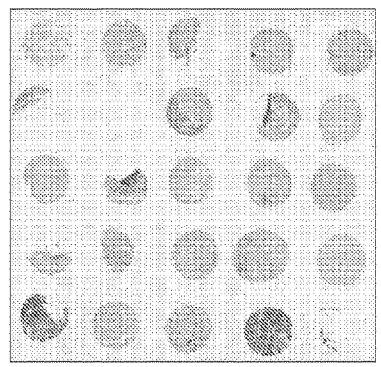
Figure 54C:
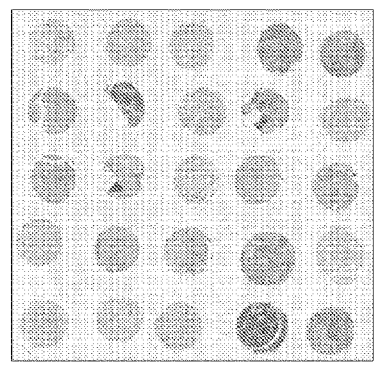
Figure 54D:
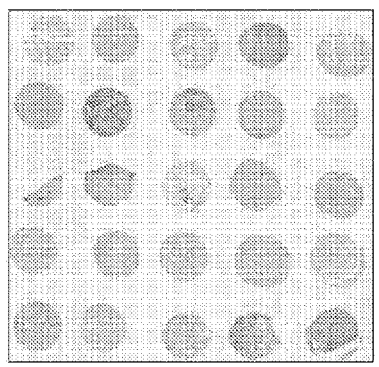
FIG. 54D shows the array stained with the 31A1 monoclonal anti-MUC1* antibody, wherein the immunogen for the antibody was the PSMGFR N+20/C−27 peptide. This figure shows that antibodies SDIX and 20A10 that both bind to the PSMGFR peptide recognize the same tumor tissue specimens, albeit to differing degrees, while antibodies that bind to the PSMGFR N+20/C−27 peptide bind to more esophageal tumor specimens as well as most of those recognized by the anti-PSMGFR antibodies. These results are consistent with the idea that antibodies that bind to the PSMGFR N+20/C−27 peptide are general more specific for esophageal cancers than antibodies that bind to the PSMGFR peptide, but that certain patients may have an esophageal cancer that is better recognized by an anti-MUC1* antibody that binds to the PSMGFR peptide.

FIG. 54A-54C shows photographs of adjacent serial sections from an esophageal cancer array, which was stained by standard IHC methods with various anti-MUC1* antibodies. FIG. 54A shows the array stained with the SDIX polyclonal anti-MUC1* antibody, wherein the immunogen for the antibody was the PSMGFR peptide. FIG. 54B shows the array stained with the 20A10 monoclonal anti-MUC1* antibody, wherein the immunogen for the antibody was the PSMGFR peptide. FIG. 54C shows the array stained with the 29H1 monoclonal anti-MUC1* antibody, wherein the immunogen for the antibody was the PSMGFR N+20/C−27 peptide. FIG. 54D shows the array stained with the 31A1 monoclonal anti-MUC1* antibody, wherein the immunogen for the antibody was the PSMGFR N+20/C−27 peptide. This figure shows that antibodies SDIX and 20A10 that both bind to the PSMGFR peptide recognize the same tumor tissue specimens, albeit to differing degrees, while antibodies that bind to the PSMGFR N+20/C−27 peptide bind to more esophageal tumor specimens as well as most of those recognized by the anti-PSMGFR antibodies. These results are consistent with the idea that antibodies that bind to the PSMGFR N+20/C−27 peptide are general more specific for esophageal cancers than antibodies that bind to the PSMGFR peptide, but that certain patients may have an esophageal cancer that is better recognized by an anti-MUC1* antibody that binds to the PSMGFR peptide.

Figures 55A, 55B, 55C, 55D:
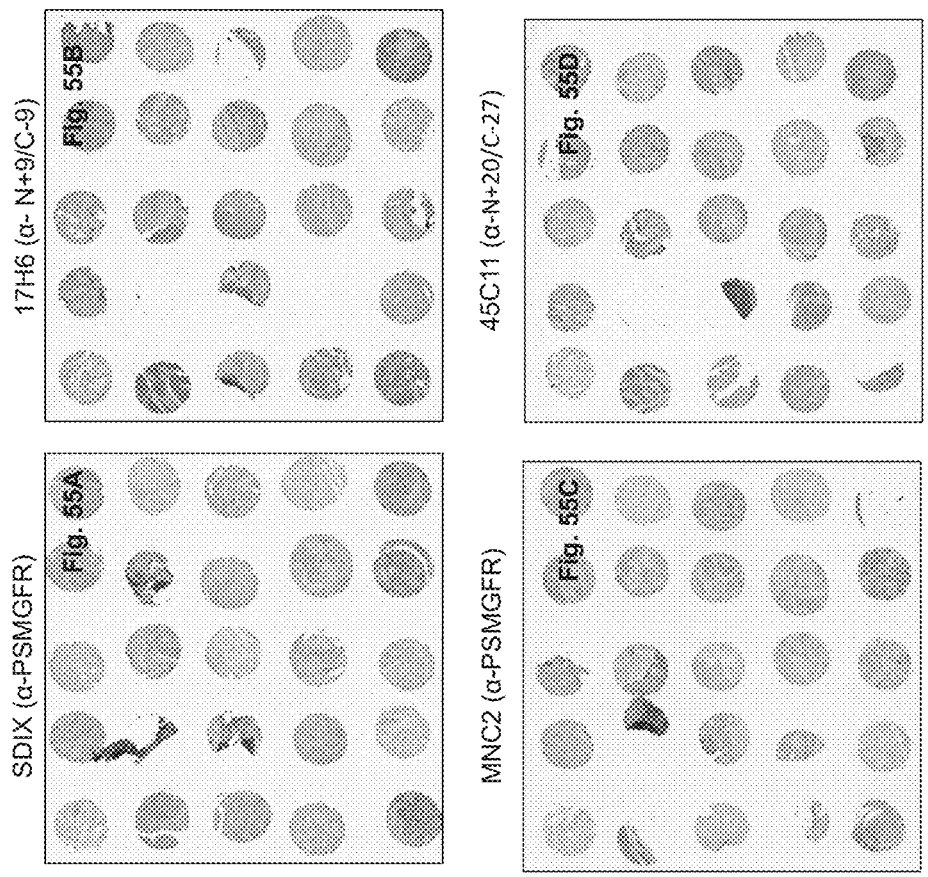
FIG. 55A-55C shows photographs of adjacent serial sections from an esophageal cancer array, which was stained by standard IHC methods with various anti-MUC1* antibodies.
FIG. 55D shows the array stained with the 45C11 monoclonal anti-MUC1* antibody, wherein the antibody binds to the PSMGFR N+20/C−27 peptide. These results are consistent with the idea that on most esophageal cancers, MUC1 is cleaved by an enzyme that exposes a cryptic epitope that is N-terminal to the PSMGFR sequence.

FIG. 55A-55C shows photographs of adjacent serial sections from an esophageal cancer array, which was stained by standard IHC methods with various anti-MUC1* antibodies. FIG. 55A shows the array stained with the SDIX polyclonal anti-MUC1* antibody, wherein the immunogen for the antibody was the PSMGFR peptide. FIG. 55B shows the array stained with the 17H6 monoclonal anti-MUC1* antibody, wherein the antibody binds to the PSMGFR N+9/C−9 peptide. FIG. 55C shows the array stained with the MNC2 monoclonal anti-MUC1* antibody, wherein the antibody binds to the PSMGFR peptide. FIG. 55D shows the array stained with the 45C11 monoclonal anti-MUC1* antibody, wherein the antibody binds to the PSMGFR N+20/C−27 peptide. These results are consistent with the idea that on most esophageal cancers, MUC1 is cleaved by an enzyme that exposes a cryptic epitope that is N-terminal to the PSMGFR sequence.

FIG. 56A-56F shows photographs and graphical representations of pathologist staining scores of adjacent serial sections from a esophageal cancer array, which was stained by standard IHC methods with either antibodies that recognize full-length MUC1 or an antibody that only recognizes MUC1*. FIG. 56A shows the esophageal cancer array stained with antibody 5E5, which is an antibody that binds to a trapped O-linked glycan in the tandem repeat domain of full-length MUC1. FIG. 56B shows the pathologist's score for each specimen in the array. FIG. 56C shows the esophageal cancer array stained with anti-MUC1* antibody 29H1, which is an antibody that binds to the PSMGFR N+20/C−27 peptide of MUC1*. FIG. 56D shows the pathologist's score for each specimen in the array. FIG. 56E shows the esophageal cancer array stained with antibody VU4H5, which is an antibody that binds to an epitope in the tandem repeat domain of full-length MUC1. FIG. 56F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C−27 peptide recognize epitopes that are prevalent on esophageal cancers.

Figure 57E:
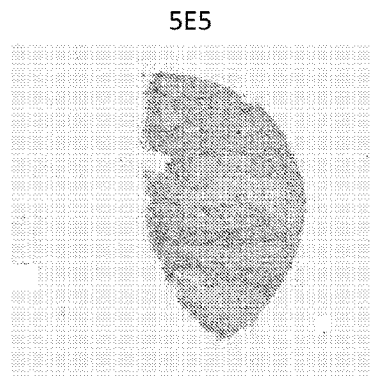
Figure 57F:
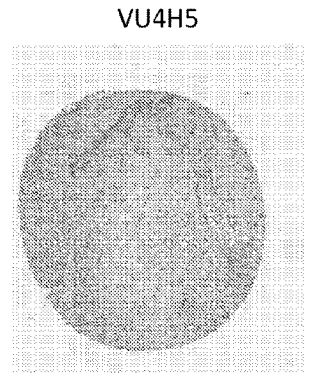
Figure 57G:
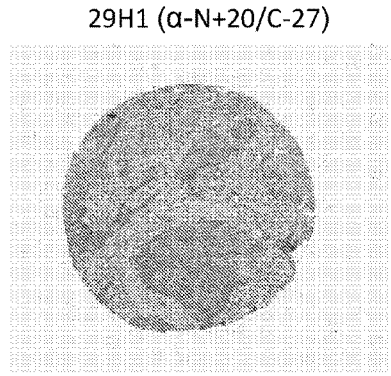

FIG. 57A-57G shows photographs of the prostate cancer array, which was stained with either antibody 5E5 or VU4H5, which both recognize full-length MUC1 or 29H1 that only recognizes MUC1* and binds to the PSMGFR N+20/C−27 peptide. FIG. 57A shows the esophageal cancer array stained with antibody 5E5. FIG. 57B shows the esophageal cancer array stained with antibody 29H1. FIG. 57B shows the esophageal cancer array stained with antibody 29H1. FIG. 57C shows the esophageal cancer array stained with antibody VU4H5. FIG. 57D shows the esophageal cancer array stained with the secondary antibody only, as a control. FIG. 57E shows the tissue marked by red box in FIG. 57A at greater magnification, wherein staining was done with 5E5. FIG. 57F shows the tissue marked by red box in FIG. 57B at greater magnification, wherein staining was done with 29H1. FIG. 57G shows the tissue marked by red box in FIG. 57C at greater magnification, wherein staining was done with VU4H5. The dashed red boxes indicate just one patient's specimen of many esophageal tumor specimens that stain negative for antibodies that recognize full-length MUC1, but highly positive when probed with anti-MUC1* antibodies, and particularly those antibodies that bind to the PSMGFR N+20/C−27 peptide.

FIG. 58A-58C shows photographs of adjacent serial sections from a prostate cancer array, which was stained by standard IHC methods with various anti-MUC1* antibodies. FIG. 58A shows the array stained with the SDIX polyclonal anti-MUC1* antibody, wherein the immunogen for the antibody was the PSMGFR peptide. FIG. 58B shows the array stained with the 18B4 monoclonal anti-MUC1* antibody, wherein the antibody binds to the PSMGFR peptide. FIG. 58C shows the array stained with the 1E4 monoclonal anti-MUC1* antibody, wherein the antibody binds to the PSMGFR N+20/C−27 peptide.

Figure 59A:
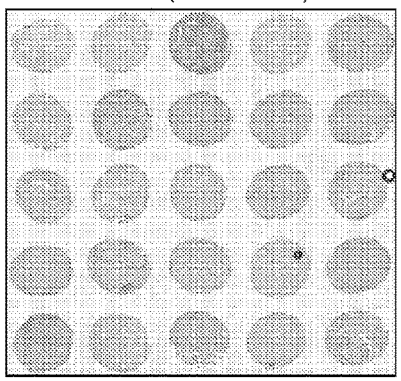
FIG. 59A-59E shows photographs of adjacent serial sections from a prostate cancer array, which was stained by standard IHC methods with various anti-MUC1* antibodies.
Figure 59B:
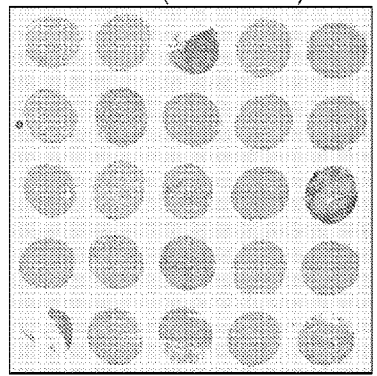
Figure 59C:
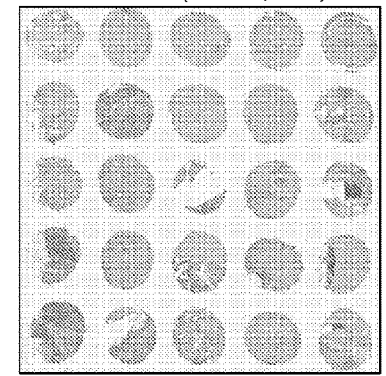
Figure 59D:
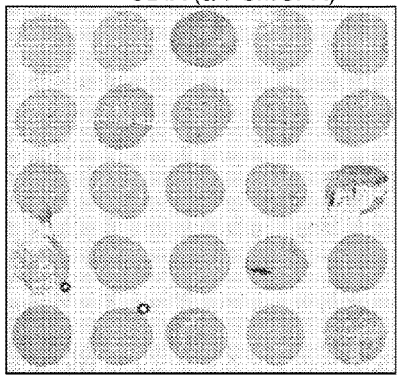
Figure 59E:
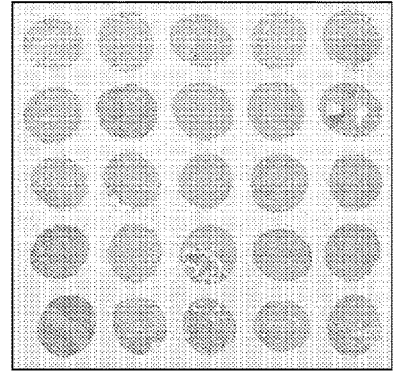

FIG. 59A-59E shows photographs of adjacent serial sections from a prostate cancer array, which was stained by standard IHC methods with various anti-MUC1* antibodies. FIG. 59A shows the array stained with the MNC2 monoclonal antibody that binds to the PSMGFR peptide but not the C−10 peptide. FIG. 59B shows the array stained with the 18B4 antibody that binds to the PSMGFR peptide. FIG. 59C shows the array stained with the 32C1 antibody that binds to the PSMGFR N+20/C−27 peptide. FIG. 59D shows the array stained with the SDIX polyclonal anti-MUC1* antibody, wherein the immunogen for the antibody was the PSMGFR peptide. FIG. 59E shows the array stained with the 31A1 monoclonal anti-MUC1* antibody that binds to the PSMGFR N+20/C−27 peptide.

FIG. 60A-60F shows photographs and graphical representations of pathologist staining scores of adjacent serial sections from a prostate cancer array, which was stained by standard IHC methods with either antibodies that recognize full-length MUC1 or an antibody that only recognizes MUC1*. FIG. 60A shows the prostate cancer array stained with antibody 5E5, which is an antibody that binds to a trapped O-linked glycan in the tandem repeat domain of full-length MUC1. FIG. 60B shows the pathologist's score for each specimen in the array. FIG. 60C shows the prostate cancer array stained with anti-MUC1* antibody 29H1, which is an antibody that binds to the PSMGFR N+20/C−27 peptide of MUC1*. FIG. 60D shows the pathologist's score for each specimen in the array. FIG. 60E shows the prostate cancer array stained with antibody VU4H5, which is an antibody that binds to an epitope in the tandem repeat domain of full-length MUC1. FIG. 60F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C−27 peptide recognize epitopes that are prevalent on prostate cancers.

FIG. 61A-61G shows photographs of the prostate cancer array, which was stained with either antibody 5E5 or VU4H5, which both recognize full-length MUC1 or 29H1 that only recognizes MUC1* and binds to the PSMGFR N+20/C−27 peptide. FIG. 61A shows the prostate cancer array stained with antibody 5E5. FIG. 61B shows the prostate cancer array stained with antibody 29H1. FIG. 61B shows the prostate cancer array stained with antibody 29H1. FIG. 61C shows the prostate cancer array stained with antibody VU4H5. FIG. 61D shows the prostate cancer array stained with the secondary antibody only, as a control. FIG. 61E shows the tissue marked by red box in FIG. 61A at greater magnification, wherein staining was done with 5E5. FIG. 61F shows the tissue marked by red box in FIG. 61B at greater magnification, wherein staining was done with 29H1. FIG. 61G shows the tissue marked by red box in FIG. 61C at greater magnification, wherein staining was done with VU4H5. The dashed red boxes indicate just one patient's specimen of many prostate tumor specimens that stain negative for antibodies that recognize full-length MUC1, but highly positive when probed with anti-MUC1* antibodies, and particularly those antibodies that bind to the PSMGFR N+20/C−27 peptide.

MNC2 recognizes a MUC1* that is present in large percentages of breast cancers. However, tumor heterogeneity and the potential of tumor escape by proliferating a population of cells in which MUC1*, the growth factor receptor, is cleaved by a different cleavage enzyme, and thereby recognized by a different anti-MUC1* antibody, suggests that treatment with more than one anti-MUC1* antibody would be beneficial. To this end, we compared more closely the recognition of new anti-MUC1* antibodies to MNC2 (FIG. 62-FIG. 73).

Figure 41:
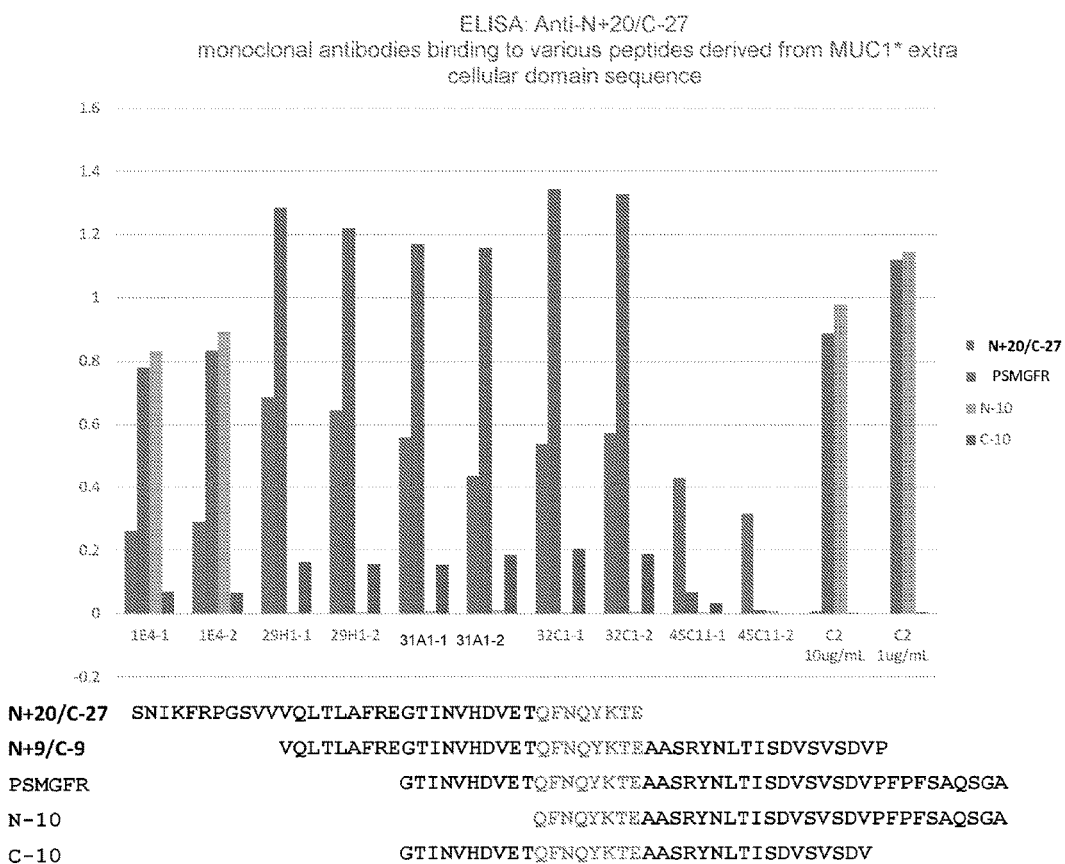
FIG. 41 shows a graph of an ELISA experiment testing the ability of monoclonal antibodies, generated by immunizing with the PSMGFR N+20/C-27 peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.
Figure 42A:
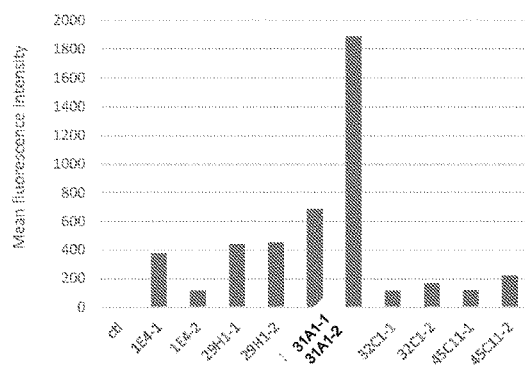
FIG. 42A-42B shows graphs of FACS analysis of the new PSMGFR N+20/C-27 anti-MUC1* monoclonal antibodies binding to T47D breast cancer cells.
Figure 42B:
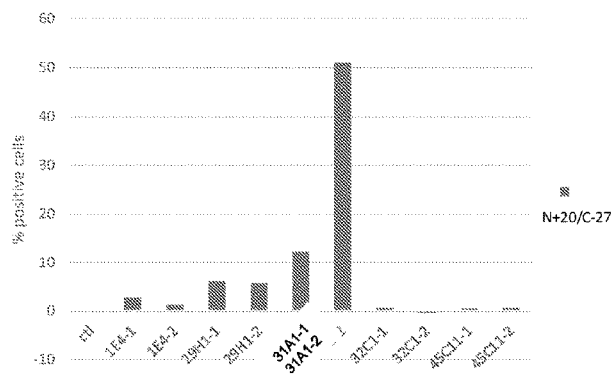
Figure 43:
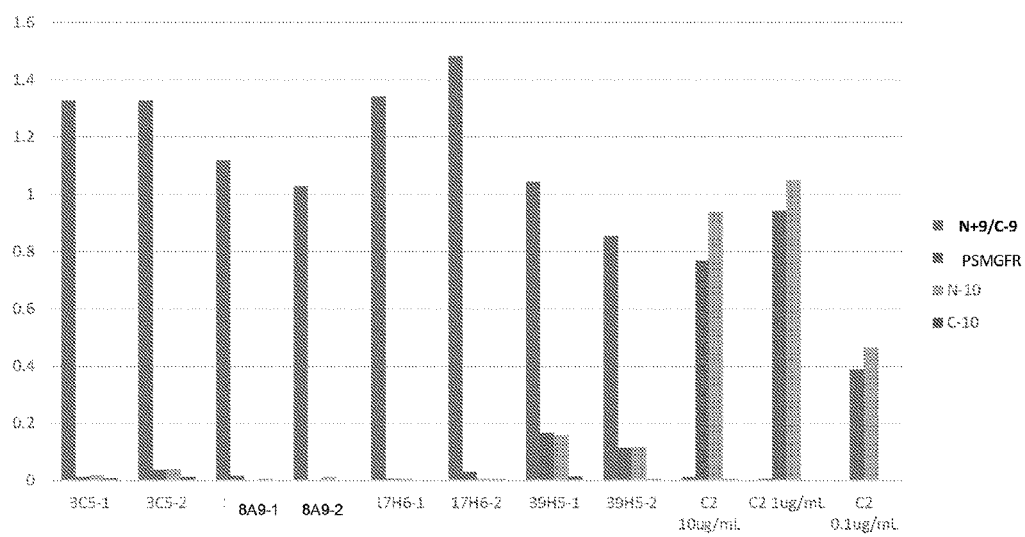
FIG. 43 shows a graph of an ELISA experiment testing the ability of monoclonal antibodies, generated by immunizing with the PSMGFR N+9/C-9 peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.
Figure 44A:
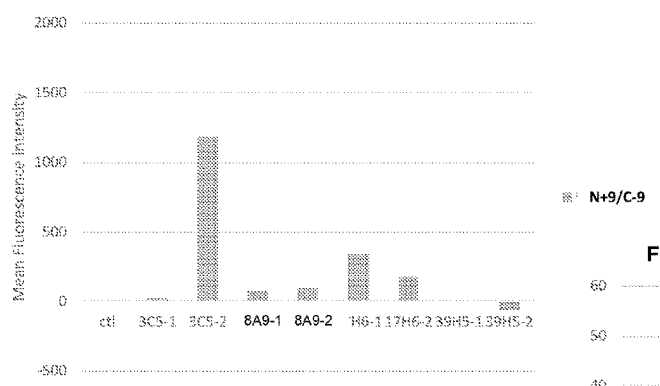
FIG. 44A-44B shows graphs of FACS analysis of the new PSMGFR N+9/C-9 anti-MUC1* monoclonal antibodies binding to T47D breast cancer cells.
Figure 44B:
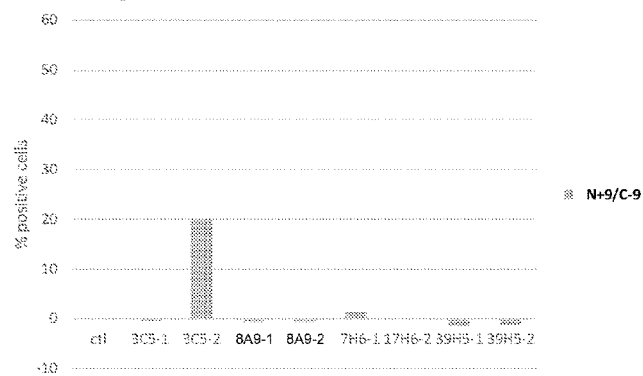
Figure 46A:
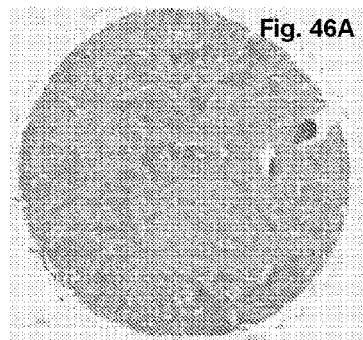
FIG. 46A-46F shows photographs of individual specimens from the pancreatic cancer array shown in FIG. 45.
Figure 46C:
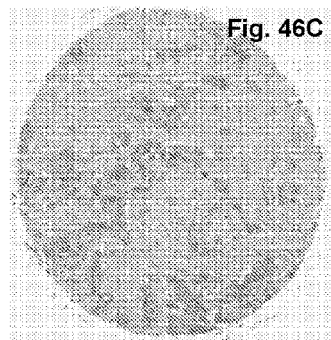
Figure 46E:
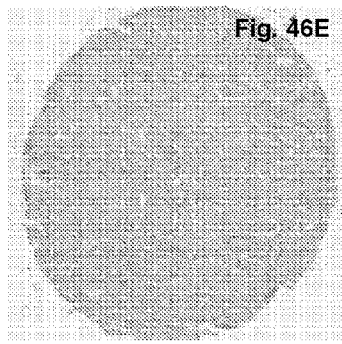
Figure 46B:
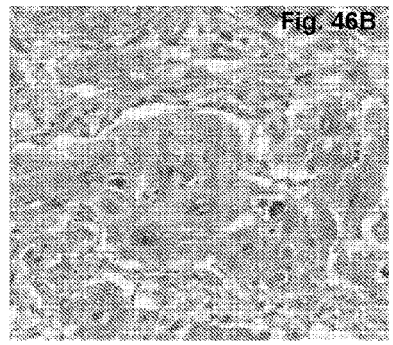
Figure 46D:
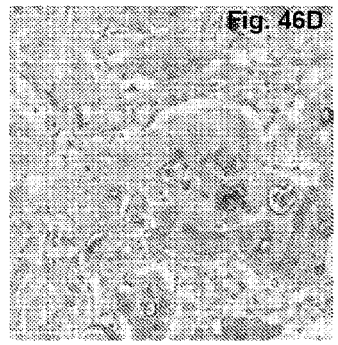
Figure 46F:
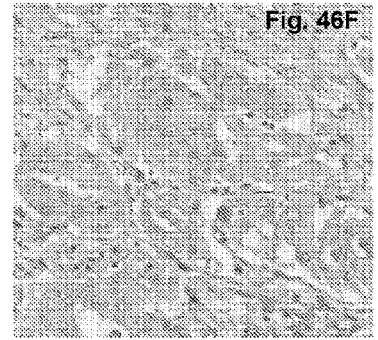
Figure 47A:
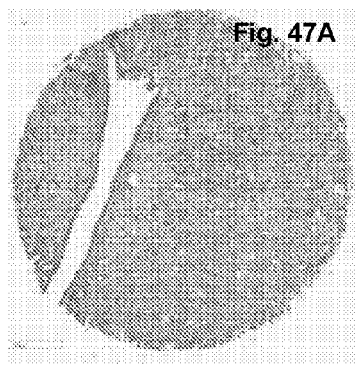
FIG. 47A-47D shows photographs of individual specimens from the pancreatic cancer array shown in FIG. 45.
Figure 47C:
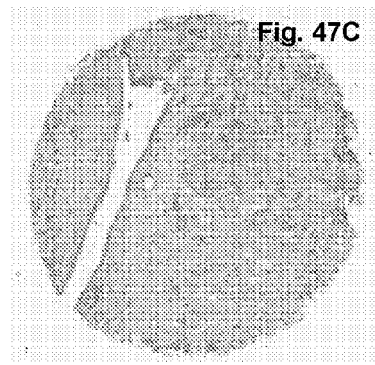
Figure 47B:
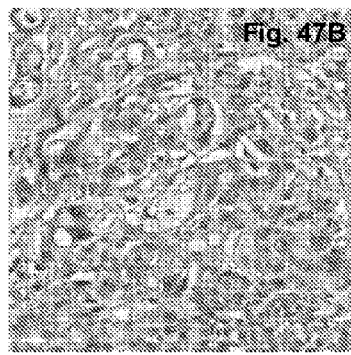
Figure 47D:
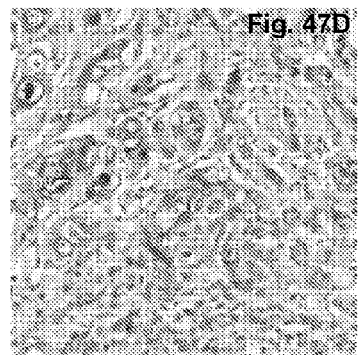
Figure 49A:
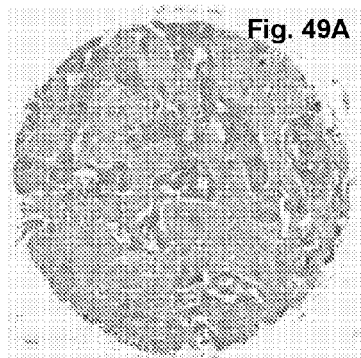
FIG. 49A-49D shows photographs of individual specimens from the pancreatic cancer array shown in FIG. 45.
Figure 49C:
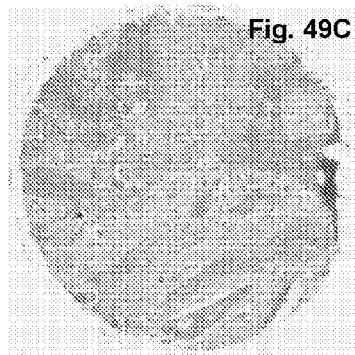
Figure 49B:
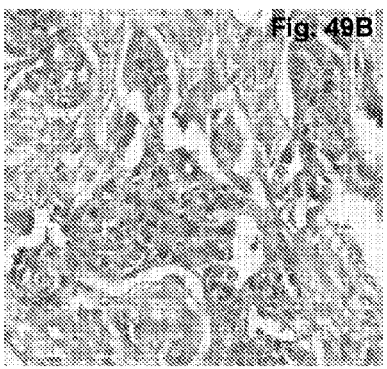
Figure 49D:
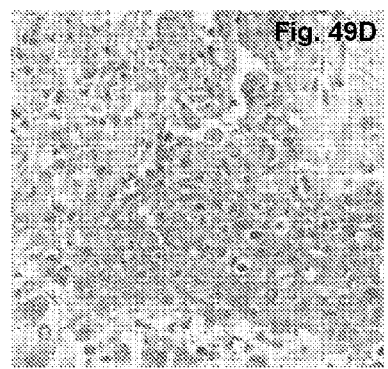
Figure 62A:
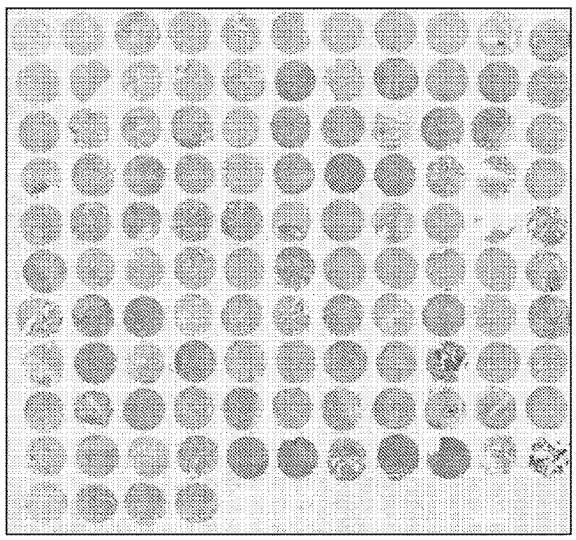
FIG. 62A-62B shows photographs of adjacent serial sections of breast cancer array BR1141 that were stained with two different anti-MUC1* monoclonal antibodies.
Figure 62B:
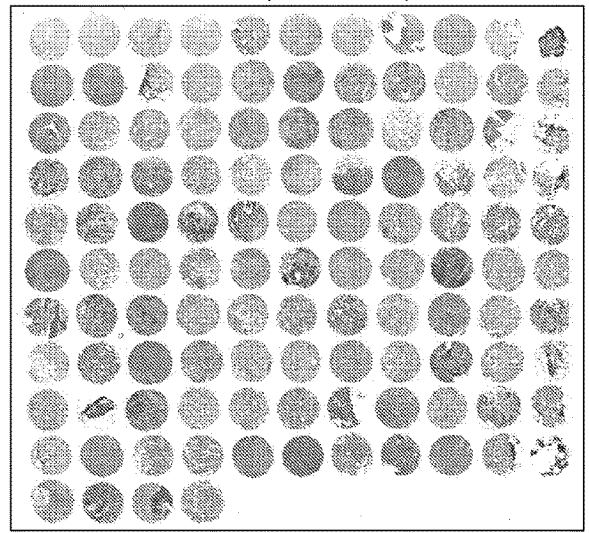
Figure 65A:
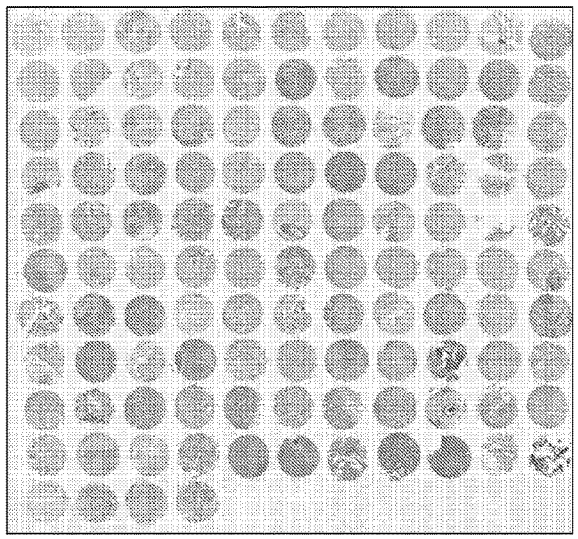
FIG. 65A-65B shows photographs of adjacent serial sections of breast cancer array BR1141 that were stained with two different anti-MUC1* monoclonal antibodies.
Figure 65B:
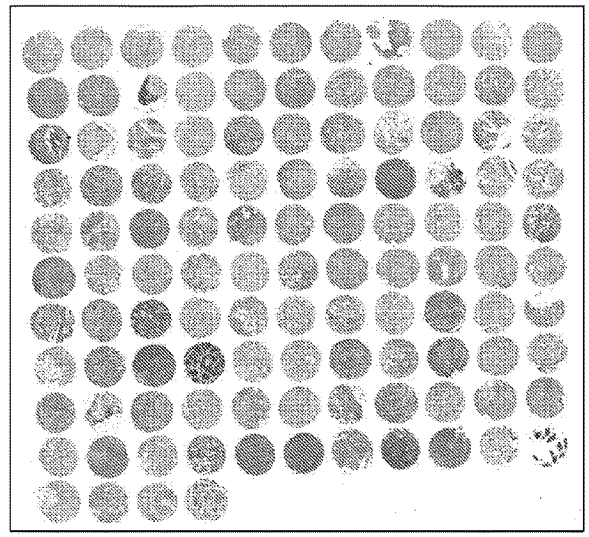
Figure 70A:
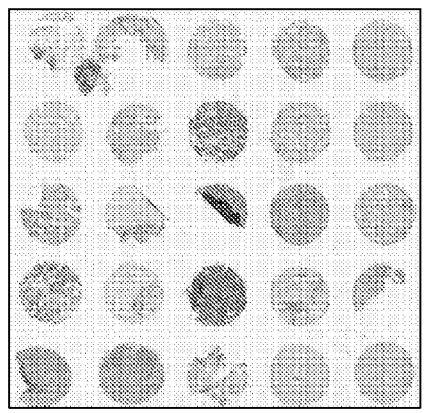
Figure 70B:
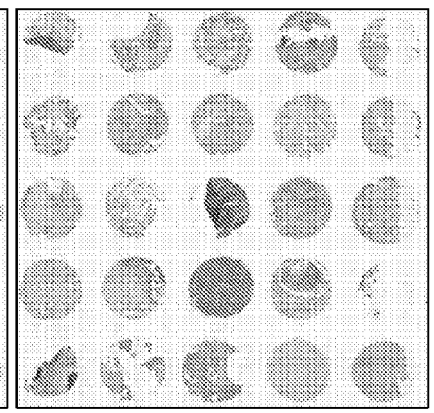
Figure 70C:
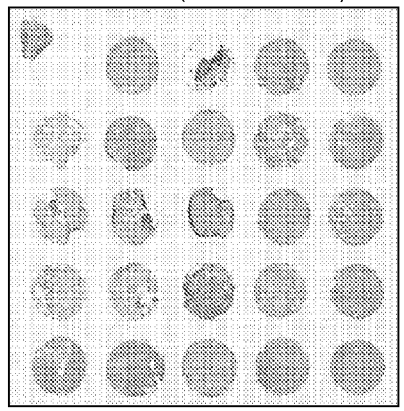
Figure 70D:
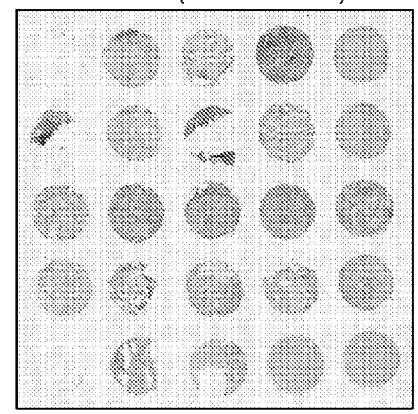

Breast cancer array BR1141 was stained with either MNC2 or 20A10, which both bind to PSMGFR peptide, N-10 peptide, but not the C-10 peptide. To a first order approximation, the two antibodies recognize the same or a very close epitope of a MUC1* that is expressed in breast cancers (FIG. 62A-62B). FIG. 63A-65B shows the same breast cancer array but MNC2 compared to 25E6, 18B4 and 18G12. Recall that unlike MNC2, this set of new anti-PSMGFR antibodies are able to bind to the C-10 peptide (FIG. 41). As can be seen in the figure, there are differences between the binding of MNC2 and these new anti-PSMGFR antibodies. Differences in recognition of breast cancer populations between patients, as well as within the same tumor, are more pronounced when MNC2 is compared to anti-PSMGFR N+9/C-9 antibody 8A9 (FIG. 66A-66B) and anti-PSMGFR antibody 28F9 (FIG. 67A-67B). Referring to FIG. 41, antibody 28F9 showed the highest degree of binding to the C-10 peptide whereas MNC2 does not bind the C-10 peptide, arguing that these antibodies bind to very different epitopes on the truncated extra cellular domain of MUC1*. Differences between the binding of anti-PSMGFR N+9/C-9 antibody 3C5 and MNC2 are clearly visible in FIG. 69A-69B. Differences in breast cancer recognition between anti-PSMGFR antibodies 20A10 and 18B4 and other antibodies that bind to peptide PSMGFR N+20/C-27, such as 29H1, 45C11 and 32C1, 31A1 or antibodies that bind to the PSMGFR N+9/C-9 peptide, such as 17H6 are shown in FIG. 70A-70G.

A smaller breast cancer array, BR1007, was probed with anti-MUC1* antibody 29H1 and compared to the recognition of the same array when probed with anti-full-length-MUC1 antibodies 5E5 and VU4H5 (FIG. 71A-71F). As can be seen in the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1.

Figure 39:
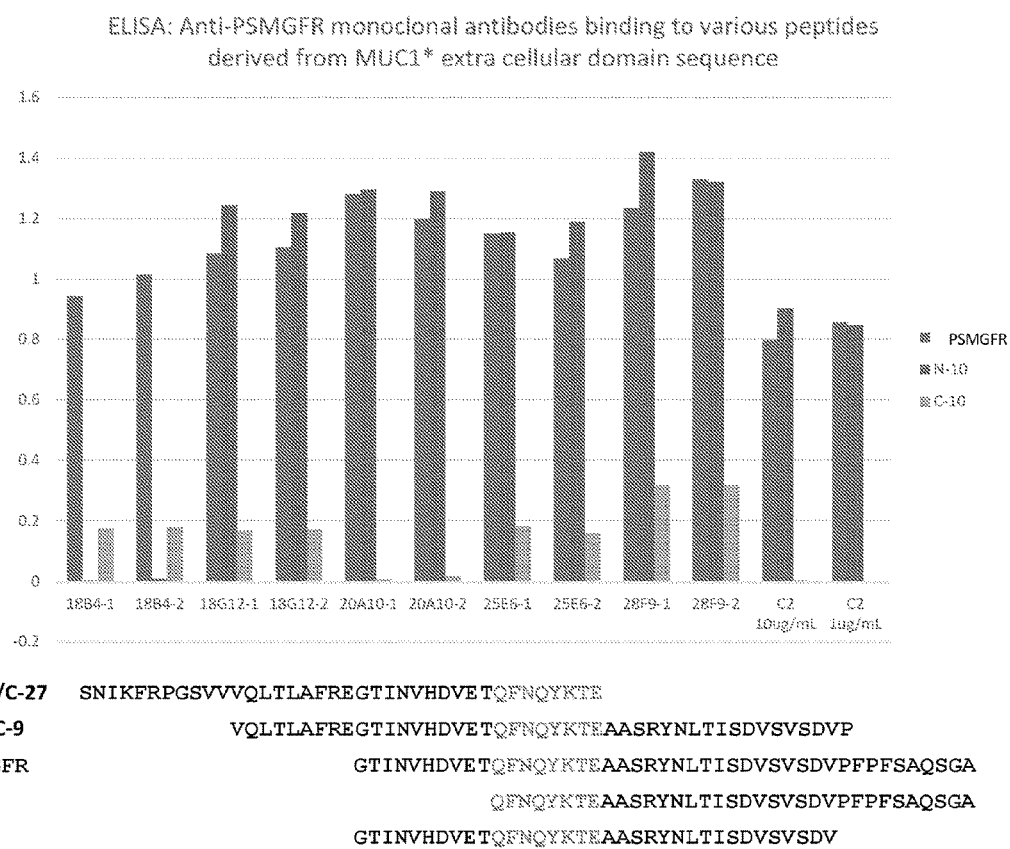
FIG. 39 shows a graph of an ELISA experiment testing the ability of monoclonal antibodies, generated by immunizing with the PSMGFR peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.
Figure 40A:
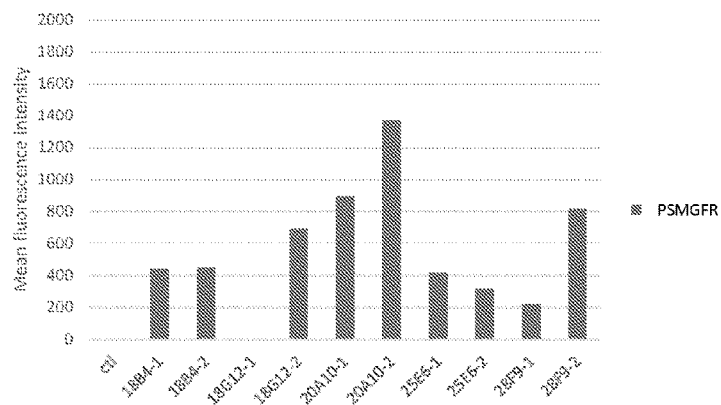
FIG. 40A-40B shows graphs of FACS analysis of the new PSMGFR anti-MUC1* monoclonal antibodies binding to T47D breast cancer cells.
Figure 40B:
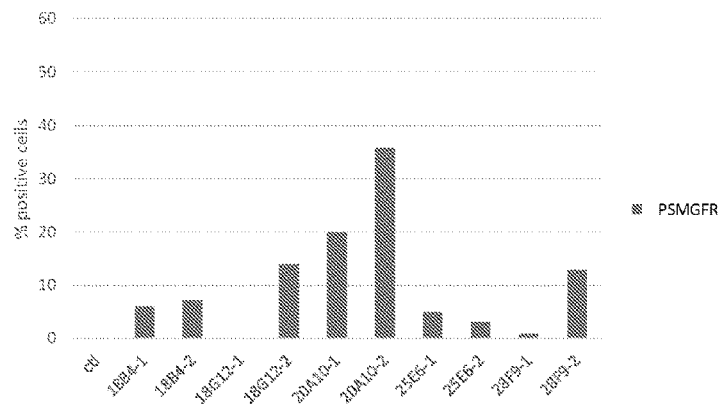

In FIG. 72A-72F, the binding of MNC2 to breast cancer array BR1141 was compared to a panel of anti-PSMGFR antibodies. All these antibodies bind to the PSMGFR peptide and roughly produce the same staining pattern of this breast cancer array. However, there are some differences in how these antibodies recognize individual specimens within the array, which could represent MUC1 to MUC1* cleavage by different enzymes. Referring to FIG. 39, MNC2 and 20A10 bind to the N-10 peptide but not to the C-10 peptide, indicating the 10 membrane proximal amino acids are important for their binding. Antibodies 18B4, 18G12 and 25E6 show some binding to the C-10 peptide and 28F9 shows even more binding to C-10 peptide. Notably, 18B4 does not bind to the N-10 peptide, indicating that it binds to an epitope that is more N-terminal within PSMGFR than the others. Albeit with the previously mentioned exceptions, the recognition of tumors within this array by anti-PSMGFR antibodies was very similar.

In contrast, antibodies that bind to the PSMGFR N+9/C-9 peptide robustly recognized a subset of tumors that was either not recognized by MNC2 or weakly recognized by MNC2 and other anti-PSMGFR antibodies (FIG. 73A-73F). The photographs shown are of adjacent serial sections of breast cancer tissue array BR1141 that have been stained with various anti-MUC1* monoclonal antibodies, wherein antibodies that bind to the PSMGFR N+9/C-9 peptide are compared to MNC2 and its humanized single chain form, huMNC2-scFv-Fc, which both bind to PSMGFR, N-10 but not to C-10 peptides. FIG. 73A shows breast cancer specimen that was stained with MNC2. FIG. 73B shows breast cancer specimen that was stained with 8A9. FIG. 73C shows breast cancer specimen that was stained with 17H6. FIG. 73D shows breast cancer specimen that was stained with huMNC2-scFv-Fc. FIG. 73E shows breast cancer specimen that was stained with 3C5. FIG. 73F shows breast cancer specimen that was stained with 39H5. Referring now to the patient specimens that are marked by red circles, it is plain to see that antibodies that bind to the PSMGFR N+9/C-9 peptide recognize a population of breast cancer cells that MNC2 anti-PSMGFR antibodies miss or bind weakly to. Anti-MUC1* antibodies 8A9, 17H6, 3C5, and 39H5 recognize a unique subset of cancer cells that are either not recognized or recognized to a lesser degree by anti-PSMGFR antibodies such as MNC2, 20A10, 25E6, 28F9, 18G12, or 18B4.

Collectively, these data show that: (i) diagnosis of MUC1 positive cancers, even within a cancer sub-type such as breast cancers, is more accurate when a tumor is probed with an anti-MUC1* antibody rather than an antibody that binds to full-length MUC1; (ii) diagnosis of MUC1 positive cancers, even within a cancer sub-type such as breast cancers, is more accurate when a tumor is probed with more than one anti-MUC1*; (iii) diagnosis of MUC1 positive cancers, even within a cancer sub-type such as breast cancers, is even more accurate when a tumor is probed with more than one anti-MUC1*, wherein the at least two different antibodies are chosen from among two different groups, wherein the groups are antibodies that bind to the PSMGFR peptide, antibodies that bind to the PSMGFR N+20/C-27 peptide, and antibodies that bind to the PSMGFR N+9/C-9 peptide.

Anti-MUC1* antibodies of the invention, which can be used for use in the diagnosis of cancers, include antibodies that bind to the PSMGFR peptide, the PSMGFR N+20/C-27 peptide, the PSMGFR N+9/C-9 peptide, or more specifically antibodies that bind to a peptide having at least 15 contiguous amino acids of the sequences below, with up to four amino acids substitutions;

(i) PSMGFR region of MUC1;

(ii) PSMGFR peptide as set forth in SEQ ID NO:4;

(iii) PSMGFR N+20/C-22, a peptide having amino acid sequence of

```
                                        (SEQ ID NO: 5)
SNIKFRPGSVVVQLTLAFREGTINVHDVETQFNQYKTEAASRY;
```

(iv) PSMGFR N+12/C-22, a peptide having amino acid sequence of

```
                                        (SEQ ID NO: 6)
     SVVVQLTLAFREGTINVHDVETQFNQYKTEAASRY;
```

(v) PSMGFR N+9/C-30, a peptide having amino acid sequence of

```
                                        (SEQ ID NO: 7)
             VQLTLAFREGTINVHDVETQFNQY;
```

(vi) PSMGFR N+20/C−41, a peptide having amino acid sequence of

```
                                        (SEQ ID NO: 8)
SNIKFRPGSVVVQLTLAFREGTIN
```

(vii) PSMGFR N+20/C−27, a peptide having amino acid sequence of

```
                                        (SEQ ID NO: 9)
SNIKFRPGSVVVQLTLAFREGTINVHDVETQFNQYKTE;
``` or (viii) PSMGFR N+9/C−9, a peptide having amino acid sequence of

```
                                       (SEQ ID NO: 10)
VQLTLAFREGTINVHDVETQFNQYKTEAASRYNLTISDVSVSDVP.
```

Specifically anti-PSMGFR antibodies MNC2, MNE6, 18B4, 18G12, 20A10, 25E6, anti-PSMGFR N+20/C−27 antibodies 1E4, 29H1, 31A1, 32C1, 45C11, and anti-PSMGFR N+9/C−9 antibodies 3C5, 8A9, 17H6, and 39H5 are antibodies that can be used to diagnose cancers. These antibodies may be human, humanized or non-human. They may be antibody intact antibodies or antibody fragments. Antibodies may be generated by immunizing animals with peptides of sequences (i)-(viii) above. The animal that is immunized with the MUC1* extra cellular domain peptides to produce the antibodies may be human, rabbit, mouse, goat, donkey, camelid, llama, alpaca or other non-human species.

An antibody of the invention can be used in a diagnostic assay wherein it may be derivatized with, or attached to an imaging agent, a dye, a fluorescent entity, a color producing reagent or any other entity that renders the antibody optically, visually, electrically or radioactively detectable. Antibodies of the invention can be used in a variety of diagnostic formats.

In another example, anti-MUC1* antibodies of the invention can be attached to an imaging agent for use in a live patient as a whole body diagnostic to determine if the patient has a MUC1* positive tumor or to determine if the patient would benefit from a therapeutic comprising all, or a fragment of, an anti-MUC1* antibody, which may be derived from or have similar binding characteristics as the antibody used in the diagnostic. The species of the diagnostic antibody and the therapeutic antibody do not need to be the same. Antibodies generated in camelid species are particularly useful for in vivo diagnostic assays because camelids generate small monovalent antibodies that have a short half-life in humans.

In yet another example, anti-MUC1* antibodies of the invention may be attached to an imaging agent and used intra-surgically to detect or mark cancerous tissues so they can be excised completely during the surgery.

In one aspect of the invention, a bodily fluid or tissue specimen from a patient diagnosed with cancer or suspected to be at risk of cancer is contacted with one or more anti-MUC1* antibodies of the invention; analysis of the binding of the antibody to the cells of the specimen indicate a level of binding or a pattern of binding that is indicative of cancer. A therapeutic agent for the treatment of cancer is then administered to the patient. In one aspect of the invention the therapeutic agent comprises all or a fragment of an anti-MUC1* antibody.

In one example, diagnostic assays employing anti-MUC1* antibodies or fragments thereof are used to screen patients to determine their potential benefit from a MUC1* targeting therapeutic. The anti-MUC1* antibody used in the diagnostic and the antibody or fragment thereof that is incorporated into the therapeutic may be derived from the same antibody. The species of the diagnostic antibody and the therapeutic antibody do not need to be the same. Diagnostic assays may encompass use of one or more anti-MUC1* antibodies. A patient specimen that reacts with one or more anti-MUC1* antibodies indicates that the patient may benefit from administration of therapeutics that contain the one or more reactive antibodies, or fragments thereof.

One example, includes the steps of: (i) a suspect cellular or tissue specimen, which may be a biopsy, from a patient diagnosed with cancer or suspected of developing cancer is contacted with an anti-MUC1* antibody; (ii) a normal cellular or tissue specimen from the patient or from a healthy donor is contacted with the same anti-MUC1* antibody, which may be an archived reference specimen; (iii) antibody binding is detected; (iv) the extent and pattern of antibody binding to the suspect specimen is compared to that of the normal specimen; (v) a determination that the suspect specimen overexpresses MUC1*, or expresses MUC1* in a uniform pattern as opposed to expression that is restricted to the apical border, indicates that the patient is suffering from a MUC1* positive cancer; (vi) a therapeutic agent for the treatment of cancer is then administered to the patient, which may be a therapeutic agent that incorporates an anti-MUC1* antibody, or fragment thereof.

In one aspect of the invention, a bodily fluid or tissue specimen from a patient diagnosed with or suspected of having cancer is contacted with an anti-MUC1* antibody of the invention and a higher than normal level of MUC1* is detected or an abnormal pattern of MUC1* is detected, indicating that the patient has a MUC1* positive cancer and a therapeutic agent is then administered to the patient, which incorporates an anti-MUC1* antibody or antibody fragment. In one case the therapeutic agent into which the antibody or antibody fragment is incorporated is an immuno-oncology agent, such as a CAR T cell, an engineered NK cell or a dendritic cell. In another case, the therapeutic agent into which the antibody or antibody fragment is incorporated is a huMNC2-CAR44 T cell. In yet another aspect of the invention the therapeutic agent into which the antibody or antibody fragment is incorporated is a bispecific antibody. In yet another aspect of the invention the therapeutic agent into which the antibody or antibody fragment is incorporated is an antibody drug conjugate (ADC). In yet another aspect of the invention the therapeutic agent into which the antibody or antibody fragment is incorporated is a bispecific T cell engager (BiTE).

In another example, the diagnostic assay may comprise an anti-MUC1* antibody and a second antibody, and the steps may comprise determining the ratio of the amount of a first antibody to a second antibody. The first antibody may bind to MUC1* extra cellular domain and the second antibody may bind to a portion of the MUC1 extra cellular domain that is N-terminal of the cleavage site, such as the tandem repeat sequences. In the case of contacting a tissue specimen, the higher the ratio of MUC1* to full-length MUC1, the more progressed is the cancer and the more likely it is that the patient would benefit from a MUC1* targeting therapeutic.

The invention includes antibodies as well as antibody-like proteins, including but not limited to polyclonal, monoclonal, chimeras, humanized, single chain, antibody fragments and the like. In addition, the invention includes the use of protein scaffolds for generating antibody mimics to obtain proteins that can be characterized by binding assays described herein and The invention further includes using methods set forth here to identify antibodies that recognize specific epitopes, within the MUC1* extra cellular domain, that are differentially expressed on cancer cells.

In one aspect, the present invention is directed to a human or humanized anti-MUC1* antibody or antibody fragment or antibody-like protein that binds to a region on extracellular domain of MUC1 isoform or cleavage product that is devoid of the tandem repeat domains. The human or humanized anti-MUC1* antibody or antibody fragment or antibody-like protein may specifically bind to (i) PSMGFR region of MUC1;
(ii) PSMGFR peptide as set forth in SEQ ID NO:4;
(iii) PSMGFR N+20/C-22, a peptide having amino acid sequence of

```
                                            (SEQ ID NO: 5)
SNIKFRPGSVVVQLTLAFREGTINVHDVETQFNQYKTEAASRY;
```

(iv) PSMGFR N+12/C-22, a peptide having amino acid sequence of

```
                                  (SEQ ID NO: 6)
SVVVQLTLAFREGTINVHDVETQFNQYKTEAASRY;
```

(v) PSMGFR N+9/C-30, a peptide having amino acid sequence of

```
                         (SEQ ID NO: 7)
VQLTLAFREGTINVHDVETQFNQY;
```

(vi) PSMGFR N+20/C-41, a peptide having amino acid sequence of

```
                          (SEQ ID NO: 8)
SNIKFRPGSVVVQLTLAFREGTIN
```

(vii) PSMGFR N+20/C-27, a peptide having amino acid sequence of

```
                                     (SEQ ID NO: 9)
SNIKFRPGSVVVQLTLAFREGTINVHDVETQFNQYKTE;
``` or (viii) PSMGFR N+9/C-9, a peptide having amino acid sequence of

```
                                           (SEQ ID NO: 10)
VQLTLAFREGTINVHDVETQFNQYKTEAASRYNLTISDVSVSDVP.
```

The human or humanized antibody may be IgG1, IgG2, IgG3, IgG4 or IgM. The human or humanized antibody fragment or antibody-like protein may be scFv or scFv-Fc.

The human or humanized antibody, antibody fragment or antibody-like protein as in above may comprise a heavy chain variable region and light chain variable region which is derived from mouse monoclonal MN-E6 antibody, and has at least 80%, 90% or 95% or 98% sequence identity to the mouse monoclonal MN-E6 antibody.

The human or humanized antibody, antibody fragment or antibody-like protein according to above may include complementarity determining regions (CDRs) in the heavy chain variable region and light chain variable region having at least 90% or 95% or 98% sequence identity to CDR1, CDR2 or CDR3 regions of the antibodies 1E4, 29H1, 31A1, 32C1, and 45C11 reactive with PSMGFR N+20/C-27; 17H6, 39H5, 3C5, 8A9 reactive with PSMGFR N+9/C-9; 18G12, 20A10, 25E6, 28F9, 18B4, MNC2, and MNE6 reactive with PSMGFR.

In another aspect, the invention is directed to a human or humanized anti-MUC1* antibody or antibody fragment or antibody-like protein according to above, which inhibits the binding of NME protein to MUC1*. The NME may be NME1, NME6, NME7AB, NME7 or NME8.

In still another aspect, the invention is directed to a chimeric antigen receptor (CAR) comprising a scFv or a humanized variable region that binds to the extracellular domain of a MUC1 that is devoid of tandem repeats, a linker molecule, a transmembrane domain and a cytoplasmic domain. The single chain antibody fragment may bind to (i) PSMGFR region of MUC1;
(ii) PSMGFR peptide as set forth in SEQ ID NO:4;
(iii) PSMGFR N+20/C-22, a peptide having amino acid sequence of

```
                                            (SEQ ID NO: 5)
SNIKFRPGSVVVQLTLAFREGTINVHDVETQFNQYKTEAASRY;
```

(iv) PSMGFR N+12/C-22, a peptide having amino acid sequence of

```
                                  (SEQ ID NO: 6)
SVVVQLTLAFREGTINVHDVETQFNQYKTEAASRY;
```

(v) PSMGFR N+9/C-30, a peptide having amino acid sequence of

```
                         (SEQ ID NO: 7)
VQLTLAFREGTINVHDVETQFNQY;
```

(vi) PSMGFR N+20/C-41, a peptide having amino acid sequence of

```
                          (SEQ ID NO: 8)
SNIKFRPGSVVVQLTLAFREGTIN
```

(vii) PSMGFR N+20/C-27, a peptide having amino acid sequence of

```
                                     (SEQ ID NO: 9)
SNIKFRPGSVVVQLTLAFREGTINVHDVETQFNQYKTE;
``` or (viii) PSMGFR N+9/C-9, a peptide having amino acid sequence of

```
                                           (SEQ ID NO: 10)
VQLTLAFREGTINVHDVETQFNQYKTEAASRYNLTISDVSVSDVP.
```

In this regard, a preferred embodiment is huMNC2-CAR44 set forth in SEQ ID NO:236)

In one aspect, the invention is directed to a method for the treatment of a person diagnosed with, suspected of having or at risk of developing a MUC1 or MUC1* positive cancer involving administering to the person an effective amount of a cancer specific antibody such as MNC2 or MNE6, or fragment thereof, wherein the antibody may be human, humanized or of a non-human species. In a particular aspect of the invention, the MUC1* targeting therapeutic is an immune cell transduced with a chimeric antigen receptor, also known as CAR T, wherein the antibody fragment of the CAR is derived from a MUC1* cancer cell specific antibody. In one aspect it is derived from MNC2. In another case it is derived from MNE6.

In another aspect, the invention is directed to a diagnostic assay for the identification of persons who might benefit from treatment of a MUC1 or MUC1* positive cancer with a therapeutic that includes an antibody, or fragment thereof, selected from the group of 1E4, 29H1, 31A1, 32C1, 45C11, 17H6, 39H5, 3C5, 8A9, 18G12, 20A10, 25E6, 28F9, 18B4, MNC2, and MNE6 antibodies. In one aspect of the invention, the anti-MUC1* antibody or a fragment thereof comprises all or part of the therapeutic and may be derived from the antibody or fragment thereof that is used for the diagnostic, wherein the therapeutic and diagnostic need not be the same species. In another instance, the anti-MUC1* antibody or fragment thereof that comprises all or part of the therapeutic is not derived from the antibody or fragment thereof that is used for the diagnostic, wherein the therapeutic and diagnostic need not be the same species.

In one aspect of the invention, the therapeutic agent targets MUC1*. In another aspect of the invention, the therapeutic that comprises some or all of an anti-MUC1* antibody is a cancer immunotherapy composition, a CAR T, a BiTE, an antibody or an antibody drug conjugate, ADC.

In one aspect of the invention, the diagnostic is a companion diagnostic to determine eligibility for treatment with the therapeutic. In another aspect of the invention, the diagnostic is used to assess efficacy of the therapeutic treatment. In yet another aspect of the invention, the diagnostic together with results of clinical trials of the therapeutic are analyzed such that results of the diagnostic can be used to predict which patients will benefit from the treatment. In another aspect of the invention, the cancer cell antibody or fragment thereof is derivatized with an imaging agent, which composition is then administered to the patient to enable visualization of reactive tumors within the patient. In this way, the antibody plus imaging agent can be used to diagnose cancer, assess response of a therapeutic treatment or assess response to a therapeutic treatment wherein the therapeutic targets MUC1* and may comprise some or all of the cancer cell antibody used in the diagnostic. In one aspect of the invention, the antibody attached to the imaging agent is a camelid antibody, including but not limited to llama, alpaca, and camel.

The diagnostic assays described here can be used on samples that may be tissues, biopsy specimens, cells, or bodily fluids taken from the test subject, patient or a normal person as a control. The diagnostic assays can be performed in vitro or in vivo. The diagnostic assays can be used intraoperatively (e.g. tissue at a surgical site can be studied without removal of the tissue from the subject). In this way, the diagnostic assay guides the surgeon to remove all the MUC1* positive tissues that are detectable, whether or not the tissues appear to be part of the tumor. In either of these studies, a primary indicator of tumorigenesis or potential for tumorigenesis is the amount of MUC1* at a cell or tissue surface that is accessible to anti-PSMGFR antibodies or cancer cell antibodies. By extension, an exposed cancer cell antibody binding epitope means that the PSMGFR region of MUC1* is also accessible to growth factors that bind to and activate growth and survival functions mediated by the MUC1* growth factor receptor. In another technique, antibodies to the MUC1* region and to the tandem repeats, IBR or UR can be exposed to the sample and a determination made of the ratio of binding of MUC1* to MUC1 full-length. A healthy sample will exhibit little or no antibody binding to the MUC1* region. A sample indicating tumorigenesis will show a non-zero ratio of anti-MUC1* antibody to anti-tandem repeat antibody or anti-IBR antibody, wherein as cancer stage/grade increases, the ratio of MUC1* to MUC1 containing tandem repeats, IBR or UR increases.

In addition to detecting an amount of MUC1* or tandem repeat containing MUC1 on cells and tissues, portions of MUC1 that contain tandem repeats, which are shed from the tissues can be detected in bodily fluids such as blood, breast milk or secretions, urine, lung efflux and the like. In these cases, a level of MUC1 cleavage to transmembrane MUC1* is inferred by measuring an amount of shed MUC1 using antibodies, including but not limited to antibodies that bind to the tandem repeats, unique regions that are N-terminal to an IBR or the IBR itself.

Measuring or inferring an amount of MUC1* on cells or tissues, that is greater than normal tissues or a prior sample from the patient, is an indicator of potential for tumor formation, existence of a tumor, or progression of a tumor, and can thereby serve as a diagnostic and/or an evaluator of the efficacy of a treatment for the patient's cancer. In one aspect, an amount of MUC1* is measured by contacting a tissue specimen with an anti-MUC1* antibody and determining that the amount of MUC1* is greater than the amount expressed on normal tissues or in a healthy person.

Sequence Listing Free Text

In the antibody sequences below, underlined sequence refers to CDR sequence and double underlined region refers to framework region.

Full-Length MUC1 Receptor (Mucin 1 Precursor, Genbank Accession Number: P15941

```
                                        (SEQ ID NO: 1)
MTPGTQSPFF LLLLLTVLTV VTGSGHASST PGGEKETSAT

QRSSVPSSTE KNAVSMTSSV LSSHSPGSGS STTQGQDVTL

APATEPASGS AATWGQDVTS VPVTRPALGS TTPPAHDVTS

APDNKPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS
```

```
-continued
APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDNRPALGS TAPPVHNVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
```

A Truncated MUC1 Receptor Isoform Having Nat-PSMGFR and PSIBR at its N-Terminus and Including the Transmembrane and Cytoplasmic Sequences of a Full-Length MUC1 Receptor which May be Cleaved after Translation and Prior to Expression of the Receptor on the Cell Surface:

```
                                    (SEQ ID NO: 2)
GFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
```

A Truncated MUC1 Receptor Isoform Having Nat-PSMGFR+PSIBR+Unique Region at its N-Terminus and Including the Transmembrane and Cytoplasmic Sequences of a Full-Length MUC1 Receptor:

```
                                    (SEQ ID NO: 3)
ATTTPASKSTPFSIPSHHSDTPTTLASHSTKTDASSTHHSTVPPLTSSNH

STSPQLSTGVSFFFLSFHISNLQFNSSLEDPSTDYYQELQRDISEMFLQI

YKQGGFLGLSNIKFRPGSVVVQLTLAFREGTINVHDVETQFNQYKTEAAS

RYNLTISDVSVSDVPFPFSAQSGAGVPGWGIALLVLVCVLVALAIVYLIA

LAVCQCRRKNYGQLDIFPARDTYHPMSEYPTYHTHGRYVPPSSTDRSPYE

KVSAGNGGSSLSYTNPAVAAASANL

PSMGFR
                                    (SEQ ID NO: 4)
GTINVHDVETQFNQYKTEAASRYNLTISDVSVSDVPFPFSAQSGA

PSMGFR N+20/C-22
                                    (SEQ ID NO: 5)
SNIKFRPGSVVVQLTLAFREGTINVHDVETQFNQYKTEAASRY

PSMGFR N+12/C-22
                                    (SEQ ID NO: 6)
SVVVQLTLAFREGTINVHDVETQFNQYKTEAASRY
```

```
-continued
PSMGFR N+9/C-30
                                    (SEQ ID NO: 7)
VQLTLAFREGTINVHDVETQFNQY PSMGFR N+20/C-41
                                    (SEQ ID NO: 8)
SNIKFRPGSVVVQLTLAFREGTIN PSMGFR N+20/C-27
                                    (SEQ ID NO: 9)
SNIKFRPGSVVVQLTLAFREGTINVHDVETQFNQYKTE PSMGFR N+9/C-9
                                    (SEQ ID NO: 10)
VQLTLAFREGTINVHDVETQFNQYKTEAASRYNLTISDVSVSDVP Antibody 17H6 Heavy Chain - Signal sequence-
FR1-CDR1-FR2-CDR2-FR3-CDR3-FR4
                                    (SEQ ID NO: 11)
ATGAAGTTGTGGCTGAACTGGATTTTCCTTGTAACACTTTTAAATGGTAT

CCAGTGTGAGGTGAAGCTGGTGGAGTCTGGAGGAGGCTTGGTACAGCCTG

GGGGTTCTCTGAGACTCTCCTGTGCAACTTCTGGGTTCACCTTCACTGAT

TACTACATGAGCTGGGTCCGCCAGCCTCCAAGAAAGGCACTTGAGTGGTT

GGGTTTTATTAGAAACAAAGCTAATGGTTACACAGCAGAGTACAGTGCGT

CTGTGAAGGGTCGGTTCACCATCTCCAGAGATGTTTCCCAAAACCTCCTC

TATCTTCAAATGAACATCCTGAGAGCTGAGGACAGTGCCACTTATTACTG

TGCAAAAGATTACTACGGTAGTAACCCTGCCTGGTTTGCTTACTGGGGCC

AAGGGACTCTGGTCACTGTCTCTGCA

Antibody 17H6 Heavy Chain - Signal peptide-
FR1-CDR1-FR2-CDR2-FR3-CDR3-FR4
                                    (SEQ ID NO: 12)
MKLWLNWIFLVTLLNGIQCEVKLVESGGGLVQPGGSLRLSCATSGFTFTD

YYMSWVRQPPRKALEWLGFIRNKANGYTAEYSASVKGRFTISRDVSQNLL

YLQMNILRAEDSATYYCAKDYYGSNPAWFAYWGQGTLVTVSA

Antibody 17H6 Light Chain - Signal sequence-
FR1-CDR1-FR2-CDR2-FR3-CDR3-FR4
                                    (SEQ ID NO: 13)
ATGAAGTTGCCTGTGAGGCTGTTGGTGCTGATGTTCTGGATTCCTGCTTC

CAACAGTGATATTTTGATGACCCAGACTCCACTCTCCCTGCCTGTCAGTC

TTGGAGATCAAGCCTCCATCTCTTGCAGATCTAGTCAGAGCATTGTACAT

AGTAGTGGAAACACCTTTTTAGAATGGTACCTGCAGAAACCTGGCCAGTC

TCCAAAGCTCCTGATCTACAAAGTTTCCAACCGATTTTCTGGGGTCCCAG

ACAGGTTCAGTGGCAGTGGATCAGGGATAGATTTCACACTCAAGATCAGC

AGAGTGGAGGCTGAGGATCTGGGAGTTTATTACTGCTTTCAAGGTTCACA

TGTTCCTTTCACGTTCGGCTCGGGGACAAAGTTGGAAATAAAA

Antibody 17H6 Light Chain - Signal peptide-
FR1-CDR1-FR2-CDR2-FR3-CDR3-FR4
                                    (SEQ ID NO: 14)
MKLPVRLLVLMFWIPASNSDILMTQTPLSLPVSLGDQASISCRSSQSIVH

SSGNTFLEWYLQKPGQSPKLLIYKVSNRFSGVPDRFSGSGSGIDFTLKIS

RVEAEDLGVYYCFQGSHVPFTFGSGTKLEIK

Antibody 17H6 Heavy Chain CDR1
                                    (SEQ ID NO: 15)
GATTACTACATGAGC Antibody 17H6 Heavy Chain CDR1
                                    (SEQ ID NO: 16)
DYYMS
```

```
Antibody 17H6 Heavy Chain CDR2
                                        (SEQ ID NO: 17)
TTTATTAGAAACAAAGCTAATGGTTACACAGCAGAGTACAGTGCGTCTGT

GAAGGGT

Antibody 17H6 Heavy Chain CDR2
                                        (SEQ ID NO: 18)
FIRNKANGYTAEYSASVKG Antibody 17H6 Heavy Chain CDR3
                                        (SEQ ID NO: 19)
GATTACTACGGTAGTAACCCTGCCTGGTTTGCTTAC Antibody 17H6 Heavy Chain CDR3
                                        (SEQ ID NO: 20)
DYYGSNPAWFAY Antibody 17H6 Light Chain CDR1
                                        (SEQ ID NO: 21)
AGATCTAGTCAGAGCATTGTACATAGTAGTGGAAACACCTTTTTAGAA Antibody 17H6 Light Chain CDR1
                                        (SEQ ID NO: 22)
RSSQSIVHSSGNTFLE Antibody 17H6 Light Chain CDR2
                                        (SEQ ID NO: 23)
AAAGTTTCCAACCGATTTTCT Antibody 17H6 Light Chain CDR2
                                        (SEQ ID NO: 24)
KVSNRFS Antibody 17H6 Light Chain CDR3
                                        (SEQ ID NO: 25)
TTTCAAGGTTCACATGTTCCTTTCACG Antibody 17H6 Light Chain CDR3
                                        (SEQ. ID. NO: 26)
FQGSHVPFT Antibody 39H5 Heavy Chain - Signal sequence-
FR1-CDR1-FR2-CDR2-FR3-CDR3-FR4
                                        (SEQ ID NO: 27)
ATGGCTTGGGTGTGGACCTTGCTATTCCTGATGGCAGCTGCCCAAAGTGC

CCAAGCACAGATCCAGTTGGTGCAGTCTGGACCTGAGCTGAAGAAGCCTG

GAGAGACAGTCAAGATCTCCTGCAAGGCTTCTGGGTATACCTTCACAAAC

TATGGAATGAACTGGGTGAAGCAGGCTCCAGGAAAGGGTTTAAAGTGGAT

GGGCTGGATAAACACCTACACTGGAGAGCCAACATATGTTGGTGACTTCA

AGGGACGGTTTGCCTTCTCTTTGGAGACCTCTGCCAGCACTGCCTATTTG

CAGATCAACAACCTCAAAAATGAGGACACGGCTACATATTTTTGTGTTAG

AGGTATCCACGGCTACGTGGACTACTGGGGCCAAGGCACCACTCTCACAG

TCTCCTCA

Antibody 39H5 Heavy Chain - Signal sequence-
FR1-CDR1-FR2-CDR2-FR3-CDR3-FR4
                                        (SEQ. ID. NO: 28)
MAWVWTLLFLMAAAQSAQAQIQLVQSGPELKKPGETVKISCKASGYTFTN

YGMNWVKQAPGKGLKWMGWINTYTGEPTYVGDFKGRFAFSLETSASTAYL

QINNLKNEDTATYFCVRGIHGYVDYWGQGTTLTVSS

Antibody 39H5 Light Chain - Signal sequence-
FR1-CDR1-FR2-CDR2-FR3-CDR3-FR4
                                        (SEQ ID NO: 29)
ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCATCTCTTGCAGATCTAGTCAGAGCATTGTACAT

AGAAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTACTGCTTTCAAGGTTCACA

TCTTCCGTGGACGTTCGGTGGAGGCACCAAGCTGGAAATCAAA

Antibody 39H5 Light Chain - Signal sequence-
FR1-CDR1-FR2-CDR2-FR3-CDR3-FR4
                                        (SEQ ID NO: 30)
MKLPVRLLVLMFWIPASSSDVLMTQTPLSLPVSLGDQASISCRSSQSIVH

RNGNTYLEWYLQKPGQSPKLLIYKVSNRFSGVPDRFSGSGSGTDFTLKIS

RVEAEDLGVYYCFQGSHLPWTFGGGTKLEIK

Antibody 39H5 Heavy Chain CDR1
                                        (SEQ ID NO: 31)
AACTATGGAATGAAC Antibody 39H5 Heavy Chain CDR1
                                        (SEQ ID NO: 32)
NYGMN Antibody 39H5 Heavy Chain CDR2
                                        (SEQ ID NO: 33)
TGGATAAACACCTACACTGGAGAGCCAACATATGTTGGTGACTTCAAGGG

A

Antibody 39H5 Heavy Chain CDR2
                                        (SEQ ID NO: 34)
WINTYTGEPTYVGDFKG Antibody 39H5 Heavy Chain CDR3
                                        (SEQ ID NO: 35)
GGTATCCACGGCTACGTGGACTAC Antibody 39H5 Heavy Chain CDR3
                                        (SEQ ID NO: 36)
GIHGYVDY Antibody 39H5 Light Chain CDR1
                                        (SEQ ID NO: 37)
AGATCTAGTCAGAGCATTGTACATAGAAATGGAAACACCTATTTAGAA Antibody 39H5 Light Chain CDR1
                                        (SEQ ID NO: 38)
RSSQSIVHRNGNTYLE Antibody 39H5 Light Chain CDR2
                                        (SEQ ID NO: 39)
AAAGTTTCCAACCGATTTTCT Antibody 39H5 Light Chain CDR2
                                        (SEQ ID NO: 40)
KVSNRFS Antibody 39H5 Light Chain CDR3
                                        (SEQ ID NO: 41)
TTTCAAGGTTCACATCTTCCGTGGACG Antibody 39H5 Light Chain CDR3
                                        (SEQ ID NO: 42)
FQGSHLPWT Antibody 3C5 Heavy Chain - Signal sequence-
FR1-CDR1-FR2-CDR2-FR3-CDR3-FR4
                                        (SEQ ID NO: 43)
ATGGCTTGGGTGTGGACCTTGCTGTTCCTGATGGCAGCTGCCCAAAGTGC

CCAAGCACAGATCCAGTTGGTGCAGTCTGGACCTGAGCTGAAGAAGCCTG

GAGAGACAGTCAAGATCTCCTGCAAGGCTTCTGGGTATACCTTCACAAAC

TATGGAATGAACTGGGTGAAGCAGGCTCCAGGAAAGGGTTTAAAGTGGAT
```

-continued

GGGCTGGATAAACACCTACACTGGAAAGCCAACATATGCTGATGACTTCA
AGGGACGGTTTGCCTTCTCTTTGGAGACCTCTGCCAGCACTGCCTATTTG
CAGATCAACAACCTCAAAAATGAGGACACGGCTACATATTTCTGTGCAAG
AGGGGGACTAGATGGTTACTACGGCTACTGGGGCCAAGGCACCACTCTCA
CAGTCTCCTCA

Antibody 3C5 Heavy Chain - Signal sequence-
FR1-CDR1-FR2-CDR2-FR3-CDR3-FR4
(SEQ ID NO: 44)
MAWVWTLLFLMAAAQSAQAQIQLVQSGPELKKPGETVKISCKASGYTFTN
YGMNWVKQAPGKGLKWMGWINTYTGKPTYADDFKGRFAFSLETSASTAYL
QINNLKNEDTATYFCARGGLDGYYGYWGQGTTLTVSS Antibody 3C5 Light Chain - Signal sequence-
FR1-CDR1-FR2-CDR2-FR3-CDR3-FR4
(SEQ ID NO: 45)
ATGAGTCCTGCCCAGTTCCTGTTTCTGCTAGTGCTCTCGATTCAGGAAAC
CAACGGTGATGTTGTGATGGCTCAGACCCCACTCACTTTGTCGGTTACCA
TTGGACAACCAGCCTCCATCTCTTGCAAATCAAGTCAGAGCCTCTTACAT
AGTAAAGGAAAGACATATTTGAATTGGTTATTACAGAGGCCAGGCCAGTC
TCCAAAGCTCCTAATCTATCTGGTGTCTAAACTGGAATCTGGAGTCCCTG
ACAGGTTCAGTGGCAGTGGATCAGGGACAGATTTCACACTGAAAATCAGC
AGAGTGGAGGCTGAAGATTTGGGAGTTTATTACTGCTTGCAAACTACACA
TTTTCCGTGGACGTTCGGTGGAGGCACCAAGCTGGAAATCAAA Antibody 3C5 Light Chain - Signal sequence-
FR1-CDR1-FR2-CDR2-FR3-CDR3-FR4
(SEQ ID NO: 46)
MSPAQFLFLLVLSIQETNGDVVMAQTPLTLSVTIGQPASISCKSSQSLLH
SKGKTYLNWLLQRPGQSPKLLIYLVSKLESGVPDRFSGSGSGTDFTLKIS
RVEAEDLGVYYCLQTTHFPWTFGGGTKLEIK Antibody 3C5 Heavy Chain CDR1
(SEQ ID NO: 47)
AACTATGGAATGAAC Antibody 3C5 Heavy Chain CDR1
(SEQ ID NO: 48)
NYGMN Antibody 3C5 Heavy Chain CDR2
(SEQ ID NO: 49)
TGGATAAACACCTACACTGGAAAGCCAACATATGCTGATGACTTCAAGGGA Antibody 3C5 Heavy Chain CDR2
(SEQ ID NO: 50)
WINTYTGKPTYADDFKG Antibody 3C5 Heavy Chain CDR3
(SEQ ID NO: 51)
GGGGGACTAGATGGTTACTACGGCTAC Antibody 3C5 Heavy Chain CDR3
(SEQ ID NO: 52)
GGLDGYYGY Antibody 3C5 Light Chain CDR1
(SEQ ID NO: 53)
AAATCAAGTCAGAGCCTCTTACATAGTAAAGGAAAGACATATTTGAAT Antibody 3C5 Light Chain CDR1
(SEQ ID NO: 54)
KSSQSLLHSKGKTYLN Antibody 3C5 Light Chain CDR2
(SEQ ID NO: 55)
CTGGTGTCTAAACTGGAATCT Antibody 3C5 Light Chain CDR2
(SEQ ID NO: 56)
LVSKLES Antibody 3C5 Light Chain CDR3
(SEQ ID NO: 57)
TTGCAAACTACACATTTTCCGTGGACG Antibody 3C5 Light Chain CDR3
(SEQ ID NO: 58)
LQTTHFPWT Antibody 8A9 Heavy Chain - Signal sequence-
FR1-CDR1-FR2-CDR2-FR3-CDR3-FR4
(SEQ ID NO: 59)
ATGAAGTTGTGGCTGAACTGGATTTTCCTTGTAACACTTTTAAATGGTAT
CCAGTGTGAGGTGGAGCTGGTGGAGTCTGGAGGAGGCTTGGTACAGCCTG
GGGGTTCTCTGAGACTCTCCTGTGCAACTTCTGGGTTCACCTTCACTGAT
CACTACATGAGCTGGGTCCGCCAGCCTCCAGGAAAGGCACTTGAGTGGTT
GGGATTTATTAGAAACAAAGCTAATGGTTACACAACAGAGTACAGTGCAT
CTGTGAAGGGTCGGTTCACCATCTCCAGAGATAATTCCCAAAGCATCCTC
TATCTTCAAATGAAAACCCTGAGAACTGAGGACAGTGCCACTTATTACTG
TGCAAGACCTTCTGACTGGGACTCCTGGTTTGCTTACTGGGGCCAAGGGA
CTCTGGTCACTGTCTCTGCA Antibody 8A9 Heavy Chain - Signal sequence-
FR1-CDR1-FR2-CDR2-FR3-CDR3-FR4
(SEQ ID NO: 60)
MKLWLNWIFLVTLLNGIQCEVELVESGGGLVQPGGSLRLSCATSGFTFTD
HYMSWVRQFPGKALEWLGFIRNKANGYTTEYSASVKGRFTISRDNSQSIL
YLQMKTLRTEDSATYYCARPSDWDSWFAYWGQGTLVTVSA Antibody 8A9 Light Chain - Signal sequence-
FR1-CDR1-FR2-CDR2-FR3-CDR3-FR4
(SEQ ID NO: 61)
ATGAAGTTGCCTGTTAGGCTGTTGGTGCTGATGTTCTGGATTCCTGCTTC
CAGCAGTGATGTTTTGATGACCCAAACTCCACTCTCCCTGCCTGTCAGTC
TTGGTGATCAAGCCTCCATCTCTTGCAGATCTAGTCAGAGCATTGTACAT
AGTAATGGCAACACCTATTTAGATTGGTACTTGCAGAAACCAGGCCAGTC
TCCAAAGCTCCTGATCTACAGAGTTTCCAACCGATTTTCTGGGGTCCCAG
ACAGGTTCAGTGGCAGTGGATCAGGGACAGATTTCACACTCAAGATCAGC
AGAGTGGAGGCTGAGGATCTGGGACTTTATTACTGTTTTCAAGGTTCACA
TGTTCCGTGGGCGTTCGGTGGAGGCACCAAGCTGGAAATCAAA Antibody 8A9 Light Chain - Signal sequence-
FR1-CDR1-FR2-CDR2-FR3-CDR3-FR4
(SEQ ID NO: 62)
MKLPVRLLVLMFWIPASSSDVLMTQTPLSLPVSLGDQASISCRSSQSIVH
SNGNTYLDWYLQKPGQSPKLLIYRVSNRFSGVPDRFSGSGSGTDFTLKIS
RVEAEDLGLYYCFQGSHVPWAFGGGTKLEIK Antibody 8A9 Heavy Chain CDR1
(SEQ ID NO: 63)
GATCACTACATGAGC Antibody 8A9 Heavy Chain CDR1
(SEQ ID NO: 64)
DHYMS

```
Antibody 8A9 Heavy Chain CDR2
                                        (SEQ ID NO: 65)
TTTATTAGAAACAAAGCTAATGGTTACACAACAGAGTACAGTGCATCTGT

GAAGGGT

Antibody 8A9 Heavy Chain CDR2
                                        (SEQ ID NO: 66)
FIRNKANGYTTEYSASVKG Antibody 8A9 Heavy Chain CDR3
                                        (SEQ ID NO: 67)
CCTTCTGACTGGGACTCCTGGTTTGCTTAC Antibody 8A9 Heavy Chain CDR3
                                        (SEQ ID NO: 68)
PSDWDSWFAY Antibody 8A9 Light Chain CDR1
                                        (SEQ ID NO: 69)
AGATCTAGTCAGAGCATTGTACATAGTAATGGCAACACCTATTTAGAT Antibody 8A9 Light Chain CDR1
                                        (SEQ ID NO: 70)
RSSQSIVHSNGNTYLD Antibody 8A9 Light Chain CDR2
                                        (SEQ ID NO: 71)
AGAGTTTCCAACCGATTTTCT Antibody 8A9 Light Chain CDR2
                                        (SEQ ID NO: 72)
RVSNRFS Antibody 8A9 Light Chain CDR3
                                        (SEQ ID NO: 73)
TTTCAAGGTTCACATGTTCCGTGGGCG Antibody 8A9 Light Chain CDR3
                                        (SEQ ID NO: 74)
FQGSHVPWA Antibody 18G12 Heavy Chain - Signal sequence-
FR1-CDR1-FR2-CDR2-FR3-CDR3-FR4
                                        (SEQ ID NO: 75)
ATGGGATGGAGCTATATCATCCTCTTTTTGGTCGCAACAGCTACAGGTGT

CCACTCCCAGGTCCAACTGCAGCAGTCTGGGGCTGAACTGGTGAAGCCTG

GGGCTTCAGTGAAGTTGTCCTGCAAGGCTTCTGGCTACACCTTCACCGGC

TACTTTTTGTACTGGGTGAAGCAGAGGCCTGGACAAGGCCTTGAGTGGAT

TGGGGGGATTAATCCTGACAATGGTGGTATTGACTTCAATGAGAAGTTCA

GGAACAAGGCCACACTGACTGTAGACAAATCCTCCAGCACAGCCTACATG

CAACTCAGCAGCCTGACATCTGAGGACTCTGCGGTCTATTATTGTACATT

ACTAATAGGGAACTATTGGGGCCAAGGCACCACTCTCACAGTCTCCTCA

Antibody 18G12 Heavy Chain - Signal sequence-
FR1-CDR1-FR2-CDR2-FR3-CDR3-FR4
                                        (SEQ ID NO: 76)
MGWSYIILFLVATATGVHSQVQLQQSGAELVKPGASVKLSCKASGYTFTG

YFLYWVKQRPGQGLEWIGGINPDNGGIDFNEKFRNKATLTVDKSSSTAYM

QLSSLTSEDSAVYYCTLLIGNYWGQGTTLTVSS

Antibody 18G12 Light Chain - Signal sequence-
FR1-CDR1-FR2-CDR2-FR3-CDR3-FR4
                                        (SEQ ID NO: 77)
ATGAGTCCTGCCCAGTTCCTGTTTCTGTTAGTGCTCTGGATTCGGGAAAC

CAATGGTGATGTTGTGATGACCCAGACTCCACTCACTTTGTCGGTAACCA

TTGGACAGCCAGCCTCCATCTCTTGCAAGTCAAGTCAGAGCCTCTTACAT

AGTGATGGAAAGACATATTTGATTTGGTTGTTACAGAGGCCAGGCCAGTC

TCCAAAGCGCCTAATCTATCTGGTGTCTAAACTGGACTCTGGAGTCCCTG

ACAGGTTCACTGGCAGTGGATCAGGGACAGATTTCACACTGAAAATCAGC

AGAGTGGAGGCTGAGGATTTGGGAGTTTATTTTTGCTGTCAAGGTACACA

TTTTCCGTGGACGTTCGGTGGAGGCACCATGCTGGAAATCAAA

Antibody 18G12 Light Chain - Signal sequence-
FR1-CDR1-FR2-CDR2-FR3-CDR3-FR4
                                        (SEQ ID NO: 78)
MSPAQFLFLLVLWIRETNGDVVMTQTPLTLSVTIGQPASISCKSSQSLLH

SDGKTYLIWLLQRPGQSPKRLIYLVSKLDSGVPDRFTGSGSGTDFTLKIS

RVEAEDLGVYFCCQGTHFPWTFGGGTMLEIK

Antibody 18G12 Heavy Chain CDR1
                                        (SEQ ID NO: 79)
GGCTACTTTTTGTAC Antibody 18G12 Heavy Chain CDR1
                                        (SEQ ID NO: 80)
GYFLY Antibody 18G12 Heavy Chain CDR2
                                        (SEQ ID NO: 81)
GGGATTAATCCTGACAATGGTGGTATTGACTTCAATGAGAAGTTCAGGAA

C

Antibody 18G12 Heavy Chain CDR2
                                        (SEQ ID NO: 82)
GINPDNGGIDFNEKFRN Antibody 18G12 Heavy Chain CDR3
                                        (SEQ ID NO: 83)
CTAATAGGGAACTAT Antibody 18G12 Heavy Chain CDR3
                                        (SEQ ID NO: 84)
LIGNY Antibody 18G12 Light Chain CDR1
                                        (SEQ ID NO: 85)
AAGTCAAGTCAGAGCCTCTTACATAGTGATGGAAAGACATATTTGATT Antibody 18G12 Light Chain CDR1
                                        (SEQ ID NO: 86)
KSSQSLLHSDGKTYLI Antibody 18G12 Light Chain CDR2
                                        (SEQ ID NO: 87)
CTGGTGTCTAAACTGGACTCT Antibody 18G12 Light Chain CDR2
                                        (SEQ ID NO: 88)
LVSKLDS Antibody 18G12 Light Chain CDR3
                                        (SEQ ID NO: 89)
TGTCAAGGTACACATTTTCCGTGGACG Antibody 18G12 Light Chain CDR3
                                        (SEQ ID NO: 90)
CQGTHFPWT Antibody 20A10 Heavy Chain - Signal sequence-
FR1-CDR1-FR2-CDR2-FR3-CDR3-FR4
                                        (SEQ ID NO: 91)
ATGAACTTCGGGTTCAGCTTGATTTTCCTTGTCCTTGTTTTAAAAGGTGT

CCAGTGTGAAGTGATGCTGGTGGAGTCTGGGGGAGGCTTAGTGAAGCCTG

GAGGGTCCCTGAAACTCTCCTGTGCAGCCTCTGGATTCACTTTCAGTACC

TATGCCATGTCTTGGATTCGCCAGACTCCAGAGAAGAGGCTGGAGTGGGT

CGCATCCATTGGTCGTGCTGGTTCCACCTACTATTCAGACAGTGTGAAGG
```

```
GCCGATTCACCATCTCCAGAGATAATGTCCGGAACATCCTGTACCTGCAA

ATGAGCAGTCTGAGGTCTGAGGACACGGCCATGTATTACTGTGCTAGAGG

CCCGATCTACAATGATTACGACGAGTTTGCTTACTGGGGCCAAGGGACTC

TGGTCACTGTCTCTGCA
```

Antibody 20A10 Heavy Chain - Signal sequence-
FR1-CDR1-FR2-CDR2-FR3-CDR3-FR4
(SEQ ID NO: 92)
MNFGFSLIFLVLVLKGVQC EVMLVESGGGLVKPGGSLKLSCAASGFTFST

YAMSWIRQTPEKRLEWVASIGRAGSTYYSDSVKGRFTISRDNVRNILYLQ

MSSLRSEDTAMYYCARGPIYNDYDEFAYWGQGTLVTVSA

Antibody 20A10 Light Chain - Signal sequence-
FR1-CDR1-FR2-CDR2-FR3-CDR3-FR4
(SEQ ID NO: 93)
ATGGAATCACAGACTCAGGTCTTCCTCTCCCTGCTGCTCTGGGTATCTGG

TACCTGTGGGAACATTATGATGACACAGTCGCCATCATCTCTGGCTGTGT

CTGCAGGAGAAAAGGTCACTATGAGCTGTAAGTCCAGTCAAAGTGTTTTA

TACAGTTCAAATCAGAAGAACTATTTGGCCTGGTACCAGCAGAAACCAGG

GCAGTCTCCTAAACTGCTGATCTACTGGGCATCCACTAGGGAATCTGGTG

TCCCTGATCGCTTCACAGGCAGTGGATCTGGGACAGATTTTACTCTTACC

ATCAGCAGTGTACAAGCTGAAGACCTGGCAGTTTATTACTGTCATCAATA

CCTCTCCTCGCTCACGTTCGGTGCTGGGACCAAGCTGGAGCTGAAA

Antibody 20A10 Light Chain - Signal sequence-
FR1-CDR1-FR2-CDR2-FR3-CDR3-FR4
(SEQ ID NO: 94)
MESQTQVFLSLLLWVSGTCG NIMMTQSPSSLAVSAGEKVTMSCKSSQSVL

YSSNQKNYLAWYQQKPGQSPKLLIYWASTRESGVPDRFTGSGSGTDFTLT

ISSVQAEDLAVYYCHQYLSSLTFGAGTKLELK

Antibody 20A10 Heavy Chain CDR1
(SEQ ID NO: 95)
ACCTATGCCATGTCT

Antibody 20A10 Heavy Chain CDR1
(SEQ ID NO: 96)
TYAMS

Antibody 20A10 Heavy Chain CDR2
(SEQ ID NO: 97)
TCCATTGGTCGTGCTGGTTCCACCTACTATTCAGACAGTGTGAAGGGC Antibody 20A10 Heavy Chain CDR2
(SEQ ID NO: 98)
SIGRAGSTYYSDSVKG Antibody 20A10 Heavy Chain CDR3
(SEQ ID NO: 99)
GGCCCGATCTACAATGATTACGACGAGTTTGCTTAC Antibody 20A10 Heavy Chain CDR3
(SEQ ID NO: 100)
GPIYNDYDEFAY Antibody 20A10 Light Chain CDR1
(SEQ ID NO: 101)
AAGTCCAGTCAAAGTGTTTTATACAGTTCAAATCAGAAGAACTATTTGGC
C Antibody 20A10 Light Chain CDR1
(SEQ ID NO: 102)
KSSQSVLYSSNQKNYLA Antibody 20A10 Light Chain CDR2
(SEQ ID NO: 103)
TGGGCATCCACTAGGGAATCT Antibody 20A10 Light Chain CDR2
(SEQ ID NO: 104)
WASTRES Antibody 20A10 Light Chain CDR3
(SEQ ID NO: 105)
CATCAATACCTCTCCTCGCTCACG Antibody 20A10 Light Chain CDR3
(SEQ ID NO: 106)
HQYLSSLT Antibody 25E6 Heavy Chain - Signal sequence-
FR1-CDR1-FR2-CDR2-FR3-CDR3-FR4
(SEQ ID NO: 107)
ATGAACTTCGGGCTCAGCTTGATTTTCCTTGCCCTCATTTTAAAAGGTGT

CCAGTGTGAGGTGCAGCTGGTGGAGTCTGGGGGAGACTTAGTGAAGCCTG

GAGGGTCCCTGAAACTCTCCTGTGCAGCCTCTGGTTTCACTTTCAGTAGT

TATGGAATGTCTTGGGTTCGCCAGACTCCAGACAAGAGGCTGGAGTGGGT

CGCAACCATTAGTAATGGTGGTAGACACACCTTCTATCCAGACAGTGTGA

AGGGGCGATTCACCATCTCCAGAGACAATGCCAAGAACACCCTGTATCTG

CAAATGAGCAGTCTGAAGTCTGAGGACACAGCCATGTATTTATGTGTAAG

ACAGACTGGGACGGAGGGCTGGTTTGCTTACTGGGGCCAAGGGACTCTGG

TCACTGTCTCTGCA

Antibody 25E6 Heavy Chain - Signal sequence-
FR1-CDR1-FR2-CDR2-FR3-CDR3-FR4
(SEQ ID NO: 108)
MNFGLSLIFLALILKGVQC EVQLVESGGDLVKPGGSLKLSCAASGFTFSS

YGMSWVRQTPDKRLEWVATISNGGRHTFYPDSVKGRFTISRDNAKNTLYL

QMSSLKSEDTAMYLCVRQTGTEGWFAYWGQGTLVTVSA

Antibody 25E6 Light Chain - Signal sequence-
FR1-CDR1-FR2-CDR2-FR3-CDR3-FR4
(SEQ ID NO: 109)
ATGAGTCCTGCCCAGTTCCTGTTTCTGTTAGTGCTCTGGATTCGGGAAAC

CAACGGTGATGTTGTGATGACCCAGACTCCACTCACTTTGTCGGTTACCA

TTGGACAACCAGCCTCCATCTCTTGCAAGTCAAGTCAGAGCCTCTTAGAT

AGTGATGGAAAGACATATTTGAATTGGTTGTTACAGAGGCCAGGCCAGTC

TCCAAAGCGCCTAATCTATCTGGTGTCTAAACTGGACTCTGGAGTCCCTG

ACAGGTTCACTGGCAGTGGATCAGGGACAGATTTCACACTGAAAATCAGC

AGAGTGGAGGCTGAGGATTTGGGAGTTTATTATTGCTGGCAAGGTACACA

TTTTCCTCAGACGTTCGGTGGAGGCACCAAGCTGGAAATCAAA

Antibody 25E6 Light Chain - Signal sequence-
FR1-CDR1-FR2-CDR2-FR3-CDR3-FR4
(SEQ ID NO: 110)
MSPAQFLFLLVLWIRETNG DVVMTQTPLTLSVTIGQPASISCKSSQSLLD

SDGKTYLNWLLQRPGQSPKRLIYLVSKLDSGVPDRFTGSGSGTDFTLKIS

RVEAEDLGVYYCWQGTHFPQTFGGGTKLEIK

Antibody 25E6 Heavy Chain CDR1
(SEQ ID NO: 111)
AGTTATGGAATGTCT

-continued

Antibody 25E6 Heavy Chain CDR1
(SEQ ID NO: 112)
SYGMS

Antibody 25E6 Heavy Chain CDR2
(SEQ ID NO: 113)
ACCATTAGTAATGGTGGTAGACACACCTTCTATCCAGACAGTGTGAAGGG

G

Antibody 25E6 Heavy Chain CDR2
(SEQ ID NO: 114)
TISNGGRHTFYPDSVKG

Antibody 25E6 Heavy Chain CDR3
(SEQ ID NO: 115)
CAGACTGGGACGGAGGGCTGGTTTGCTTAC

Antibody 25E6 Heavy Chain CDR3
(SEQ ID NO: 116)
QTGTEGWFAY

Antibody 25E6 Light Chain CDR1
(SEQ ID NO: 117)
AAGTCAAGTCAGAGCCTCTTAGATAGTGATGGAAAGACATATTTGAAT Antibody 25E6 Light Chain CDR1
(SEQ ID NO: 118)
KSSQSLLDSDGKTYLN Antibody 25E6 Light Chain CDR2
(SEQ ID NO: 119)
CTGGTGTCTAAACTGGACTCT Antibody 25E6 Light Chain CDR2
(SEQ ID NO: 120)
LVSKLDS Antibody 25E6 Light Chain CDR3
(SEQ ID NO: 121)
TGGCAAGGTACACATTTTCCTCAGACG Antibody 25E6 Light Chain CDR3
(SEQ ID NO: 122)
WQGTHFPQT Antibody 28F9 Heavy Chain - Signal sequence-
FR1-CDR1-FR2-CDR2-FR3-CDR3-FR4
(SEQ ID NO: 123)
ATGGGATGGAGCTATATCATCCTCTTTTTGGTAGCAACAGCTACAGGTGT

CCACTCCCAGGTCCAACTGCAGCAGCCTGGGGCTGAACTGGTGCAGCCTG

GGGCTTCAGTGAAGTTGTCCTGCAAGGCTTCTGGCTACACCTTCACCGGC

TACTTTTTGTACTGGGTGAAGCAGAGGCCTGGACATGGCCTTGAGTGGAT

TGGGGGAATTCATCCTAGCAATGGTGATACTGACTTCAATGAGAAGTTCA

AGAACAAGGCCACACTGACTGTAGACATATCCTCCAGCACTGCCTACATG

CAACTCAGCAGCCTGACATCTGAGGACTCTGCGGTCTATTATTGTACATT

ACTAATAGGGGTCTACTGGGGCCAAGGCACCACTCTCACAGTCTCCTCA

Antibody 28F9 Heavy Chain - Signal sequence-
FR1-CDR1-FR2-CDR2-FR3-CDR3-FR4
(SEQ ID NO: 124)
MGWSYIILFLVATATGVHSQVQLQQPGAELVQPGASVKLSCKASGYTFTG

YFLYWVKQRPGHGLEWIGGIHPSNGDTDFNEKFKNKATLTVDISSSTAYM

QLSSLTSEDSAVYYCTLLIGVYWGQGTTLTVSS

Antibody 28F9 Light Chain - Signal sequence-
FR1-CDR1-FR2-CDR2-FR3-CDR3-FR4
(SEQ ID NO: 125)
ATGAGTCCTGCCCAGTTCCTGTTTCTGTTAGTGCTCTGGATTCGGGAAAC

CAACGGTGATGTTGTGATGACCCAGACTCCACTCACTTTGTCGGTTACCA

TTGGACAACCAGCCTCCATCTCTTGCAAGTCAAGTCAGAGCCTCTTACAT

AGTGATGGAAAGACATATTTGATTTGGTTGTTACAGAGGCCAGGCCAGTC

TCCAAAGCGCCTAATCTATCTGGTGTCTAAACTGGACTCTGGAGTCCCTG

ACAGGTTCACCGGCAGTGGATCAGGGACAGATTTCACACTGAAAATCAGC

AGAGTGGAGGCTGAGGATTTGGGAGTTTATTTTTGCTGTCAAGGTACACA

TTTTCCGTGGACGTTCGGTGGAGGCACCATGCTGGAAATCAAA

Antibody 28F9 Light Chain - Signal sequence-
FR1-CDR1-FR2-CDR2-FR3-CDR3-FR4
(SEQ ID NO: 126)
MSPAQFLFLLVLWIRETNGDVVMTQTPLTLSVTIGQPASISCKSSQSLLH

SDGKTYLIWLLQRPGQSPKRLIYLVSKLDSGVPDRFTGSGSGTDFTLKIS

RVEAEDLGVYFCCQGTHFPWTFGGGTMLEIK

Antibody 28F9 Heavy Chain CDR1
(SEQ ID NO: 127)
GGCTACTTTTTGTAC

Antibody 28F9 Heavy Chain CDR1
(SEQ ID NO: 128)
GYFLY

Antibody 28F9 Heavy Chain CDR2
(SEQ ID NO: 129)
GGAATTCATCCTAGCAATGGTGATACTGACTTCAATGAGAAGTTCAAGAA

C

Antibody 28F9 Heavy Chain CDR2
(SEQ ID NO: 130)
GIHPSNGDTDFNEKFKN

Antibody 28F9 Heavy Chain CDR3
(SEQ ID NO: 131)
CTAATAGGGGTCTAC

Antibody 28F9 Heavy Chain CDR3
(SEQ ID NO: 132)
LIGVY

Antibody 28F9 Light Chain CDR1
(SEQ ID NO: 133)
AAGTCAAGTCAGAGCCTCTTACATAGTGATGGAAAGACATATTTGATT Antibody 28F9 Light Chain CDR1
(SEQ ID NO: 134)
KSSQSLLHSDGKTYLI Antibody 28F9 Light Chain CDR2
(SEQ ID NO: 135)
CTGGTGTCTAAACTGGACTCT Antibody 28F9 Light Chain CDR2
(SEQ ID NO: 136)
LVSKLDS Antibody 28F9 Light Chain CDR3
(SEQ ID NO: 137)
TGTCAAGGTACACATTTTCCGTGGACG Antibody 28F9 Light Chain CDR3
(SEQ ID NO: 138)
CQGTHFPWT Antibody 18B4 Heavy Chain - Signal sequence-
FR1-CDR1-FR2-CDR2-FR3-CDR3-FR4
(SEQ ID NO: 139)
ATGTACTTGGGACTGAACTATGTATTCATAGTTTTTCTCTTAAATGGTGT

CCAGAGTGAAGTGAAACTTGAGGAGTCTGGAGGAGGCTTGGTGCAACCTG

GGGGATCCATGAAACTCTCTTGTGCTGCCTCTGGATTCACTTTTAATGAC

-continued

GCCTGGATGGACTGGGTCCGCCAGTCTCCAGAGAAGGGGCTTGAGTGGGT

TGCTGAAATTAGAAGCACAGCTAATATTCATACAACATACTATGCTGAGT

CTGTCCAAGGGAGGTTCACCATCTCAAGAGATGATTCCAAAAGTAGTGTC

TACCTGCAAATGAACAGCTTGAGAGCTGAAGACACTGGCATTTATTATTG

TACCCCATTACTCTACGGATTTGCTTACTGGGGCCAAGGGACTCTGGTCA

CTGTCTCTGCA

Antibody 18B4 Heavy Chain - Signal sequence-
FR1-CDR1-FR2-CDR2-FR3-CDR3-FR4
(SEQ ID NO: 140)
MYLGLNYVFIVFLLNGVQSEVKLEESGGGLVQPGGSMKLSCAASGFTFND

AWMDWVRQSPEKGLEWVAEIRSTANIHTTYYAESVQGRFTISRDDSKSSV

YLQMNSLRAEDTGIYYCTPLLYGFAYWGQGTLVTVSA

Antibody 18B4 Light Chain - Signal sequence-
FR1-CDR1-FR2-CDR2-FR3-CDR3-FR4
(SEQ ID NO: 141)
ATGAAGTTGCCTGTTAGGCTGTTGGTGCTGATGTTCTGGATTCCTGCTTC

CAGCAGTGATGTTGTGATGACCCAAAGTCCACTCTCCCTGCCTGTCAGTC

TTGGAGATCAAGCCTCCATCTCTTGCAGAACTAGTCAGAGCCTTGTACAC

AGTAATGGAAACACCTATTTACATTGGCACCTGCAGAAGCCAGGCCAGTC

TCCAAAGGTCCTGATCTACAAAGTTTCCAGCCGATTTTCTGGGGTCCCAG

ACAGGTTCAGTGGCAGTGGATCGGGGACAGATTTCACACTCAAGATCAGC

AGAGTGGAGGCTGAGGATCTGGGAGTTTATTTCTGCTCTCAAAATACACA

TGTTCCGTACACGTTCGGAGGGGGGACCAAGCTGGAAATAAAA

Antibody 18B4 Heavy Chain - Signal sequence-
FR1-CDR1-FR2-CDR2-FR3-CDR3-FR4
(SEQ ID NO: 142)
MKLPVRLLVLMFWIPASSSDVVMTQSPLSLPVSLGDQASISCRTSQSLVH

SNGNTYLHWHLQKPGQSPKVLIYKVSSRFSGVPDRFSGSGSGTDFTLKIS

RVEAEDLGVYFCSQNTHVPYTFGGGTKLEIK

Antibody 18B4 Heavy Chain CDR1
(SEQ ID NO: 143)
GACGCCTGGATGGAC

Antibody 18B4 Heavy Chain CDR1
(SEQ ID NO: 144)
DAWMD

Antibody 18B4 Heavy Chain CDR2
(SEQ ID NO: 145)
GAAATTAGAAGCACAGCTAATATTCATACAACATACTATGCTGAGTCTGT

CCAAGGG

Antibody 18B4 Heavy Chain CDR2
(SEQ ID NO: 146)
EIRSTANIHTTYYAESVQG

Antibody 18B4 Heavy Chain CDR3
(SEQ ID NO: 147)
TTACTCTACGGATTTGCTTAC

Antibody 18B4 Heavy Chain CDR3
(SEQ ID NO: 148)
LLYGFAY

Antibody 18B4 Light Chain CDR1
(SEQ ID NO: 149)
AGAACTAGTCAGAGCCTTGTACACAGTAATGGAAACACCTATTTACAT Antibody 18B4 Light Chain CDR1
(SEQ ID NO: 150)
RTSQSLVHSNGNTYLH Antibody 18B4 Light Chain CDR2
(SEQ ID NO: 151)
AAAGTTTCCAGCCGATTTTCT Antibody 18B4 Light Chain CDR2
(SEQ ID NO: 152)
KVSSRFS Antibody 18B4 Light Chain CDR3
(SEQ ID NO: 153)
TCTCAAAATACACATGTTCCGTACACG Antibody 18B4 Light Chain CDR3
(SEQ ID NO: 154)
SQNTHVPYT Antibody 1E4 Heavy Chain - Signal sequence-
FR1-CDR1-FR2-CDR2-FR3-CDR3-FR4
(SEQ ID NO: 155)
ATGGAATGGCCTTGTATCTTTCTCTTCCTCCTGTCAGTAACTGAAGGTGT

CCACTCCCAGGTTCAGCTGCAGCAGTCTGGGGCTGAGCTGGTGAGGCCTG

GGTCCTCAGTGAAGATTTCCTGTAAGGCTTCTGGCTATGCATTCAGTACC

TACTGGATGAACTGGGTGAAGCAGAGGCCTGGACAGGGTCTTGAGTGGAT

TGGACAGATTTATCCTGGAGATAGTGATACTAACTACAATGGAAAGTTCA

AGGGTAAAGCCACACTGACTGCAGACAAGTCCTCCAACACAGCCTACATG

CAGCTCAGCAGCCTAACATCTGAGGACTCTGCGGTCTTTTTCTGTGCAAG

AGGTAACCACGCCTCTATGGACTACTGGGGTCAAGGAACCTCAGTCACCG

TCTCCTCA

Antibody 1E4 Heavy Chain - Signal sequence-
FR1-CDR1-FR2-CDR2-FR3-CDR3-FR4
(SEQ ID NO: 156)
MEWPCIFLFLLSVTEGVHSQVQLQQSGAELVRPGSSVKISCKASGYAFST

YWMNWVKQRPGQGLEWIGQIYPGDSDTNYNGKFKGKATLTADKSSNTAYM

QLSSLTSEDSAVFFCARGNHASMDYWGQGTSVTVSS

Antibody 1E4 Light Chain - Signal sequence-FR1-
CDR1-FR2-CDR2-FR3-CDR3-FR4
(SEQ ID NO: 157)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTTCTGCTCTCAAAAACACA

TGTTCCGTGGACGTTCGGTGGAGGCACCAAGCTGGAAATCAAA

Antibody 1E4 Light Chain - Signal sequence-
FR1-CDR1-FR2-CDR2-FR3-CDR3-FR4
(SEQ ID NO: 158)
MKLPVRLLVLMFWIPASSSDVVMTQTPLSLPVSLGDQASISCRSSQSLVH

SNGNTYLHWYLQKPGQSPKLLIYKVSNRFSGVPDRFSGSGSGTDFTLKIS

RVEAEDLGVYFCSQKTHVPWTFGGGTKLEIK

Antibody 1E4 Heavy Chain CDR1
(SEQ ID NO: 159)
ACCTACTGGATGAAC

Antibody 1E4 Heavy Chain CDR1
(SEQ ID NO: 160)
TYWMN

Antibody 1E4 Heavy Chain CDR2
(SEQ ID NO: 161)
CAGATTTATCCTGGAGATAGTGATACTAACTACAATGGAAAGTTCAAGGG
T Antibody 1E4 Heavy Chain CDR2
(SEQ ID NO: 162)
QIYPGDSDTNYNGKFKG Antibody 1E4 Heavy Chain CDR3
(SEQ ID NO: 163)
GGTAACCACGCCTCTATGGACTAC Antibody 1E4 Heavy Chain CDR3
(SEQ ID NO: 164)
GNHASMDY Antibody 1E4 Light Chain CDR1
(SEQ ID NO: 165)
AGATCTAGTCAGAGCCTTGTACACAGTAATGGAAACACCTATTTACAT Antibody 1E4 Light Chain CDR1
(SEQ ID NO: 166)
RSSQSLVHSNGNTYLH Antibody 1E4 Light Chain CDR2
(SEQ ID NO: 167)
AAAGTTTCCAACCGATTTTCT Antibody 1E4 Light Chain CDR2
(SEQ ID NO: 168)
KVSNRFS Antibody 1E4 Light Chain CDR3
(SEQ ID NO: 169)
TCTCAAAAAACACATGTTCCGTGGACG Antibody 1E4 Light Chain CDR3
(SEQ ID NO: 170)
SQKTHVPWT Antibody 29H1 Heavy Chain - Signal sequence-FR1-CDR1-FR2-CDR2-FR3-CDR3-FR4
(SEQ ID NO: 171)
ATGTACTTGGGACTGAACTATGTATTCATAGTTTTTCTCTTAAATGGTGT
CCAGAGTGAAGTGAAGCTTGAGGAGTCTGGAGGAGGCTTGGTACAACCTG
GAGGATCCATGAAACTCTCTTGTGCTGCCTCTGGATTCACTTTTAGTGAC
GCCTGGATGGACTGGGTCCGCCAGTCTCCAGAGAAGGGGCTTGAATGGGT
TGCTGAAATTAGAAGCAAAGCTACTAATCATGCAACATACTATGCTGAGT
CTGTGAAAGGGAGGTTCACCATCTCAAGAGATGATTCCAAAAGTAGTGTC
TACCTGCAAATGAACAGCTTAAGAGCTGAAGACACTGGCATTTATTACTG
TACCCCCCTACTTTACGGGTTTGCTTACTGGGGCCAAGGGACTCTGGTCA
CTGTCTCTGCA Antibody 29H1 Heavy Chain - Signal sequence-FR1-CDR1-FR2-CDR2-FR3-CDR3-FR4
(SEQ ID NO: 172)
MYLGLNYVFIVFLLNGVQSEVKLEESGGGLVQPGGSMKLSCAASGFTFSD
AWMDWVRQSPEKGLEWVAEIRSKATNHATYYAESVKGRFTISRDDSKSSV
YLQMNSLRAEDTGIYYCTPLLYGFAYWGQGTLVTVSA Antibody 29H1 Light Chain - Signal sequence-FR1-CDR1-FR2-CDR2-FR3-CDR3-FR4
(SEQ ID NO: 173)
ATGAAGTTGCCTGTTAGGCTGTTGGTGCTGATGTTCTGGATTCCTGCTTC
CAGCAGTGATGTTGTGATGACCCAAACTCCACTCTCCCTGCCTGTCAGTC
TTGGAGATCAAGCCTCCATCTCTTGCAGATCTGGTCAGAGCCTTGTACAC
AGTAATGGACACACCTATTTACATTGGTACCTGCAGAAGCCAGGCCAGTC
TCCAAGGCTCCTGATCTACAAAGTTTCCAACCGATTTTCTGGGGTCCCAG
ACAGGTTCAGTGGCAGTGGATCAAGGGCAGATTTCACACTCAAGATCAGC
AGAGTGGAGGCTGAGGATCTGGGAGTTTATTTCTGCTCTCAAACTACACA
TGTTCCGTGGACGTTCGGTGGAGGCACCAAGCTGGAAATCAAA Antibody 29H1 Light Chain - Signal sequence-FR1-CDR1-FR2-CDR2-FR3-CDR3-FR4
(SEQ ID NO: 174)
MKLPVRLLVLMFWIPASSSDVVMTQTPLSLPVSLGDQASISCRSGQSLVH
SNGHTYLHWYLQKPGQSPRLLIYKVSNRFSGVPDRFSGSGSRADFTLKIS
RVEAEDLGVYFCSQTTHVPWTFGGGTKLEIK Antibody 29H1 Heavy Chain CDR1
(SEQ ID NO: 175)
GACGCCTGGATGGAC Antibody 29H1 Heavy Chain CDR1
(SEQ ID NO: 176)
DAWMD Antibody 29H1 Heavy Chain CDR2
(SEQ ID NO: 177)
GAAATTAGAAGCAAAGCTACTAATCATGCAACATACTATGCTGAGTCTGT
GAAAGGG Antibody 29H1 Heavy Chain CDR2
(SEQ ID NO: 178)
EIRSKATNHATYYAESVKG Antibody 29H1 Heavy Chain CDR3
(SEQ ID NO: 179)
CTACTTTACGGGTTTGCTTAC Antibody 29H1 Heavy Chain CDR3
(SEQ ID NO: 180)
LLYGFAY Antibody 29H1 Light Chain CDR1
(SEQ ID NO: 181)
AGATCTGGTCAGAGCCTTGTACACAGTAATGGACACACCTATTTACAT Antibody 29H1 Light Chain CDR1
(SEQ ID NO: 182)
RSGQSLVHSNGHTYLH Antibody 29H1 Light Chain CDR2
(SEQ ID NO: 183)
AAAGTTTCCAACCGATTTTCT Antibody 29H1 Light Chain CDR2
(SEQ ID NO: 184)
KVSNRFS Antibody 29H1 Light Chain CDR3
(SEQ ID NO: 185)
TCTCAAACTACACATGTTCCGTGGACG Antibody 29H1 Light Chain CDR3
(SEQ ID NO: 186)
SQTTHVPWT Antibody 31A1 Heavy Chain - Signal sequence-
FR1-CDR1-FR2-CDR2-FR3-CDR3-FR4
(SEQ ID NO: 187)
ATGGAAAGGCACTGGATCTTTCTCTTCCTGTTTTCAGTAACTGCAGGTGT

CCACTCCCAGGTCCAGCTTCAGCAGTCTGGGGCTGAACTGGCAAAACCTG

GGGCCTCAGTGAAGATGTCCTGCAAGGCTTCTGGCTACACCTTTACTAGC

TACTGGATGCACTGGGTAAAACAGAGGCCTGGACAGGGTCTGGAATGGAT

TGGATACATTAATCCTAGCACTGGTTATACTGAGTACAATCAGAAGTTCA

AGGACAAGGCCACATTGACTGCAGACAAATCCTCCAGCACAGCCTACATG

CAACTGAGCAGCCTGACATCTGAGGACTCTGCAGTCTATTACTGTGCAAG

AGCCTACATTGACTACTGGGGCCAAGGCACCACTCTCACAGTCTCCTCA

Antibody 31A1 Heavy Chain - Signal sequence-
FR1-CDR1-FR2-CDR2-FR3-CDR3-FR4
(SEQ ID NO: 188)
MERHWIFLFLFSVTAGVHSQVQLQQSGAELAKPGASVKMSCKASGYTFTS

YWMHWVKQRPGQGLEWIGYINPSTGYTEYNQKFKDKATLTADKSSSTAYM

QLSSLTSEDSAVYYCARAYIDYWGQGTTLTVSS

Antibody 31A1 Light Chain - Signal sequence-
FR1-CDR1-FR2-CDR2-FR3-CDR3-FR4
(SEQ ID NO: 189)
ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCTTCTCTTGCAGATCTAGTCAGAGCATTGTACAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAAC

AGAGTGGAGGCTGAGGATCTGGGAGTTTATTACTGCTTTCAAGTTTCACA

TTTTCCGTGGACGTTCGGTGGAGGCACCAAGCTGGAAATCAAA

Antibody 31A1 Light Chain - Signal sequence-
FR1-CDR1-FR2-CDR2-FR3-CDR3-FR4
(SEQ ID NO: 190)
MKLPVRLLVLMFWIPASSSDVLMTQTPLSLPVSLGDQASFSCRSSQSIVH

SNGNTYLEWYLQKPGQSPKLLIYKVSNRFSGVPDRFSGSGSGTDFTLKIN

RVEAEDLGVYYCFQVSHFPWTFGGGTKLEIK

Antibody 31A1 Heavy Chain CDR1
(SEQ ID NO: 191)
AGCTACTGGATGCAC

Antibody 31A1 Heavy Chain CDR1
(SEQ ID NO: 192)
SYWMH

Antibody 31A1 Heavy Chain CDR2
(SEQ ID NO: 193)
TACATTAATCCTAGCACTGGTTATACTGAGTACAATCAGAAGTTCAAGGA
C Antibody 31A1 Heavy Chain CDR2
(SEQ ID NO: 194)
YINPSTGYTEYNQKFKD Antibody 31A1 Heavy Chain CDR3
(SEQ ID NO: 195)
GCCTACATTGACTAC Antibody 31A1 Heavy Chain CDR3
(SEQ ID NO: 196)
AYIDY Antibody 31A1 Light Chain CDR1
(SEQ ID NO: 197)
AGATCTAGTCAGAGCATTGTACATAGTAATGGAAACACCTATTTAGAA Antibody 31A1 Light Chain CDR1
(SEQ ID NO: 198)
RSSQSIVHSNGNTYLE Antibody 31A1 Light Chain CDR2
(SEQ ID NO: 199)
AAAGTTTCCAACCGATTTTCT Antibody 31A1 Light Chain CDR2
(SEQ ID NO: 200)
KVSNRFS Antibody 31A1 Light Chain CDR3
(SEQ ID NO: 201)
TTTCAAGTTTCACATTTTCCGTGGACG Antibody 31A1 Light Chain CDR3
(SEQ ID NO: 202)
FQVSHFPWT Antibody 32C1 Heavy Chain - Signal sequence-
FR1-CDR1-FR2-CDR2-FR3-CDR3-FR4
(SEQ ID NO: 203)
ATGTACTTGGGACTGAACTGTGTATTCATAGTTTTTCTCTTAAAAGGTGT

CCAGAGTGAAGTGAAGCTTGAGGAGTCTGGAGGAGGCTTGGTGCAATCTG

GAGGATCCATGAAACTCTCCTGTGTTGCCTCTGGATTCACTTTCAGTAAT

TACTGGATGAACTGGGTCCGCCAGTCTCCAGAGAAGGGGCTTGAGTGGGT

TGCTGAAATTAGATTGAAATCTAATAATTATGCAATACATTATGCGGAGT

CTGTGAAGGGGAGGTTCACCATCTCAAGAGATGATTCCAAAAGTAGTGTC

TACCTGCAAATGAACAACTTAAGAGCTGAAGACACTGGCATTTATTACTG

TACCAGGGTCCCGGGACTGGATGCTTACTGGGGCCAAGGGACTCTGGTCA

CTGTCTCTGCA

Antibody 32C1 Heavy Chain - Signal sequence-
FR1-CDR1-FR2-CDR2-FR3-CDR3-FR4
(SEQ ID NO: 204)
MYLGLNCVFIVFLLKGVQSEVKLEESGGGLVQSGGSMKLSCVASGFTFSN

YWMNWVRQSPEKGLEWVAEIRLKSNNYAIHYAESVKGRFTISRDDSKSSV

YLQMNNLRAEDTGIYYCTRVPGLDAYWGQGTLVTVSA

Antibody 32C1 Light Chain - Signal sequence-
FR1-CDR1-FR2-CDR2-FR3-CDR3-FR4
(SEQ ID NO: 205)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGTGGAGGCTGAGGATCTGGGAGTTTATTCTGCTCTCAAATTACACA

TGTTCCGTACACGTTCGGAGGGGGGACCAATCTGGAAATAAAA

```
Antibody 32C1 Light Chain - Signal sequence-
FR1-CDR1-FR2-CDR2-FR3-CDR3-FR4
                                       (SEQ ID NO: 206)
MKLPVRLLVLMFWIPASSSDVVMTQTPLSLPVSLGDQASISCRSSQSLVH

SNGNTYLHWYLQKPGQSPKLLIYKVSNRFSGVPDRFSGSGSGTDFTLKIS

SVEAEDLGVYFCSQITHVPYTFGGGTNLEIK

Antibody 32C1 Heavy Chain CDR1
                                       (SEQ ID NO: 207)
AATTACTGGATGAAC Antibody 32C1 Heavy Chain CDR1
                                       (SEQ ID NO: 208)
NYWMN Antibody 32C1 Heavy Chain CDR2
                                       (SEQ ID NO: 209)
GAAATTAGATTGAAATCTAATAATTATGCAATACATTATGCGGAGTCTGT

GAAGGGG

Antibody 32C1 Heavy Chain CDR2
                                       (SEQ ID NO: 210)
EIRLKSNNYAIHYAESVKG Antibody 32C1 Heavy Chain CDR3
                                       (SEQ ID NO: 211)
GTCCCGGGACTGGATGCTTAC Antibody 32C1 Heavy Chain CDR3
                                       (SEQ ID NO: 212)
VPGLDAY Antibody 32C1 Light Chain CDR1
                                       (SEQ ID NO: 213)
AGATCTAGTCAGAGCCTTGTACACAGTAATGGAAACACCTATTTACAT Antibody 32C1 Light Chain CDR1
                                       (SEQ ID NO: 214)
RSSQSLVHSNGNTYLH Antibody 32C1 Light Chain CDR2
                                       (SEQ ID NO: 215)
AAAGTTTCCAACCGATTTTCT Antibody 32C1 Light Chain CDR2
                                       (SEQ ID NO: 216)
KVSNRFS Antibody 32C1 Light Chain CDR3
                                       (SEQ ID NO: 217)
TCTCAAATTACACATGTTCCGTACACG Antibody 32C1 Light Chain CDR3
                                       (SEQ ID NO: 218)
SQITHVPYT Antibody 45C11 Heavy Chain - Signal sequence-
FR1-CDR1-FR2-CDR2-FR3-CDR3-FR4
                                       (SEQ ID NO: 219)
ATGAAATGCAGCTGGGTTATCTTCTTCCTGATGGCAGTGGTTACAGGGGT

CAATTCAGAGGTTCAGCTGCAGCAGTCTGGGGCAGACCTTGTGAAGCCAG

GGGCCTCAGTCAAGTTGTCCTGCACAGCTTCTGGCTTCAACATTAAAGAC

ACCTTTATGCACTGGGTGAAGCAGAGGCCTGAACAGGGCCTGGAGTGGAT

TGGAAGGATTGATCCTGCGAATGGTAATACTAAATATGACCCGAAATTCC

AGGGCAAGGCCACTATAACAGCAGACACATCCTCCAACACAGCCTACCTG

CAGCTCAGCAGCCTGACATCTGAGGACACTGCCGTCTATTACTGTGCTAA

ACCGTATGGTAACTACGGCTATTACTATGCTTTGGACTACTGGGGTCAAG

GAACCTCAGTCACCGTCTCCTCA

Antibody 45C11 Heavy Chain - Signal sequence-
FR1-CDR1-FR2-CDR2-FR3-CDR3-FR4
                                       (SEQ ID NO: 220)
MKCSWVIFFLMAVVTGVNSEVQLQQSGADLVKPGASVKLSCTASGFNIKD

TFMHWVKQRPEQGLEWIGRIDPANGNTKYDPKFQGKATITADTSSNTAYL

QLSSLTSEDTAVYYCAKPYGNYGYYYALDYWGQGTSVTVSS

Antibody 45C11 Light Chain - Signal sequence-
FR1-CDR1-FR2-CDR2-FR3-CDR3-FR4
                                       (SEQ ID NO: 221)
ATGAGGTTCCAGGTTCAGGTTCTGGGGCTCCTTCTGCTCTGGATATCAGG

TGCCCAGTGTGATGTCCAGATAACCCAGTCTCCATCTTATCTTGCTGCAT

CTCCTGGAGAAACCATTACTATTAATTGCAGGGCAAGTAAGAGCATTAGC

AAATATTTAGCCTGGTATCAAGAGAAACCTGGGAAAACTAATAAGCTTCT

TATCTACTCTGGATCCACTTTGCAATCTGGAATTCCATCAAGGTTCAGTG

GCAGTGGATCTGGTACAGATTTCACTCTCACCATCAGTAGCCTGGAGCCT

GAAGATTTTGCAATGTATTACTGTCAACAGCATAATGAATTCCCGTGGAC

GTTCGGTGGAGGCACCAAGCTGGAAATCAAA

Antibody 45C11 Light Chain - Signal sequence-
FR1-CDR1-FR2-CDR2-FR3-CDR3-FR4
                                       (SEQ ID NO: 222)
MRFQVQVLGLLLLWISGAQCDVQITQSPSYLAASPGETITINCRASKSIS

KYLAWYQEKPGKTNKLLIYSGSTLQSGIPSRFSGSGSGTDFTLTISSLEP

EDFAMYYCQQHNEFPWTFGGGTKLEIK

Antibody 45C11 Heavy Chain CDR1
                                       (SEQ ID NO: 223)
GACACCTTTATGCAC Antibody 45C11 Heavy Chain CDR1
                                       (SEQ ID NO: 224)
DTFMH Antibody 45C11 Heavy Chain CDR2
                                       (SEQ ID NO: 225)
AGGATTGATCCTGCGAATGGTAATACTAAATATGACCCGAAATTCCAGGG

C

Antibody 45C11 Heavy Chain CDR2
                                       (SEQ ID NO: 226)
RIDPANGNTKYDPKFQG Antibody 45C11 Heavy Chain CDR3
                                       (SEQ ID NO: 227)
CCGTATGGTAACTACGGCTATTACTATGCTTTGGACTAC Antibody 45C11 Heavy Chain CDR3
                                       (SEQ ID NO: 228)
PYGNYGYYYALDY Antibody 45C11 Light Chain CDR1
                                       (SEQ ID NO: 229)
AGGGCAAGTAAGAGCATTAGCAAATATTTAGCC Antibody 45C11 Light Chain CDR1
                                       (SEQ ID NO: 230)
RASKSISKYLA Antibody 45C11 Light Chain CDR2
                                       (SEQ ID NO: 231)
TCTGGATCCACTTTGCAATCT Antibody 45C11 Light Chain CDR2
                                       (SEQ ID NO: 232)
SGSTLQS
```

-continued

Antibody 45C11 Light Chain CDR3
(SEQ ID NO: 233)
CAACAGCATAATGAATTCCCGTGGACG

Antibody 45C11 Light Chain CDR3
(SEQ ID NO: 234)
QQHNEFPWT

Tandem repeat domain peptide
(SEQ ID NO: 235)
PDTRPAPGSTAPPAHGVTSA

CAR44: CD8/HUMNC2/CD8/4-1BB/CD3
(SEQ ID NO: 236)
MALPVTALLLPLALLLHAARPEVQLVESGGGLVKPGGSLRLSCAASGFTF

SGYAMSWVRQAPGKGLEWVSTISSGGTYIYYPDSVKGRFTISRDNAKNSL

YLQMNSLRAEDTAVYYCARLGGDNYYEYFDVWGKGTTVTVSSGGGGSGGG

GSGGGGSDIVLTQSPASLAVSPGQRATITCRASKSVSTSGYSYMHWYQQK

PGQPPKLLIYLASNLESGVPARFSGSGSGTDFTLTINPVEANDTANYYCQ

HSRELPFTFGGGTKVEIKRTTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYKQGNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR

MIN-A2-1 LIGHT CHAIN VARIABLE REGION
AMINO ACID SEQUENCE
(SEQ ID NO: 237)
DIVLTQSTEIMSASPGEKVTITCSASSSISYIHWFQQKPGTSPKLWIFGT

SNLASGVPARFSGSGSGTSYSLTVSRMEAEDTATYYCQQRSNYPFTFGSG

TKLQIKRADAAPTVS

MIN-A2-2 LIGHT CHAIN VARIABLE REGION
AMINO ACID SEQUENCE
(SEQ ID NO: 238)
DIVMTQSPAIMSASPGEKVTMTCSASSSVSYMHWFQQKPGTSPKLWIYST

SNLASGAPARFSGSGSGTSYSLTVSRMESEDAATYYCQQRSSYPSTFGGG

TKLEIKRADAAPTVS

MIN-C9-1 LIGHT CHAIN VARIABLE REGION
AMINO ACID SEQUENCE
(SEQ ID NO: 239)
DIVLTQTTAIMSASPGEKVTITCSASSSVSYMYWFQQKPGTSPKLWIYST

SNLASGVPARFSGSGSGTSYSLTISRMEAEDAATYYCQQRSSYPSTFGGG

TKLEIKRADAAPTVS

MIN-C9-2 LIGHT CHAIN VARIABLE REGION
AMINO ACID SEQUENCE
(SEQ ID NO: 240)
DIVITQSTAIMSASPGEKVTITCSASSSVSYTYWFQQKPGTSPKLWIYST

SNLASGVPARFSGSGSGTSYSLTISRMEAEDAATYYCQQRSSYPSTFGGG

TKLEIKRADAAPTVS

MIN-D7-1 LIGHT CHAIN VARIABLE REGION
AMINO ACID SEQUENCE
(SEQ ID NO: 241)
DIVITQTPAIMSASPGEKVTMTCSASSSVSYMHWFQQKPGTSPKLWIYST

SNLASGVPARFSGSGSGTSYSLTVSRMESEDAATYYCQQRSSYPSTFGGG

TKLEIKRADAAPTVS

MIN-D7-2 LIGHT CHAIN VARIABLE REGION
AMINO ACID SEQUENCE
(SEQ ID NO: 242)
DIVLTQSTAIMSASPGEKVTMTCSASSSVSYMHWFQQKPGTSPKLWIYST

SNLASGVPARFSGSGSGTSYSLTVSRMESEDAATYYCQQRSSYPSTFGGG

TKLEIKRADAAPTVS

MIN-F2-1 LIGHT CHAIN VARIABLE REGION
AMINO ACID SEQUENCE
(SEQ ID NO: 243)
DIVMTQSPEIMSASPGEKVTITCSASSSISYIHWFQQKPGTSPKLWIFGT

SNLASGVPARFSGSGSGTSYSLTVSRMEAEDTATYYCQQRSNYPFTFGSG

TKLQIKRADAAPTVS

MIN-F2-2 LIGHT CHAIN VARIABLE REGION
AMINO ACID SEQUENCE
(SEQ ID NO: 244)
DIVITQSTEIMSASPGEKVTITCSASSSISYIHWFQQKPGTSPKLWIFGT

SNLASGVPARFSGSGSGTSYSLTVSRMEAEDTATYYCQQRSNYPFTFGSG

TKLQIKRADAAPTVS

MIN-A2-1 HEAVY CHAIN VARIABLE REGION
AMINO ACID SEQUENCE
(SEQ ID NO: 245)
EVKLQESGPELKKPGETVEISCKASGYTFTNYGMNWVKQAPGKGLKWMGW

INTYTGEPTYAGDFKGRFAFSLETSASTAYLQINTLKNEDTATYFCARSG

DGYWYYAMDYWGQGTSVTVSSAKTTPPSVY

MIN-A2-2 HEAVY CHAIN VARIABLE REGION
AMINO ACID SEQUENCE
(SEQ ID NO: 246)
EVQLQQSGPELKKPGETVKISCKASGYTFTNYGMNWVKQAPGKGLKWMGW

INTYTGEPTYAGDFKGRFAFSLETSASTAYLQINTLKNEDTATYFCARSG

DGYWYYAMDYWGQGTSVTVSSAKTTPPSVY

MIN-C9-1 HEAVY CHAIN VARIABLE REGION
AMINO ACID SEQUENCE
(SEQ ID NO: 247)
QVQLQESGPELKQPGETVKISCKASGYTFTNNGMNWVKQAPGKGLKWMGW

INTYTGEPTYADDFKGRFAFSLDTSASTAYLQINNLKNEDMATYFCARTG

TARAFYAMDYWGQGTSVTVSSTKTTAPSVY

MIN-C9-2 HEAVY CHAIN VARIABLE REGION
AMINO ACID SEQUENCE
(SEQ ID NO: 248)
QVQLQQSGPELKQPGETVKISCKASGYTFTNNGMNWVKQAPGKGLKWMGW

INTYTGEPTYADDFKGRFAFSLGTSASTAYLQINNLKNEDMATYFCARTG

TARAFYAMDYWGQGTSVTVSSTKTTAPSVY

MIN-D7-1 HEAVY CHAIN VARIABLE REGION
AMINO ACID SEQUENCE
(SEQ ID NO: 249)
EVQLEQSGPELKKPGETVKISCKASGYTFINYGMNWVKQAPGKGLKWMGW

INTYTGEPTYVDDFKGRFAFSLETSARTAYLQINNLKNEDMATYFCARTG

TTAILNGMDYWGQGTSVTVSSAKTTPPSVY

MIN-D7-2 HEAVY CHAIN VARIABLE REGION
AMINO ACID SEQUENCE
(SEQ ID NO: 250)
EVQLQQSGPELKKPGETVKISCKASGYTFTNYGMNWVKQAPGKGLKWMGW

INTYTGEPTYAGDFKGRFAFSLETSASTAYLQINTLKNEDTATYFCARSG

DGYWYYAMDYWGQGTSVTVSSAKTTPPSVY

MIN-F2-1 HEAVY CHAIN VARIABLE REGION
AMINO ACID SEQUENCE
(SEQ ID NO: 251)
EVKLEESGPELKKPGETVKISCKASGYTFINYGMNWVKQAPGKGLKWMGW

INTYTGEPTYVDDFKGRFAFSLETSARTAYLQINNLKNEDMATYFCARTG

TTAILNGMDYWGQGTSVTVSSAKTTPPSVY

MIN-F2-2 HEAVY CHAIN VARIABLE REGION
AMINO ACID SEQUENCE
(SEQ ID NO: 252)
EVQLEQSGAELVRPGASVKLSCKALGYTFTDYEMHWVKQTPVHGLEWIGA

IHPGSGGTAYNQKFKGKATLTADKSSSTAYMELSSLTSEDSAVYYCTNYG

SFAYWGQGTLVTVSAAKTTPPSVY

MIN-F2-3 HEAVY CHAIN VARIABLE REGION
AMINO ACID SEQUENCE
(SEQ ID NO: 253)
RCRLQQSGPELKKPGETVKISCKASGYTFINYGMNWVKQAPGKGLKWMGW

INTYTGEPTYVDDFKGRFAFSLETSARTAYLQINNLKNEDMATYFCARTG

TTAILNGMDYWGQGTSVTVSSAKTTPPSCL

MIN-F2-4 HEAVY CHAIN VARIABLE REGION
AMINO ACID SEQUENCE
(SEQ ID NO: 254)
EVQLEQSGPELKKPGETVKISCKASGYTFINYGMNWVKQAPGKGLKWMGW

INTYTGEPTYVDDFKGRFAFSLETSARTAYLQINNLKNEDMATYFCARTG

TTAILNGMDYWGQGTSVTVSSAKTTPPSVY

MIN-14 LIGHT CHAIN VARIABLE REGION
AMINO ACID SEQUENCE
(SEQ ID NO: 255)
DIQMTQSPSSLSASLGERVSLTCRASQDIGSSLNWLQQEPDGTIKRLIYA

TSSLDSGVPKRFSGSRSGSDYSLTISSLESEDFVDYYCLQYASSPHVRCW

DQAGAETGCCTNC

MIN-17-1 LIGHT CHAIN VARIABLE REGION
AMINO ACID SEQUENCE
(SEQ ID NO: 256)
DIVLTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSW

MIN-17-2 LIGHT CHAIN VARIABLE REGION
AMINO ACID SEQUENCE
(SEQ ID NO: 257)
DIQMTQSPASQSASLGESVTITCLASQTIGTWLAWYQQKPGKSPQLLIYA

ATSLADGVPSRFSGSGSGTKFSFKISSLQAEDFVSYYCQQLYSTPWTFGG

GTKLEIKRADAAPTV

MIN-29 LIGHT CHAIN VARIABLE REGION
AMINO ACID SEQUENCE
(SEQ ID NO: 258)
DIVLTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSW

MIN-34 LIGHT CHAIN VARIABLE REGION
AMINO ACID SEQUENCE
(SEQ ID NO: 259)
DIVLTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSW

MIN-42 LIGHT CHAIN VARIABLE REGION
AMINO ACID SEQUENCE
(SEQ ID NO: 260)
DIVMTQSQKFMSTSVGDRVSVTCKASQNVGTNVGWYQQKPGQSPKALIYS

ASYRYSGVPDRFTGSGSGTDFTLTISNVQSEDLAEYFCQQYNNYPYTFGG

GTKLEIKRADAAPTV

MIN-45 LIGHT CHAIN VARIABLE REGION
AMINO ACID SEQUENCE
(SEQ ID NO: 261)
DIQMTQPPASLSASVGETVTITCRASGNIHNFLAWYQQKQGKSPQLLVYN

AKTLADGVPSRFSGSGSGTQYSLKINSLQPEDFGSYYCQHFWSTPWTFGG

GTKLEIKRADAAPTV

MIN-14 HEAVY CHAIN VARIABLE REGION
AMINO ACID SEQUENCE
(SEQ ID NO: 262)
QVQLQQPGAELVKPGASVKLSCKASGYTFTSYWMHWVKQRPGQGLEWIGE

INPSNGRTNYNEKFKSKATLTVDKSSSTAYMQLSSLTSEDSAVYYCATYG

NYWYF

MIN-17-2 HEAVY CHAIN VARIABLE REGION
AMINO ACID SEQUENCE
(SEQ ID NO: 263)
QITLKESGPGIVQPSQPFRLTCTFSGFSLSTSGIGVTWIRQPSGKGLEWL

ATIWWDDDNRYNPSLKSRLTVSKDTSNNQAFLNIITVETADTAIYYCAQS

TMVTA

MIN-17-1 HEAVY CHAIN VARIABLE REGION
AMINO ACID SEQUENCE
(SEQ ID NO: 264)
QVQLQQPGAELVKPGASVKLSCKASGYTFTSYWMHWVKQRPGQGLEWIGE

INPSNGRTNYNEK-FKSKATLTVDKSSSTAYMQLSSLTSEDSAVYYCATY

GNYWYF

MIN-29 HEAVY CHAIN VARIABLE REGION
AMINO ACID SEQUENCE
(SEQ ID NO: 265)
DVKLVESGGDLXKLTEGEDIWEGLTLCRDSDQSPLAPVSKPGRVVRPQRS

CTVIQGCVLRLQTAHLQVQGVLGIVSGDGESALHSVWIVGATTITINGCD

QLQPLLWSLANPRHVIATESESRGCTG

MIN-34 HEAVY CHAIN VARIABLE REGION
AMINO ACID SEQUENCE
(SEQ ID NO: 266)
QVQLKQSGPGLVQPSQSLSITCTVSGFSLTSYGVHWVRQSPGKGLEWLGV

IWGGGSTDYNAAFISRLSISKDNSKSQVFFKMNSLQANDTAIYYCARNDY

PAWF

MIN-42 HEAVY CHAIN VARIABLE REGION
AMINO ACID SEQUENCE
(SEQ ID NO: 267)
EVQLVESGGDLVKPGRSLKLSCAASGFTFSSFGMSWVRQTPDKRLEWVAT

ISSGGTYTYYPDSVKGRFTISRDNAKNTLYLQMSSLKSEDTAMYYCSRRF

YYDYD

MIN-45 HEAVY CHAIN VARIABLE REGION
AMINO ACID SEQUENCE
(SEQ ID NO: 268)
EVQQQSGPELVKPGASVKISCKASGYSFTGYFMSWVMQSHGKSLEWIGR

INPYNGDTFYNQKFKGKATLTVDKSSTTAHIELRSLASEDSAVYYCARKG

LYG

DESCRIBES MIN-A2-1 LIGHT CHAIN VARIABLE
COMPLEMENTARITY DETERMINING REGION1 (CDR1)
AMINO ACID SEQUENCE.
(SEQ ID NO: 269)
SASSSISYIH

DESCRIBES MIN-A2-2 LIGHT CHAIN VARIABLE
COMPLEMENTARITY DETERMINING REGION1 (CDR1)
AMINO ACID SEQUENCE.
(SEQ ID NO: 270)
SASSSVSYMH

DESCRIBES MIN-C9-1 LIGHT CHAIN VARIABLE
COMPLEMENTARITY DETERMINING REGION1 (CDR1)
AMINO ACID SEQUENCE.
(SEQ ID NO: 271)
SASSSVSYMY

DESCRIBES MIN-C9-2 LIGHT CHAIN VARIABLE
COMPLEMENTARITY DETERMINING REGION1 (CDR1)
AMINO ACID SEQUENCE.
(SEQ ID NO: 272)
SASSSVSYTY

DESCRIBES MIN-D7-1 LIGHT CHAIN VARIABLE
COMPLEMENTARITY DETERMINING REGION1 (CDR1)
AMINO ACID SEQUENCE.
(SEQ ID NO: 273)
SASSSVSYMH

DESCRIBES MIN-D7-2 LIGHT CHAIN VARIABLE
COMPLEMENTARITY DETERMINING REGION1 (CDR1)
AMINO ACID SEQUENCE.
(SEQ ID NO: 274)
SASSSVSYMH

DESCRIBES MIN-F2-1 LIGHT CHAIN VARIABLE
COMPLEMENTARITY DETERMINING REGION1 (CDR1)
AMINO ACID SEQUENCE.
(SEQ ID NO: 275)
SASSSISYIH

DESCRIBES MIN-F2-2 LIGHT CHAIN VARIABLE
COMPLEMENTARITY DETERMINING REGION1 (CDR1)
AMINO ACID SEQUENCE.
(SEQ ID NO: 276)
SASSSISYIH

DESCRIBES MIN-A2-1 LIGHT CHAIN VARIABLE
COMPLEMENTARITY DETERMINING REGION2 (CDR2)
AMINO ACID SEQUENCE.
(SEQ ID NO: 277)
GTSNLAS

DESCRIBES MIN-A2-2 LIGHT CHAIN VARIABLE
COMPLEMENTARITY DETERMINING REGION2 (CDR2)
AMINO ACID SEQUENCE.
(SEQ ID NO: 278)
STSNLAS

DESCRIBES MIN-C9-1 LIGHT CHAIN VARIABLE
COMPLEMENTARITY DETERMINING REGION2 (CDR2)
AMINO ACID SEQUENCE.
(SEQ ID NO: 279)
STSNLAS

DESCRIBES MIN-C9-2 LIGHT CHAIN VARIABLE
COMPLEMENTARITY DETERMINING REGION2 (CDR2)
AMINO ACID SEQUENCE.
(SEQ ID NO: 280)
STSNLAS

DESCRIBES MIN-D7-1 LIGHT CHAIN VARIABLE
COMPLEMENTARITY DETERMINING REGION2 (CDR2)
AMINO ACID SEQUENCE.
(SEQ ID NO: 281)
STSNLAS

DESCRIBES MIN-D7-2 LIGHT CHAIN VARIABLE
COMPLEMENTARITY DETERMINING REGION2 (CDR2)
AMINO ACID SEQUENCE.
(SEQ ID NO: 282)
STSNLAS

DESCRIBES MIN-F2-1 LIGHT CHAIN VARIABLE
COMPLEMENTARITY DETERMINING REGION2 (CDR2)
AMINO ACID SEQUENCE.
(SEQ ID NO: 283)
GTSNLAS

DESCRIBES MIN-F2-2 LIGHT CHAIN VARIABLE
COMPLEMENTARITY DETERMINING REGION2 (CDR2)
AMINO ACID SEQUENCE.
(SEQ ID NO: 284)
GTSNLAS

DESCRIBES MIN-A2-1 LIGHT CHAIN VARIABLE
COMPLEMENTARITY DETERMINING REGION3 (CDR3)
AMINO ACID SEQUENCE.
(SEQ ID NO: 285)
QQRSNYPFT

DESCRIBES MIN-A2-2 LIGHT CHAIN VARIABLE
COMPLEMENTARITY DETERMINING REGION3 (CDR3)
AMINO ACID SEQUENCE.
(SEQ ID NO: 286)
QQRSSYPST

DESCRIBES MIN-C9-1 LIGHT CHAIN VARIABLE
COMPLEMENTARITY DETERMINING REGION3 (CDR3)
AMINO ACID SEQUENCE.
(SEQ ID NO: 287)
QQRSSYPST

DESCRIBES MIN-C9-2 LIGHT CHAIN VARIABLE
COMPLEMENTARITY DETERMINING REGION3 (CDR3)
AMINO ACID SEQUENCE.
(SEQ ID NO: 288)
QQRSSYPST

DESCRIBES MIN-D7-1 LIGHT CHAIN VARIABLE
COMPLEMENTARITY DETERMINING REGION3 (CDR3)
AMINO ACID SEQUENCE.
(SEQ ID NO: 289)
QQRSSYPST

DESCRIBES MIN-D7-2 LIGHT CHAIN VARIABLE
COMPLEMENTARITY DETERMINING REGION3 (CDR3)
AMINO ACID SEQUENCE.
(SEQ ID NO: 290)
QQRSSYPST

DESCRIBES MIN-F2-1 LIGHT CHAIN VARIABLE
COMPLEMENTARITY DETERMINING REGION3 (CDR3)
AMINO ACID SEQUENCE.
(SEQ ID NO: 291)
QQRSNYPFT

DESCRIBES MIN-F2-2 LIGHT CHAIN VARIABLE
COMPLEMENTARITY DETERMINING REGION3 (CDR3)
AMINO ACID SEQUENCE.
(SEQ ID NO: 292)
QQRSNYPFT

DESCRIBES MIN-A2-1 HEAVY CHAIN VARIABLE
COMPLEMENTARITY DETERMINING REGION1 (CDR1)
AMINO ACID SEQUENCE.
(SEQ ID NO: 293)
NYGMN

DESCRIBES MIN-A2-2 HEAVY CHAIN VARIABLE
COMPLEMENTARITY DETERMINING REGION1 (CDR1)
AMINO ACID SEQUENCE.
(SEQ ID NO: 294)
NYGMN

DESCRIBES MIN-C9-1 HEAVY CHAIN VARIABLE
COMPLEMENTARITY DETERMINING REGION1 (CDR1)
AMINO ACID SEQUENCE.

(SEQ ID NO: 295)
NNGMN

DESCRIBES MIN-C9-2 HEAVY CHAIN VARIABLE
COMPLEMENTARITY DETERMINING REGION1 (CDR1)
AMINO ACID SEQUENCE.

(SEQ ID NO: 296)
NNGMN

DESCRIBES MIN-D7-1 HEAVY CHAIN VARIABLE
COMPLEMENTARITY DETERMINING REGION1 (CDR1)
AMINO ACID SEQUENCE.

(SEQ ID NO: 297)
NYGMN

DESCRIBES MIN-D7-2 HEAVY CHAIN VARIABLE
COMPLEMENTARITY DETERMINING REGION1 (CDR1)
AMINO ACID SEQUENCE.

(SEQ ID NO: 298)
NYGMN

DESCRIBES MIN-F2-1 HEAVY CHAIN VARIABLE
COMPLEMENTARITY DETERMINING REGION1 (CDR1)
AMINO ACID SEQUENCE.

(SEQ ID NO: 299)
NYGMN

DESCRIBES MIN-F2-2 HEAVY CHAIN VARIABLE
COMPLEMENTARITY DETERMINING REGION1 (CDR1)
AMINO ACID SEQUENCE.

(SEQ ID NO: 300)
DYEMH

DESCRIBES MIN-F2-3 HEAVY CHAIN VARIABLE
COMPLEMENTARITY DETERMINING REGION1 (CDR1)
AMINO ACID SEQUENCE.

(SEQ ID NO: 301)
NYGMN

DESCRIBES MIN-F2-4 HEAVY CHAIN VARIABLE
COMPLEMENTARITY DETERMINING REGION1 (CDR1)
AMINO ACID SEQUENCE.

(SEQ ID NO: 302)
NYGMN

DESCRIBES MIN-A2-1 HEAVY CHAIN
VARIABLE COMPLEMENTARITY DETERMINING
REGION2 (CDR2) AMINO ACID SEQUENCE.

(SEQ ID NO: 303)
WINTYTGEPTYAGDFKG

DESCRIBES MIN-A2-2 HEAVY CHAIN
VARIABLE COMPLEMENTARITY DETERMINING
REGION2 (CDR2) AMINO ACID SEQUENCE.

(SEQ ID NO: 304)
WINTYTGEPTYAGDFKG

DESCRIBES MIN-C9-1 HEAVY CHAIN
VARIABLE COMPLEMENTARITY DETERMINING
REGION2 (CDR2) AMINO ACID SEQUENCE.

(SEQ ID NO: 305)
WINTYTGEPTYADDFKG

DESCRIBES MIN-C9-2 HEAVY CHAIN
VARIABLE COMPLEMENTARITY DETERMINING
REGION2 (CDR2) AMINO ACID SEQUENCE.

(SEQ ID NO: 306)
WINTYTGEPTYADDFKG

DESCRIBES MIN-D7-1 HEAVY CHAIN
VARIABLE COMPLEMENTARITY DETERMINING
REGION2 (CDR2) AMINO ACID SEQUENCE.

(SEQ ID NO: 307)
WINTYTGEPTYVDDFKG

DESCRIBES MIN-D7-2 HEAVY CHAIN
VARIABLE COMPLEMENTARITY DETERMINING
REGION2 (CDR2) AMINO ACID SEQUENCE.

(SEQ ID NO: 308)
WINTYTGEPTYAGDFKG

DESCRIBES MIN-F2-1 HEAVY CHAIN
VARIABLE COMPLEMENTARITY DETERMINING
REGION2 (CDR2) AMINO ACID SEQUENCE.

(SEQ ID NO: 309)
WINTYTGEPTYVDDFKG

DESCRIBES MIN-F2-2 HEAVY CHAIN
VARIABLE COMPLEMENTARITY DETERMINING
REGION2 (CDR2) AMINO ACID SEQUENCE.

(SEQ ID NO: 310)
AIHPGSGGTAYNQKFKG

DESCRIBES MIN-F2-3 HEAVY CHAIN
VARIABLE COMPLEMENTARITY DETERMINING
REGION2 (CDR2) AMINO ACID SEQUENCE.

(SEQ ID NO: 311)
WINTYTGEPTYVDDFKG

DESCRIBES MIN-F2-4 HEAVY CHAIN
VARIABLE COMPLEMENTARITY DETERMINING
REGION2 (CDR2) AMINO ACID SEQUENCE.

(SEQ ID NO: 312)
WINTYTGEPTYVDDFKG

DESCRIBES MIN-A2-1 HEAVY CHAIN
VARIABLE COMPLEMENTARITY DETERMINING
REGION3 (CDR3) AMINO ACID SEQUENCE.

(SEQ ID NO: 313)
SGDGYWYYA

DESCRIBES MIN-A2-2 HEAVY CHAIN
VARIABLE COMPLEMENTARITY DETERMINING
REGION3 (CDR3) AMINO ACID SEQUENCE.

(SEQ ID NO: 314)
SGDGYWYYA

DESCRIBES MIN-C9-1 HEAVY CHAIN
VARIABLECOMPLEMENTARITY DETERMINING
REGION3 (CDR3) AMINO ACID SEQUENCE.

(SEQ ID NO: 315)
TGTARAFYA

DESCRIBES MIN-C9-2 HEAVY CHAIN
VARIABLECOMPLEMENTARITY DETERMINING
REGION3 (CDR3) AMINO ACID SEQUENCE.

(SEQ ID NO: 316)
TGTARAFYA

DESCRIBES MIN-D7-1 HEAVY CHAIN
VARIABLE COMPLEMENTARITY DETERMINING
REGION3 (CDR3) AMINO ACID SEQUENCE.

(SEQ ID NO: 317)
TGTTAILNG

DESCRIBES MIN-D7-2 HEAVY CHAIN
VARIABLE COMPLEMENTARITY DETERMINING
REGION3 (CDR3) AMINO ACID SEQUENCE.

(SEQ ID NO: 318)
SGDGYWYYA

DESCRIBES MIN-F2-1 HEAVY CHAIN
VARIABLE COMPLEMENTARITY DETERMINING
REGION3 (CDR3) AMINO ACID SEQUENCE.

(SEQ ID NO: 319)
TGTTAILNG

DESCRIBES MIN-F2-2 HEAVY CHAIN
VARIABLE COMPLEMENTARITY DETERMINING
REGION3 (CDR3) AMINO ACID SEQUENCE.

(SEQ ID NO: 320)
YGSFA

DESCRIBES MIN-F2-3 HEAVY CHAIN VARIABLE COMPLEMENTARITY DETERMINING REGION3 (CDR3) AMINO ACID SEQUENCE.

(SEQ ID NO: 321)
TGTTAILNG

DESCRIBES MIN-F2-4 HEAVY CHAIN VARIABLE COMPLEMENTARITY DETERMINING REGION3 (CDR3) AMINO ACID SEQUENCE.

(SEQ ID NO: 322)
TGTTAILNG

DESCRIBES MIN-14 LIGHT CHAIN VARIABLE COMPLEMENTARITY DETERMINING REGION1 (CDR1) AMINO ACID SEQUENCE.

(SEQ ID NO: 323)
RASQDIGSSLN

DESCRIBES MIN-17-1 LIGHT CHAIN VARIABLE COMPLEMENTARITY DETERMINING REGION1 (CDR1) AMINO ACID SEQUENCE.

(SEQ ID NO: 324)
RASKSVSTSGYSYMH

DESCRIBES MIN-17-2 LIGHT CHAIN VARIABLE COMPLEMENTARITY DETERMINING REGION1 (CDR1) AMINO ACID SEQUENCE.

(SEQ ID NO: 325)
LASQTIGTWLA

DESCRIBES MIN-29 LIGHT CHAIN VARIABLE COMPLEMENTARITY DETERMINING REGION1 (CDR1) AMINO ACID SEQUENCE.

(SEQ ID NO: 326)
RASKSVSTSGYSYMH

DESCRIBES MIN-34 LIGHT CHAIN VARIABLE COMPLEMENTARITY DETERMINING REGION1 (CDR1) AMINO ACID SEQUENCE.

(SEQ ID NO: 327)
RASKSVSTSGYSYMH

DESCRIBES MIN-42 LIGHT CHAIN VARIABLE COMPLEMENTARITY DETERMINING REGION1 (CDR1) AMINO ACID SEQUENCE.

(SEQ ID NO: 328)
KASQNVGTNVG

DESCRIBES MIN-45 LIGHT CHAIN VARIABLE COMPLEMENTARITY DETERMINING REGION1 (CDR1) AMINO ACID SEQUENCE.

(SEQ ID NO: 329)
RASGNIHNFLA

DESCRIBES MIN-14 LIGHT CHAIN VARIABLE COMPLEMENTARITY DETERMINING REGION2 (CDR2) AMINO ACID SEQUENCE.

(SEQ ID NO: 330)
ATSSLDS

DESCRIBES MIN-17-1 LIGHT CHAIN VARIABLE COMPLEMENTARITY DETERMINING REGION2 (CDR2) AMINO ACID SEQUENCE.

(SEQ ID NO: 331)
LVSNLES

DESCRIBES MIN-17-2 LIGHT CHAIN VARIABLE COMPLEMENTARITY DETERMINING REGION2 (CDR2) AMINO ACID SEQUENCE.

(SEQ ID NO: 332)
AATSLAD

DESCRIBES MIN-29 LIGHT CHAIN VARIABLE COMPLEMENTARITY DETERMINING REGION2 (CDR2) AMINO ACID SEQUENCE.

(SEQ ID NO: 333)
LVSNLES

DESCRIBES MIN-34 LIGHT CHAIN VARIABLE COMPLEMENTARITY DETERMINING REGION2 (CDR2) AMINO ACID SEQUENCE.

(SEQ ID NO: 334)
LVSNLES

DESCRIBES MIN-42 LIGHT CHAIN VARIABLE COMPLEMENTARITY DETERMINING REGION2 (CDR2) AMINO ACID SEQUENCE.

(SEQ ID NO: 335)
SASYRYS

DESCRIBES MIN-45 LIGHT CHAIN VARIABLE COMPLEMENTARITY DETERMINING REGION2 (CDR2) AMINO ACID SEQUENCE.

(SEQ ID NO: 336)
NAKTLAD

DESCRIBES MIN-14 HEAVY CHAIN COMPLEMENTARITY DETERMINING REGION1 (CDR1) AMINO ACID SEQUENCE.

(SEQ ID NO: 337)
SYWMH

DESCRIBES MIN-17-1 HEAVY CHAIN COMPLEMENTARITY DETERMINING REGION1 (CDR1) AMINO ACID SEQUENCE.

(SEQ ID NO: 338)
SYWMH

DESCRIBES MIN-17-2 HEAVY CHAIN COMPLEMENTARITY DETERMINING REGION1 (CDR1) AMINO ACID SEQUENCE.

(SEQ ID NO: 339)
GIGVT

DESCRIBES MIN-34 HEAVY CHAIN COMPLEMENTARITY DETERMINING REGION1 (CDR1) AMINO ACID SEQUENCE.

(SEQ ID NO: 340)
SYGVH

DESCRIBES MIN-42 HEAVY CHAIN COMPLEMENTARITY DETERMINING REGION1 (CDR1) AMINO ACID SEQUENCE.

(SEQ ID NO: 341)
SFGMS

DESCRIBES MIN-45 HEAVY CHAIN COMPLEMENTARITY DETERMINING REGION1 (CDR1) AMINO ACID SEQUENCE.

(SEQ ID NO: 342)
GYFMS

DESCRIBES MIN-14 HEAVY CHAIN COMPLEMENTARITY DETERMINING REGION2 (CDR2) AMINO ACID SEQUENCE.

(SEQ ID NO: 343)
EINPSNGRTNYNEKFKS

DESCRIBES MIN-17-1 HEAVY CHAIN COMPLEMENTARITY DETERMINING REGION2 (CDR2) AMINO ACID SEQUENCE.

(SEQ ID NO: 344)
EINPSNGRTNYNEKFKS

DESCRIBES MIN-17-2 HEAVY CHAIN COMPLEMENTARITY DETERMINING REGION2 (CDR2) AMINO ACID SEQUENCE.

(SEQ ID NO: 345)
TIWWDDDNRYNPSLKS

DESCRIBES MIN-29 HEAVY CHAIN COMPLEMENTARITY DETERMINING REGION2 (CDR2) AMINO ACID SEQUENCE.

(SEQ ID NO: 346)
GIVSGDGESALHSVWIVG

DESCRIBES MIN-34 HEAVY CHAIN
COMPLEMENTARITY DETERMINING REGION2
(CDR2) AMINO ACID SEQUENCE.
(SEQ ID NO: 347)
VIWGGGSTDYNAAFIS

DESCRIBES MIN-42 HEAVY CHAIN
COMPLEMENTARITY DETERMINING REGION2
(CDR2) AMINO ACID SEQUENCE.
(SEQ ID NO: 348)
TISSGGTYTYYPDSVKG

DESCRIBES MIN-45 HEAVY CHAIN
COMPLEMENTARITY DETERMINING REGION2
(CDR2) AMINO ACID SEQUENCE.
(SEQ ID NO: 349)
RINPYNGDTFYNQKFKG

HUMANIZED E6 HEAVY CHAIN VARIABLE
REGION SEQUENCE:
(SEQ ID NO: 350)
EVQLVESGGGLVKPGGSLRLSCAASGFTFSRYGMSWVRQAPGKRLEWVST
ISGGGTYIYYPDSVKGRFTISRDNAKNTLYLQMNSLRAEDTAVYYCTRDN
YGRNYDYGMDYWGQGTLVTVSS

HUMANIZED E6 HEAVY CHAIN VARIABLE
COMPLEMENTARITY DETERMINING REGIONS
1 (CDR1) SEQUENCE:
(SEQ ID NO: 351)
RYGMS

HUMANIZED E6 HEAVY CHAIN VARIABLE
COMPLEMENTARITY DETERMINING REGIONS
2 (CDR2) SEQUENCE:
(SEQ ID NO: 352)
TISGGGTYIYYPDSVKG

HUMANIZED E6 HEAVY CHAIN VARIABLE
COMPLEMENTARITY DETERMINING REGIONS
3 (CDR3) SEQUENCE:
(SEQ ID NO: 353)
DNYGRNYDYGMDY

HUMANIZED E6 LIGHT CHAIN VARIABLE
REGION SEQUENCE:
(SEQ ID NO: 354)
EIVLTQSPATLSLSPGERATLTCSATSSVSYIHWYQQRPGQSPRLLIYST
SNLASGIPARFSGSGSGSDYTLTISSLEPEDFAVYYCQQRSSSPFTFGSG
TKVEIK

HUMANIZED E6 LIGHT CHAIN VARIABLE
COMPLEMENTARITY DETERMINING REGIONS
1 (CDR1) SEQUENCE:
(SEQ ID NO: 355)
SATSSVSYIH

HUMANIZED E6 LIGHT CHAIN VARIABLE
COMPLEMENTARITY DETERMINING REGIONS
2 (CDR2) SEQUENCE:
(SEQ ID NO: 356)
STSNLAS

HUMANIZED E6 LIGHT CHAIN VARIABLE
COMPLEMENTARITY DETERMINING REGIONS
3 (CDR3) SEQUENCE:
(SEQ ID NO: 357)
QQRSSSPFT

HUMANIZED C2 HEAVY CHAIN VARIABLE
REGION SEQUENCE:
(SEQ ID NO: 358)
EVQLVESGGGLVKPGGSLRLSCAASGFTFSGYAMSWVRQAPGKGLEWVST
ISSGGTYIYYPDSVKGRFTISRDNAKNSLYLQMNSLRAEDTAVYYCARLG
GDNYYEYFDVWGKGTTVTVSS

HUMANIZED C2 HEAVY CHAIN VARIABLE
COMPLEMENTARITY DETERMINING REGIONS
1 (CDR1) SEQUENCE:
(SEQ ID NO: 359)
GYAMS

HUMANIZED C2 HEAVY CHAIN VARIABLE
COMPLEMENTARITY DETERMINING REGIONS
2 (CDR2) SEQUENCE:
(SEQ ID NO: 360)
TISSGGTYIYYPDSVKG

HUMANIZED C2 HEAVY CHAIN VARIABLE
COMPLEMENTARITY DETERMINING REGIONS
3 (CDR3) SEQUENCE:
(SEQ ID NO: 361)
LGGDNYYEYFDV

HUMANIZED C2 LIGHT CHAIN VARIABLE
REGION SEQUENCE:
(SEQ ID NO: 362)
DIVLTQSPASLAVSPGQRATITCRASKSVSTSGYSYMHWYQQKPGQPPKL
LIYLASNLESGVPARFSGSGSGTDFTLTINPVEANDTANYYCQHSRELPF
TFGGGTKVEIKRT

HUMANIZED C2 LIGHT CHAIN VARIABLE
COMPLEMENTARITY DETERMINING REGIONS
1 (CDR1) SEQUENCE:
(SEQ ID NO: 363)
RASKSVSTSGYSYMH

HUMANIZED C2 LIGHT CHAIN VARIABLE
COMPLEMENTARITY DETERMINING REGIONS
2 (CDR2) SEQUENCE:
(SEQ ID NO: 364)
LASNLES

HUMANIZED C2 LIGHT CHAIN VARIABLE
COMPLEMENTARITY DETERMINING REGIONS
3 (CDR3) SEQUENCE:
(SEQ ID NO: 365)
QHSRELPFT

HUMANIZED C2 LIGHT CHAIN VARIABLE
COMPLEMENTARITY DETERMINING REGIONS
3 (CDR3) SEQUENCE:
(SEQ ID NO: 366)
LQSKNFPPT

PSECTAG2C2SCFV-FC
(SEQ ID NO: 367)
METDTLLLWVLLLWVPGSTGDAAQPAEVQLVESGGGLVKPGGSLRLSCAA
SGFTFSGYAMSWVRQAPGKGLEWVSTISSGGTYIYYPDSVKGRFTISRDN
AKNSLYLQMNSLRAEDTAVYYCARLGGDNYYEYFDVWGKGTTVTVSSGGG
GSGGGGSGGGGSDIVLTQSPASLAVSPGQRATITCRASKSVSTSGYSYMH
WYQQKPGQPPKLLIYLASNLESGVPARFSGSGSGTDFTLTINPVEANDTA
NYYCQHSRELPFTFGGGTKVEIKRTEPKSCDKTHTCPPCPAPELLGGPSV
FLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKS
LSLSPGK**

PSECTAG2E6SCFV-FC
(SEQ ID NO: 368)
METDTLLLWVLLLWVPGSTGDAAQPAEVQLVESGGGLVKPGGSLRLSCAA
SGFTFSRYGMSWVRQAPGKRLEWVSTISGGGTYIYYPDSVKGRFTISRDN
AKNTLYLQMNSLRAEDTAVYYCTRDNYGRNYDYGMDYWGQGTLVTVSSGG
GGSGGGGSGGGGSEIVLTQSPATLSLSPGERATLTCSATSSVSYIHWYQQ
RPGQSPRLLIYSTSNLASGIPARFSGSGSGSDYTLTISSLEPEDFAVYYC

QQRSSSPFTFGSGTKVEIKEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K**

HUMANIZED C2SCFV (VH-VL) SEQUENCE:
(SEQ ID NO: 369)
EVQLVESGGGLVKPGGSLRLSCAASGFTFSGYAMSWVRQAPGKGLEWVST

ISSGGTYIYYPDSVKGRFTISRDNAKNSLYLQMNSLRAEDTAVYYCARLG

GDNYYEYFDVWGKGTTVTVSSGGGGSGGGGSGGGGSDIVLTQSPASLAVS

PGQRATITCRASKSVSTSGYSYMHWYQQKPGQPPKLLIYLASNLESGVPA

RFSGSGSGTDFTLTINPVEANDTANYYCQHSRELPFTFGGGTKVEIKRT

HUMANIZED E6SCFV (VL-VH) SEQUENCE:
(SEQ ID NO: 370)
DIVLTQSPASLAVSPGQRATITCRASKSVSTSGYSYMHWYQQKPGQPPKL

LIYLASNLESGVPARFSGSGSGTDFTLTINPVEANDTANYYCQHSRELPF

TFGGGTKVEIKRTGGGGSGGGGSGGGGSEVQLVESGGGLVKPGGSLRLSC

AASGFTFSGYAMSWVRQAPGKGLEWVSTISSGGTYIYYPDSVKGRFTISR

DNAKNSLYLQMNSLRAEDTAVYYCARLGGDNYYEYFDVWGKGTTVTVSS

HUMANIZED C3 HEAVY CHAIN VARIABLE
REGION SEQUENCE:
(SEQ ID NO: 371)
QVQLVQSGAEVKKPGASVKVSCKASGYTFTDYAMNWVRQAPGQGLEWMGV

ISTFSGNTNFNQKFKGRVTMTTDTSTSTAYMELRSLRSDDTAVYYCARSD

YYGPYFDYWGQGTTLTVSS

HUMANIZED C3 HEAVY CHAIN VARIABLE
COMPLEMENTARITY DETERMINING REGIONS
1 (CDR1) SEQUENCE:
(SEQ ID NO: 372)
DYAMN

HUMANIZED C3 HEAVY CHAIN VARIABLE
COMPLEMENTARITY DETERMINING REGIONS
2 (CDR2) SEQUENCE:
(SEQ ID NO: 373)
VISTFSGNTNFNQKFKG

HUMANIZED C3 HEAVY CHAIN VARIABLE
COMPLEMENTARITY DETERMINING REGIONS
3 (CDR3) SEQUENCE:
(SEQ ID NO: 374)
SDYYGPYFDY

HUMANIZED C3 LIGHT CHAIN VARIABLE
REGION SEQUENCE:
(SEQ ID NO: 375)
DIVMTQTPLSLSVTPGQPASISCRSSQTIVHSNGNTYLEWYLQKPGQSPQ

LLIYKVSNRFSGVPDRFSGSGSGTDFTLKISRVEAEDVGVYYCFQGSHVP

FTFGGGTKVEIKRT

HUMANIZED C3 LIGHT CHAIN VARIABLE
COMPLEMENTARITY DETERMINING REGIONS
1 (CDR1) SEQUENCE:
(SEQ ID NO: 376)
RSSQTIVHSNGNTYLE

HUMANIZED C3 LIGHT CHAIN VARIABLE
COMPLEMENTARITY DETERMINING REGIONS
2 (CDR2) SEQUENCE:
(SEQ ID NO: 377)
KVSNRFS

HUMANIZED C3 LIGHT CHAIN VARIABLE
COMPLEMENTARITY DETERMINING REGIONS
3 (CDR3) SEQUENCE:
(SEQ ID NO: 378)
FQGSHVPFT

HUMANIZED C8 HEAVY CHAIN VARIABLE
REGION SEQUENCE:
(SEQ ID NO: 379)
EVQLVESGGGLVKPGGSLRLSCAASGFTFSGYAMSWVRQAPGKGLEWVST

ISSGGTYIYYPDSVKGRFTISRDNAKNSLYLQMNSLRAEDTAVYYCARLG

GDNYYEYWGKGTTVTVSS

HUMANIZED C8 HEAVY CHAIN VARIABLE
COMPLEMENTARITY DETERMINING REGION1
(CDR1) SEQUENCE:
(SEQ ID NO: 380)
GYAMS

HUMANIZED C8 HEAVY CHAIN VARIABLE
COMPLEMENTARITY DETERMINING REGION2
(CDR2) SEQUENCE:
(SEQ ID NO: 381)
TISSGGTYIYYPDSVKG

HUMANIZED C8 HEAVY CHAIN VARIABLE
COMPLEMENTARITY DETERMINING REGION3
(CDR3) SEQUENCE:
(SEQ ID NO: 382)
LGGDNYYEY

HUMANIZED C8 LIGHT CHAIN VARIABLE
REGION SEQUENCE
(SEQ ID NO: 383)
DIVMTQSPDSLAVSLGERATINCRASKSVSTSGYSYMHWYQQKPGQPPKL

LIYLVSNLESGVPDRFSGSGSGTDFTLTISSLQAEDVAVYYCQHIRELTR

SEFGGGTKVEIKRT

HUMANIZED C8 LIGHT CHAIN VARIABLE
COMPLEMENTARITY DETERMINING REGION1
(CDR1) SEQUENCE:
(SEQ ID NO: 384)
RASKSVSTSGYSYM

HUMANIZED C8 LIGHT CHAIN VARIABLE
COMPLEMENTARITY DETERMINING REGION2
(CDR2) SEQUENCE:
(SEQ ID NO: 385)
LVSNLES

HUMANIZED C8 LIGHT CHAIN VARIABLE
COMPLEMENTARITY DETERMINING REGION3
(CDR3) SEQUENCE:
(SEQ ID NO: 386)
QHIRELTRSE

All of the references cited herein are incorporated by reference in their entirety.

Those skilled in the art will recognize, or be able to ascertain using no more than routine experimentation, many equivalents to the specific embodiments of the invention specifically described herein.

What is claimed is:

1. An antibody or antibody fragment that binds to PSMGFR peptide as set forth in SEQ ID NO: 4, wherein the antibody or antibody fragment comprises three heavy chain (HC) complementarity determining regions (CDR) and three light chain (LC) CDRs, wherein:
   HC-CDR1 comprises SEQ ID NO: 96,
   HC-CDR2 comprises SEQ ID NO: 98,
   HC-CDR2 comprises SEQ ID NO: 100,
   LC-CDR1 comprises SEQ ID NO: 102,
   LC-CDR2 comprises SEQ ID NO: 104, AND
   LC-CDR2 comprises SEQ ID NO: 106.

2. A compound comprising the antibody or antibody fragment of claim 1 attached to an imaging agent, a dye, a fluorescent entity, a color producing reagent or any other entity that renders the antibody or antibody fragment optically, visually, electrically or radioactively detectable.

3. The antibody or antibody fragment of claim 1, wherein the antibody or antibody fragment is human or humanized.

4. A method of diagnosing cancer comprising contacting cells or tissue of a subject with the antibody or antibody fragment of claim 1.

5. The method of claim 4, wherein the contacting is carried out in vitro.

6. The method of claim 4, wherein the contacting is carried out in vivo.

7. The method of claim 4, further comprising:
   detecting presence of the antibody or antibody fragment bound to the cells or tissue;
   comparing an amount or pattern of the antibody or antibody fragment binding to the cells or tissue to an amount or pattern of the antibody or antibody fragment binding to normal cells or tissue; and
   determining that:
      the amount of the antibody or antibody fragment binding to the cells or tissue of the subject is greater than the amount of the antibody or antibody fragment binding to the normal cells or tissue, or
      the pattern of the antibody or antibody fragment binding to the cells or tissue of the subject is not restricted to an apical border of the cells or tissue; and
   concluding that the subject is suffering from a MUC1 * positive cancer.

8. A method of determining suitability of treating a patient suffering from cancer or metastasis of cancer with a MUC1* targeting therapeutic agent, comprising:
   contacting cells or tissue of the patient a compound comprising the antibody or antibody fragment of claim 1,
   wherein specific binding of the antibody or antibody fragment to the cells or tissue indicates that the MUC1* targeting therapeutic agent is suitable for treating the patient.

9. The method of claim 8, wherein the MUC1* targeting therapeutic agent comprises the antibody or antibody fragment of claim 1.

10. The method of claim 8, wherein the MUC1* targeting therapeutic agent comprises a cancer immunotherapy agent.

11. The method of claim 8, wherein the MUC1* targeting therapeutic agent comprises in a CAR T cell.

12. The method of claim 8, wherein the MUC1* targeting therapeutic agent comprises in a bispecific T cell engager (BiTE).

13. The method of claim 8, wherein the MUC1* targeting therapeutic agent comprises in an antibody drug conjugate (ADC).

14. A chimeric antigen receptor (CAR) comprising the antibody or antibody fragment of claim 1.

15. An immune cell comprising the CAR of claim 14.

16. A T cell comprising the CAR of claim 14.

17. A bispecific T cell engager comprising the antibody or antibody fragment of claim 1.

18. An antibody drug conjugate (ADC) comprising the antibody or antibody fragment of claim 1.

* * * * *

SEQUENCE LISTING

<160> NUMBER OF SEQ ID NOS: 386

<210> SEQ ID NO 1
<211> LENGTH: 1255
<212> TYPE: PRT
<213> ORGANISM: Artificial Sequence
<220> FEATURE:
<223> OTHER INFORMATION: Full-length MUC1 Receptor (Mucin 1 precursor,
      Genbank Accession number: P15941

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

```
Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
        450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
        530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
        610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
        690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
```

```
              770             775             780
Arg Pro Ala Pro Gly Ser Thr Ala Pro Pro Ala His Gly Val Thr Ser
785             790             795             800

Ala Pro Asp Thr Arg Pro Ala Pro Gly Ser Thr Ala Pro Pro Ala His
            805             810             815

Gly Val Thr Ser Ala Pro Asp Thr Arg Pro Ala Pro Gly Ser Thr Ala
            820             825             830

Pro Pro Ala His Gly Val Thr Ser Ala Pro Asp Thr Arg Pro Ala Pro
            835             840             845

Gly Ser Thr Ala Pro Pro Ala His Gly Val Thr Ser Ala Pro Asp Thr
850             855             860

Arg Pro Ala Pro Gly Ser Thr Ala Pro Pro Ala His Gly Val Thr Ser
865             870             875             880

Ala Pro Asp Thr Arg Pro Ala Pro Gly Ser Thr Ala Pro Pro Ala His
            885             890             895

Gly Val Thr Ser Ala Pro Asp Thr Arg Pro Ala Pro Gly Ser Thr Ala
            900             905             910

Pro Pro Ala His Gly Val Thr Ser Ala Pro Asp Thr Arg Pro Ala Pro
            915             920             925

Gly Ser Thr Ala Pro Pro Ala His Gly Val Thr Ser Ala Pro Asp Asn
930             935             940

Arg Pro Ala Leu Gly Ser Thr Ala Pro Val His Asn Val Thr Ser
945             950             955             960

Ala Ser Gly Ser Ala Ser Gly Ser Ala Ser Thr Leu Val His Asn Gly
            965             970             975

Thr Ser Ala Arg Ala Thr Thr Thr Pro Ala Ser Lys Ser Thr Pro Phe
            980             985             990

Ser Ile Pro Ser His His Ser Asp Thr Pro Thr Thr Leu Ala Ser His
            995             1000            1005

Ser Thr Lys Thr Asp Ala Ser Ser Thr His His Ser Ser Val Pro
    1010            1015            1020

Pro Leu Thr Ser Ser Asn His Ser Thr Ser Pro Gln Leu Ser Thr
    1025            1030            1035

Gly Val Ser Phe Phe Phe Leu Ser Phe His Ile Ser Asn Leu Gln
    1040            1045            1050

Phe Asn Ser Ser Leu Glu Asp Pro Ser Thr Asp Tyr Tyr Gln Glu
    1055            1060            1065

Leu Gln Arg Asp Ile Ser Glu Met Phe Leu Gln Ile Tyr Lys Gln
    1070            1075            1080

Gly Gly Phe Leu Gly Leu Ser Asn Ile Lys Phe Arg Pro Gly Ser
    1085            1090            1095

Val Val Val Gln Leu Thr Leu Ala Phe Arg Glu Gly Thr Ile Asn
    1100            1105            1110

Val His Asp Val Glu Thr Gln Phe Asn Gln Tyr Lys Thr Glu Ala
    1115            1120            1125

Ala Ser Arg Tyr Asn Leu Thr Ile Ser Asp Val Ser Val Ser Asp
    1130            1135            1140

Val Pro Phe Pro Phe Ser Ala Gln Ser Gly Ala Gly Val Pro Gly
    1145            1150            1155

Trp Gly Ile Ala Leu Leu Val Leu Val Cys Val Leu Val Ala Leu
    1160            1165            1170

Ala Ile Val Tyr Leu Ile Ala Leu Ala Val Cys Gln Cys Arg Arg
    1175            1180            1185
```

```
Lys Asn Tyr Gly Gln Leu Asp Ile Phe Pro Ala Arg Asp Thr Tyr
    1190             1195                 1200

His Pro Met Ser Glu Tyr Pro Thr Tyr His Thr His Gly Arg Tyr
    1205             1210                 1215

Val Pro Pro Ser Ser Thr Asp Arg Ser Pro Tyr Glu Lys Val Ser
    1220             1225                 1230

Ala Gly Asn Gly Gly Ser Ser Leu Ser Tyr Thr Asn Pro Ala Val
    1235             1240                 1245

Ala Ala Ala Ser Ala Asn Leu
    1250             1255

<210> SEQ ID NO 2
<211> LENGTH: 171
<212> TYPE: PRT
<213> ORGANISM: Artificial Sequence
<220> FEATURE:
<223> OTHER INFORMATION: A truncated MUC1 receptor isoform having
      nat-PSMGFR and PSIBR at its N-terminus and including the
      transmembrane and cytoplasmic sequences of a full-length MUC1
      receptor which may be cleaved after translation and prior to
      expression of the receptor on the

<400> SEQUENCE: 2

Gly Phe Leu Gly Leu Ser Asn Ile Lys Phe Arg Pro Gly Ser Val Val
1               5                   10                  15

Val Gln Leu Thr Leu Ala Phe Arg Glu Gly Thr Ile Asn Val His Asp
                20                  25                  30

Val Glu Thr Gln Phe Asn Gln Tyr Lys Thr Glu Ala Ala Ser Arg Tyr
            35                  40                  45

Asn Leu Thr Ile Ser Asp Val Ser Val Ser Asp Val Pro Phe Pro Phe
50                  55                  60

Ser Ala Gln Ser Gly Ala Gly Val Pro Gly Trp Gly Ile Ala Leu Leu
65                  70                  75                  80

Val Leu Val Cys Val Leu Val Ala Leu Ala Ile Val Tyr Leu Ile Ala
                85                  90                  95

Leu Ala Val Cys Gln Cys Arg Arg Lys Asn Tyr Gly Gln Leu Asp Ile
                100                 105                 110

Phe Pro Ala Arg Asp Thr Tyr His Pro Met Ser Glu Tyr Pro Thr Tyr
            115                 120                 125

His Thr His Gly Arg Tyr Val Pro Pro Ser Ser Thr Asp Arg Ser Pro
130                 135                 140

Tyr Glu Lys Val Ser Ala Gly Asn Gly Gly Ser Ser Leu Ser Tyr Thr
145                 150                 155                 160

Asn Pro Ala Val Ala Ala Ala Ser Ala Asn Leu
                165                 170

<210> SEQ ID NO 3
<211> LENGTH: 275
<212> TYPE: PRT
<213> ORGANISM: Artificial Sequence
<220> FEATURE:
<223> OTHER INFORMATION: A truncated MUC1 receptor isoform having
      nat-PSMGFR + PSIBR + Unique Region at its N-terminus and including
      the transmembrane and cytoplasmic sequences of a full-length MUC1
      receptor

<400> SEQUENCE: 3

Ala Thr Thr Thr Pro Ala Ser Lys Ser Thr Pro Phe Ser Ile Pro Ser
1               5                   10                  15
```

```
His His Ser Asp Thr Pro Thr Thr Leu Ala Ser His Ser Thr Lys Thr
             20                  25                  30

Asp Ala Ser Ser Thr His Ser Thr Val Pro Pro Leu Thr Ser Ser
         35                  40                  45

Asn His Ser Thr Ser Pro Gln Leu Ser Thr Gly Val Ser Phe Phe Phe
 50                  55                  60

Leu Ser Phe His Ile Ser Asn Leu Gln Phe Asn Ser Ser Leu Glu Asp
 65                  70                  75                  80

Pro Ser Thr Asp Tyr Tyr Gln Glu Leu Gln Arg Asp Ile Ser Glu Met
                 85                  90                  95

Phe Leu Gln Ile Tyr Lys Gln Gly Phe Leu Gly Leu Ser Asn Ile
                100                 105                 110

Lys Phe Arg Pro Gly Ser Val Val Gln Leu Thr Leu Ala Phe Arg
             115                 120                 125

Glu Gly Thr Ile Asn Val His Asp Val Glu Thr Gln Phe Asn Gln Tyr
             130                 135                 140

Lys Thr Glu Ala Ala Ser Arg Tyr Asn Leu Thr Ile Ser Asp Val Ser
145                 150                 155                 160

Val Ser Asp Val Pro Phe Pro Phe Ser Ala Gln Ser Gly Ala Gly Val
                 165                 170                 175

Pro Gly Trp Gly Ile Ala Leu Leu Val Leu Val Cys Val Leu Val Ala
             180                 185                 190

Leu Ala Ile Val Tyr Leu Ile Ala Leu Ala Val Cys Gln Cys Arg Arg
             195                 200                 205

Lys Asn Tyr Gly Gln Leu Asp Ile Phe Pro Ala Arg Asp Thr Tyr His
210                 215                 220

Pro Met Ser Glu Tyr Pro Thr Tyr His Thr His Gly Arg Tyr Val Pro
225                 230                 235                 240

Pro Ser Ser Thr Asp Arg Ser Pro Tyr Glu Lys Val Ser Ala Gly Asn
                 245                 250                 255

Gly Gly Ser Ser Leu Ser Tyr Thr Asn Pro Ala Val Ala Ala Ala Ser
             260                 265                 270

Ala Asn Leu
     275

<210> SEQ ID NO 4
<211> LENGTH: 45
<212> TYPE: PRT
<213> ORGANISM: Artificial Sequence
<220> FEATURE:
<223> OTHER INFORMATION: PSMGFR

<400> SEQUENCE: 4

Gly Thr Ile Asn Val His Asp Val Glu Thr Gln Phe Asn Gln Tyr Lys
 1               5                  10                  15

Thr Glu Ala Ala Ser Arg Tyr Asn Leu Thr Ile Ser Asp Val Ser Val
                 20                  25                  30

Ser Asp Val Pro Phe Pro Phe Ser Ala Gln Ser Gly Ala
             35                  40                  45

<210> SEQ ID NO 5
<211> LENGTH: 43
<212> TYPE: PRT
<213> ORGANISM: Artificial Sequence
<220> FEATURE:
<223> OTHER INFORMATION: PSMGFR N+20/C-22

<400> SEQUENCE: 5
```

Ser Asn Ile Lys Phe Arg Pro Gly Ser Val Val Gln Leu Thr Leu
1               5                   10                  15

Ala Phe Arg Glu Gly Thr Ile Asn Val His Asp Val Glu Thr Gln Phe
                20                  25                  30

Asn Gln Tyr Lys Thr Glu Ala Ala Ser Arg Tyr
        35                  40

<210> SEQ ID NO 6
<211> LENGTH: 35
<212> TYPE: PRT
<213> ORGANISM: Artificial Sequence
<220> FEATURE:
<223> OTHER INFORMATION: PSMGFR N+12/C-22

<400> SEQUENCE: 6

Ser Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
                20                  25                  30

Ser Arg Tyr
        35

<210> SEQ ID NO 7
<211> LENGTH: 24
<212> TYPE: PRT
<213> ORGANISM: Artificial Sequence
<220> FEATURE:
<223> OTHER INFORMATION: PSMGFR N+9/C-30

<400> SEQUENCE: 7

Val Gln Leu Thr Leu Ala Phe Arg Glu Gly Thr Ile Asn Val His Asp
1               5                   10                  15

Val Glu Thr Gln Phe Asn Gln Tyr
                20

<210> SEQ ID NO 8
<211> LENGTH: 24
<212> TYPE: PRT
<213> ORGANISM: Artificial Sequence
<220> FEATURE:
<223> OTHER INFORMATION: PSMGFR N+20/C-41

<400> SEQUENCE: 8

Ser Asn Ile Lys Phe Arg Pro Gly Ser Val Val Gln Leu Thr Leu
1               5                   10                  15

Ala Phe Arg Glu Gly Thr Ile Asn
                20

<210> SEQ ID NO 9
<211> LENGTH: 38
<212> TYPE: PRT
<213> ORGANISM: Artificial Sequence
<220> FEATURE:
<223> OTHER INFORMATION: PSMGFR N+20/C-27

<400> SEQUENCE: 9

Ser Asn Ile Lys Phe Arg Pro Gly Ser Val Val Gln Leu Thr Leu
1               5                   10                  15

Ala Phe Arg Glu Gly Thr Ile Asn Val His Asp Val Glu Thr Gln Phe
                20                  25                  30

Asn Gln Tyr Lys Thr Glu
        35

<210> SEQ ID NO 10
<211> LENGTH: 45
<212> TYPE: PRT
<213> ORGANISM: Artificial Sequence
<220> FEATURE:
<223> OTHER INFORMATION: PSMGFR N+9/C-9

<400> SEQUENCE: 10

Val Gln Leu Thr Leu Ala Phe Arg Glu Gly Thr Ile Asn Val His Asp
1               5                   10                  15

Val Glu Thr Gln Phe Asn Gln Tyr Lys Thr Glu Ala Ala Ser Arg Tyr
            20                  25                  30

Asn Leu Thr Ile Ser Asp Val Ser Val Ser Asp Val Pro
        35                  40                  45

<210> SEQ ID NO 11
<211> LENGTH: 426
<212> TYPE: DNA
<213> ORGANISM: Artificial Sequence
<220> FEATURE:
<223> OTHER INFORMATION: Antibody 17H6 Heavy chain - Signal
      sequence-FR1-CDR1-FR2-CDR2-FR3-CDR3-FR4

<400> SEQUENCE: 11
atgaagttgt ggctgaactg gattttcctt gtaacacttt taaatggtat ccagtgtgag    60
gtgaagctgg tggagtctgg aggaggcttg gtacagcctg ggggttctct gagactctcc   120
tgtgcaactt ctgggttcac cttcactgat tactacatga gctgggtccg ccagcctcca   180
agaaaggcac ttgagtggtt gggttttatt agaaacaaag ctaatggtta cacagcagag   240
tacagtgcgt ctgtgaaggg tcggttcacc atctccagag atgtttccca aaacctcctc   300
tatcttcaaa tgaacatcct gagagctgag gacagtgcca ttattactg tgcaaaagat    360 tactacggta gtaaccctgc ctggtttgct tactggggcc aagggactct ggtcactgtc    420
tctgca                                                              426

<210> SEQ ID NO 12
<211> LENGTH: 142
<212> TYPE: PRT
<213> ORGANISM: Artificial Sequence
<220> FEATURE:
<223> OTHER INFORMATION: Antibody 17H6 Heavy chain - Signal
      peptide-FR1-CDR1-FR2-CDR2-FR3-CDR3-FR4

<400> SEQUENCE: 12

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Arg Lys Ala Leu
    50                  55                  60

Glu Trp Leu Gly Phe Ile Arg Asn Lys Ala Asn Gly Tyr Thr Ala Glu
65                  70                  75                  80

Tyr Ser Ala Ser Val Lys Gly Arg Phe Thr Ile Ser Arg Asp Val Ser
                85                  90                  95

Gln Asn Leu Leu Tyr Leu Gln Met Asn Ile Leu Arg Ala Glu Asp Ser
            100                 105                 110

```
Ala Thr Tyr Tyr Cys Ala Lys Asp Tyr Tyr Gly Ser Asn Pro Ala Trp
        115                 120                 125

Phe Ala Tyr Trp Gly Gln Gly Thr Leu Val Thr Val Ser Ala
        130                 135                 140
```

<210> SEQ ID NO 13
<211> LENGTH: 393
<212> TYPE: DNA
<213> ORGANISM: Artificial Sequence
<220> FEATURE:
<223> OTHER INFORMATION: Antibody 17H6 Light chain - Signal
      sequence-FR1-CDR1-FR2-CDR2-FR3-CDR3-FR4

<400> SEQUENCE: 13

```
atgaagttgc ctgtgaggct gttggtgctg atgttctgga ttcctgcttc caacagtgat      60
attttgatga cccagactcc actctccctg cctgtcagtc ttggagatca agcctccatc     120
tcttgcagat ctagtcagag cattgtacat agtagtggaa acacctttt  agaatggtac     180
ctgcagaaac ctggccagtc tccaaagctc ctgatctaca aagtttccaa ccgattttct     240
ggggtcccag acaggttcag tggcagtgga tcagggatag atttcacact caagatcagc     300
agagtggagg ctgaggatct gggagtttat tactgctttc aaggttcaca tgttcctttc     360
acgttcggct cggggacaaa gttggaaata aaa                                  393
```

<210> SEQ ID NO 14
<211> LENGTH: 131
<212> TYPE: PRT
<213> ORGANISM: Artificial Sequence
<220> FEATURE:
<223> OTHER INFORMATION: Antibody 17H6 Light chain - Signal
      peptide-FR1-CDR1-FR2-CDR2-FR3-CDR3-FR4

<400> SEQUENCE: 14

```
Met Lys Leu Pro Val Arg Leu Val Leu Met Phe Trp Ile Pro Ala
1               5                   10                  15

Ser Asn Ser Asp Ile Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Ser Gly Asn Thr Phe Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Ile Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys
        130
```

<210> SEQ ID NO 15
<211> LENGTH: 15
<212> TYPE: DNA
<213> ORGANISM: Artificial Sequence
<220> FEATURE:
<223> OTHER INFORMATION: Antibody 17H6 Heavy Chain CDR1

<400> SEQUENCE: 15

```
gattactaca tgagc                                              15
```

<210> SEQ ID NO 16
<211> LENGTH: 5
<212> TYPE: PRT
<213> ORGANISM: Artificial Sequence
<220> FEATURE:
<223> OTHER INFORMATION: Antibody 17H6 Heavy Chain CDR1

<400> SEQUENCE: 16

Asp Tyr Tyr Met Ser
1               5

<210> SEQ ID NO 17
<211> LENGTH: 57
<212> TYPE: DNA
<213> ORGANISM: Artificial Sequence
<220> FEATURE:
<223> OTHER INFORMATION: Antibody 17H6 Heavy Chain CDR2

<400> SEQUENCE: 17

```
tttattagaa acaaagctaa tggttacaca gcagagtaca gtgcgtctgt gaagggt    57
```

<210> SEQ ID NO 18
<211> LENGTH: 19
<212> TYPE: PRT
<213> ORGANISM: Artificial Sequence
<220> FEATURE:
<223> OTHER INFORMATION: Antibody 17H6 Heavy Chain CDR

<400> SEQUENCE: 18

Phe Ile Arg Asn Lys Ala Asn Gly Tyr Thr Ala Glu Tyr Ser Ala Ser
1               5                   10                  15

Val Lys Gly

<210> SEQ ID NO 19
<211> LENGTH: 36
<212> TYPE: DNA
<213> ORGANISM: Artificial Sequence
<220> FEATURE:
<223> OTHER INFORMATION: Antibody 17H6 Heavy Chain CDR3

<400> SEQUENCE: 19

```
gattactacg gtagtaaccc tgcctggttt gcttac                       36
```

<210> SEQ ID NO 20
<211> LENGTH: 12
<212> TYPE: PRT
<213> ORGANISM: Artificial Sequence
<220> FEATURE:
<223> OTHER INFORMATION: Antibody 17H6 Heavy Chain CDR3

<400> SEQUENCE: 20

Asp Tyr Tyr Gly Ser Asn Pro Ala Trp Phe Ala Tyr
1               5                   10

<210> SEQ ID NO 21
<211> LENGTH: 48
<212> TYPE: DNA
<213> ORGANISM: Artificial Sequence
<220> FEATURE:
<223> OTHER INFORMATION: Antibody 17H6 Light Chain CDR1

<400> SEQUENCE: 21

```
agatctagtc agagcattgt acatagtagt ggaaacacct ttttagaa          48
```

```
<210> SEQ ID NO 22
<211> LENGTH: 16
<212> TYPE: PRT
<213> ORGANISM: Artificial Sequence
<220> FEATURE:
<223> OTHER INFORMATION: Antibody 17H6 Light Chain CDR1

<400> SEQUENCE: 22

Arg Ser Ser Gln Ser Ile Val His Ser Ser Gly Asn Thr Phe Leu Glu
 1               5                   10                  15

<210> SEQ ID NO 23
<211> LENGTH: 21
<212> TYPE: DNA
<213> ORGANISM: Artificial Sequence
<220> FEATURE:
<223> OTHER INFORMATION: Antibody 17H6 Light Chain CDR2

<400> SEQUENCE: 23
aaagtttcca accgattttc t                                           21

<210> SEQ ID NO 24
<211> LENGTH: 7
<212> TYPE: PRT
<213> ORGANISM: Artificial Sequence
<220> FEATURE:
<223> OTHER INFORMATION: Antibody 17H6 Light Chain CDR2

<400> SEQUENCE: 24

Lys Val Ser Asn Arg Phe Ser
 1               5

<210> SEQ ID NO 25
<211> LENGTH: 27
<212> TYPE: DNA
<213> ORGANISM: Artificial Sequence
<220> FEATURE:
<223> OTHER INFORMATION: Antibody 17H6 Light Chain CDR3

<400> SEQUENCE: 25
tttcaaggtt cacatgttcc tttcacg                                     27

<210> SEQ ID NO 26
<211> LENGTH: 9
<212> TYPE: PRT
<213> ORGANISM: Artificial Sequence
<220> FEATURE:
<223> OTHER INFORMATION: Antibody 17H6 Light Chain CDR3

<400> SEQUENCE: 26

Phe Gln Gly Ser His Val Pro Phe Thr
 1               5

<210> SEQ ID NO 27
<211> LENGTH: 408
<212> TYPE: DNA
<213> ORGANISM: Artificial Sequence
<220> FEATURE:
<223> OTHER INFORMATION: Antibody 39H5 Heavy chain - Signal
      sequence-FR1-CDR1-FR2-CDR2-FR3-CDR3-FR4

<400> SEQUENCE: 27
atggcttggg tgtggacctt gctattcctg atggcagctg cccaaagtgc ccaagcacag    60
atccagttgg tgcagtctgg acctgagctg aagaagcctg agagacagt caagatctcc   120 tgcaaggctt ctgggtatac cttcacaaac tatggaatga actgggtgaa gcaggctcca   180
```

```
ggaaagggtt taaagtggat gggctggata acacctaca ctggagagcc aacatatgtt      240
ggtgacttca agggacggtt tgccttctct ttggagacct ctgccagcac tgcctatttg      300
cagatcaaca acctcaaaaa tgaggacacg gctacatatt tttgtgttag aggtatccac      360
ggctacgtgg actactgggg ccaaggcacc actctcacag tctcctca                  408
```

<210> SEQ ID NO 28
<211> LENGTH: 136
<212> TYPE: PRT
<213> ORGANISM: Artificial Sequence
<220> FEATURE:
<223> OTHER INFORMATION: Antibody 39H5 Heavy chain - Signal
      sequence-FR1-CDR1-FR2-CDR2-FR3-CDR3-FR4

<400> SEQUENCE: 28

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Val
65                  70                  75                  80

Gly Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Arg Gly Ile His Gly Tyr Val Asp Tyr Trp Gly Gln
        115                 120                 125

Gly Thr Thr Leu Thr Val Ser Ser
    130                 135

<210> SEQ ID NO 29
<211> LENGTH: 393
<212> TYPE: DNA
<213> ORGANISM: Artificial Sequence
<220> FEATURE:
<223> OTHER INFORMATION: Antibody 39H5 Light chain - Signal
      sequence-FR1-CDR1-FR2-CDR2-FR3-CDR3-FR4

<400> SEQUENCE: 29

```
atgaagttgc ctgttaggct gttggtgctg atgttctgga ttcctgcttc cagcagtgat       60
gttttgatga cccaaactcc actctccctg cctgtcagtc ttggagatca agcctccatc      120
tcttgcagat ctagtcagag cattgtacat agaaatggaa acacctattt gaatggtac       180 ctgcagaaac caggccagtc tccaaagctc ctgatctaca agtttccaa ccgattttct       240 ggggtcccag acaggttcag tggcagtgga tcagggacag atttcacact caagatcagc      300
agagtggagg ctgaggatct gggagtttat tactgctttc aaggttcaca tcttccgtgg      360
acgttcggtg aggcaccaa gctggaaatc aaa                                    393
```

<210> SEQ ID NO 30
<211> LENGTH: 131
<212> TYPE: PRT
<213> ORGANISM: Artificial Sequence
<220> FEATURE:
<223> OTHER INFORMATION: Antibody 39H5 Light chain - Signal sequence-FR1-CDR1-FR2-CDR2-FR3-CDR3-FR4

<400> SEQUENCE: 30

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Arg Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Leu Pro Trp Thr Phe Gly Gly Gly Thr Lys Leu
        115                 120                 125

Glu Ile Lys
    130

<210> SEQ ID NO 31
<211> LENGTH: 15
<212> TYPE: DNA
<213> ORGANISM: Artificial Sequence
<220> FEATURE:
<223> OTHER INFORMATION: Antibody 39H5 Heavy Chain CDR1

<400> SEQUENCE: 31
aactatggaa tgaac                                                    15

<210> SEQ ID NO 32
<211> LENGTH: 5
<212> TYPE: PRT
<213> ORGANISM: Artificial Sequence
<220> FEATURE:
<223> OTHER INFORMATION: Antibody 39H5 Heavy Chain CDR1

<400> SEQUENCE: 32

Asn Tyr Gly Met Asn
1               5

<210> SEQ ID NO 33
<211> LENGTH: 51
<212> TYPE: DNA
<213> ORGANISM: Artificial Sequence
<220> FEATURE:
<223> OTHER INFORMATION: Antibody 39H5 Heavy Chain CDR2

<400> SEQUENCE: 33
tggataaaca cctacactgg agagccaaca tatgttggtg acttcaaggg a            51

<210> SEQ ID NO 34
<211> LENGTH: 17
<212> TYPE: PRT
<213> ORGANISM: Artificial Sequence
<220> FEATURE:
<223> OTHER INFORMATION: Antibody 39H5 Heavy Chain CDR2

<400> SEQUENCE: 34

Trp Ile Asn Thr Tyr Thr Gly Glu Pro Thr Tyr Val Gly Asp Phe Lys

Gly

<210> SEQ ID NO 35
<211> LENGTH: 24
<212> TYPE: DNA
<213> ORGANISM: Artificial Sequence
<220> FEATURE:
<223> OTHER INFORMATION: Antibody 39H5 Heavy Chain CDR3

<400> SEQUENCE: 35
ggtatccacg gctacgtgga ctac                                          24

<210> SEQ ID NO 36
<211> LENGTH: 8
<212> TYPE: PRT
<213> ORGANISM: Artificial Sequence
<220> FEATURE:
<223> OTHER INFORMATION: Antibody 39H5 Heavy Chain CDR3

<400> SEQUENCE: 36

Gly Ile His Gly Tyr Val Asp Tyr
1               5

<210> SEQ ID NO 37
<211> LENGTH: 48
<212> TYPE: DNA
<213> ORGANISM: Artificial Sequence
<220> FEATURE:
<223> OTHER INFORMATION: Antibody 39H5 Light Chain CDR1

<400> SEQUENCE: 37
agatctagtc agagcattgt acatagaaat ggaaacacct atttagaa                48

<210> SEQ ID NO 38
<211> LENGTH: 16
<212> TYPE: PRT
<213> ORGANISM: Artificial Sequence
<220> FEATURE:
<223> OTHER INFORMATION: Antibody 39H5 Light Chain CDR1

<400> SEQUENCE: 38

Arg Ser Ser Gln Ser Ile Val His Arg Asn Gly Asn Thr Tyr Leu Glu
1               5                   10                  15

<210> SEQ ID NO 39
<211> LENGTH: 21
<212> TYPE: DNA
<213> ORGANISM: Artificial Sequence
<220> FEATURE:
<223> OTHER INFORMATION: Antibody 39H5 Light Chain CDR2

<400> SEQUENCE: 39
aaagtttcca accgattttc t                                             21

<210> SEQ ID NO 40
<211> LENGTH: 7
<212> TYPE: PRT
<213> ORGANISM: Artificial Sequence
<220> FEATURE:
<223> OTHER INFORMATION: Antibody 39H5 Light Chain CDR2

<400> SEQUENCE: 40

Lys Val Ser Asn Arg Phe Ser
1               5

<210> SEQ ID NO 41
<211> LENGTH: 27
<212> TYPE: DNA
<213> ORGANISM: Artificial Sequence
<220> FEATURE:
<223> OTHER INFORMATION: Antibody 39H5 Light Chain CDR3

<400> SEQUENCE: 41
tttcaaggtt cacatcttcc gtggacg                                27

<210> SEQ ID NO 42
<211> LENGTH: 9
<212> TYPE: PRT
<213> ORGANISM: Artificial Sequence
<220> FEATURE:
<223> OTHER INFORMATION: Antibody 39H5 Light Chain CDR3

<400> SEQUENCE: 42

Phe Gln Gly Ser His Leu Pro Trp Thr
1               5

<210> SEQ ID NO 43
<211> LENGTH: 411
<212> TYPE: DNA
<213> ORGANISM: Artificial Sequence
<220> FEATURE:
<223> OTHER INFORMATION: Antibody 3C5 Heavy chain - Signal
      sequence-FR1-CDR1-FR2-CDR2-FR3-CDR3-FR4

<400> SEQUENCE: 43
atggcttggg tgtggacctt gctgttcctg atggcagctg cccaaagtgc ccaagcacag    60
atccagttgg tgcagtctgg acctgagctg aagaagcctg agagacagt caagatctcc    120 tgcaaggctt ctgggtatac cttcacaaac tatggaatga actgggtgaa gcaggctcca   180
ggaaagggtt taaagtggat gggctggata acacctaca ctggaaagcc aacatatgct    240
gatgacttca aggacggtt tgccttctct ttggagacct ctgccagcac tgcctatttg    300
cagatcaaca acctcaaaaa tgaggacacg gctacatatt tctgtgcaag ggggggacta   360
gatggttact acggctactg gggccaaggc accactctca cagtctcctc a            411

<210> SEQ ID NO 44
<211> LENGTH: 137
<212> TYPE: PRT
<213> ORGANISM: Artificial Sequence
<220> FEATURE:
<223> OTHER INFORMATION: Antibody 3C5 Heavy chain - Signal
      sequence-FR1-CDR1-FR2-CDR2-FR3-CDR3-FR4

<400> SEQUENCE: 44

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Lys Pro Thr Tyr Ala
65                  70                  75                  80

Asp Asp Phe Lys Gly Arg Phe Ala Phe Ser Leu Glu Thr Ser Ala Ser
                85                  90                  95

```
Thr Ala Tyr Leu Gln Ile Asn Asn Leu Lys Asn Glu Asp Thr Ala Thr
            100                 105                 110

Tyr Phe Cys Ala Arg Gly Gly Leu Asp Gly Tyr Tyr Gly Tyr Trp Gly
        115                 120                 125

Gln Gly Thr Thr Leu Thr Val Ser Ser
    130                 135

<210> SEQ ID NO 45
<211> LENGTH: 393
<212> TYPE: DNA
<213> ORGANISM: Artificial Sequence
<220> FEATURE:
<223> OTHER INFORMATION: Antibody 3C5 Light chain - Signal
      sequence-FR1-CDR1-FR2-CDR2-FR3-CDR3-FR4

<400> SEQUENCE: 45
atgagtcctg cccagttcct gtttctgcta gtgctctcga ttcaggaaac caacggtgat    60
gttgtgatgg ctcagacccc actcactttg tcggttacca ttggacaacc agcctccatc   120
tcttgcaaat caagtcagag cctcttacat agtaaaggaa agacatattt gaattggtta   180
ttacagaggc caggccagtc tccaaagctc ctaatctatc tggtgtctaa actggaatct   240
ggagtccctg acaggttcag tggcagtgga tcagggacag atttcacact gaaaatcagc   300
agagtggagg ctgaagattt gggagtttat tactgcttgc aaactacaca ttttccgtgg   360
acgttcggtg aggcaccaa gctggaaatc aaa                                  393

<210> SEQ ID NO 46
<211> LENGTH: 131
<212> TYPE: PRT
<213> ORGANISM: Artificial Sequence
<220> FEATURE:
<223> OTHER INFORMATION: Antibody 3C5 Light chain - Signal
      sequence-FR1-CDR1-FR2-CDR2-FR3-CDR3-FR4

<400> SEQUENCE: 46

Met Ser Pro Ala Gln Phe Leu Phe Leu Leu Val Leu Ser Ile Gln Glu
1               5                   10                  15

Thr Asn Gly Asp Val Val Met Ala Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu His Ser Lys Gly Lys Thr Tyr Leu Asn Trp Leu Leu Gln Arg Pro
    50                  55                  60

Gly Gln Ser Pro Lys Leu Leu Ile Tyr Leu Val Ser Lys Leu Glu Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Leu Gln Thr Thr His Phe Pro Trp Thr Phe Gly Gly Gly Thr Lys Leu
        115                 120                 125

Glu Ile Lys
    130

<210> SEQ ID NO 47
<211> LENGTH: 15
<212> TYPE: DNA
<213> ORGANISM: Artificial Sequence
<220> FEATURE:
<223> OTHER INFORMATION: Antibody 3C5 Heavy Chain CDR1
```

<400> SEQUENCE: 47
aactatggaa tgaac                                                    15

<210> SEQ ID NO 48
<211> LENGTH: 5
<212> TYPE: PRT
<213> ORGANISM: Artificial Sequence
<220> FEATURE:
<223> OTHER INFORMATION: Antibody 3C5 Heavy Chain CDR1

<400> SEQUENCE: 48

Asn Tyr Gly Met Asn
1               5

<210> SEQ ID NO 49
<211> LENGTH: 51
<212> TYPE: DNA
<213> ORGANISM: Artificial Sequence
<220> FEATURE:
<223> OTHER INFORMATION: Antibody 3C5 Heavy Chain CDR2

<400> SEQUENCE: 49
tggataaaca cctacactgg aaagccaaca tatgctgatg acttcaaggg a            51

<210> SEQ ID NO 50
<211> LENGTH: 17
<212> TYPE: PRT
<213> ORGANISM: Artificial Sequence
<220> FEATURE:
<223> OTHER INFORMATION: Antibody 3C5 Heavy Chain CDR2

<400> SEQUENCE: 50

Trp Ile Asn Thr Tyr Thr Gly Lys Pro Thr Tyr Ala Asp Asp Phe Lys
1               5                   10                  15
Gly

<210> SEQ ID NO 51
<211> LENGTH: 27
<212> TYPE: DNA
<213> ORGANISM: Artificial Sequence
<220> FEATURE:
<223> OTHER INFORMATION: Antibody 3C5 Heavy Chain CDR3

<400> SEQUENCE: 51
gggggactag atggttacta cggctac                                       27

<210> SEQ ID NO 52
<211> LENGTH: 9
<212> TYPE: PRT
<213> ORGANISM: Artificial Sequence
<220> FEATURE:
<223> OTHER INFORMATION: Antibody 3C5 Heavy Chain CDR3

<400> SEQUENCE: 52

Gly Gly Leu Asp Gly Tyr Tyr Gly Tyr
1               5

<210> SEQ ID NO 53
<211> LENGTH: 48
<212> TYPE: DNA
<213> ORGANISM: Artificial Sequence
<220> FEATURE:
<223> OTHER INFORMATION: Antibody 3C5 Light Chain CDR1

<400> SEQUENCE: 53
aaatcaagtc agagcctctt acatagtaaa ggaaagacat atttgaat         48

<210> SEQ ID NO 54
<211> LENGTH: 16
<212> TYPE: PRT
<213> ORGANISM: Artificial Sequence
<220> FEATURE:
<223> OTHER INFORMATION: Antibody 3C5 Light Chain CDR1

<400> SEQUENCE: 54

Lys Ser Ser Gln Ser Leu Leu His Ser Lys Gly Lys Thr Tyr Leu Asn
1               5                   10                  15

<210> SEQ ID NO 55
<211> LENGTH: 21
<212> TYPE: DNA
<213> ORGANISM: Artificial Sequence
<220> FEATURE:
<223> OTHER INFORMATION: Antibody 3C5 Light Chain CDR2

<400> SEQUENCE: 55
ctggtgtcta aactggaatc t                                     21

<210> SEQ ID NO 56
<211> LENGTH: 7
<212> TYPE: PRT
<213> ORGANISM: Artificial Sequence
<220> FEATURE:
<223> OTHER INFORMATION: Antibody 3C5 Light Chain CDR2

<400> SEQUENCE: 56

Leu Val Ser Lys Leu Glu Ser
1               5

<210> SEQ ID NO 57
<211> LENGTH: 27
<212> TYPE: DNA
<213> ORGANISM: Artificial Sequence
<220> FEATURE:
<223> OTHER INFORMATION: Antibody 3C5 Light Chain CDR3

<400> SEQUENCE: 57
ttgcaaacta cacattttcc gtggacg                               27

<210> SEQ ID NO 58
<211> LENGTH: 9
<212> TYPE: PRT
<213> ORGANISM: Artificial Sequence
<220> FEATURE:
<223> OTHER INFORMATION: Antibody 3C5 Light Chain CDR3

<400> SEQUENCE: 58

Leu Gln Thr Thr His Phe Pro Trp Thr
1               5

<210> SEQ ID NO 59
<211> LENGTH: 420
<212> TYPE: DNA
<213> ORGANISM: Artificial Sequence
<220> FEATURE:
<223> OTHER INFORMATION: Antibody 8A9 Heavy chain - Signal
      sequence-FR1-CDR1-FR2-CDR2-FR3-CDR3-FR4

<400> SEQUENCE: 59
atgaagttgt ggctgaactg gattttcctt gtaacacttt taaatggtat ccagtgtgag    60

```
gtggagctgg tggagtctgg aggaggcttg gtacagcctg ggggttctct gagactctcc    120
tgtgcaactt ctgggttcac cttcactgat cactacatga gctgggtccg ccagcctcca    180
ggaaaggcac ttgagtggtt gggatttatt agaaacaaag ctaatggtta cacaacagag    240
tacagtgcat ctgtgaaggg tcggttcacc atctccagag ataattccca aagcatcctc    300
tatcttcaaa tgaaaaccct gagaactgag gacagtgcca cttattactg tgcaagacct    360
tctgactggg actcctggtt tgcttactgg ggccaaggga ctctggtcac tgtctctgca    420
```

<210> SEQ ID NO 60
<211> LENGTH: 140
<212> TYPE: PRT
<213> ORGANISM: Artificial Sequence
<220> FEATURE:
<223> OTHER INFORMATION: Antibody 8A9 Heavy chain - Signal
      sequence-FR1-CDR1-FR2-CDR2-FR3-CDR3-FR4

<400> SEQUENCE: 60

Met Lys Leu Trp Leu Asn Trp Ile Phe Leu Val Thr Leu Leu Asn Gly
1               5                   10                  15

Ile Gln Cys Glu Val Glu Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp His Tyr Met Ser Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Lys Thr Leu Arg Thr Glu Asp Ser
            100                 105                 110

Ala Thr Tyr Tyr Cys Ala Arg Pro Ser Asp Trp Asp Ser Trp Phe Ala
        115                 120                 125

Tyr Trp Gly Gln Gly Thr Leu Val Thr Val Ser Ala
    130                 135                 140

<210> SEQ ID NO 61
<211> LENGTH: 393
<212> TYPE: DNA
<213> ORGANISM: Artificial Sequence
<220> FEATURE:
<223> OTHER INFORMATION: Antibody 8A9 Light chain - Signal
      sequence-FR1-CDR1-FR2-CDR2-FR3-CDR3-FR4

<400> SEQUENCE: 61

```
atgaagttgc ctgttaggct gttggtgctg atgttctgga ttcctgcttc cagcagtgat     60
gttttgatga cccaaactcc actctccctg cctgtcagtc ttggtgatca agcctccatc    120
tcttgcagat ctagtcagag cattgtacat agtaatggca cacctattt agattggtac    180 ttgcagaaac caggccagtc tccaaagctc ctgatctaca gagtttccaa ccgatttct    240 ggggtcccag acaggttcag tggcagtgga tcaggacag atttcacact caagatcagc    300
agagtggagg ctgaggatct gggactttat tactgttttc aaggttcaca tgttccgtgg    360
gcgttcggtg gaggcaccaa gctggaaatc aaa                                  393
```

<210> SEQ ID NO 62
<211> LENGTH: 131
<212> TYPE: PRT

```
<213> ORGANISM: Artificial Sequence
<220> FEATURE:
<223> OTHER INFORMATION: Antibody 8A9 Light chain - Signal
      sequence-FR1-CDR1-FR2-CDR2-FR3-CDR3-FR4

<400> SEQUENCE: 62

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Asp Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Tyr Cys
            100                 105                 110

Phe Gln Gly Ser His Val Pro Trp Ala Phe Gly Gly Gly Thr Lys Leu
        115                 120                 125

Glu Ile Lys
    130

<210> SEQ ID NO 63
<211> LENGTH: 15
<212> TYPE: DNA
<213> ORGANISM: Artificial Sequence
<220> FEATURE:
<223> OTHER INFORMATION: Antibody 8A9 Heavy Chain CDR1

<400> SEQUENCE: 63
gatcactaca tgagc                                                      15

<210> SEQ ID NO 64
<211> LENGTH: 5
<212> TYPE: PRT
<213> ORGANISM: Artificial Sequence
<220> FEATURE:
<223> OTHER INFORMATION: Antibody 8A9 Heavy Chain CDR1

<400> SEQUENCE: 64

Asp His Tyr Met Ser
1               5

<210> SEQ ID NO 65
<211> LENGTH: 57
<212> TYPE: DNA
<213> ORGANISM: Artificial Sequence
<220> FEATURE:
<223> OTHER INFORMATION: Antibody 8A9 Heavy Chain CDR2

<400> SEQUENCE: 65
tttattagaa acaaagctaa tggttacaca acagagtaca gtgcatctgt gaagggt        57

<210> SEQ ID NO 66
<211> LENGTH: 19
<212> TYPE: PRT
<213> ORGANISM: Artificial Sequence
<220> FEATURE:
<223> OTHER INFORMATION: Antibody 8A9 Heavy Chain CDR2
```

<400> SEQUENCE: 66

Phe Ile Arg Asn Lys Ala Asn Gly Tyr Thr Thr Glu Tyr Ser Ala Ser
1               5                   10                  15

Val Lys Gly

<210> SEQ ID NO 67
<211> LENGTH: 30
<212> TYPE: DNA
<213> ORGANISM: Artificial Sequence
<220> FEATURE:
<223> OTHER INFORMATION: Antibody 8A9 Heavy Chain CDR3

<400> SEQUENCE: 67
ccttctgact gggactcctg gtttgcttac                                      30

<210> SEQ ID NO 68
<211> LENGTH: 10
<212> TYPE: PRT
<213> ORGANISM: Artificial Sequence
<220> FEATURE:
<223> OTHER INFORMATION: Antibody 8A9 Heavy Chain CDR3

<400> SEQUENCE: 68

Pro Ser Asp Trp Asp Ser Trp Phe Ala Tyr
1               5                   10

<210> SEQ ID NO 69
<211> LENGTH: 48
<212> TYPE: DNA
<213> ORGANISM: Artificial Sequence
<220> FEATURE:
<223> OTHER INFORMATION: Antibody 8A9 Light Chain CDR1

<400> SEQUENCE: 69
agatctagtc agagcattgt acatagtaat ggcaacacct atttagat                  48

<210> SEQ ID NO 70
<211> LENGTH: 16
<212> TYPE: PRT
<213> ORGANISM: Artificial Sequence
<220> FEATURE:
<223> OTHER INFORMATION: Antibody 8A9 Light Chain CDR1

<400> SEQUENCE: 70

Arg Ser Ser Gln Ser Ile Val His Ser Asn Gly Asn Thr Tyr Leu Asp
1               5                   10                  15

<210> SEQ ID NO 71
<211> LENGTH: 21
<212> TYPE: DNA
<213> ORGANISM: Artificial Sequence
<220> FEATURE:
<223> OTHER INFORMATION: Antibody 8A9 Light Chain CDR2

<400> SEQUENCE: 71
agagtttcca accgattttc t                                               21

<210> SEQ ID NO 72
<211> LENGTH: 7
<212> TYPE: PRT
<213> ORGANISM: Artificial Sequence
<220> FEATURE:
<223> OTHER INFORMATION: Antibody 8A9 Light Chain CDR2

<400> SEQUENCE: 72

Arg Val Ser Asn Arg Phe Ser
1               5

<210> SEQ ID NO 73
<211> LENGTH: 27
<212> TYPE: DNA
<213> ORGANISM: Artificial Sequence
<220> FEATURE:
<223> OTHER INFORMATION: Antibody 8A9 Light Chain CDR3

<400> SEQUENCE: 73
tttcaaggtt cacatgttcc gtgggcg                                27

<210> SEQ ID NO 74
<211> LENGTH: 9
<212> TYPE: PRT
<213> ORGANISM: Artificial Sequence
<220> FEATURE:
<223> OTHER INFORMATION: Antibody 8A9 Light Chain CDR3

<400> SEQUENCE: 74

Phe Gln Gly Ser His Val Pro Trp Ala
1               5

<210> SEQ ID NO 75
<211> LENGTH: 399
<212> TYPE: DNA
<213> ORGANISM: Artificial Sequence
<220> FEATURE:
<223> OTHER INFORMATION: Antibody 18G12 Heavy chain - Signal
      sequence-FR1-CDR1-FR2-CDR2-FR3-CDR3-FR4

<400> SEQUENCE: 75
atgggatgga gctatatcat cctctttttg gtcgcaacag ctacaggtgt ccactcccag    60
gtccaactgc agcagtctgg ggctgaactg gtgaagcctg ggcttcagt gaagttgtcc    120 tgcaaggctt ctggctacac cttcaccggc tacttttttgt actgggtgaa gcagaggcct    180
ggacaaggcc ttgagtggat tggggggatt aatcctgaca tggtggtat tgacttcaat    240 gagaagttca ggaacaaggc cacactgact gtagacaaat cctccagcac agcctacatg    300
caactcagca gcctgacatc tgaggactct gcggtctatt attgtacatt actaataggg    360
aactattggg gccaaggcac cactctcaca gtctcctca                          399

<210> SEQ ID NO 76
<211> LENGTH: 133
<212> TYPE: PRT
<213> ORGANISM: Artificial Sequence
<220> FEATURE:
<223> OTHER INFORMATION: Antibody 18G12 Heavy chain - Signal
      sequence-FR1-CDR1-FR2-CDR2-FR3-CDR3-FR4

<400> SEQUENCE: 76

Met Gly Trp Ser Tyr Ile Ile Leu Phe Leu Val Ala Thr Ala Thr Gly
1               5                   10                  15

Val His Ser Gln Val Gln Leu Gln Gln Ser Gly Ala Glu Leu Val Lys
                20                  25                  30

Pro Gly Ala Ser Val Lys Leu Ser Cys Lys Ala Ser Gly Tyr Thr Phe
            35                  40                  45

Thr Gly Tyr Phe Leu Tyr Trp Val Lys Gln Arg Pro Gly Gln Gly Leu
        50                  55                  60

Glu Trp Ile Gly Gly Ile Asn Pro Asp Asn Gly Gly Ile Asp Phe Asn
65                  70                  75                  80

```
Glu Lys Phe Arg Asn Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Leu Leu Ile Gly Asn Tyr Trp Gly Gln Gly Thr Thr
        115                 120                 125

Leu Thr Val Ser Ser
    130
```

```
<210> SEQ ID NO 77
<211> LENGTH: 393
<212> TYPE: DNA
<213> ORGANISM: Artificial Sequence
<220> FEATURE:
<223> OTHER INFORMATION: Antibody 18G12 Light chain - Signal
      sequence-FR1-CDR1-FR2-CDR2-FR3-CDR3-FR4

<400> SEQUENCE: 77
atgagtcctg cccagttcct gtttctgtta gtgctctgga ttcgggaaac caatggtgat      60
gttgtgatga cccagactcc actcactttg tcggtaacca ttggacagcc agcctccatc    120
tcttgcaagt caagtcagag cctcttacat agtgatggaa agacatattt gatttggttg    180
ttacagaggc caggccagtc tccaaagcgc ctaatctatc tggtgtctaa actggactct    240
ggagtccctg acaggttcac tggcagtgga tcagggacag atttcacact gaaaatcagc    300
agagtggagg ctgaggattt gggagtttat ttttgctgtc aaggtacaca ttttccgtgg    360
acgttcggtg gaggcaccat gctggaaatc aaa                                 393
```

```
<210> SEQ ID NO 78
<211> LENGTH: 131
<212> TYPE: PRT
<213> ORGANISM: Artificial Sequence
<220> FEATURE:
<223> OTHER INFORMATION: Antibody 18G12 Light chain - Signal
      sequence-FR1-CDR1-FR2-CDR2-FR3-CDR3-FR4

<400> SEQUENCE: 78

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu His Ser Asp Gly Lys Thr Tyr Leu Ile Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Cys Gln Gly Thr His Phe Pro Trp Thr Phe Gly Gly Gly Thr Met Leu
        115                 120                 125

Glu Ile Lys
    130
```

```
<210> SEQ ID NO 79
<211> LENGTH: 15
<212> TYPE: DNA
```

```
<213> ORGANISM: Artificial Sequence
<220> FEATURE:
<223> OTHER INFORMATION: Antibody 18G12 Heavy Chain CDR1

<400> SEQUENCE: 79
ggctactttt tgtac                                                      15

<210> SEQ ID NO 80
<211> LENGTH: 5
<212> TYPE: PRT
<213> ORGANISM: Artificial Sequence
<220> FEATURE:
<223> OTHER INFORMATION: Antibody 18G12 Heavy Chain CDR1

<400> SEQUENCE: 80

Gly Tyr Phe Leu Tyr
1               5

<210> SEQ ID NO 81
<211> LENGTH: 51
<212> TYPE: DNA
<213> ORGANISM: Artificial Sequence
<220> FEATURE:
<223> OTHER INFORMATION: Antibody 18G12 Heavy Chain CDR2

<400> SEQUENCE: 81
gggattaatc ctgacaatgg tggtattgac ttcaatgaga agttcaggaa c              51

<210> SEQ ID NO 82
<211> LENGTH: 17
<212> TYPE: PRT
<213> ORGANISM: Artificial Sequence
<220> FEATURE:
<223> OTHER INFORMATION: Antibody 18G12 Heavy Chain CDR2

<400> SEQUENCE: 82

Gly Ile Asn Pro Asp Asn Gly Gly Ile Asp Phe Asn Glu Lys Phe Arg
1               5                   10                  15
Asn

<210> SEQ ID NO 83
<211> LENGTH: 15
<212> TYPE: DNA
<213> ORGANISM: Artificial Sequence
<220> FEATURE:
<223> OTHER INFORMATION: Antibody 18G12 Heavy Chain CDR3

<400> SEQUENCE: 83
ctaataggga actat                                                      15

<210> SEQ ID NO 84
<211> LENGTH: 5
<212> TYPE: PRT
<213> ORGANISM: Artificial Sequence
<220> FEATURE:
<223> OTHER INFORMATION: Antibody 18G12 Heavy Chain CDR3

<400> SEQUENCE: 84

Leu Ile Gly Asn Tyr
1               5

<210> SEQ ID NO 85
<211> LENGTH: 48
<212> TYPE: DNA
<213> ORGANISM: Artificial Sequence
<220> FEATURE:
```

<223> OTHER INFORMATION: Antibody 18G12 Light Chain CDR1

<400> SEQUENCE: 85
aagtcaagtc agagcctctt acatagtgat ggaaagacat atttgatt                48

<210> SEQ ID NO 86
<211> LENGTH: 16
<212> TYPE: PRT
<213> ORGANISM: Artificial Sequence
<220> FEATURE:
<223> OTHER INFORMATION: Antibody 18G12 Light Chain CDR1

<400> SEQUENCE: 86

Lys Ser Ser Gln Ser Leu Leu His Ser Asp Gly Lys Thr Tyr Leu Ile
1               5                   10                  15

<210> SEQ ID NO 87
<211> LENGTH: 21
<212> TYPE: DNA
<213> ORGANISM: Artificial Sequence
<220> FEATURE:
<223> OTHER INFORMATION: Antibody 18G12 Light Chain CDR2

<400> SEQUENCE: 87
ctggtgtcta aactggactc t                                              21

<210> SEQ ID NO 88
<211> LENGTH: 7
<212> TYPE: PRT
<213> ORGANISM: Artificial Sequence
<220> FEATURE:
<223> OTHER INFORMATION: Antibody 18G12 Light Chain CDR2

<400> SEQUENCE: 88

Leu Val Ser Lys Leu Asp Ser
1               5

<210> SEQ ID NO 89
<211> LENGTH: 27
<212> TYPE: DNA
<213> ORGANISM: Artificial Sequence
<220> FEATURE:
<223> OTHER INFORMATION: Antibody 18G12 Light Chain CDR3

<400> SEQUENCE: 89
tgtcaaggta cacattttcc gtggacg                                        27

<210> SEQ ID NO 90
<211> LENGTH: 9
<212> TYPE: PRT
<213> ORGANISM: Artificial Sequence
<220> FEATURE:
<223> OTHER INFORMATION: Antibody 18G12 Light Chain CDR3

<400> SEQUENCE: 90

Cys Gln Gly Thr His Phe Pro Trp Thr
1               5

<210> SEQ ID NO 91
<211> LENGTH: 417
<212> TYPE: DNA
<213> ORGANISM: Artificial Sequence
<220> FEATURE:
<223> OTHER INFORMATION: Antibody 20A10 Heavy chain - Signal
      sequence-FR1-CDR1-FR2-CDR2-FR3-CDR3-FR4

<400> SEQUENCE: 91

```
atgaacttcg ggttcagctt gattttcctt gtccttgttt taaaaggtgt ccagtgtgaa      60
gtgatgctgg tggagtctgg gggaggctta gtgaagcctg agggtccct gaaactctcc      120 tgtgcagcct ctggattcac tttcagtacc tatgccatgt cttggattcg ccagactcca     180
gagaagaggc tggagtgggt cgcatccatt ggtcgtgctg gttccaccta ctattcagac    240
agtgtgaagg gccgattcac catctccaga gataatgtcc ggaacatcct gtacctgcaa    300
atgagcagtc tgaggtctga ggacacggcc atgtattact gtgctagagg cccgatctac    360
aatgattacg acgagtttgc ttactggggc caagggactc tggtcactgt ctctgca       417
```

```
<210> SEQ ID NO 92
<211> LENGTH: 139
<212> TYPE: PRT
<213> ORGANISM: Artificial Sequence
<220> FEATURE:
<223> OTHER INFORMATION: Antibody 20A10 Heavy chain - Signal
      sequence-FR1-CDR1-FR2-CDR2-FR3-CDR3-FR4

<400> SEQUENCE: 92
```

Met Asn Phe Gly Phe Ser Leu Ile Phe Leu Val Leu Val Leu Lys Gly
1               5                   10                  15

Val Gln Cys Glu Val Met Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Tyr Ala Met Ser Trp Ile Arg Gln Thr Pro Glu Lys Arg Leu
    50                  55                  60

Glu Trp Val Ala Ser Ile Gly Arg Ala Gly Ser Thr Tyr Tyr Ser Asp
65                  70                  75                  80

Ser Val Lys Gly Arg Phe Thr Ile Ser Arg Asp Asn Val Arg Asn Ile
                85                  90                  95

Leu Tyr Leu Gln Met Ser Ser Leu Arg Ser Glu Asp Thr Ala Met Tyr
            100                 105                 110

Tyr Cys Ala Arg Gly Pro Ile Tyr Asn Asp Tyr Asp Glu Phe Ala Tyr
        115                 120                 125

Trp Gly Gln Gly Thr Leu Val Thr Val Ser Ala
    130                 135

```
<210> SEQ ID NO 93
<211> LENGTH: 396
<212> TYPE: DNA
<213> ORGANISM: Artificial Sequence
<220> FEATURE:
<223> OTHER INFORMATION: Antibody 20A10 Light chain - Signal
      sequence-FR1-CDR1-FR2-CDR2-FR3-CDR3-FR4

<400> SEQUENCE: 93
```

```
atggaatcac agactcaggt cttcctctcc ctgctgctct gggtatctgg tacctgtggg      60
aacattatga tgacacagtc gccatcatct ctggctgtgt ctgcaggaga aaaggtcact    120
atgagctgta gtccagtca aagtgtttta tacagttcaa atcagaagaa ctatttggcc     180
tggtaccagc agaaaccagg gcagtctcct aaactgctga tctactgggc atccactagg    240
gaatctggtg tccctgatcg cttcacaggc agtggatctg ggacagattt tactcttacc    300
atcagcagtg tacaagctga agacctggca gtttattact gtcatcaata cctctcctcg   360
ctcacgttcg gtgctgggac caagctggag ctgaaa                              396
```

<210> SEQ ID NO 94
<211> LENGTH: 132
<212> TYPE: PRT
<213> ORGANISM: Artificial Sequence
<220> FEATURE:
<223> OTHER INFORMATION: Antibody 20A10 Light chain - Signal
      sequence-FR1-CDR1-FR2-CDR2-FR3-CDR3-FR4

<400> SEQUENCE: 94

```
Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Ser Leu Ala
            20                  25                  30

Val Ser Ala Gly Glu Lys Val Thr Met Ser Cys Lys Ser Gln Ser
        35                  40                  45

Val Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Leu Ser Ser Leu Thr Phe Gly Ala Gly Thr Lys
        115                 120                 125

Leu Glu Leu Lys
    130
```

<210> SEQ ID NO 95
<211> LENGTH: 15
<212> TYPE: DNA
<213> ORGANISM: Artificial Sequence
<220> FEATURE:
<223> OTHER INFORMATION: Antibody 20A10 Heavy Chain CDR1

<400> SEQUENCE: 95
acctatgcca tgtct                                                     15

<210> SEQ ID NO 96
<211> LENGTH: 5
<212> TYPE: PRT
<213> ORGANISM: Artificial Sequence
<220> FEATURE:
<223> OTHER INFORMATION: Antibody 20A10 Heavy Chain CDR1

<400> SEQUENCE: 96

```
Thr Tyr Ala Met Ser
1               5
```

<210> SEQ ID NO 97
<211> LENGTH: 48
<212> TYPE: DNA
<213> ORGANISM: Artificial Sequence
<220> FEATURE:
<223> OTHER INFORMATION: Antibody 20A10 Heavy Chain CDR2

<400> SEQUENCE: 97
tccattggtc gtgctggttc cacctactat tcagacagtg tgaagggc                 48

<210> SEQ ID NO 98
<211> LENGTH: 16
<212> TYPE: PRT
<213> ORGANISM: Artificial Sequence
<220> FEATURE:
<223> OTHER INFORMATION: Antibody 20A10 Heavy Chain CDR2

<400> SEQUENCE: 98

Ser Ile Gly Arg Ala Gly Ser Thr Tyr Tyr Ser Asp Ser Val Lys Gly
1               5                   10                  15

<210> SEQ ID NO 99
<211> LENGTH: 36
<212> TYPE: DNA
<213> ORGANISM: Artificial Sequence
<220> FEATURE:
<223> OTHER INFORMATION: Antibody 20A10 Heavy Chain CDR3

<400> SEQUENCE: 99
ggcccgatct acaatgatta cgacgagttt gcttac                          36

<210> SEQ ID NO 100
<211> LENGTH: 12
<212> TYPE: PRT
<213> ORGANISM: Artificial Sequence
<220> FEATURE:
<223> OTHER INFORMATION: Antibody 20A10 Heavy Chain CDR3

<400> SEQUENCE: 100

Gly Pro Ile Tyr Asn Asp Tyr Asp Glu Phe Ala Tyr
1               5                   10

<210> SEQ ID NO 101
<211> LENGTH: 51
<212> TYPE: DNA
<213> ORGANISM: Artificial Sequence
<220> FEATURE:
<223> OTHER INFORMATION: Antibody 20A10 Light Chain CDR1

<400> SEQUENCE: 101
aagtccagtc aaagtgtttt atacagttca atcagaaga actatttggc c          51

<210> SEQ ID NO 102
<211> LENGTH: 17
<212> TYPE: PRT
<213> ORGANISM: Artificial Sequence
<220> FEATURE:
<223> OTHER INFORMATION: Antibody 20A10 Light Chain CDR1

<400> SEQUENCE: 102

Lys Ser Ser Gln Ser Val Leu Tyr Ser Ser Asn Gln Lys Asn Tyr Leu
1               5                   10                  15
Ala

<210> SEQ ID NO 103
<211> LENGTH: 21
<212> TYPE: DNA
<213> ORGANISM: Artificial Sequence
<220> FEATURE:
<223> OTHER INFORMATION: Antibody 20A10 Light Chain CDR2

<400> SEQUENCE: 103
tgggcatcca ctagggaatc t                                          21

<210> SEQ ID NO 104
<211> LENGTH: 7
<212> TYPE: PRT
<213> ORGANISM: Artificial Sequence
<220> FEATURE:
<223> OTHER INFORMATION: Antibody 20A10 Light Chain CDR2

<400> SEQUENCE: 104

Trp Ala Ser Thr Arg Glu Ser
1               5

<210> SEQ ID NO 105
<211> LENGTH: 24
<212> TYPE: DNA
<213> ORGANISM: Artificial Sequence
<220> FEATURE:
<223> OTHER INFORMATION: Antibody 20A10 Light Chain CDR3

<400> SEQUENCE: 105
catcaatacc tctcctcgct cacg                                          24

<210> SEQ ID NO 106
<211> LENGTH: 8
<212> TYPE: PRT
<213> ORGANISM: Artificial Sequence
<220> FEATURE:
<223> OTHER INFORMATION: Antibody 20A10 Light Chain CDR3

<400> SEQUENCE: 106

His Gln Tyr Leu Ser Ser Leu Thr
1               5

<210> SEQ ID NO 107
<211> LENGTH: 414
<212> TYPE: DNA
<213> ORGANISM: Artificial Sequence
<220> FEATURE:
<223> OTHER INFORMATION: Antibody 25E6 Heavy chain - Signal
      sequence-FR1-CDR1-FR2-CDR2-FR3-CDR3-FR4

<400> SEQUENCE: 107
atgaacttcg ggctcagctt gattttcctt gccctcattt taaaaggtgt ccagtgtgag    60
gtgcagctgg tggagtctgg gggagactta gtgaagcctg agggtccct gaaactctcc   120 tgtgcagcct ctggtttcac tttcagtagt tatggaatgt cttgggttcg ccagactcca   180
gacaagaggc tggagtgggt cgcaaccatt agtaatggtg gtagcacac cttctatcca   240 gacagtgtga aggggcgatt caccatctcc agagacaatg ccaagaacac cctgtatctg   300
caaatgagca gtctgaagtc tgaggacaca gccatgtatt tatgtgtaag acagactggg   360
acggagggct ggtttgctta ctggggccaa gggactctgg tcactgtctc tgca         414

<210> SEQ ID NO 108
<211> LENGTH: 138
<212> TYPE: PRT
<213> ORGANISM: Artificial Sequence
<220> FEATURE:
<223> OTHER INFORMATION: Antibody 25E6 Heavy chain - Signal
      sequence-FR1-CDR1-FR2-CDR2-FR3-CDR3-FR4

<400> SEQUENCE: 108

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

```
Glu Trp Val Ala Thr Ile Ser Asn Gly Gly Arg His Thr Phe Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Leu Cys Val Arg Gln Thr Gly Thr Glu Gly Trp Phe Ala Tyr Trp
        115                 120                 125

Gly Gln Gly Thr Leu Val Thr Val Ser Ala
    130                 135

<210> SEQ ID NO 109
<211> LENGTH: 393
<212> TYPE: DNA
<213> ORGANISM: Artificial Sequence
<220> FEATURE:
<223> OTHER INFORMATION: Antibody 25E6 Light chain - Signal
      sequence-FR1-CDR1-FR2-CDR2-FR3-CDR3-FR4

<400> SEQUENCE: 109
atgagtcctg cccagttcct gtttctgtta gtgctctgga ttcgggaaac caacggtgat      60
gttgtgatga cccagactcc actcactttg tcggttacca ttggacaacc agcctccatc    120
tcttgcaagt caagtcagag cctcttagat agtgatggaa agacatattt gaattggttg    180
ttacagaggc caggccagtc tccaaagcgc ctaatctatc tggtgtctaa actggactct    240
ggagtccctg acaggttcac tggcagtgga tcagggacag atttcacact gaaaatcagc    300
agagtggagg ctgaggattt gggagtttat tattgctggc aaggtacaca ttttcctcag    360
acgttcggtg aggcaccaa gctggaaatc aaa                                  393

<210> SEQ ID NO 110
<211> LENGTH: 131
<212> TYPE: PRT
<213> ORGANISM: Artificial Sequence
<220> FEATURE:
<223> OTHER INFORMATION: Antibody 25E6 Light chain - Signal
      sequence-FR1-CDR1-FR2-CDR2-FR3-CDR3-FR4

<400> SEQUENCE: 110

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
                20                  25                  30

Thr Ile Gly Gln Pro Ala Ser Ile Ser Cys Lys Ser Ser Gln Ser Leu
            35                  40                  45

Leu Asp Ser Asp Gly Lys Thr Tyr Leu Asn Trp Leu Leu Gln Arg Pro
        50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Thr His Phe Pro Gln Thr Phe Gly Gly Gly Thr Lys Leu
        115                 120                 125

Glu Ile Lys
    130
```

<210> SEQ ID NO 111
<211> LENGTH: 15
<212> TYPE: DNA
<213> ORGANISM: Artificial Sequence
<220> FEATURE:
<223> OTHER INFORMATION: Antibody 25E6 Heavy Chain CDR1

<400> SEQUENCE: 111
agttatggaa tgtct                                                     15

<210> SEQ ID NO 112
<211> LENGTH: 5
<212> TYPE: PRT
<213> ORGANISM: Artificial Sequence
<220> FEATURE:
<223> OTHER INFORMATION: Antibody 25E6 Heavy Chain CDR1

<400> SEQUENCE: 112

Ser Tyr Gly Met Ser
1               5

<210> SEQ ID NO 113
<211> LENGTH: 51
<212> TYPE: DNA
<213> ORGANISM: Artificial Sequence
<220> FEATURE:
<223> OTHER INFORMATION: Antibody 25E6 Heavy Chain CDR2

<400> SEQUENCE: 113
accattagta atggtggtag acacaccttc tatccagaca gtgtgaaggg g              51

<210> SEQ ID NO 114
<211> LENGTH: 17
<212> TYPE: PRT
<213> ORGANISM: Artificial Sequence
<220> FEATURE:
<223> OTHER INFORMATION: Antibody 25E6 Heavy Chain CDR2

<400> SEQUENCE: 114

Thr Ile Ser Asn Gly Gly Arg His Thr Phe Tyr Pro Asp Ser Val Lys
1               5                   10                  15

Gly

<210> SEQ ID NO 115
<211> LENGTH: 30
<212> TYPE: DNA
<213> ORGANISM: Artificial Sequence
<220> FEATURE:
<223> OTHER INFORMATION: Antibody 25E6 Heavy Chain CDR3

<400> SEQUENCE: 115
cagactggga cggagggctg gtttgcttac                                     30

<210> SEQ ID NO 116
<211> LENGTH: 10
<212> TYPE: PRT
<213> ORGANISM: Artificial Sequence
<220> FEATURE:
<223> OTHER INFORMATION: Antibody 25E6 Heavy Chain CDR3

<400> SEQUENCE: 116

Gln Thr Gly Thr Glu Gly Trp Phe Ala Tyr
1               5                   10

<210> SEQ ID NO 117
<211> LENGTH: 48

<210> SEQ ID NO 117
<211> LENGTH: 48
<212> TYPE: DNA
<213> ORGANISM: Artificial Sequence
<220> FEATURE:
<223> OTHER INFORMATION: Antibody 25E6 Light Chain CDR1

<400> SEQUENCE: 117
aagtcaagtc agagcctctt agatagtgat ggaaagacat atttgaat          48

<210> SEQ ID NO 118
<211> LENGTH: 16
<212> TYPE: PRT
<213> ORGANISM: Artificial Sequence
<220> FEATURE:
<223> OTHER INFORMATION: Antibody 25E6 Light Chain CDR1

<400> SEQUENCE: 118

Lys Ser Ser Gln Ser Leu Leu Asp Ser Asp Gly Lys Thr Tyr Leu Asn
1               5                   10                  15

<210> SEQ ID NO 119
<211> LENGTH: 21
<212> TYPE: DNA
<213> ORGANISM: Artificial Sequence
<220> FEATURE:
<223> OTHER INFORMATION: Antibody 25E6 Light Chain CDR2

<400> SEQUENCE: 119
ctggtgtcta aactggactc t                                     21

<210> SEQ ID NO 120
<211> LENGTH: 7
<212> TYPE: PRT
<213> ORGANISM: Artificial Sequence
<220> FEATURE:
<223> OTHER INFORMATION: Antibody 25E6 Light Chain CDR2

<400> SEQUENCE: 120

Leu Val Ser Lys Leu Asp Ser
1               5

<210> SEQ ID NO 121
<211> LENGTH: 27
<212> TYPE: DNA
<213> ORGANISM: Artificial Sequence
<220> FEATURE:
<223> OTHER INFORMATION: Antibody 25E6 Light Chain CDR3

<400> SEQUENCE: 121
tggcaaggta cacattttcc tcagacg                               27

<210> SEQ ID NO 122
<211> LENGTH: 9
<212> TYPE: PRT
<213> ORGANISM: Artificial Sequence
<220> FEATURE:
<223> OTHER INFORMATION: Antibody 25E6 Light Chain CDR3

<400> SEQUENCE: 122

Trp Gln Gly Thr His Phe Pro Gln Thr
1               5

<210> SEQ ID NO 123
<211> LENGTH: 399
<212> TYPE: DNA
<213> ORGANISM: Artificial Sequence
<220> FEATURE:
<223> OTHER INFORMATION: Antibody 28F9 Heavy chain - Signal sequence-FR1-CDR1-FR2-CDR2-FR3-CDR3-FR4

<400> SEQUENCE: 123

```
atgggatgga gctatatcat cctcttttg gtagcaacag ctacaggtgt ccactcccag    60
gtccaactgc agcagcctgg ggctgaactg gtgcagcctg ggcttcagt gaagttgtcc   120
tgcaaggctt ctggctacac cttcaccggc tacttttgt actgggtgaa gcagaggcct   180
ggacatggcc ttgagtggat tgggggaatt catcctagca atggtgatac tgacttcaat   240
gagaagttca gaacaaggc cacactgact gtagacatat cctccagcac tgcctacatg   300
caactcagca gcctgacatc tgaggactct gcggtctatt attgtacatt actaataggg   360
gtctactggg gccaaggcac cactctcaca gtctcctca                         399
```

<210> SEQ ID NO 124
<211> LENGTH: 133
<212> TYPE: PRT
<213> ORGANISM: Artificial Sequence
<220> FEATURE:
<223> OTHER INFORMATION: Antibody 28F9 Heavy chain - Signal
      sequence-FR1-CDR1-FR2-CDR2-FR3-CDR3-FR4

<400> SEQUENCE: 124

Met Gly Trp Ser Tyr Ile Ile Leu Phe Leu Val Ala Thr Ala Thr Gly
1               5                   10                  15

Val His Ser Gln Val Gln Leu Gln Gln Pro Gly Ala Glu Leu Val Gln
            20                  25                  30

Pro Gly Ala Ser Val Lys Leu Ser Cys Lys Ala Ser Gly Tyr Thr Phe
        35                  40                  45

Thr Gly Tyr Phe Leu Tyr Trp Val Lys Gln Arg Pro Gly His Gly Leu
    50                  55                  60

Glu Trp Ile Gly Gly Ile His Pro Ser Asn Gly Asp Thr Asp Phe Asn
65                  70                  75                  80

Glu Lys Phe Lys Asn Lys Ala Thr Leu Thr Val Asp Ile Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Leu Leu Ile Gly Val Tyr Trp Gly Gln Gly Thr Thr
        115                 120                 125

Leu Thr Val Ser Ser
    130

<210> SEQ ID NO 125
<211> LENGTH: 393
<212> TYPE: DNA
<213> ORGANISM: Artificial Sequence
<220> FEATURE:
<223> OTHER INFORMATION: Antibody 28F9 Light chain - Signal
      sequence-FR1-CDR1-FR2-CDR2-FR3-CDR3-FR4

<400> SEQUENCE: 125

```
atgagtcctg cccagttcct gtttctgtta gtgctctgga ttcgggaaac caacggtgat    60
gttgtgatga cccagactcc actcactttg tcggttacca ttggacaacc agcctccatc   120
tcttgcaagt caagtcagag cctcttacat agtgatggaa agacatattt gatttggttg   180
ttacagaggc caggccagtc tccaaagcgc ctaatctatc tggtgtctaa actggactct   240
ggagtccctg acaggttcac cggcagtgga tcagggacag atttcacact gaaaatcagc   300
agagtggagg ctgaggattt gggagtttat ttttgctgtc aagtacaca ttttccgtgg   360
```
acgttcggtg gaggcaccat gctggaaatc aaa                                    393

```
<210> SEQ ID NO 126
<211> LENGTH: 131
<212> TYPE: PRT
<213> ORGANISM: Artificial Sequence
<220> FEATURE:
<223> OTHER INFORMATION: Antibody 28F9 Light chain - Signal
      sequence-FR1-CDR1-FR2-CDR2-FR3-CDR3-FR4

<400> SEQUENCE: 126
```

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu His Ser Asp Gly Lys Thr Tyr Leu Ile Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Cys Gln Gly Thr His Phe Pro Trp Thr Phe Gly Gly Gly Thr Met Leu
        115                 120                 125

Glu Ile Lys
    130

```
<210> SEQ ID NO 127
<211> LENGTH: 15
<212> TYPE: DNA
<213> ORGANISM: Artificial Sequence
<220> FEATURE:
<223> OTHER INFORMATION: Antibody 28F9 Heavy Chain CDR1

<400> SEQUENCE: 127
```
ggctactttt tgtac                                                        15

```
<210> SEQ ID NO 128
<211> LENGTH: 5
<212> TYPE: PRT
<213> ORGANISM: Artificial Sequence
<220> FEATURE:
<223> OTHER INFORMATION: Antibody 28F9 Heavy Chain CDR1

<400> SEQUENCE: 128
```

Gly Tyr Phe Leu Tyr
1               5

```
<210> SEQ ID NO 129
<211> LENGTH: 51
<212> TYPE: DNA
<213> ORGANISM: Artificial Sequence
<220> FEATURE:
<223> OTHER INFORMATION: Antibody 28F9 Heavy Chain CDR2

<400> SEQUENCE: 129
```
ggaattcatc ctagcaatgg tgatactgac ttcaatgaga agttcaagaa c                 51

```
<210> SEQ ID NO 130
```

-continued

```
<211> LENGTH: 17
<212> TYPE: PRT
<213> ORGANISM: Artificial Sequence
<220> FEATURE:
<223> OTHER INFORMATION: Antibody 28F9 Heavy Chain CDR2

<400> SEQUENCE: 130

Gly Ile His Pro Ser Asn Gly Asp Thr Asp Phe Asn Glu Lys Phe Lys
1               5                   10                  15
Asn

<210> SEQ ID NO 131
<211> LENGTH: 15
<212> TYPE: DNA
<213> ORGANISM: Artificial Sequence
<220> FEATURE:
<223> OTHER INFORMATION: Antibody 28F9 Heavy Chain CDR3

<400> SEQUENCE: 131
ctaatagggg tctac                                                    15

<210> SEQ ID NO 132
<211> LENGTH: 5
<212> TYPE: PRT
<213> ORGANISM: Artificial Sequence
<220> FEATURE:
<223> OTHER INFORMATION: Antibody 28F9 Heavy Chain CDR3

<400> SEQUENCE: 132

Leu Ile Gly Val Tyr
1               5

<210> SEQ ID NO 133
<211> LENGTH: 48
<212> TYPE: DNA
<213> ORGANISM: Artificial Sequence
<220> FEATURE:
<223> OTHER INFORMATION: Antibody 28F9 Light Chain CDR1

<400> SEQUENCE: 133
aagtcaagtc agagcctctt acatagtgat ggaaagacat atttgatt                48

<210> SEQ ID NO 134
<211> LENGTH: 16
<212> TYPE: PRT
<213> ORGANISM: Artificial Sequence
<220> FEATURE:
<223> OTHER INFORMATION: Antibody 28F9 Light Chain CDR1

<400> SEQUENCE: 134

Lys Ser Ser Gln Ser Leu Leu His Ser Asp Gly Lys Thr Tyr Leu Ile
1               5                   10                  15

<210> SEQ ID NO 135
<211> LENGTH: 21
<212> TYPE: DNA
<213> ORGANISM: Artificial Sequence
<220> FEATURE:
<223> OTHER INFORMATION: Antibody 28F9 Light Chain CDR2

<400> SEQUENCE: 135
ctggtgtcta aactggactc t                                             21

<210> SEQ ID NO 136
<211> LENGTH: 7
<212> TYPE: PRT
```

<213> ORGANISM: Artificial Sequence
<220> FEATURE:
<223> OTHER INFORMATION: Antibody 28F9 Light Chain CDR2

<400> SEQUENCE: 136

Leu Val Ser Lys Leu Asp Ser
1               5

<210> SEQ ID NO 137
<211> LENGTH: 27
<212> TYPE: DNA
<213> ORGANISM: Artificial Sequence
<220> FEATURE:
<223> OTHER INFORMATION: Antibody 28F9 Light Chain CDR3

<400> SEQUENCE: 137
tgtcaaggta cacattttcc gtggacg                                        27

<210> SEQ ID NO 138
<211> LENGTH: 9
<212> TYPE: PRT
<213> ORGANISM: Artificial Sequence
<220> FEATURE:
<223> OTHER INFORMATION: Antibody 28F9 Light Chain CDR3

<400> SEQUENCE: 138

Cys Gln Gly Thr His Phe Pro Trp Thr
1               5

<210> SEQ ID NO 139
<211> LENGTH: 411
<212> TYPE: DNA
<213> ORGANISM: Artificial Sequence
<220> FEATURE:
<223> OTHER INFORMATION: Antibody 18B4 Heavy chain - Signal
      sequence-FR1-CDR1-FR2-CDR2-FR3-CDR3-FR4

<400> SEQUENCE: 139
atgtacttgg gactgaacta tgtattcata gttttttctct taaatggtgt ccagagtgaa     60
gtgaaacttg aggagtctgg aggaggcttg gtgcaacctg ggggatccat gaaactctct    120
tgtgctgcct ctggattcac ttttaatgac gcctggatgg actgggtccg ccagtctcca    180 gagaagggc ttgagtgggt tgctgaaatt agaagcacag ctaatattca tacaacatac    240
tatgctgagt ctgtccaagg gaggttcacc atctcaagag atgattccaa agtagtgtc    300 tacctgcaaa tgaacagctt gagagctgaa gacactggca tttattattg tacccccatta    360 ctctacggat ttgcttactg gggccaaggg actctggtca ctgtctctgc a              411

<210> SEQ ID NO 140
<211> LENGTH: 137
<212> TYPE: PRT
<213> ORGANISM: Artificial Sequence
<220> FEATURE:
<223> OTHER INFORMATION: Antibody 18B4 Heavy chain - Signal
      sequence-FR1-CDR1-FR2-CDR2-FR3-CDR3-FR4

<400> SEQUENCE: 140

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

```
Asn Asp Ala Trp Met Asp Trp Val Arg Gln Ser Pro Glu Lys Gly Leu
 50                  55                  60

Glu Trp Val Ala Glu Ile Arg Ser Thr Ala Asn Ile His Thr Thr Tyr
 65                  70                  75                  80

Tyr Ala Glu Ser Val Gln Gly Arg Phe Thr Ile Ser Arg Asp Asp Ser
                 85                  90                  95

Lys Ser Ser Val Tyr Leu Gln Met Asn Ser Leu Arg Ala Glu Asp Thr
            100                 105                 110

Gly Ile Tyr Tyr Cys Thr Pro Leu Leu Tyr Gly Phe Ala Tyr Trp Gly
        115                 120                 125

Gln Gly Thr Leu Val Thr Val Ser Ala
    130                 135

<210> SEQ ID NO 141
<211> LENGTH: 393
<212> TYPE: DNA
<213> ORGANISM: Artificial Sequence
<220> FEATURE:
<223> OTHER INFORMATION: Antibody 18B4 Light chain - Signal
      sequence-FR1-CDR1-FR2-CDR2-FR3-CDR3-FR4

<400> SEQUENCE: 141
atgaagttgc ctgttaggct gttggtgctg atgttctgga ttcctgcttc cagcagtgat    60
gttgtgatga cccaaagtcc actctccctg cctgtcagtc ttggagatca agcctccatc   120
tcttgcagaa ctagtcagag ccttgtacac agtaatggaa acacctattt acattggcac   180
ctgcagaagc caggccagtc tccaaaggtc ctgatctaca agtttccag ccgattttct    240 ggggtcccag acaggttcag tggcagtgga tcggggacag atttcacact caagatcagc   300
agagtggagg ctgaggatct gggagtttat ttctgctctc aaaatacaca tgttccgtac   360
acgttcggag gggggaccaa gctggaaata aaa                                393

<210> SEQ ID NO 142
<211> LENGTH: 131
<212> TYPE: PRT
<213> ORGANISM: Artificial Sequence
<220> FEATURE:
<223> OTHER INFORMATION: Antibody 18B4 Heavy chain - Signal
      sequence-FR1-CDR1-FR2-CDR2-FR3-CDR3-FR4

<400> SEQUENCE: 142

Met Lys Leu Pro Val Arg Leu Leu Val Leu Met Phe Trp Ile Pro Ala
 1               5                  10                  15

Ser Ser Ser Asp Val Val Met Thr Gln Ser Pro Leu Ser Leu Pro Val
             20                  25                  30

Ser Leu Gly Asp Gln Ala Ser Ile Ser Cys Arg Thr Ser Gln Ser Leu
         35                  40                  45

Val His Ser Asn Gly Asn Thr Tyr Leu His Trp His Leu Gln Lys Pro
 50                  55                  60

Gly Gln Ser Pro Lys Val Leu Ile Tyr Lys Val Ser Ser Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Asn Thr His Val Pro Tyr Thr Phe Gly Gly Gly Thr Lys Leu
        115                 120                 125

Glu Ile Lys
```

-continued

130

<210> SEQ ID NO 143
<211> LENGTH: 15
<212> TYPE: DNA
<213> ORGANISM: Artificial Sequence
<220> FEATURE:
<223> OTHER INFORMATION: Antibody 18B4 Heavy Chain CDR1

<400> SEQUENCE: 143
gacgcctgga tggac                                                     15

<210> SEQ ID NO 144
<211> LENGTH: 5
<212> TYPE: PRT
<213> ORGANISM: Artificial Sequence
<220> FEATURE:
<223> OTHER INFORMATION: Antibody 18B4 Heavy Chain CDR1

<400> SEQUENCE: 144

Asp Ala Trp Met Asp
1               5

<210> SEQ ID NO 145
<211> LENGTH: 57
<212> TYPE: DNA
<213> ORGANISM: Artificial Sequence
<220> FEATURE:
<223> OTHER INFORMATION: Antibody 18B4 Heavy Chain CDR2

<400> SEQUENCE: 145
gaaattagaa gcacagctaa tattcataca acatactatg ctgagtctgt ccaaggg      57

<210> SEQ ID NO 146
<211> LENGTH: 19
<212> TYPE: PRT
<213> ORGANISM: Artificial Sequence
<220> FEATURE:
<223> OTHER INFORMATION: Antibody 18B4 Heavy Chain CDR2

<400> SEQUENCE: 146

Glu Ile Arg Ser Thr Ala Asn Ile His Thr Thr Tyr Tyr Ala Glu Ser
1               5                   10                  15

Val Gln Gly

<210> SEQ ID NO 147
<211> LENGTH: 21
<212> TYPE: DNA
<213> ORGANISM: Artificial Sequence
<220> FEATURE:
<223> OTHER INFORMATION: Antibody 18B4 Heavy Chain CDR3

<400> SEQUENCE: 147
ttactctacg gatttgctta c                                              21

<210> SEQ ID NO 148
<211> LENGTH: 7
<212> TYPE: PRT
<213> ORGANISM: Artificial Sequence
<220> FEATURE:
<223> OTHER INFORMATION: Antibody 18B4 Heavy Chain CDR3

<400> SEQUENCE: 148

Leu Leu Tyr Gly Phe Ala Tyr
1               5

<210> SEQ ID NO 149
<211> LENGTH: 48
<212> TYPE: DNA
<213> ORGANISM: Artificial Sequence
<220> FEATURE:
<223> OTHER INFORMATION: Antibody 18B4 Light Chain CDR1

<400> SEQUENCE: 149
agaactagtc agagccttgt acacagtaat ggaaacacct atttacat        48

<210> SEQ ID NO 150
<211> LENGTH: 16
<212> TYPE: PRT
<213> ORGANISM: Artificial Sequence
<220> FEATURE:
<223> OTHER INFORMATION: Antibody 18B4 Light Chain CDR1

<400> SEQUENCE: 150

Arg Thr Ser Gln Ser Leu Val His Ser Asn Gly Asn Thr Tyr Leu His
1               5                   10                  15

<210> SEQ ID NO 151
<211> LENGTH: 21
<212> TYPE: DNA
<213> ORGANISM: Artificial Sequence
<220> FEATURE:
<223> OTHER INFORMATION: Antibody 18B4 Light Chain CDR2

<400> SEQUENCE: 151
aaagtttcca gccgattttc t        21

<210> SEQ ID NO 152
<211> LENGTH: 7
<212> TYPE: PRT
<213> ORGANISM: Artificial Sequence
<220> FEATURE:
<223> OTHER INFORMATION: Antibody 18B4 Light Chain CDR2

<400> SEQUENCE: 152

Lys Val Ser Ser Arg Phe Ser
1               5

<210> SEQ ID NO 153
<211> LENGTH: 27
<212> TYPE: DNA
<213> ORGANISM: Artificial Sequence
<220> FEATURE:
<223> OTHER INFORMATION: Antibody 18B4 Light Chain CDR3

<400> SEQUENCE: 153
tctcaaaata cacatgttcc gtacacg        27

<210> SEQ ID NO 154
<211> LENGTH: 9
<212> TYPE: PRT
<213> ORGANISM: Artificial Sequence
<220> FEATURE:
<223> OTHER INFORMATION: Antibody 18B4 Light Chain CDR3

<400> SEQUENCE: 154

Ser Gln Asn Thr His Val Pro Tyr Thr
1               5

<210> SEQ ID NO 155
<211> LENGTH: 408
<212> TYPE: DNA

<213> ORGANISM: Artificial Sequence
<220> FEATURE:
<223> OTHER INFORMATION: Antibody 1E4 Heavy chain - Signal sequence-FR1-CDR1-FR2-CDR2-FR3-CDR3-FR4

<400> SEQUENCE: 155

```
atggaatggc cttgtatctt tctcttcctc ctgtcagtaa ctgaaggtgt ccactcccag      60
gttcagctgc agcagtctgg ggctgagctg gtgaggcctg gtcctcagt gaagatttcc      120
tgtaaggctt ctggctatgc attcagtacc tactggatga actgggtgaa gcagaggcct     180
ggacagggtc ttgagtggat tggacagatt tatcctggag atagtgatac taactacaat     240
ggaaagttca gggtaaagc cacactgact gcagacaagt cctccaacac agcctacatg      300
cagctcagca gcctaacatc tgaggactct gcggtctttt tctgtgcaag aggtaaccac     360
gcctctatgg actactgggg tcaaggaacc tcagtcaccg tctcctca                  408
```

<210> SEQ ID NO 156
<211> LENGTH: 136
<212> TYPE: PRT
<213> ORGANISM: Artificial Sequence
<220> FEATURE:
<223> OTHER INFORMATION: Antibody 1E4 Heavy chain - Signal sequence-FR1-CDR1-FR2-CDR2-FR3-CDR3-FR4

<400> SEQUENCE: 156

```
Met Glu Trp Pro Cys Ile Phe Leu Phe Leu Leu Ser Val Thr Glu Gly
1               5                   10                  15
Val His Ser Gln Val Gln Leu Gln Gln Ser Gly Ala Glu Leu Val Arg
            20                  25                  30
Pro Gly Ser Ser Val Lys Ile Ser Cys Lys Ala Ser Gly Tyr Ala Phe
        35                  40                  45
Ser Thr Tyr Trp Met Asn Trp Val Lys Gln Arg Pro Gly Gln Gly Leu
    50                  55                  60
Glu Trp Ile Gly Gln Ile Tyr Pro Gly Asp Ser Asp Thr Asn Tyr Asn
65                  70                  75                  80
Gly Lys Phe Lys Gly Lys Ala Thr Leu Thr Ala Asp Lys Ser Ser Asn
                85                  90                  95
Thr Ala Tyr Met Gln Leu Ser Ser Leu Thr Ser Glu Asp Ser Ala Val
            100                 105                 110
Phe Phe Cys Ala Arg Gly Asn His Ala Ser Met Asp Tyr Trp Gly Gln
        115                 120                 125
Gly Thr Ser Val Thr Val Ser Ser
    130                 135
```

<210> SEQ ID NO 157
<211> LENGTH: 393
<212> TYPE: DNA
<213> ORGANISM: Artificial Sequence
<220> FEATURE:
<223> OTHER INFORMATION: Antibody 1E4 Light chain - Signal sequence-FR1-CDR1-FR2-CDR2-FR3-CDR3-FR4

<400> SEQUENCE: 157

```
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca aagttccaa ccgattttct      240
ggggtcccag acaggttcag tggcagtgga tcagggacag atttcacact caagatcagc     300
```

```
agagtggagg ctgaggatct gggagtttat ttctgctctc aaaaaacaca tgttccgtgg    360
acgttcggtg gaggcaccaa gctggaaatc aaa                                 393
```

<210> SEQ ID NO 158
<211> LENGTH: 131
<212> TYPE: PRT
<213> ORGANISM: Artificial Sequence
<220> FEATURE:
<223> OTHER INFORMATION: Antibody 1E4 Light chain - Signal
      sequence-FR1-CDR1-FR2-CDR2-FR3-CDR3-FR4

<400> SEQUENCE: 158

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Lys Thr His Val Pro Trp Thr Phe Gly Gly Gly Thr Lys Leu
        115                 120                 125

Glu Ile Lys
    130
```

<210> SEQ ID NO 159
<211> LENGTH: 15
<212> TYPE: DNA
<213> ORGANISM: Artificial Sequence
<220> FEATURE:
<223> OTHER INFORMATION: Antibody 1E4 Heavy Chain CDR1

<400> SEQUENCE: 159

```
acctactgga tgaac                                                     15
```

<210> SEQ ID NO 160
<211> LENGTH: 5
<212> TYPE: PRT
<213> ORGANISM: Artificial Sequence
<220> FEATURE:
<223> OTHER INFORMATION: Antibody 1E4 Heavy Chain CDR1

<400> SEQUENCE: 160

```
Thr Tyr Trp Met Asn
1               5
```

<210> SEQ ID NO 161
<211> LENGTH: 51
<212> TYPE: DNA
<213> ORGANISM: Artificial Sequence
<220> FEATURE:
<223> OTHER INFORMATION: Antibody 1E4 Heavy Chain CDR2

<400> SEQUENCE: 161

```
cagatttatc ctggagatag tgatactaac tacaatggaa agttcaaggg t             51
```

<210> SEQ ID NO 162
<211> LENGTH: 17
<212> TYPE: PRT
<213> ORGANISM: Artificial Sequence
<220> FEATURE:
<223> OTHER INFORMATION: Antibody 1E4 Heavy Chain CDR2

<400> SEQUENCE: 162

Gln Ile Tyr Pro Gly Asp Ser Asp Thr Asn Tyr Asn Gly Lys Phe Lys
1               5                   10                  15

Gly

<210> SEQ ID NO 163
<211> LENGTH: 24
<212> TYPE: DNA
<213> ORGANISM: Artificial Sequence
<220> FEATURE:
<223> OTHER INFORMATION: Antibody 1E4 Heavy Chain CDR3

<400> SEQUENCE: 163
ggtaaccacg cctctatgga ctac                                          24

<210> SEQ ID NO 164
<211> LENGTH: 8
<212> TYPE: PRT
<213> ORGANISM: Artificial Sequence
<220> FEATURE:
<223> OTHER INFORMATION: Antibody 1E4 Heavy Chain CDR3

<400> SEQUENCE: 164

Gly Asn His Ala Ser Met Asp Tyr
1               5

<210> SEQ ID NO 165
<211> LENGTH: 48
<212> TYPE: DNA
<213> ORGANISM: Artificial Sequence
<220> FEATURE:
<223> OTHER INFORMATION: Antibody 1E4 Light Chain CDR1

<400> SEQUENCE: 165
agatctagtc agagccttgt acacagtaat ggaaacacct atttacat                48

<210> SEQ ID NO 166
<211> LENGTH: 16
<212> TYPE: PRT
<213> ORGANISM: Artificial Sequence
<220> FEATURE:
<223> OTHER INFORMATION: Antibody 1E4 Light Chain CDR1

<400> SEQUENCE: 166

Arg Ser Ser Gln Ser Leu Val His Ser Asn Gly Asn Thr Tyr Leu His
1               5                   10                  15

<210> SEQ ID NO 167
<211> LENGTH: 21
<212> TYPE: DNA
<213> ORGANISM: Artificial Sequence
<220> FEATURE:
<223> OTHER INFORMATION: Antibody 1E4 Light Chain CDR2

<400> SEQUENCE: 167
aaagtttcca accgattttc t                                             21

<210> SEQ ID NO 168
<211> LENGTH: 7
<212> TYPE: PRT
<213> ORGANISM: Artificial Sequence
<220> FEATURE:
<223> OTHER INFORMATION: Antibody 1E4 Light Chain CDR2

<400> SEQUENCE: 168

Lys Val Ser Asn Arg Phe Ser
1               5

<210> SEQ ID NO 169
<211> LENGTH: 27
<212> TYPE: DNA
<213> ORGANISM: Artificial Sequence
<220> FEATURE:
<223> OTHER INFORMATION: Antibody 1E4 Light Chain CDR3

<400> SEQUENCE: 169
tctcaaaaaa cacatgttcc gtggacg                                        27

<210> SEQ ID NO 170
<211> LENGTH: 9
<212> TYPE: PRT
<213> ORGANISM: Artificial Sequence
<220> FEATURE:
<223> OTHER INFORMATION: Antibody 1E4 Light Chain CDR3

<400> SEQUENCE: 170

Ser Gln Lys Thr His Val Pro Trp Thr
1               5

<210> SEQ ID NO 171
<211> LENGTH: 411
<212> TYPE: DNA
<213> ORGANISM: Artificial Sequence
<220> FEATURE:
<223> OTHER INFORMATION: Antibody 29H1 Heavy chain - Signal
      sequence-FR1-CDR1-FR2-CDR2-FR3-CDR3-FR4

<400> SEQUENCE: 171
atgtacttgg gactgaacta tgtattcata gtttttctct taaatggtgt ccagagtgaa    60
gtgaagcttg aggagtctgg aggaggcttg gtacaacctg gaggatccat gaaactctct   120
tgtgctgcct ctggattcac ttttagtgac gcctggatgg actgggtccg ccagtctcca   180
gagaaggggc ttgaatgggt tgctgaaatt agaagcaaag ctactaatca tgcaacatac   240
tatgctgagt ctgtgaaagg gaggttcacc atctcaagag atgattccaa agtagtgtc   300 tacctgcaaa tgaacagctt aagagctgaa gacactggca tttattactg tacccccta   360 ctttacgggt tgcttactg gggccaaggg actctggtca ctgtctctgc a             411

<210> SEQ ID NO 172
<211> LENGTH: 137
<212> TYPE: PRT
<213> ORGANISM: Artificial Sequence
<220> FEATURE:
<223> OTHER INFORMATION: Antibody 29H1 Heavy chain - Signal
      sequence-FR1-CDR1-FR2-CDR2-FR3-CDR3-FR4

<400> SEQUENCE: 172

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
          35                  40                  45

Ser Asp Ala Trp Met Asp Trp Val Arg Gln Ser Pro Glu Lys Gly Leu
 50                  55                  60

Glu Trp Val Ala Glu Ile Arg Ser Lys Ala Thr Asn His Ala Thr Tyr
 65                  70                  75                  80

Tyr Ala Glu Ser Val Lys Gly Arg Phe Thr Ile Ser Arg Asp Asp Ser
                 85                  90                  95

Lys Ser Ser Val Tyr Leu Gln Met Asn Ser Leu Arg Ala Glu Asp Thr
             100                 105                 110

Gly Ile Tyr Tyr Cys Thr Pro Leu Leu Tyr Gly Phe Ala Tyr Trp Gly
             115                 120                 125

Gln Gly Thr Leu Val Thr Val Ser Ala
    130                 135

<210> SEQ ID NO 173
<211> LENGTH: 393
<212> TYPE: DNA
<213> ORGANISM: Artificial Sequence
<220> FEATURE:
<223> OTHER INFORMATION: Antibody 29H1 Light chain - Signal
      sequence-FR1-CDR1-FR2-CDR2-FR3-CDR3-FR4

<400> SEQUENCE: 173
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctggtcagag ccttgtacac agtaatggac acacctattt acattggtac     180
ctgcagaagc caggccagtc tccaaggctc ctgatctaca agtttccaa ccgatttct      240 ggggtcccag acaggttcag tggcagtgga tcagggcag atttcacact caagatcagc     300
agagtggagg ctgaggatct gggagtttat ttctgctctc aaactacaca tgttccgtgg     360
acgttcggtg aggcaccaa gctggaaatc aaa                                   393

<210> SEQ ID NO 174
<211> LENGTH: 131
<212> TYPE: PRT
<213> ORGANISM: Artificial Sequence
<220> FEATURE:
<223> OTHER INFORMATION: Antibody 29H1 Light chain - Signal
      sequence-FR1-CDR1-FR2-CDR2-FR3-CDR3-FR4

<400> SEQUENCE: 174

Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
                 20                  25                  30

Ser Leu Gly Asp Gln Ala Ser Ile Ser Cys Arg Ser Gly Gln Ser Leu
             35                  40                  45

Val His Ser Asn Gly His Thr Tyr Leu His Trp Tyr Leu Gln Lys Pro
         50                  55                  60

Gly Gln Ser Pro Arg Leu Leu Ile Tyr Lys Val Ser Asn Arg Phe Ser
 65                  70                  75                  80

Gly Val Pro Asp Arg Phe Ser Gly Ser Gly Ser Arg Ala Asp Phe Thr
                 85                  90                  95

Leu Lys Ile Ser Arg Val Glu Ala Glu Asp Leu Gly Val Tyr Phe Cys
             100                 105                 110

Ser Gln Thr Thr His Val Pro Trp Thr Phe Gly Gly Gly Thr Lys Leu

<210> SEQ ID NO 175
<211> LENGTH: 15
<212> TYPE: DNA
<213> ORGANISM: Artificial Sequence
<220> FEATURE:
<223> OTHER INFORMATION: Antibody 29H1 Heavy Chain CDR1

<400> SEQUENCE: 175
gacgcctgga tggac                                                    15

<210> SEQ ID NO 176
<211> LENGTH: 5
<212> TYPE: PRT
<213> ORGANISM: Artificial Sequence
<220> FEATURE:
<223> OTHER INFORMATION: Antibody 29H1 Heavy Chain CDR1

<400> SEQUENCE: 176

Asp Ala Trp Met Asp
1               5

<210> SEQ ID NO 177
<211> LENGTH: 57
<212> TYPE: DNA
<213> ORGANISM: Artificial Sequence
<220> FEATURE:
<223> OTHER INFORMATION: Antibody 29H1 Heavy Chain CDR2

<400> SEQUENCE: 177
gaaattagaa gcaaagctac taatcatgca acatactatg ctgagtctgt gaaaggg      57

<210> SEQ ID NO 178
<211> LENGTH: 19
<212> TYPE: PRT
<213> ORGANISM: Artificial Sequence
<220> FEATURE:
<223> OTHER INFORMATION: Antibody 29H1 Heavy Chain CDR2

<400> SEQUENCE: 178

Glu Ile Arg Ser Lys Ala Thr Asn His Ala Thr Tyr Tyr Ala Glu Ser
1               5                   10                  15

Val Lys Gly

<210> SEQ ID NO 179
<211> LENGTH: 21
<212> TYPE: DNA
<213> ORGANISM: Artificial Sequence
<220> FEATURE:
<223> OTHER INFORMATION: Antibody 29H1 Heavy Chain CDR3

<400> SEQUENCE: 179
ctactttacg ggtttgctta c                                             21

<210> SEQ ID NO 180
<211> LENGTH: 7
<212> TYPE: PRT
<213> ORGANISM: Artificial Sequence
<220> FEATURE:
<223> OTHER INFORMATION: Antibody 29H1 Heavy Chain CDR3

<400> SEQUENCE: 180

```
Leu Leu Tyr Gly Phe Ala Tyr
1               5
```

<210> SEQ ID NO 181
<211> LENGTH: 48
<212> TYPE: DNA
<213> ORGANISM: Artificial Sequence
<220> FEATURE:
<223> OTHER INFORMATION: Antibody 29H1 Light Chain CDR1

<400> SEQUENCE: 181

```
agatctggtc agagccttgt acacagtaat ggacacacct atttacat          48
```

<210> SEQ ID NO 182
<211> LENGTH: 16
<212> TYPE: PRT
<213> ORGANISM: Artificial Sequence
<220> FEATURE:
<223> OTHER INFORMATION: Antibody 29H1 Light Chain CDR1

<400> SEQUENCE: 182

```
Arg Ser Gly Gln Ser Leu Val His Ser Asn Gly His Thr Tyr Leu His
1               5                   10                  15
```

<210> SEQ ID NO 183
<211> LENGTH: 21
<212> TYPE: DNA
<213> ORGANISM: Artificial Sequence
<220> FEATURE:
<223> OTHER INFORMATION: Antibody 29H1 Light Chain CDR2

<400> SEQUENCE: 183

```
aaagtttcca accgattttc t                                       21
```

<210> SEQ ID NO 184
<211> LENGTH: 7
<212> TYPE: PRT
<213> ORGANISM: Artificial Sequence
<220> FEATURE:
<223> OTHER INFORMATION: Antibody 29H1 Light Chain CDR2

<400> SEQUENCE: 184

```
Lys Val Ser Asn Arg Phe Ser
1               5
```

<210> SEQ ID NO 185
<211> LENGTH: 27
<212> TYPE: DNA
<213> ORGANISM: Artificial Sequence
<220> FEATURE:
<223> OTHER INFORMATION: Antibody 29H1 Light Chain CDR3

<400> SEQUENCE: 185

```
tctcaaacta cacatgttcc gtggacg                                 27
```

<210> SEQ ID NO 186
<211> LENGTH: 9
<212> TYPE: PRT
<213> ORGANISM: Artificial Sequence
<220> FEATURE:
<223> OTHER INFORMATION: Antibody 29H1 Light Chain CDR3

<400> SEQUENCE: 186

```
Ser Gln Thr Thr His Val Pro Trp Thr
1               5
```

<210> SEQ ID NO 187
<211> LENGTH: 399
<212> TYPE: DNA
<213> ORGANISM: Artificial Sequence
<220> FEATURE:
<223> OTHER INFORMATION: Antibody 31A1 Heavy chain - Signal
      sequence-FR1-CDR1-FR2-CDR2-FR3-CDR3-FR4

<400> SEQUENCE: 187

```
atggaaaggc actggatctt tctcttcctg ttttcagtaa ctgcaggtgt ccactcccag    60
gtccagcttc agcagtctgg ggctgaactg gcaaaacctg gggcctcagt gaagatgtcc   120
tgcaaggctt ctggctacac ctttactagc tactggatgc actgggtaaa acagaggcct   180
ggacagggtc tggaatggat tggatacatt aatcctagca ctggttatac tgagtacaat   240
cagaagttca aggacaaggc cacattgact gcagacaaat cctccagcac agcctacatg   300
caactgagca gcctgacatc tgaggactct gcagtctatt actgtgcaag agcctacatt   360
gactactggg gccaaggcac cactctcaca gtctcctca                           399
```

<210> SEQ ID NO 188
<211> LENGTH: 133
<212> TYPE: PRT
<213> ORGANISM: Artificial Sequence
<220> FEATURE:
<223> OTHER INFORMATION: Antibody 31A1 Heavy chain - Signal
      sequence-FR1-CDR1-FR2-CDR2-FR3-CDR3-FR4

<400> SEQUENCE: 188

```
Met Glu Arg His Trp Ile Phe Leu Phe Leu Phe Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Tyr Ile Asn Pro Ser Thr Gly Tyr Thr Glu Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ala Tyr Ile Asp Tyr Trp Gly Gln Gly Thr Thr
        115                 120                 125

Leu Thr Val Ser Ser
    130
```

<210> SEQ ID NO 189
<211> LENGTH: 393
<212> TYPE: DNA
<213> ORGANISM: Artificial Sequence
<220> FEATURE:
<223> OTHER INFORMATION: Antibody 31A1 Light chain - Signal
      sequence-FR1-CDR1-FR2-CDR2-FR3-CDR3-FR4

<400> SEQUENCE: 189

```
atgaagttgc ctgttaggct gttggtgctg atgttctgga ttcctgcttc cagcagtgat    60
gttttgatga cccaaactcc actctccctg cctgtcagtc ttggagatca agcctccttc   120
tcttgcagat ctagtcagag cattgtacat agtaatggaa acacctattt agaatggtac   180
```

```
ctgcagaaac caggccagtc tccaaagctc ctgatctaca aagtttccaa ccgatttct      240 ggggtcccag acaggttcag tgcagtgga tcagggacag atttcacact caagatcaac       300
agagtggagg ctgaggatct gggagtttat tactgctttc aagtttcaca ttttccgtgg      360
acgttcggtg gaggcaccaa gctggaaatc aaa                                   393
```

```
<210> SEQ ID NO 190
<211> LENGTH: 131
<212> TYPE: PRT
<213> ORGANISM: Artificial Sequence
<220> FEATURE:
<223> OTHER INFORMATION: Antibody 31A1 Light chain - Signal
      sequence-FR1-CDR1-FR2-CDR2-FR3-CDR3-FR4

<400> SEQUENCE: 190
```

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Phe Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Asn Arg Val Glu Ala Glu Asp Leu Gly Val Tyr Tyr Cys
            100                 105                 110

Phe Gln Val Ser His Phe Pro Trp Thr Phe Gly Gly Gly Thr Lys Leu
        115                 120                 125

Glu Ile Lys
    130

```
<210> SEQ ID NO 191
<211> LENGTH: 15
<212> TYPE: DNA
<213> ORGANISM: Artificial Sequence
<220> FEATURE:
<223> OTHER INFORMATION: Antibody 31A1 Heavy Chain CDR1

<400> SEQUENCE: 191
agctactgga tgcac                                                       15

<210> SEQ ID NO 192
<211> LENGTH: 5
<212> TYPE: PRT
<213> ORGANISM: Artificial Sequence
<220> FEATURE:
<223> OTHER INFORMATION: Antibody 31A1 Heavy Chain CDR1

<400> SEQUENCE: 192
```

Ser Tyr Trp Met His
1               5

```
<210> SEQ ID NO 193
<211> LENGTH: 51
<212> TYPE: DNA
<213> ORGANISM: Artificial Sequence
<220> FEATURE:
<223> OTHER INFORMATION: Antibody 31A1 Heavy Chain CDR2
```

<400> SEQUENCE: 193
tacattaatc ctagcactgg ttatactgag tacaatcaga agttcaagga c        51

<210> SEQ ID NO 194
<211> LENGTH: 17
<212> TYPE: PRT
<213> ORGANISM: Artificial Sequence
<220> FEATURE:
<223> OTHER INFORMATION: Antibody 31A1 Heavy Chain CDR2

<400> SEQUENCE: 194

Tyr Ile Asn Pro Ser Thr Gly Tyr Thr Glu Tyr Asn Gln Lys Phe Lys
1               5                   10                  15
Asp

<210> SEQ ID NO 195
<211> LENGTH: 15
<212> TYPE: DNA
<213> ORGANISM: Artificial Sequence
<220> FEATURE:
<223> OTHER INFORMATION: Antibody 31A1 Heavy Chain CDR3

<400> SEQUENCE: 195
gcctacattg actac                                                  15

<210> SEQ ID NO 196
<211> LENGTH: 5
<212> TYPE: PRT
<213> ORGANISM: Artificial Sequence
<220> FEATURE:
<223> OTHER INFORMATION: Antibody 31A1 Heavy Chain CDR3

<400> SEQUENCE: 196

Ala Tyr Ile Asp Tyr
1               5

<210> SEQ ID NO 197
<211> LENGTH: 48
<212> TYPE: DNA
<213> ORGANISM: Artificial Sequence
<220> FEATURE:
<223> OTHER INFORMATION: Antibody 31A1 Light Chain CDR1

<400> SEQUENCE: 197
agatctagtc agagcattgt acatagtaat ggaaacacct atttagaa             48

<210> SEQ ID NO 198
<211> LENGTH: 16
<212> TYPE: PRT
<213> ORGANISM: Artificial Sequence
<220> FEATURE:
<223> OTHER INFORMATION: Antibody 31A1 Light Chain CDR1

<400> SEQUENCE: 198

Arg Ser Ser Gln Ser Ile Val His Ser Asn Gly Asn Thr Tyr Leu Glu
1               5                   10                  15

<210> SEQ ID NO 199
<211> LENGTH: 21
<212> TYPE: DNA
<213> ORGANISM: Artificial Sequence
<220> FEATURE:
<223> OTHER INFORMATION: Antibody 31A1 Light Chain CDR2

<400> SEQUENCE: 199

```
aaagtttcca accgattttc t                                              21
```

```
<210> SEQ ID NO 200
<211> LENGTH: 7
<212> TYPE: PRT
<213> ORGANISM: Artificial Sequence
<220> FEATURE:
<223> OTHER INFORMATION: Antibody 31A1 Light Chain CDR2

<400> SEQUENCE: 200

Lys Val Ser Asn Arg Phe Ser
1               5
```

```
<210> SEQ ID NO 201
<211> LENGTH: 27
<212> TYPE: DNA
<213> ORGANISM: Artificial Sequence
<220> FEATURE:
<223> OTHER INFORMATION: Antibody 31A1 Light Chain CDR3

<400> SEQUENCE: 201
tttcaagttt cacattttcc gtggacg                                        27
```

```
<210> SEQ ID NO 202
<211> LENGTH: 9
<212> TYPE: PRT
<213> ORGANISM: Artificial Sequence
<220> FEATURE:
<223> OTHER INFORMATION: Antibody 31A1 Light Chain CDR3

<400> SEQUENCE: 202

Phe Gln Val Ser His Phe Pro Trp Thr
1               5
```

```
<210> SEQ ID NO 203
<211> LENGTH: 411
<212> TYPE: DNA
<213> ORGANISM: Artificial Sequence
<220> FEATURE:
<223> OTHER INFORMATION: Antibody 32C1 Heavy chain - Signal
      sequence-FR1-CDR1-FR2-CDR2-FR3-CDR3-FR4

<400> SEQUENCE: 203
atgtacttgg gactgaactg tgtattcata gtttttctct taaaaggtgt ccagagtgaa     60
gtgaagcttg aggagtctgg aggaggcttg gtgcaatctg gaggatccat gaaactctcc    120
tgtgttgcct ctggattcac tttcagtaat tactggatga actgggtccg ccagtctcca    180
gagaaggggc ttgagtgggt tgctgaaatt agattgaaat ctaataatta tgcaatacat    240
tatgcggagt ctgtgaaggg gaggttcacc atctcaagag atgattccaa agtagtgtc    300
tacctgcaaa tgaacaactt aagagctgaa gacactggca tttattactg taccagggtc    360
ccgggactgg atgcttactg gggccaaggg actctggtca ctgtctctgc a             411
```

```
<210> SEQ ID NO 204
<211> LENGTH: 137
<212> TYPE: PRT
<213> ORGANISM: Artificial Sequence
<220> FEATURE:
<223> OTHER INFORMATION: Antibody 32C1 Heavy chain - Signal
      sequence-FR1-CDR1-FR2-CDR2-FR3-CDR3-FR4

<400> SEQUENCE: 204

Met Tyr Leu Gly Leu Asn Cys Val Phe Ile Val Phe Leu Leu Lys Gly
1               5                   10                  15
```

Val Gln Ser Glu Val Lys Leu Glu Glu Ser Gly Gly Gly Leu Val Gln
            20                  25                  30

Ser Gly Gly Ser Met Lys Leu Ser Cys Val Ala Ser Gly Phe Thr Phe
            35                  40                  45

Ser Asn Tyr Trp Met Asn Trp Val Arg Gln Ser Pro Glu Lys Gly Leu
        50                  55                  60

Glu Trp Val Ala Glu Ile Arg Leu Lys Ser Asn Asn Tyr Ala Ile His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Arg Val Pro Gly Leu Asp Ala Tyr Trp Gly
        115                 120                 125

Gln Gly Thr Leu Val Thr Val Ser Ala
    130                 135

<210> SEQ ID NO 205
<211> LENGTH: 393
<212> TYPE: DNA
<213> ORGANISM: Artificial Sequence
<220> FEATURE:
<223> OTHER INFORMATION: Antibody 32C1 Light chain - Signal
      sequence-FR1-CDR1-FR2-CDR2-FR3-CDR3-FR4

<400> SEQUENCE: 205
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgatttttct     240 ggggtcccag acaggttcag tggcagtgga tcagggacag atttcacact caagatcagc     300
agtgtggagg ctgaggatct gggagtttat ttctgctctc aaattacaca tgttccgtac     360
acgttcggag gggggaccaa tctggaaata aaa                                  393

<210> SEQ ID NO 206
<211> LENGTH: 131
<212> TYPE: PRT
<213> ORGANISM: Artificial Sequence
<220> FEATURE:
<223> OTHER INFORMATION: Antibody 32C1 Light chain - Signal
      sequence-FR1-CDR1-FR2-CDR2-FR3-CDR3-FR4

<400> SEQUENCE: 206

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Ser Val Glu Ala Glu Asp Leu Gly Val Tyr Phe Cys

```
                    100                 105                 110
Ser Gln Ile Thr His Val Pro Tyr Thr Phe Gly Gly Gly Thr Asn Leu
        115                 120                 125

Glu Ile Lys
    130

<210> SEQ ID NO 207
<211> LENGTH: 15
<212> TYPE: DNA
<213> ORGANISM: Artificial Sequence
<220> FEATURE:
<223> OTHER INFORMATION: Antibody 32C1 Heavy Chain CDR1

<400> SEQUENCE: 207
aattactgga tgaac                                                    15

<210> SEQ ID NO 208
<211> LENGTH: 5
<212> TYPE: PRT
<213> ORGANISM: Artificial Sequence
<220> FEATURE:
<223> OTHER INFORMATION: Antibody 32C1 Heavy Chain CDR1

<400> SEQUENCE: 208

Asn Tyr Trp Met Asn
1               5

<210> SEQ ID NO 209
<211> LENGTH: 57
<212> TYPE: DNA
<213> ORGANISM: Artificial Sequence
<220> FEATURE:
<223> OTHER INFORMATION: Antibody 32C1 Heavy Chain CDR2

<400> SEQUENCE: 209
gaaattagat tgaaatctaa taattatgca atacattatg cggagtctgt gaagggg     57

<210> SEQ ID NO 210
<211> LENGTH: 19
<212> TYPE: PRT
<213> ORGANISM: Artificial Sequence
<220> FEATURE:
<223> OTHER INFORMATION: Antibody 32C1 Heavy Chain CDR2

<400> SEQUENCE: 210

Glu Ile Arg Leu Lys Ser Asn Asn Tyr Ala Ile His Tyr Ala Glu Ser
1               5                   10                  15

Val Lys Gly

<210> SEQ ID NO 211
<211> LENGTH: 21
<212> TYPE: DNA
<213> ORGANISM: Artificial Sequence
<220> FEATURE:
<223> OTHER INFORMATION: Antibody 32C1 Heavy Chain CDR3

<400> SEQUENCE: 211
gtcccgggac tggatgctta c                                             21

<210> SEQ ID NO 212
<211> LENGTH: 7
<212> TYPE: PRT
<213> ORGANISM: Artificial Sequence
<220> FEATURE:
<223> OTHER INFORMATION: Antibody 32C1 Heavy Chain CDR3
```

<400> SEQUENCE: 212

Val Pro Gly Leu Asp Ala Tyr
1               5

<210> SEQ ID NO 213
<211> LENGTH: 48
<212> TYPE: DNA
<213> ORGANISM: Artificial Sequence
<220> FEATURE:
<223> OTHER INFORMATION: Antibody 32C1 Light Chain CDR1

<400> SEQUENCE: 213
agatctagtc agagccttgt acacagtaat ggaaacacct atttacat          48

<210> SEQ ID NO 214
<211> LENGTH: 16
<212> TYPE: PRT
<213> ORGANISM: Artificial Sequence
<220> FEATURE:
<223> OTHER INFORMATION: Antibody 32C1 Light Chain CDR1

<400> SEQUENCE: 214

Arg Ser Ser Gln Ser Leu Val His Ser Asn Gly Asn Thr Tyr Leu His
1               5                   10                  15

<210> SEQ ID NO 215
<211> LENGTH: 21
<212> TYPE: DNA
<213> ORGANISM: Artificial Sequence
<220> FEATURE:
<223> OTHER INFORMATION: Antibody 32C1 Light Chain CDR2

<400> SEQUENCE: 215
aaagtttcca accgattttc t                                       21

<210> SEQ ID NO 216
<211> LENGTH: 7
<212> TYPE: PRT
<213> ORGANISM: Artificial Sequence
<220> FEATURE:
<223> OTHER INFORMATION: Antibody 32C1 Light Chain CDR2

<400> SEQUENCE: 216

Lys Val Ser Asn Arg Phe Ser
1               5

<210> SEQ ID NO 217
<211> LENGTH: 27
<212> TYPE: DNA
<213> ORGANISM: Artificial Sequence
<220> FEATURE:
<223> OTHER INFORMATION: Antibody 32C1 Light Chain CDR3

<400> SEQUENCE: 217
tctcaaatta cacatgttcc gtacacg                                 27

<210> SEQ ID NO 218
<211> LENGTH: 9
<212> TYPE: PRT
<213> ORGANISM: Artificial Sequence
<220> FEATURE:
<223> OTHER INFORMATION: Antibody 32C1 Light Chain CDR3

<400> SEQUENCE: 218

Ser Gln Ile Thr His Val Pro Tyr Thr

<210> SEQ ID NO 219
<211> LENGTH: 423
<212> TYPE: DNA
<213> ORGANISM: Artificial Sequence
<220> FEATURE:
<223> OTHER INFORMATION: Antibody 45C11 Heavy chain - Signal
      sequence-FR1-CDR1-FR2-CDR2-FR3-CDR3-FR4

<400> SEQUENCE: 219

```
atgaaatgca gctgggttat cttcttcctg atggcagtgg ttacaggggt caattcagag      60
gttcagctgc agcagtctgg ggcagacctt gtgaagccag ggcctcagt caagttgtcc     120
tgcacagctt ctggcttcaa cattaaagac acctttatgc actgggtgaa gcagaggcct    180
gaacagggcc tggagtggat tggaaggatt gatcctgcga atggtaatac taaatatgac    240
ccgaaattcc agggcaaggc cactataaca gcagacacat cctccaacac agcctacctg    300
cagctcagca gcctgacatc tgaggacact gccgtctatt actgtgctaa accgtatggt    360
aactacggct attactatgc tttggactac tggggtcaag gaacctcagt caccgtctcc    420
tca                                                                  423
```

<210> SEQ ID NO 220
<211> LENGTH: 141
<212> TYPE: PRT
<213> ORGANISM: Artificial Sequence
<220> FEATURE:
<223> OTHER INFORMATION: Antibody 45C11 Heavy chain - Signal
      sequence-FR1-CDR1-FR2-CDR2-FR3-CDR3-FR4

<400> SEQUENCE: 220

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Asp Leu Val Lys
            20                  25                  30

Pro Gly Ala Ser Val Lys Leu Ser Cys Thr Ala Ser Gly Phe Asn Ile
        35                  40                  45

Lys Asp Thr Phe Met His Trp Val Lys Gln Arg Pro Glu Gln Gly Leu
    50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Lys Pro Tyr Gly Asn Tyr Gly Tyr Tyr Tyr Ala Leu
        115                 120                 125

Asp Tyr Trp Gly Gln Gly Thr Ser Val Thr Val Ser Ser
    130                 135                 140

<210> SEQ ID NO 221
<211> LENGTH: 381
<212> TYPE: DNA
<213> ORGANISM: Artificial Sequence
<220> FEATURE:
<223> OTHER INFORMATION: Antibody 45C11 Light chain - Signal
      sequence-FR1-CDR1-FR2-CDR2-FR3-CDR3-FR4

<400> SEQUENCE: 221

```
atgaggttcc aggttcaggt tctggggctc cttctgctct ggatatcagg tgcccagtgt      60
```

```
gatgtccaga taacccagtc tccatcttat cttgctgcat ctcctggaga aaccattact    120
attaattgca gggcaagtaa gagcattagc aaatatttag cctggtatca agagaaacct    180
gggaaaacta ataagcttct tatctactct ggatccactt tgcaatctgg aattccatca    240
aggttcagtg gcagtggatc tggtacagat ttcactctca ccatcagtag cctggagcct    300
gaagattttg caatgtatta ctgtcaacag cataatgaat cccgtggac gttcggtgga    360 ggcaccaagc tggaaatcaa a                                              381
```

<210> SEQ ID NO 222
<211> LENGTH: 127
<212> TYPE: PRT
<213> ORGANISM: Artificial Sequence
<220> FEATURE:
<223> OTHER INFORMATION: Antibody 45C11 Light chain - Signal
      sequence-FR1-CDR1-FR2-CDR2-FR3-CDR3-FR4

<400> SEQUENCE: 222

```
Met Arg Phe Gln Val Gln Val Leu Gly Leu Leu Leu Leu Trp Ile Ser
1               5                   10                  15

Gly Ala Gln Cys Asp Val Gln Ile Thr Gln Ser Pro Ser Tyr Leu Ala
            20                  25                  30

Ala Ser Pro Gly Glu Thr Ile Thr Ile Asn Cys Arg Ala Ser Lys Ser
        35                  40                  45

Ile Ser Lys Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Ile Pro Ser
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Met Tyr Tyr Cys Gln Gln His Asn
            100                 105                 110

Glu Phe Pro Trp Thr Phe Gly Gly Gly Thr Lys Leu Glu Ile Lys
        115                 120                 125
```

<210> SEQ ID NO 223
<211> LENGTH: 15
<212> TYPE: DNA
<213> ORGANISM: Artificial Sequence
<220> FEATURE:
<223> OTHER INFORMATION: Antibody 45C11 Heavy Chain CDR1

<400> SEQUENCE: 223

```
gacaccttta tgcac                                                      15
```

<210> SEQ ID NO 224
<211> LENGTH: 5
<212> TYPE: PRT
<213> ORGANISM: Artificial Sequence
<220> FEATURE:
<223> OTHER INFORMATION: Antibody 45C11 Heavy Chain CDR1

<400> SEQUENCE: 224

```
Asp Thr Phe Met His
1               5
```

<210> SEQ ID NO 225
<211> LENGTH: 51
<212> TYPE: DNA
<213> ORGANISM: Artificial Sequence
<220> FEATURE:

<223> OTHER INFORMATION: Antibody 45C11 Heavy Chain CDR2

<400> SEQUENCE: 225
aggattgatc ctgcgaatgg taatactaaa tatgacccga aattccaggg c        51

<210> SEQ ID NO 226
<211> LENGTH: 17
<212> TYPE: PRT
<213> ORGANISM: Artificial Sequence
<220> FEATURE:
<223> OTHER INFORMATION: Antibody 45C11 Heavy Chain CDR2

<400> SEQUENCE: 226

Arg Ile Asp Pro Ala Asn Gly Asn Thr Lys Tyr Asp Pro Lys Phe Gln
1               5                   10                  15

Gly

<210> SEQ ID NO 227
<211> LENGTH: 39
<212> TYPE: DNA
<213> ORGANISM: Artificial Sequence
<220> FEATURE:
<223> OTHER INFORMATION: Antibody 45C11 Heavy Chain CDR3

<400> SEQUENCE: 227
ccgtatggta actacggcta ttactatgct ttggactac                       39

<210> SEQ ID NO 228
<211> LENGTH: 13
<212> TYPE: PRT
<213> ORGANISM: Artificial Sequence
<220> FEATURE:
<223> OTHER INFORMATION: Antibody 45C11 Heavy Chain CDR3

<400> SEQUENCE: 228

Pro Tyr Gly Asn Tyr Gly Tyr Tyr Tyr Ala Leu Asp Tyr
1               5                   10

<210> SEQ ID NO 229
<211> LENGTH: 33
<212> TYPE: DNA
<213> ORGANISM: Artificial Sequence
<220> FEATURE:
<223> OTHER INFORMATION: Antibody 45C11 Light Chain CDR1

<400> SEQUENCE: 229
agggcaagta agagcattag caaatattta gcc                             33

<210> SEQ ID NO 230
<211> LENGTH: 11
<212> TYPE: PRT
<213> ORGANISM: Artificial Sequence
<220> FEATURE:
<223> OTHER INFORMATION: Antibody 45C11 Light Chain CDR1

<400> SEQUENCE: 230

Arg Ala Ser Lys Ser Ile Ser Lys Tyr Leu Ala
1               5                   10

<210> SEQ ID NO 231
<211> LENGTH: 21
<212> TYPE: DNA
<213> ORGANISM: Artificial Sequence
<220> FEATURE:
<223> OTHER INFORMATION: Antibody 45C11 Light Chain CDR2

```
<400> SEQUENCE: 231
tctggatcca ctttgcaatc t                                              21

<210> SEQ ID NO 232
<211> LENGTH: 7
<212> TYPE: PRT
<213> ORGANISM: Artificial Sequence
<220> FEATURE:
<223> OTHER INFORMATION: Antibody 45C11 Light Chain CDR2

<400> SEQUENCE: 232

Ser Gly Ser Thr Leu Gln Ser
1               5

<210> SEQ ID NO 233
<211> LENGTH: 27
<212> TYPE: DNA
<213> ORGANISM: Artificial Sequence
<220> FEATURE:
<223> OTHER INFORMATION: Antibody 45C11 Light Chain CDR3

<400> SEQUENCE: 233
caacagcata atgaattccc gtggacg                                        27

<210> SEQ ID NO 234
<211> LENGTH: 9
<212> TYPE: PRT
<213> ORGANISM: Artificial Sequence
<220> FEATURE:
<223> OTHER INFORMATION: Antibody 45C11 Light Chain CDR3

<400> SEQUENCE: 234

Gln Gln His Asn Glu Phe Pro Trp Thr
1               5

<210> SEQ ID NO 235
<211> LENGTH: 20
<212> TYPE: PRT
<213> ORGANISM: Artificial Sequence
<220> FEATURE:
<223> OTHER INFORMATION: Tandem repeat domain peptide

<400> SEQUENCE: 235

Pro Asp Thr Arg Pro Ala Pro Gly Ser Thr Ala Pro Pro Ala His Gly
1               5                   10                  15

Val Thr Ser Ala
            20

<210> SEQ ID NO 236
<211> LENGTH: 493
<212> TYPE: PRT
<213> ORGANISM: Artificial Sequence
<220> FEATURE:
<223> OTHER INFORMATION: CAR44: CD8/HUMNC2/CD8/4-1BB/CD3

<400> SEQUENCE: 236

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Gly Tyr Ala Met Ser Trp Val Arg Gln Ala Pro Gly Lys
    50                  55                  60
```

```
Gly Leu Glu Trp Val Ser Thr Ile Ser Ser Gly Thr Tyr Ile Tyr
65                  70                  75                  80

Tyr Pro Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Leu Gly Gly Asp Asn Tyr Tyr Glu Tyr
        115                 120                 125

Phe Asp Val Trp Gly Lys Gly Thr Thr Val Thr Val Ser Ser Gly Gly
130                 135                 140

Gly Gly Ser Gly Gly Gly Gly Ser Gly Gly Gly Gly Ser Asp Ile Val
145                 150                 155                 160

Leu Thr Gln Ser Pro Ala Ser Leu Ala Val Ser Pro Gly Gln Arg Ala
                165                 170                 175

Thr Ile Thr Cys Arg Ala Ser Lys Ser Val Ser Thr Ser Gly Tyr Ser
            180                 185                 190

Tyr Met His Trp Tyr Gln Gln Lys Pro Gly Gln Pro Pro Lys Leu Leu
        195                 200                 205

Ile Tyr Leu Ala Ser Asn Leu Glu Ser Gly Val Pro Ala Arg Phe Ser
210                 215                 220

Gly Ser Gly Ser Gly Thr Asp Phe Thr Leu Thr Ile Asn Pro Val Glu
225                 230                 235                 240

Ala Asn Asp Thr Ala Asn Tyr Tyr Cys Gln His Ser Arg Glu Leu Pro
                245                 250                 255

Phe Thr Phe Gly Gly Gly Thr Lys Val Glu Ile Lys Arg Thr Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Gly Gly Cys Glu Leu Arg Val Lys
        370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
        450                 455                 460

Lys Gly His Asp Gly Leu Tyr Gln Gly Leu Ser Thr Ala Thr Lys Asp
465                 470                 475                 480
```

Thr Tyr Asp Ala Leu His Met Gln Ala Leu Pro Pro Arg
              485                 490

<210> SEQ ID NO 237
<211> LENGTH: 115
<212> TYPE: PRT
<213> ORGANISM: Artificial Sequence
<220> FEATURE:
<223> OTHER INFORMATION: MIN- A2-1 light chain variable region amino
      acid sequence

<400> SEQUENCE: 237

Asp Ile Val Leu Thr Gln Ser Thr Glu Ile Met Ser Ala Ser Pro Gly
1               5                   10                  15

Glu Lys Val Thr Ile Thr Cys Ser Ala Ser Ser Ser Ile Ser Tyr Ile
            20                  25                  30

His Trp Phe Gln Gln Lys Pro Gly Thr Ser Pro Lys Leu Trp Ile Phe
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Thr Ala Thr Tyr Tyr Cys Gln Gln Arg Ser Asn Tyr Pro Phe Thr
                85                  90                  95

Phe Gly Ser Gly Thr Lys Leu Gln Ile Lys Arg Ala Asp Ala Ala Pro
            100                 105                 110

Thr Val Ser
        115

<210> SEQ ID NO 238
<211> LENGTH: 115
<212> TYPE: PRT
<213> ORGANISM: Artificial Sequence
<220> FEATURE:
<223> OTHER INFORMATION: MIN-A2-2 light chain variable region amino acid
      sequence

<400> SEQUENCE: 238

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Ala Pro Ala Arg Phe Ser Gly Ser
    50                  55                  60

Gly Ser Gly Thr Ser Tyr Ser Leu Thr Val Ser Arg Met Glu Ser Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115

<210> SEQ ID NO 239
<211> LENGTH: 115
<212> TYPE: PRT
<213> ORGANISM: Artificial Sequence
<220> FEATURE:

<223> OTHER INFORMATION: MIN-C9-1 light chain variable region amino acid
      sequence

<400> SEQUENCE: 239

Asp Ile Val Leu Thr Gln Thr Thr Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115

<210> SEQ ID NO 240
<211> LENGTH: 115
<212> TYPE: PRT
<213> ORGANISM: Artificial Sequence
<220> FEATURE:
<223> OTHER INFORMATION: MIN-C9-2 light chain variable region amino acid
      sequence

<400> SEQUENCE: 240

Asp Ile Val Ile Thr Gln Ser Thr Ala Ile Met Ser Ala Ser Pro Gly
1               5                   10                  15

Glu Lys Val Thr Ile Thr Cys Ser Ala Ser Ser Ser Val Ser Tyr Thr
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115

<210> SEQ ID NO 241
<211> LENGTH: 115
<212> TYPE: PRT
<213> ORGANISM: Artificial Sequence
<220> FEATURE:
<223> OTHER INFORMATION: MIN-D7-1 light chain variable region amino acid
      sequence

<400> SEQUENCE: 241

Asp Ile Val Ile Thr Gln Thr Pro Ala Ile Met Ser Ala Ser Pro Gly
1               5                   10                  15

Glu Lys Val Thr Met Thr Cys Ser Ala Ser Ser Ser Val Ser Tyr Met

```
                20                  25                  30
His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Val Ser Arg Met Glu Ser Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115

<210> SEQ ID NO 242
<211> LENGTH: 115
<212> TYPE: PRT
<213> ORGANISM: Artificial Sequence
<220> FEATURE:
<223> OTHER INFORMATION: MIN-D7-2 light chain variable region amino acid
      sequence

<400> SEQUENCE: 242

Asp Ile Val Leu Thr Gln Ser Thr Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ser Glu
65                  70                  75                  80

Asp Ala Ala Thr Tyr Tyr Cys Gln Gln Arg Ser Ser Tyr Pro Ser Thr
                85                  90                  95

Phe Gly Gly Gly Thr Lys Leu Glu Ile Lys Arg Ala Asp Ala Ala Pro
            100                 105                 110

Thr Val Ser
        115

<210> SEQ ID NO 243
<211> LENGTH: 115
<212> TYPE: PRT
<213> ORGANISM: Artificial Sequence
<220> FEATURE:
<223> OTHER INFORMATION: MIN-F2-1 light chain variable region amino acid
      sequence

<400> SEQUENCE: 243

Asp Ile Val Met Thr Gln Ser Pro Glu Ile Met Ser Ala Ser Pro Gly
1               5                   10                  15

Glu Lys Val Thr Ile Thr Cys Ser Ala Ser Ser Ser Ile Ser Tyr Ile
            20                  25                  30

His Trp Phe Gln Gln Lys Pro Gly Thr Ser Pro Lys Leu Trp Ile Phe
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
```

```
                65                  70                  75                  80
Asp Thr Ala Thr Tyr Tyr Cys Gln Gln Arg Ser Asn Tyr Pro Phe Thr
                    85                  90                  95

Phe Gly Ser Gly Thr Lys Leu Gln Ile Lys Arg Ala Asp Ala Ala Pro
                100                 105                 110

Thr Val Ser
        115

<210> SEQ ID NO 244
<211> LENGTH: 115
<212> TYPE: PRT
<213> ORGANISM: Artificial Sequence
<220> FEATURE:
<223> OTHER INFORMATION: MIN-F2-2 light chain variable region amino acid
      sequence

<400> SEQUENCE: 244

Asp Ile Val Ile Thr Gln Ser Thr Glu Ile Met Ser Ala Ser Pro Gly
1               5                   10                  15

Glu Lys Val Thr Ile Thr Cys Ser Ala Ser Ser Ile Ser Tyr Ile
                20                  25                  30

His Trp Phe Gln Gln Lys Pro Gly Thr Ser Pro Lys Leu Trp Ile Phe
                35                  40                  45

Gly Thr Ser Asn Leu Ala Ser Gly Val Pro Ala Arg Phe Ser Gly Ser
        50                  55                  60

Gly Ser Gly Thr Ser Tyr Ser Leu Thr Val Ser Arg Met Glu Ala Glu
65                  70                  75                  80

Asp Thr Ala Thr Tyr Tyr Cys Gln Gln Arg Ser Asn Tyr Pro Phe Thr
                    85                  90                  95

Phe Gly Ser Gly Thr Lys Leu Gln Ile Lys Arg Ala Asp Ala Ala Pro
                100                 105                 110

Thr Val Ser
        115

<210> SEQ ID NO 245
<211> LENGTH: 130
<212> TYPE: PRT
<213> ORGANISM: Artificial Sequence
<220> FEATURE:
<223> OTHER INFORMATION: MIN-A2-1 heavy chain variable region amino acid
      sequence

<400> SEQUENCE: 245

Glu Val Lys Leu Gln Glu Ser Gly Pro Glu Leu Lys Lys Pro Gly Glu
1               5                   10                  15

Thr Val Glu Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
                35                  40                  45

Gly Trp Ile Asn Thr Tyr Thr Gly Glu Pro Thr Tyr Ala Gly Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                    85                  90                  95

Ala Arg Ser Gly Asp Gly Tyr Trp Tyr Tyr Ala Met Asp Tyr Trp Gly
                100                 105                 110

Gln Gly Thr Ser Val Thr Val Ser Ser Ala Lys Thr Thr Pro Pro Ser
```

-continued

```
                115                 120                 125

Val Tyr
    130

<210> SEQ ID NO 246
<211> LENGTH: 130
<212> TYPE: PRT
<213> ORGANISM: Artificial Sequence
<220> FEATURE:
<223> OTHER INFORMATION: MIN-A2-2 heavy chain variable region amino acid
      sequence

<400> SEQUENCE: 246

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Gly Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                85                  90                  95

Ala Arg Ser Gly Asp Gly Tyr Trp Tyr Tyr Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130

<210> SEQ ID NO 247
<211> LENGTH: 130
<212> TYPE: PRT
<213> ORGANISM: Artificial Sequence
<220> FEATURE:
<223> OTHER INFORMATION: MIN-C9-1 heavy chain variable region amino acid
      sequence

<400> SEQUENCE: 247

Gln Val Gln Leu Gln Glu Ser Gly Pro Glu Leu Lys Gln Pro Gly Glu
1               5                   10                  15

Thr Val Lys Ile Ser Cys Lys Ala Ser Gly Tyr Thr Phe Thr Asn Asn
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Asp Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Ala Arg Ala Phe Tyr Ala Met Asp Tyr Trp Gly
            100                 105                 110

Gln Gly Thr Ser Val Thr Val Ser Ser Thr Lys Thr Thr Ala Pro Ser
        115                 120                 125

Val Tyr
```

<210> SEQ ID NO 248
<211> LENGTH: 130
<212> TYPE: PRT
<213> ORGANISM: Artificial Sequence
<220> FEATURE:
<223> OTHER INFORMATION: MIN-C9-2 heavy chain variable region amino acid sequence

<400> SEQUENCE: 248

Gln Val Gln Leu Gln Gln Ser Gly Pro Glu Leu Lys Gln Pro Gly Glu
1               5                   10                  15

Thr Val Lys Ile Ser Cys Lys Ala Ser Gly Tyr Thr Phe Thr Asn Asn
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Gly Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Ala Arg Ala Phe Tyr Ala Met Asp Tyr Trp Gly
            100                 105                 110

Gln Gly Thr Ser Val Thr Val Ser Ser Thr Lys Thr Ala Pro Ser
        115                 120                 125

Val Tyr
    130

<210> SEQ ID NO 249
<211> LENGTH: 130
<212> TYPE: PRT
<213> ORGANISM: Artificial Sequence
<220> FEATURE:
<223> OTHER INFORMATION: MIN-D7-1 heavy chain variable region amino acid sequence

<400> SEQUENCE: 249

Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Ala Ile Leu Asn Gly Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130

```
<210> SEQ ID NO 250
<211> LENGTH: 130
<212> TYPE: PRT
<213> ORGANISM: Artificial Sequence
<220> FEATURE:
<223> OTHER INFORMATION: MIN-D7-2 heavy chain variable region amino acid
      sequence

<400> SEQUENCE: 250
```

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Gly Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                85                  90                  95

Ala Arg Ser Gly Asp Gly Tyr Trp Tyr Tyr Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130

```
<210> SEQ ID NO 251
<211> LENGTH: 130
<212> TYPE: PRT
<213> ORGANISM: Artificial Sequence
<220> FEATURE:
<223> OTHER INFORMATION: MIN-F2-1 heavy chain variable region amino acid
      sequence

<400> SEQUENCE: 251
```

Glu Val Lys Leu Glu Glu Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Thr Ala Ile Leu Asn Gly Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130

```
<210> SEQ ID NO 252
<211> LENGTH: 124
<212> TYPE: PRT
```

<213> ORGANISM: Artificial Sequence
<220> FEATURE:
<223> OTHER INFORMATION: MIN-F2-2 heavy chain variable region amino acid sequence

<400> SEQUENCE: 252

Glu Val Gln Leu Glu Gln Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Ser Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Ser Ala Val Tyr Tyr Cys
            85                  90                  95

Thr Asn Tyr Gly Ser Phe Ala Tyr Trp Gly Gln Gly Thr Leu Val Thr
                100                 105                 110

Val Ser Ala Ala Lys Thr Thr Pro Pro Ser Val Tyr
            115                 120

<210> SEQ ID NO 253
<211> LENGTH: 130
<212> TYPE: PRT
<213> ORGANISM: Artificial Sequence
<220> FEATURE:
<223> OTHER INFORMATION: MIN-F2-3 heavy chain variable region amino acid sequence

<400> SEQUENCE: 253

Arg Cys Arg Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
            85                  90                  95

Ala Arg Thr Gly Thr Thr Ala Ile Leu Asn Gly Met Asp Tyr Trp Gly
                100                 105                 110

Gln Gly Thr Ser Val Thr Val Ser Ser Ala Lys Thr Thr Pro Pro Ser
            115                 120                 125

Cys Leu
    130

<210> SEQ ID NO 254
<211> LENGTH: 130
<212> TYPE: PRT
<213> ORGANISM: Artificial Sequence
<220> FEATURE:
<223> OTHER INFORMATION: MIN-F2-4 heavy chain variable region amino acid sequence

<400> SEQUENCE: 254

-continued

```
Glu Val Gln Leu Glu Gln Ser Gly Pro Glu Leu Lys Lys Pro Gly Glu
1               5                   10                  15

Thr Val Lys Ile Ser Cys Lys Ala Ser Gly Tyr Thr Phe Ile Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Met Ala Thr Tyr Phe Cys
                85                  90                  95

Ala Arg Thr Gly Thr Thr Ala Ile Leu Asn Gly Met Asp Tyr Trp Gly
            100                 105                 110

Gln Gly Thr Ser Val Thr Val Ser Ser Ala Lys Thr Thr Pro Pro Ser
        115                 120                 125

Val Tyr
    130

<210> SEQ ID NO 255
<211> LENGTH: 113
<212> TYPE: PRT
<213> ORGANISM: Artificial Sequence
<220> FEATURE:
<223> OTHER INFORMATION: MIN-14 light chain variable region amino acid
      sequence

<400> SEQUENCE: 255

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro His
                85                  90                  95

Val Arg Cys Trp Asp Gln Ala Gly Ala Glu Thr Gly Cys Cys Thr Asn
            100                 105                 110

Cys

<210> SEQ ID NO 256
<211> LENGTH: 107
<212> TYPE: PRT
<213> ORGANISM: Artificial Sequence
<220> FEATURE:
<223> OTHER INFORMATION: MIN-17-1 light chain variable region amino acid
      sequence

<400> SEQUENCE: 256

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30
```

```
Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
 50                      55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp
                100                 105
```

<210> SEQ ID NO 257
<211> LENGTH: 115
<212> TYPE: PRT
<213> ORGANISM: Artificial Sequence
<220> FEATURE:
<223> OTHER INFORMATION: MIN-17-2 light chain variable region amino acid
      sequence

<400> SEQUENCE: 257

```
Asp Ile Gln Met Thr Gln Ser Pro Ala Ser Gln Ser Ala Ser Leu Gly
 1               5                  10                  15

Glu Ser Val Thr Ile Thr Cys Leu Ala Ser Gln Thr Ile Gly Thr Trp
                 20                  25                  30

Leu Ala Trp Tyr Gln Gln Lys Pro Gly Lys Ser Pro Gln Leu Leu Ile
            35                  40                  45

Tyr Ala Ala Thr Ser Leu Ala Asp Gly Val Pro Ser Arg Phe Ser Gly
 50                      55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Leu Tyr Ser Thr Pro Trp
                 85                  90                  95

Thr Phe Gly Gly Gly Thr Lys Leu Glu Ile Lys Arg Ala Asp Ala Ala
                100                 105                 110

Pro Thr Val
        115
```

<210> SEQ ID NO 258
<211> LENGTH: 107
<212> TYPE: PRT
<213> ORGANISM: Artificial Sequence
<220> FEATURE:
<223> OTHER INFORMATION: MIN-29 light chain variable region amino acid
      sequence

<400> SEQUENCE: 258

```
Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
                 20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
 50                      55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95
```

```
Glu Leu Thr Arg Ser Glu Gly Gly Pro Ser Trp
            100                 105
```

<210> SEQ ID NO 259
<211> LENGTH: 107
<212> TYPE: PRT
<213> ORGANISM: Artificial Sequence
<220> FEATURE:
<223> OTHER INFORMATION: MIN-34 light chain variable region amino acid
      sequence

<400> SEQUENCE: 259

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp
            100                 105
```

<210> SEQ ID NO 260
<211> LENGTH: 115
<212> TYPE: PRT
<213> ORGANISM: Artificial Sequence
<220> FEATURE:
<223> OTHER INFORMATION: MIN-42 light chain variable region amino acid
      sequence

<400> SEQUENCE: 260

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Gly Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Tyr
                85                  90                  95

Thr Phe Gly Gly Gly Thr Lys Leu Glu Ile Lys Arg Ala Asp Ala Ala
            100                 105                 110

Pro Thr Val
        115
```

<210> SEQ ID NO 261
<211> LENGTH: 115
<212> TYPE: PRT
<213> ORGANISM: Artificial Sequence
<220> FEATURE:
<223> OTHER INFORMATION: MIN-45 light chain variable region amino acid
      sequence -continued

<400> SEQUENCE: 261

Asp Ile Gln Met Thr Gln Pro Pro Ala Ser Leu Ser Ala Ser Val Gly
1               5                   10                  15

Glu Thr Val Thr Ile Thr Cys Arg Ala Ser Gly Asn Ile His Asn Phe
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Arg Ala Asp Ala Ala
            100                 105                 110

Pro Thr Val
        115

<210> SEQ ID NO 262
<211> LENGTH: 105
<212> TYPE: PRT
<213> ORGANISM: Artificial Sequence
<220> FEATURE:
<223> OTHER INFORMATION: MIN-14 heavy chain variable region amino acid
      sequence

<400> SEQUENCE: 262

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Tyr Gly Asn Tyr Trp Tyr Phe
            100                 105

<210> SEQ ID NO 263
<211> LENGTH: 105
<212> TYPE: PRT
<213> ORGANISM: Artificial Sequence
<220> FEATURE:
<223> OTHER INFORMATION: MIN-17-2 heavy chain variable region amino acid
      sequence

<400> SEQUENCE: 263

Gln Ile Thr Leu Lys Glu Ser Gly Pro Gly Ile Val Gln Pro Ser Gln
1               5                   10                  15

Pro Phe Arg Leu Thr Cys Thr Phe Ser Gly Phe Ser Leu Ser Thr Ser
            20                  25                  30

Gly Ile Gly Val Thr Trp Ile Arg Gln Pro Ser Gly Lys Gly Leu Glu
        35                  40                  45

Trp Leu Ala Thr Ile Trp Trp Asp Asp Asp Asn Arg Tyr Asn Pro Ser

```
                50                  55                  60
Leu Lys Ser Arg Leu Thr Val Ser Lys Asp Thr Ser Asn Asn Gln Ala
 65                  70                  75                  80

Phe Leu Asn Ile Ile Thr Val Glu Thr Ala Asp Thr Ala Ile Tyr Tyr
                 85                  90                  95

Cys Ala Gln Ser Thr Met Val Thr Ala
                100                 105

<210> SEQ ID NO 264
<211> LENGTH: 105
<212> TYPE: PRT
<213> ORGANISM: Artificial Sequence
<220> FEATURE:
<223> OTHER INFORMATION: MIN-17-1 heavy chain variable region amino acid
      sequence

<400> SEQUENCE: 264

Gln Val Gln Leu Gln Gln Pro Gly Ala Glu Leu Val Lys Pro Gly Ala
 1                5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Ile
                 35                  40                  45

Gly Glu Ile Asn Pro Ser Asn Gly Arg Thr Asn Tyr Asn Glu Lys Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Thr Tyr Gly Asn Tyr Trp Tyr Phe
                100                 105

<210> SEQ ID NO 265
<211> LENGTH: 127
<212> TYPE: PRT
<213> ORGANISM: Artificial Sequence
<220> FEATURE:
<223> OTHER INFORMATION: MIN-29 heavy chain variable region amino acid
      sequence
<220> FEATURE:
<221> NAME/KEY: misc_feature
<222> LOCATION: (12)..(12)
<223> OTHER INFORMATION: Xaa can be any naturally occurring amino acid

<400> SEQUENCE: 265

Asp Val Lys Leu Val Glu Ser Gly Gly Asp Leu Xaa Lys Leu Thr Glu
 1                5                  10                  15

Gly Glu Asp Ile Trp Glu Gly Leu Thr Leu Cys Arg Asp Ser Asp Gln
                 20                  25                  30

Ser Pro Leu Ala Pro Val Ser Lys Pro Gly Arg Val Val Arg Pro Gln
                 35                  40                  45

Arg Ser Cys Thr Val Ile Gln Gly Cys Val Leu Arg Leu Gln Thr Ala
 50                  55                  60

His Leu Gln Val Gln Gly Val Leu Gly Ile Val Ser Gly Asp Gly Glu
 65                  70                  75                  80

Ser Ala Leu His Ser Val Trp Ile Val Gly Ala Thr Ile Thr Ile
                 85                  90                  95

Asn Gly Cys Asp Gln Leu Gln Pro Leu Leu Trp Ser Leu Ala Asn Pro
                100                 105                 110
```

Arg His Val Ile Ala Thr Glu Ser Glu Ser Arg Gly Cys Thr Gly
            115                 120                 125

<210> SEQ ID NO 266
<211> LENGTH: 104
<212> TYPE: PRT
<213> ORGANISM: Artificial Sequence
<220> FEATURE:
<223> OTHER INFORMATION: MIN-34 heavy chain variable region amino acid
      sequence

<400> SEQUENCE: 266

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Asp Tyr Pro Ala Trp Phe
            100

<210> SEQ ID NO 267
<211> LENGTH: 105
<212> TYPE: PRT
<213> ORGANISM: Artificial Sequence
<220> FEATURE:
<223> OTHER INFORMATION: MIN-42 heavy chain variable region amino acid
      sequence

<400> SEQUENCE: 267

Glu Val Gln Leu Val Glu Ser Gly Gly Asp Leu Val Lys Pro Gly Arg
1               5                   10                  15

Ser Leu Lys Leu Ser Cys Ala Ala Ser Gly Phe Thr Phe Ser Ser Phe
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg Arg Phe Tyr Tyr Asp Tyr Asp
            100                 105

<210> SEQ ID NO 268
<211> LENGTH: 103
<212> TYPE: PRT
<213> ORGANISM: Artificial Sequence
<220> FEATURE:
<223> OTHER INFORMATION: MIN-45 heavy chain variable region amino acid
      sequence

<400> SEQUENCE: 268

Glu Val Gln Leu Gln Gln Ser Gly Pro Glu Leu Val Lys Pro Gly Ala

```
1               5                   10                  15
Ser Val Lys Ile Ser Cys Lys Ala Ser Gly Tyr Ser Phe Thr Gly Tyr
                20                  25                  30
Phe Met Ser Trp Val Met Gln Ser His Gly Lys Ser Leu Glu Trp Ile
        35                  40                  45
Gly Arg Ile Asn Pro Tyr Asn Gly Asp Thr Phe Tyr Asn Gln Lys Phe
        50                  55                  60
Lys Gly Lys Ala Thr Leu Thr Val Asp Lys Ser Ser Thr Thr Ala His
65                  70                  75                  80
Ile Glu Leu Arg Ser Leu Ala Ser Glu Asp Ser Ala Val Tyr Tyr Cys
                85                  90                  95
Ala Arg Lys Gly Leu Tyr Gly
                100
```

<210> SEQ ID NO 269
<211> LENGTH: 10
<212> TYPE: PRT
<213> ORGANISM: Artificial Sequence
<220> FEATURE:
<223> OTHER INFORMATION: MIN-A2-1 light chain variable complementarity determining region 1 (CDR1) amino acid sequence

<400> SEQUENCE: 269

```
Ser Ala Ser Ser Ser Ile Ser Tyr Ile His
1               5                   10
```

<210> SEQ ID NO 270
<211> LENGTH: 10
<212> TYPE: PRT
<213> ORGANISM: Artificial Sequence
<220> FEATURE:
<223> OTHER INFORMATION: MIN-A2-2 light chain variable complementarity determining region 1 (CDR1) amino acid sequence

<400> SEQUENCE: 270

```
Ser Ala Ser Ser Ser Val Ser Tyr Met His
1               5                   10
```

<210> SEQ ID NO 271
<211> LENGTH: 10
<212> TYPE: PRT
<213> ORGANISM: Artificial Sequence
<220> FEATURE:
<223> OTHER INFORMATION: MIN-C9-1 light chain variable complementarity determining region 1 (CDR1) amino acid sequence

<400> SEQUENCE: 271

```
Ser Ala Ser Ser Ser Val Ser Tyr Met Tyr
1               5                   10
```

<210> SEQ ID NO 272
<211> LENGTH: 10
<212> TYPE: PRT
<213> ORGANISM: Artificial Sequence
<220> FEATURE:
<223> OTHER INFORMATION: MIN-C9-2 light chain variable complementarity determining region 1 (CDR1) amino acid sequence

<400> SEQUENCE: 272

```
Ser Ala Ser Ser Ser Val Ser Tyr Thr Tyr
1               5                   10
```

<210> SEQ ID NO 273
<211> LENGTH: 10

```
<212> TYPE: PRT
<213> ORGANISM: Artificial Sequence
<220> FEATURE:
<223> OTHER INFORMATION: MIN-D7-1 light chain variable complementarity
      determining region 1 (CDR1) amino acid sequence

<400> SEQUENCE: 273

Ser Ala Ser Ser Ser Val Ser Tyr Met His
1               5                   10

<210> SEQ ID NO 274
<211> LENGTH: 10
<212> TYPE: PRT
<213> ORGANISM: Artificial Sequence
<220> FEATURE:
<223> OTHER INFORMATION: MIN-D7-2 light chain variable complementarity
      determining region 1 (CDR1) amino acid sequence

<400> SEQUENCE: 274

Ser Ala Ser Ser Ser Val Ser Tyr Met His
1               5                   10

<210> SEQ ID NO 275
<211> LENGTH: 10
<212> TYPE: PRT
<213> ORGANISM: Artificial Sequence
<220> FEATURE:
<223> OTHER INFORMATION: MIN-F2-1 light chain variable complementarity
      determining region 1 (CDR1) amino acid sequence

<400> SEQUENCE: 275

Ser Ala Ser Ser Ser Ile Ser Tyr Ile His
1               5                   10

<210> SEQ ID NO 276
<211> LENGTH: 10
<212> TYPE: PRT
<213> ORGANISM: Artificial Sequence
<220> FEATURE:
<223> OTHER INFORMATION: MIN-F2-2 light chain variable complementarity
      determining region 1 (CDR1) amino acid sequence

<400> SEQUENCE: 276

Ser Ala Ser Ser Ser Ile Ser Tyr Ile His
1               5                   10

<210> SEQ ID NO 277
<211> LENGTH: 7
<212> TYPE: PRT
<213> ORGANISM: Artificial Sequence
<220> FEATURE:
<223> OTHER INFORMATION: MIN-A2-1 light chain variable complementarity
      determining region 2 (CDR2) amino acid sequence

<400> SEQUENCE: 277

Gly Thr Ser Asn Leu Ala Ser
1               5

<210> SEQ ID NO 278
<211> LENGTH: 7
<212> TYPE: PRT
<213> ORGANISM: Artificial Sequence
<220> FEATURE:
<223> OTHER INFORMATION: MIN-A2-2 light chain variable complementarity
      determining region 2 (CDR2) amino acid sequence

<400> SEQUENCE: 278

Ser Thr Ser Asn Leu Ala Ser
```

```
<210> SEQ ID NO 279
<211> LENGTH: 7
<212> TYPE: PRT
<213> ORGANISM: Artificial Sequence
<220> FEATURE:
<223> OTHER INFORMATION: MIN-C9-1 light chain variable complementarity
      determining region 2 (CDR2) amino acid sequence

<400> SEQUENCE: 279

Ser Thr Ser Asn Leu Ala Ser
1               5

<210> SEQ ID NO 280
<211> LENGTH: 7
<212> TYPE: PRT
<213> ORGANISM: Artificial Sequence
<220> FEATURE:
<223> OTHER INFORMATION: MIN-C9-2 light chain variable complementarity
      determining region 2 (CDR2) amino acid sequence

<400> SEQUENCE: 280

Ser Thr Ser Asn Leu Ala Ser
1               5

<210> SEQ ID NO 281
<211> LENGTH: 7
<212> TYPE: PRT
<213> ORGANISM: Artificial Sequence
<220> FEATURE:
<223> OTHER INFORMATION: MIN-D7-1 light chain variable complementarity
      determining region 2 (CDR2) amino acid sequence

<400> SEQUENCE: 281

Ser Thr Ser Asn Leu Ala Ser
1               5

<210> SEQ ID NO 282
<211> LENGTH: 7
<212> TYPE: PRT
<213> ORGANISM: Artificial Sequence
<220> FEATURE:
<223> OTHER INFORMATION: MIN-D7-2 light chain variable complementarity
      determining region 2 (CDR2) amino acid sequence

<400> SEQUENCE: 282

Ser Thr Ser Asn Leu Ala Ser
1               5

<210> SEQ ID NO 283
<211> LENGTH: 7
<212> TYPE: PRT
<213> ORGANISM: Artificial Sequence
<220> FEATURE:
<223> OTHER INFORMATION: MIN-F2-1 light chain variable complementarity
      determining region 2 (CDR2) amino acid sequence

<400> SEQUENCE: 283

Gly Thr Ser Asn Leu Ala Ser
1               5

<210> SEQ ID NO 284
<211> LENGTH: 7
<212> TYPE: PRT
<213> ORGANISM: Artificial Sequence
<220> FEATURE:
<223> OTHER INFORMATION: MIN-F2-2 light chain variable complementarity
``` determining region 2 (CDR2) amino acid sequence

<400> SEQUENCE: 284

Gly Thr Ser Asn Leu Ala Ser
1               5

<210> SEQ ID NO 285
<211> LENGTH: 9
<212> TYPE: PRT
<213> ORGANISM: Artificial Sequence
<220> FEATURE:
<223> OTHER INFORMATION: MIN-A2-1 light chain variable complementarity
      determining region 3 (CDR3) amino acid sequence

<400> SEQUENCE: 285

Gln Gln Arg Ser Asn Tyr Pro Phe Thr
1               5

<210> SEQ ID NO 286
<211> LENGTH: 9
<212> TYPE: PRT
<213> ORGANISM: Artificial Sequence
<220> FEATURE:
<223> OTHER INFORMATION: MIN-A2-2 light chain variable complementarity
      determining region 3 (CDR3) amino acid sequence

<400> SEQUENCE: 286

Gln Gln Arg Ser Ser Tyr Pro Ser Thr
1               5

<210> SEQ ID NO 287
<211> LENGTH: 9
<212> TYPE: PRT
<213> ORGANISM: Artificial Sequence
<220> FEATURE:
<223> OTHER INFORMATION: MIN-C9-1 light chain variable complementarity
      determining region 3 (CDR3) amino acid sequence

<400> SEQUENCE: 287

Gln Gln Arg Ser Ser Tyr Pro Ser Thr
1               5

<210> SEQ ID NO 288
<211> LENGTH: 9
<212> TYPE: PRT
<213> ORGANISM: Artificial Sequence
<220> FEATURE:
<223> OTHER INFORMATION: MIN-C9-2 light chain variable complementarity
      determining region 3 (CDR3) amino acid sequence

<400> SEQUENCE: 288

Gln Gln Arg Ser Ser Tyr Pro Ser Thr
1               5

<210> SEQ ID NO 289
<211> LENGTH: 9
<212> TYPE: PRT
<213> ORGANISM: Artificial Sequence
<220> FEATURE:
<223> OTHER INFORMATION: MIN-D7-1 light chain variable complementarity
      determining region 3 (CDR3) amino acid sequence

<400> SEQUENCE: 289

Gln Gln Arg Ser Ser Tyr Pro Ser Thr
1               5

<210> SEQ ID NO 290

```
<211> LENGTH: 9
<212> TYPE: PRT
<213> ORGANISM: Artificial Sequence
<220> FEATURE:
<223> OTHER INFORMATION: MIN-D7-2 light chain variable complementarity
      determining region 3 (CDR3) amino acid sequence

<400> SEQUENCE: 290

Gln Gln Arg Ser Ser Tyr Pro Ser Thr
1               5

<210> SEQ ID NO 291
<211> LENGTH: 9
<212> TYPE: PRT
<213> ORGANISM: Artificial Sequence
<220> FEATURE:
<223> OTHER INFORMATION: MIN-F2-1 light chain variable complementarity
      determining region 3 (CDR3) amino acid sequence

<400> SEQUENCE: 291

Gln Gln Arg Ser Asn Tyr Pro Phe Thr
1               5

<210> SEQ ID NO 292
<211> LENGTH: 9
<212> TYPE: PRT
<213> ORGANISM: Artificial Sequence
<220> FEATURE:
<223> OTHER INFORMATION: MIN-F2-2 light chain variable complementarity
      determining region 3 (CDR3) amino acid sequence

<400> SEQUENCE: 292

Gln Gln Arg Ser Asn Tyr Pro Phe Thr
1               5

<210> SEQ ID NO 293
<211> LENGTH: 5
<212> TYPE: PRT
<213> ORGANISM: Artificial Sequence
<220> FEATURE:
<223> OTHER INFORMATION: MIN-A2-1 heavy chain variable complementarity
      determining region 1 (CDR1) amino acid sequence

<400> SEQUENCE: 293

Asn Tyr Gly Met Asn
1               5

<210> SEQ ID NO 294
<211> LENGTH: 5
<212> TYPE: PRT
<213> ORGANISM: Artificial Sequence
<220> FEATURE:
<223> OTHER INFORMATION: MIN-A2-2 heavy chain variable complementarity
      determining region 1 (CDR1) amino acid sequence

<400> SEQUENCE: 294

Asn Tyr Gly Met Asn
1               5

<210> SEQ ID NO 295
<211> LENGTH: 5
<212> TYPE: PRT
<213> ORGANISM: Artificial Sequence
<220> FEATURE:
<223> OTHER INFORMATION: MIN-C9-1 heavy chain variable complementarity
      determining region 1 (CDR1) amino acid sequence

<400> SEQUENCE: 295
```

```
Asn Asn Gly Met Asn
1               5

<210> SEQ ID NO 296
<211> LENGTH: 5
<212> TYPE: PRT
<213> ORGANISM: Artificial Sequence
<220> FEATURE:
<223> OTHER INFORMATION: MIN-C9-2 heavy chain variable complementarity
      determining region 1 (CDR1) amino acid sequence

<400> SEQUENCE: 296

Asn Asn Gly Met Asn
1               5

<210> SEQ ID NO 297
<211> LENGTH: 5
<212> TYPE: PRT
<213> ORGANISM: Artificial Sequence
<220> FEATURE:
<223> OTHER INFORMATION: MIN-D7-1 heavy chain variable complementarity
      determining region 1 (CDR1) amino acid sequence

<400> SEQUENCE: 297

Asn Tyr Gly Met Asn
1               5

<210> SEQ ID NO 298
<211> LENGTH: 5
<212> TYPE: PRT
<213> ORGANISM: Artificial Sequence
<220> FEATURE:
<223> OTHER INFORMATION: MIN-D7-2 heavy chain variable complementarity
      determining region 1 (CDR1) amino acid sequence

<400> SEQUENCE: 298

Asn Tyr Gly Met Asn
1               5

<210> SEQ ID NO 299
<211> LENGTH: 5
<212> TYPE: PRT
<213> ORGANISM: Artificial Sequence
<220> FEATURE:
<223> OTHER INFORMATION: MIN-F2-1 heavy chain variable complementarity
      determining region 1 (CDR1) amino acid sequence

<400> SEQUENCE: 299

Asn Tyr Gly Met Asn
1               5

<210> SEQ ID NO 300
<211> LENGTH: 5
<212> TYPE: PRT
<213> ORGANISM: Artificial Sequence
<220> FEATURE:
<223> OTHER INFORMATION: MIN-F2-2 heavy chain variable complementarity
      determining region 1 (CDR1) amino acid sequence

<400> SEQUENCE: 300

Asp Tyr Glu Met His
1               5

<210> SEQ ID NO 301
<211> LENGTH: 5
<212> TYPE: PRT
<213> ORGANISM: Artificial Sequence
<220> FEATURE:
```

<223> OTHER INFORMATION: MIN-F2-3 heavy chain variable complementarity
      determining region 1 (CDR1) amino acid sequence

<400> SEQUENCE: 301

Asn Tyr Gly Met Asn
1               5

<210> SEQ ID NO 302
<211> LENGTH: 5
<212> TYPE: PRT
<213> ORGANISM: Artificial Sequence
<220> FEATURE:
<223> OTHER INFORMATION: MIN-F2-4 heavy chain variable complementarity
      determining region 1 (CDR1) amino acid sequence

<400> SEQUENCE: 302

Asn Tyr Gly Met Asn
1               5

<210> SEQ ID NO 303
<211> LENGTH: 17
<212> TYPE: PRT
<213> ORGANISM: Artificial Sequence
<220> FEATURE:
<223> OTHER INFORMATION: MIN-A2-1 heavy chain variable complementarity
      determining region 2 (CDR2) amino acid sequence

<400> SEQUENCE: 303

Trp Ile Asn Thr Tyr Thr Gly Glu Pro Thr Tyr Ala Gly Asp Phe Lys
1               5                   10                  15

Gly

<210> SEQ ID NO 304
<211> LENGTH: 17
<212> TYPE: PRT
<213> ORGANISM: Artificial Sequence
<220> FEATURE:
<223> OTHER INFORMATION: MIN-A2-2 heavy chain variable complementarity
      determining region 2 (CDR2) amino acid sequence

<400> SEQUENCE: 304

Trp Ile Asn Thr Tyr Thr Gly Glu Pro Thr Tyr Ala Gly Asp Phe Lys
1               5                   10                  15

Gly

<210> SEQ ID NO 305
<211> LENGTH: 17
<212> TYPE: PRT
<213> ORGANISM: Artificial Sequence
<220> FEATURE:
<223> OTHER INFORMATION: MIN-C9-1 heavy chain variable complementarity
      determining region 2 (CDR2) amino acid sequence

<400> SEQUENCE: 305

Trp Ile Asn Thr Tyr Thr Gly Glu Pro Thr Tyr Ala Asp Asp Phe Lys
1               5                   10                  15

Gly

<210> SEQ ID NO 306
<211> LENGTH: 17
<212> TYPE: PRT
<213> ORGANISM: Artificial Sequence
<220> FEATURE:
<223> OTHER INFORMATION: MIN-C9-2 heavy chain variable complementarity
      determining region 2 (CDR2) amino acid sequence

<400> SEQUENCE: 306

Trp Ile Asn Thr Tyr Thr Gly Glu Pro Thr Tyr Ala Asp Asp Phe Lys
1               5                   10                  15
Gly

<210> SEQ ID NO 307
<211> LENGTH: 17
<212> TYPE: PRT
<213> ORGANISM: Artificial Sequence
<220> FEATURE:
<223> OTHER INFORMATION: MIN-D7-1 heavy chain variable complementarity
      determining region 2 (CDR2) amino acid sequence

<400> SEQUENCE: 307

Trp Ile Asn Thr Tyr Thr Gly Glu Pro Thr Tyr Val Asp Asp Phe Lys
1               5                   10                  15
Gly

<210> SEQ ID NO 308
<211> LENGTH: 17
<212> TYPE: PRT
<213> ORGANISM: Artificial Sequence
<220> FEATURE:
<223> OTHER INFORMATION: MIN-D7-2 heavy chain variable complementarity
      determining region 2 (CDR2) amino acid sequence

<400> SEQUENCE: 308

Trp Ile Asn Thr Tyr Thr Gly Glu Pro Thr Tyr Ala Gly Asp Phe Lys
1               5                   10                  15
Gly

<210> SEQ ID NO 309
<211> LENGTH: 17
<212> TYPE: PRT
<213> ORGANISM: Artificial Sequence
<220> FEATURE:
<223> OTHER INFORMATION: MIN-F2-1 heavy chain variable complementarity
      determining region 2 (CDR2) amino acid sequence

<400> SEQUENCE: 309

Trp Ile Asn Thr Tyr Thr Gly Glu Pro Thr Tyr Val Asp Asp Phe Lys
1               5                   10                  15
Gly

<210> SEQ ID NO 310
<211> LENGTH: 17
<212> TYPE: PRT
<213> ORGANISM: Artificial Sequence
<220> FEATURE:
<223> OTHER INFORMATION: MIN-F2-2 heavy chain variable complementarity
      determining region 2 (CDR2) amino acid sequence

<400> SEQUENCE: 310

Ala Ile His Pro Gly Ser Gly Gly Thr Ala Tyr Asn Gln Lys Phe Lys
1               5                   10                  15
Gly

<210> SEQ ID NO 311
<211> LENGTH: 17
<212> TYPE: PRT
<213> ORGANISM: Artificial Sequence
<220> FEATURE:
<223> OTHER INFORMATION: MIN-F2-3 heavy chain variable complementarity
      determining region 2 (CDR2) amino acid sequence

```
<400> SEQUENCE: 311

Trp Ile Asn Thr Tyr Thr Gly Glu Pro Thr Tyr Val Asp Asp Phe Lys
1               5                   10                  15

Gly

<210> SEQ ID NO 312
<211> LENGTH: 17
<212> TYPE: PRT
<213> ORGANISM: Artificial Sequence
<220> FEATURE:
<223> OTHER INFORMATION: MIN-F2-4 heavy chain variable complementarity
      determining region 2 (CDR2) amino acid sequence

<400> SEQUENCE: 312

Trp Ile Asn Thr Tyr Thr Gly Glu Pro Thr Tyr Val Asp Asp Phe Lys
1               5                   10                  15

Gly

<210> SEQ ID NO 313
<211> LENGTH: 9
<212> TYPE: PRT
<213> ORGANISM: Artificial Sequence
<220> FEATURE:
<223> OTHER INFORMATION: MIN-A2-1 heavy chain variable complementarity
      determining region 3 (CDR3) amino acid sequence

<400> SEQUENCE: 313

Ser Gly Asp Gly Tyr Trp Tyr Tyr Ala
1               5

<210> SEQ ID NO 314
<211> LENGTH: 9
<212> TYPE: PRT
<213> ORGANISM: Artificial Sequence
<220> FEATURE:
<223> OTHER INFORMATION: MIN-A2-2 heavy chain variable complementarity
      determining region 3 (CDR3) amino acid sequence

<400> SEQUENCE: 314

Ser Gly Asp Gly Tyr Trp Tyr Tyr Ala
1               5

<210> SEQ ID NO 315
<211> LENGTH: 9
<212> TYPE: PRT
<213> ORGANISM: Artificial Sequence
<220> FEATURE:
<223> OTHER INFORMATION: MIN-C9-1 heavy chain variable complementarity
      determining region 3 (CDR3) amino acid sequence

<400> SEQUENCE: 315

Thr Gly Thr Ala Arg Ala Phe Tyr Ala
1               5

<210> SEQ ID NO 316
<211> LENGTH: 9
<212> TYPE: PRT
<213> ORGANISM: Artificial Sequence
<220> FEATURE:
<223> OTHER INFORMATION: MIN-C9-2 heavy chain variable complementarity
      determining region 3 (CDR3) amino acid sequence

<400> SEQUENCE: 316

Thr Gly Thr Ala Arg Ala Phe Tyr Ala
1               5
```

```
<210> SEQ ID NO 317
<211> LENGTH: 9
<212> TYPE: PRT
<213> ORGANISM: Artificial Sequence
<220> FEATURE:
<223> OTHER INFORMATION: MIN-D7-1 heavy chain variable complementarity
      determining region 3(CDR3) amino acid sequence

<400> SEQUENCE: 317

Thr Gly Thr Thr Ala Ile Leu Asn Gly
1               5

<210> SEQ ID NO 318
<211> LENGTH: 9
<212> TYPE: PRT
<213> ORGANISM: Artificial Sequence
<220> FEATURE:
<223> OTHER INFORMATION: MIN-D7-2 heavy chain variable complementarity
      determining region3 (CDR3) amino acid sequence

<400> SEQUENCE: 318

Ser Gly Asp Gly Tyr Trp Tyr Tyr Ala
1               5

<210> SEQ ID NO 319
<211> LENGTH: 9
<212> TYPE: PRT
<213> ORGANISM: Artificial Sequence
<220> FEATURE:
<223> OTHER INFORMATION: MIN-F2-1 heavy chain variable complementarity
      determining region 3 (CDR3) amino acid sequence

<400> SEQUENCE: 319

Thr Gly Thr Thr Ala Ile Leu Asn Gly
1               5

<210> SEQ ID NO 320
<211> LENGTH: 5
<212> TYPE: PRT
<213> ORGANISM: Artificial Sequence
<220> FEATURE:
<223> OTHER INFORMATION: MIN-F2-2 heavy chain variable complementarity
      determining region 3(CDR3) amino acid sequence

<400> SEQUENCE: 320

Tyr Gly Ser Phe Ala
1               5

<210> SEQ ID NO 321
<211> LENGTH: 9
<212> TYPE: PRT
<213> ORGANISM: Artificial Sequence
<220> FEATURE:
<223> OTHER INFORMATION: MIN-F2-3 heavy chain variable complementarity
      determining region 3 (CDR3) amino acid sequence

<400> SEQUENCE: 321

Thr Gly Thr Thr Ala Ile Leu Asn Gly
1               5

<210> SEQ ID NO 322
<211> LENGTH: 9
<212> TYPE: PRT
<213> ORGANISM: Artificial Sequence
<220> FEATURE:
<223> OTHER INFORMATION: MIN-F2-4 heavy chain variable complementarity
      determining region 3(CDR3) amino acid sequence
```

<400> SEQUENCE: 322

Thr Gly Thr Thr Ala Ile Leu Asn Gly
1               5

<210> SEQ ID NO 323
<211> LENGTH: 11
<212> TYPE: PRT
<213> ORGANISM: Artificial Sequence
<220> FEATURE:
<223> OTHER INFORMATION: MIN-14 light chain variable complementarity
      determining region 1 (CDR1) amino acid sequence

<400> SEQUENCE: 323

Arg Ala Ser Gln Asp Ile Gly Ser Ser Leu Asn
1               5                   10

<210> SEQ ID NO 324
<211> LENGTH: 15
<212> TYPE: PRT
<213> ORGANISM: Artificial Sequence
<220> FEATURE:
<223> OTHER INFORMATION: MIN-17-1 light chain variable complementarity
      determining region 1 (CDR1) amino acid sequence

<400> SEQUENCE: 324

Arg Ala Ser Lys Ser Val Ser Thr Ser Gly Tyr Ser Tyr Met His
1               5                   10                  15

<210> SEQ ID NO 325
<211> LENGTH: 11
<212> TYPE: PRT
<213> ORGANISM: Artificial Sequence
<220> FEATURE:
<223> OTHER INFORMATION: MIN-17-2 light chain variable complementarity
      determining region 1 (CDR1) amino acid sequence

<400> SEQUENCE: 325

Leu Ala Ser Gln Thr Ile Gly Thr Trp Leu Ala
1               5                   10

<210> SEQ ID NO 326
<211> LENGTH: 15
<212> TYPE: PRT
<213> ORGANISM: Artificial Sequence
<220> FEATURE:
<223> OTHER INFORMATION: MIN-29 light chain variable complementarity
      determining region 1 (CDR1) amino acid sequence

<400> SEQUENCE: 326

Arg Ala Ser Lys Ser Val Ser Thr Ser Gly Tyr Ser Tyr Met His
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: MIN-34 light chain variable complementarity
      determining region 1 (CDR1) amino acid sequence

<400> SEQUENCE: 327

Arg Ala Ser Lys Ser Val Ser Thr Ser Gly Tyr Ser Tyr Met His
1               5                   10                  15

<210> SEQ ID NO 328
<211> LENGTH: 11

```
<212> TYPE: PRT
<213> ORGANISM: Artificial Sequence
<220> FEATURE:
<223> OTHER INFORMATION: MIN-42 light chain variable complementarity
      determining region 1 (CDR1) amino acid sequence

<400> SEQUENCE: 328

Lys Ala Ser Gln Asn Val Gly Thr Asn Val Gly
1               5                   10

<210> SEQ ID NO 329
<211> LENGTH: 11
<212> TYPE: PRT
<213> ORGANISM: Artificial Sequence
<220> FEATURE:
<223> OTHER INFORMATION: MIN-45 light chain variable complementarity
      determining region 1 (CDR1) amino acid sequence

<400> SEQUENCE: 329

Arg Ala Ser Gly Asn Ile His Asn Phe Leu Ala
1               5                   10

<210> SEQ ID NO 330
<211> LENGTH: 7
<212> TYPE: PRT
<213> ORGANISM: Artificial Sequence
<220> FEATURE:
<223> OTHER INFORMATION: MIN-14 light chain variable complementarity
      determining region 2 (CDR2) amino acid sequence

<400> SEQUENCE: 330

Ala Thr Ser Ser Leu Asp Ser
1               5

<210> SEQ ID NO 331
<211> LENGTH: 7
<212> TYPE: PRT
<213> ORGANISM: Artificial Sequence
<220> FEATURE:
<223> OTHER INFORMATION: MIN-17-1 light chain variable complementarity
      determining region 2 (CDR2) amino acid sequence

<400> SEQUENCE: 331

Leu Val Ser Asn Leu Glu Ser
1               5

<210> SEQ ID NO 332
<211> LENGTH: 7
<212> TYPE: PRT
<213> ORGANISM: Artificial Sequence
<220> FEATURE:
<223> OTHER INFORMATION: MIN-17-2 light chain variable complementarity
      determining region 2 (CDR2) amino acid sequence

<400> SEQUENCE: 332

Ala Ala Thr Ser Leu Ala Asp
1               5

<210> SEQ ID NO 333
<211> LENGTH: 7
<212> TYPE: PRT
<213> ORGANISM: Artificial Sequence
<220> FEATURE:
<223> OTHER INFORMATION: MIN-29 light chain variable complementarity
      determining region 2 (CDR2) amino acid sequence

<400> SEQUENCE: 333

Leu Val Ser Asn Leu Glu Ser
```

```
1               5
```

<210> SEQ ID NO 334
<211> LENGTH: 7
<212> TYPE: PRT
<213> ORGANISM: Artificial Sequence
<220> FEATURE:
<223> OTHER INFORMATION: MIN-34 light chain variable complementarity
      determining region 2 (CDR2) amino acid sequence

<400> SEQUENCE: 334

```
Leu Val Ser Asn Leu Glu Ser
1               5
```

<210> SEQ ID NO 335
<211> LENGTH: 7
<212> TYPE: PRT
<213> ORGANISM: Artificial Sequence
<220> FEATURE:
<223> OTHER INFORMATION: MIN-42 light chain variable complementarity
      determining region 2 (CDR2) amino acid sequence

<400> SEQUENCE: 335

```
Ser Ala Ser Tyr Arg Tyr Ser
1               5
```

<210> SEQ ID NO 336
<211> LENGTH: 7
<212> TYPE: PRT
<213> ORGANISM: Artificial Sequence
<220> FEATURE:
<223> OTHER INFORMATION: MIN-45 light chain variable complementarity
      determining region 2 (CDR2) amino acid sequence

<400> SEQUENCE: 336

```
Asn Ala Lys Thr Leu Ala Asp
1               5
```

<210> SEQ ID NO 337
<211> LENGTH: 5
<212> TYPE: PRT
<213> ORGANISM: Artificial Sequence
<220> FEATURE:
<223> OTHER INFORMATION: MIN-14 heavy chain complementarity determining
      region 1 (CDR1) amino acid sequence

<400> SEQUENCE: 337

```
Ser Tyr Trp Met His
1               5
```

<210> SEQ ID NO 338
<211> LENGTH: 5
<212> TYPE: PRT
<213> ORGANISM: Artificial Sequence
<220> FEATURE:
<223> OTHER INFORMATION: MIN-17-1 heavy chain complementarity
      determining region 1 (CDR1) amino acid sequence

<400> SEQUENCE: 338

```
Ser Tyr Trp Met His
1               5
```

<210> SEQ ID NO 339
<211> LENGTH: 5
<212> TYPE: PRT
<213> ORGANISM: Artificial Sequence
<220> FEATURE:
<223> OTHER INFORMATION: MIN-17-2 heavy chain complementarity -continued determining region 1 (CDR1) amino acid sequence

<400> SEQUENCE: 339

Gly Ile Gly Val Thr
1               5

<210> SEQ ID NO 340
<211> LENGTH: 5
<212> TYPE: PRT
<213> ORGANISM: Artificial Sequence
<220> FEATURE:
<223> OTHER INFORMATION: MIN-34 heavy chain complementarity determining
      region 1 (CDR1) amino acid sequence

<400> SEQUENCE: 340

Ser Tyr Gly Val His
1               5

<210> SEQ ID NO 341
<211> LENGTH: 5
<212> TYPE: PRT
<213> ORGANISM: Artificial Sequence
<220> FEATURE:
<223> OTHER INFORMATION: MIN-42 heavy chain complementarity determining
      region 1 (CDR1) amino acid sequence

<400> SEQUENCE: 341

Ser Phe Gly Met Ser
1               5

<210> SEQ ID NO 342
<211> LENGTH: 5
<212> TYPE: PRT
<213> ORGANISM: Artificial Sequence
<220> FEATURE:
<223> OTHER INFORMATION: MIN-45 heavy chain complementarity determining
      region 1 (CDR1) amino acid sequence

<400> SEQUENCE: 342

Gly Tyr Phe Met Ser
1               5

<210> SEQ ID NO 343
<211> LENGTH: 17
<212> TYPE: PRT
<213> ORGANISM: Artificial Sequence
<220> FEATURE:
<223> OTHER INFORMATION: MIN-14 heavy chain complementarity determining
      region 2 (CDR2) amino acid sequence

<400> SEQUENCE: 343

Glu Ile Asn Pro Ser Asn Gly Arg Thr Asn Tyr Asn Glu Lys Phe Lys
1               5                   10                  15

Ser

<210> SEQ ID NO 344
<211> LENGTH: 17
<212> TYPE: PRT
<213> ORGANISM: Artificial Sequence
<220> FEATURE:
<223> OTHER INFORMATION: MIN-17-1 heavy chain complementarity
      determining region 2 (CDR2) amino acid sequence

<400> SEQUENCE: 344

Glu Ile Asn Pro Ser Asn Gly Arg Thr Asn Tyr Asn Glu Lys Phe Lys
1               5                   10                  15

Ser

<210> SEQ ID NO 345
<211> LENGTH: 16
<212> TYPE: PRT
<213> ORGANISM: Artificial Sequence
<220> FEATURE:
<223> OTHER INFORMATION: MIN-17-2 heavy chain complementarity
      determining region 2 (CDR2) amino acid sequence

<400> SEQUENCE: 345

Thr Ile Trp Trp Asp Asp Asn Arg Tyr Asn Pro Ser Leu Lys Ser
1               5                   10                  15

<210> SEQ ID NO 346
<211> LENGTH: 18
<212> TYPE: PRT
<213> ORGANISM: Artificial Sequence
<220> FEATURE:
<223> OTHER INFORMATION: MIN-29 heavy chain complementarity determining
      region 2 (CDR2) amino acid sequence

<400> SEQUENCE: 346

Gly Ile Val Ser Gly Asp Gly Glu Ser Ala Leu His Ser Val Trp Ile
1               5                   10                  15

Val Gly

<210> SEQ ID NO 347
<211> LENGTH: 16
<212> TYPE: PRT
<213> ORGANISM: Artificial Sequence
<220> FEATURE:
<223> OTHER INFORMATION: MIN-34 heavy chain complementarity determining
      region 2 (CDR2) amino acid sequence

<400> SEQUENCE: 347

Val Ile Trp Gly Gly Gly Ser Thr Asp Tyr Asn Ala Ala Phe Ile Ser
1               5                   10                  15

<210> SEQ ID NO 348
<211> LENGTH: 17
<212> TYPE: PRT
<213> ORGANISM: Artificial Sequence
<220> FEATURE:
<223> OTHER INFORMATION: MIN-42 heavy chain complementarity determining
      region 2 (CDR2) amino acid sequence

<400> SEQUENCE: 348

Thr Ile Ser Ser Gly Gly Thr Tyr Thr Tyr Tyr Pro Asp Ser Val Lys
1               5                   10                  15

Gly

<210> SEQ ID NO 349
<211> LENGTH: 17
<212> TYPE: PRT
<213> ORGANISM: Artificial Sequence
<220> FEATURE:
<223> OTHER INFORMATION: MIN-45 heavy chain complementarity determining
      region 2 (CDR2) amino acid sequence

<400> SEQUENCE: 349

Arg Ile Asn Pro Tyr Asn Gly Asp Thr Phe Tyr Asn Gln Lys Phe Lys
1               5                   10                  15

Gly

```
<210> SEQ ID NO 350
<211> LENGTH: 122
<212> TYPE: PRT
<213> ORGANISM: Artificial Sequence
<220> FEATURE:
<223> OTHER INFORMATION: Humanized E6 heavy chain variable region
      sequence

<400> SEQUENCE: 350
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Arg Leu Glu Trp Val
        35                  40                  45

Ser Thr Ile Ser Gly Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Asn Tyr Gly Arg Asn Tyr Asp Tyr Gly Met Asp Tyr Trp
            100                 105                 110

Gly Gln Gly Thr Leu Val Thr Val Ser Ser
        115                 120

```
<210> SEQ ID NO 351
<211> LENGTH: 5
<212> TYPE: PRT
<213> ORGANISM: Artificial Sequence
<220> FEATURE:
<223> OTHER INFORMATION: Humanized E6 heavy chain variable
      complementarity determining regions 1 (CDR1) sequence

<400> SEQUENCE: 351
```

Arg Tyr Gly Met Ser
1               5

```
<210> SEQ ID NO 352
<211> LENGTH: 17
<212> TYPE: PRT
<213> ORGANISM: Artificial Sequence
<220> FEATURE:
<223> OTHER INFORMATION: Humanized E6 heavy chain variable
      complementarity determining regions 2 (CDR2) sequence

<400> SEQUENCE: 352
```

Thr Ile Ser Gly Gly Gly Thr Tyr Ile Tyr Tyr Pro Asp Ser Val Lys
1               5                   10                  15

Gly

```
<210> SEQ ID NO 353
<211> LENGTH: 13
<212> TYPE: PRT
<213> ORGANISM: Artificial Sequence
<220> FEATURE:
<223> OTHER INFORMATION: Humanized E6 heavy chain variable
      complementarity determining regions 3 (CDR3) sequence

<400> SEQUENCE: 353
```

Asp Asn Tyr Gly Arg Asn Tyr Asp Tyr Gly Met Asp Tyr
1               5                   10

<210> SEQ ID NO 354
<211> LENGTH: 106
<212> TYPE: PRT
<213> ORGANISM: Artificial Sequence
<220> FEATURE:
<223> OTHER INFORMATION: Humanized E6 light chain variable region
      sequence

<400> SEQUENCE: 354

Glu Ile Val Leu Thr Gln Ser Pro Ala Thr Leu Ser Leu Ser Pro Gly
1               5                   10                  15

Glu Arg Ala Thr Leu Thr Cys Ser Ala Thr Ser Ser Val Ser Tyr Ile
            20                  25                  30

His Trp Tyr Gln Gln Arg Pro Gly Gln Ser Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Ser Asp Tyr Thr Leu Thr Ile Ser Ser Leu Glu Pro Glu
65                  70                  75                  80

Asp Phe Ala Val Tyr Tyr Cys Gln Gln Arg Ser Ser Pro Phe Thr
                85                  90                  95

Phe Gly Ser Gly Thr Lys Val Glu Ile Lys
            100                 105

<210> SEQ ID NO 355
<211> LENGTH: 10
<212> TYPE: PRT
<213> ORGANISM: Artificial Sequence
<220> FEATURE:
<223> OTHER INFORMATION: Humanized E6 light chain variable
      complementarity determining regions 1 (CDR1) sequence

<400> SEQUENCE: 355

Ser Ala Thr Ser Ser Val Ser Tyr Ile His
1               5                   10

<210> SEQ ID NO 356
<211> LENGTH: 7
<212> TYPE: PRT
<213> ORGANISM: Artificial Sequence
<220> FEATURE:
<223> OTHER INFORMATION: Humanized E6 light chain variable
      complementarity determining regions 2 (CDR2) sequence

<400> SEQUENCE: 356

Ser Thr Ser Asn Leu Ala Ser
1               5

<210> SEQ ID NO 357
<211> LENGTH: 9
<212> TYPE: PRT
<213> ORGANISM: Artificial Sequence
<220> FEATURE:
<223> OTHER INFORMATION: Humanized E6 light chain variable
      complementarity determining regions 3 (CDR3) sequence

<400> SEQUENCE: 357

Gln Gln Arg Ser Ser Pro Phe Thr
1               5

<210> SEQ ID NO 358
<211> LENGTH: 121
<212> TYPE: PRT
<213> ORGANISM: Artificial Sequence
<220> FEATURE:

<223> OTHER INFORMATION: Humanized C2 heavy chain variable region
      sequence

<400> SEQUENCE: 358

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Asp Asn Tyr Tyr Glu Tyr Phe Asp Val Trp Gly
            100                 105                 110

Lys Gly Thr Thr Val Thr Val Ser Ser
        115                 120

<210> SEQ ID NO 359
<211> LENGTH: 5
<212> TYPE: PRT
<213> ORGANISM: Artificial Sequence
<220> FEATURE:
<223> OTHER INFORMATION: Humanized C2 heavy chain variable
      complementarity determining regions 1 (CDR1) sequence

<400> SEQUENCE: 359

Gly Tyr Ala Met Ser
1               5

<210> SEQ ID NO 360
<211> LENGTH: 17
<212> TYPE: PRT
<213> ORGANISM: Artificial Sequence
<220> FEATURE:
<223> OTHER INFORMATION: Humanized C2 heavy chain variable
      complementarity determining regions 2 (CDR2) sequence

<400> SEQUENCE: 360

Thr Ile Ser Ser Gly Gly Thr Tyr Ile Tyr Tyr Pro Asp Ser Val Lys
1               5                   10                  15

Gly

<210> SEQ ID NO 361
<211> LENGTH: 12
<212> TYPE: PRT
<213> ORGANISM: Artificial Sequence
<220> FEATURE:
<223> OTHER INFORMATION: Humanized C2 heavy chain variable
      complementarity determining regions 3 (CDR3) sequence

<400> SEQUENCE: 361

Leu Gly Gly Asp Asn Tyr Tyr Glu Tyr Phe Asp Val
1               5                   10

<210> SEQ ID NO 362
<211> LENGTH: 113
<212> TYPE: PRT
<213> ORGANISM: Artificial Sequence
<220> FEATURE:

<223> OTHER INFORMATION: Humanized C2 light chain variable region
      sequence

<400> SEQUENCE: 362

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Leu Pro Phe Thr Phe Gly Gly Gly Thr Lys Val Glu Ile Lys Arg
            100                 105                 110

Thr

<210> SEQ ID NO 363
<211> LENGTH: 15
<212> TYPE: PRT
<213> ORGANISM: Artificial Sequence
<220> FEATURE:
<223> OTHER INFORMATION: Humanized C2 light chain variable
      complementarity determining regions 1 (CDR1) sequence

<400> SEQUENCE: 363

Arg Ala Ser Lys Ser Val Ser Thr Ser Gly Tyr Ser Tyr Met His
1               5                   10                  15

<210> SEQ ID NO 364
<211> LENGTH: 7
<212> TYPE: PRT
<213> ORGANISM: Artificial Sequence
<220> FEATURE:
<223> OTHER INFORMATION: Humanized C2 light chain variable
      complementarity determining regions 2 (CDR2) sequence

<400> SEQUENCE: 364

Leu Ala Ser Asn Leu Glu Ser
1               5

<210> SEQ ID NO 365
<211> LENGTH: 9
<212> TYPE: PRT
<213> ORGANISM: Artificial Sequence
<220> FEATURE:
<223> OTHER INFORMATION: Humanized C2 light chain variable
      complementarity determining regions 3 (CDR3) sequence

<400> SEQUENCE: 365

Gln His Ser Arg Glu Leu Pro Phe Thr
1               5

<210> SEQ ID NO 366
<211> LENGTH: 9
<212> TYPE: PRT
<213> ORGANISM: Artificial Sequence
<220> FEATURE:
<223> OTHER INFORMATION: Humanized C2 light chain variable
      complementarity determining regions 3 (CDR3) sequence

<400> SEQUENCE: 366

Leu Gln Ser Lys Asn Phe Pro Pro Thr
1               5

<210> SEQ ID NO 367
<211> LENGTH: 507
<212> TYPE: PRT
<213> ORGANISM: Artificial Sequence
<220> FEATURE:
<223> OTHER INFORMATION: pSECTag2 C2 scFV-FC

<400> SEQUENCE: 367

Met Glu Thr Asp Thr Leu Leu Leu Trp Val Leu Leu Leu Trp Val Pro
1               5                   10                  15

Gly Ser Thr Gly Asp Ala Ala Gln Pro Ala Glu Val Gln Leu Val Glu
            20                  25                  30

Ser Gly Gly Gly Leu Val Lys Pro Gly Gly Ser Leu Arg Leu Ser Cys
        35                  40                  45

Ala Ala Ser Gly Phe Thr Phe Ser Gly Tyr Ala Met Ser Trp Val Arg
    50                  55                  60

Gln Ala Pro Gly Lys Gly Leu Glu Trp Val Ser Thr Ile Ser Ser Gly
65                  70                  75                  80

Gly Thr Tyr Ile Tyr Tyr Pro Asp Ser Val Lys Gly Arg Phe Thr Ile
                85                  90                  95

Ser Arg Asp Asn Ala Lys Asn Ser Leu Tyr Leu Gln Met Asn Ser Leu
            100                 105                 110

Arg Ala Glu Asp Thr Ala Val Tyr Tyr Cys Ala Arg Leu Gly Gly Asp
        115                 120                 125

Asn Tyr Tyr Glu Tyr Phe Asp Val Trp Gly Lys Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Val Leu Thr Gln Ser Pro Ala Ser Leu Ala Val Ser
                165                 170                 175

Pro Gly Gln Arg Ala Thr Ile Thr Cys Arg Ala Ser Lys Ser Val Ser
            180                 185                 190

Thr Ser Gly Tyr Ser Tyr Met His Trp Tyr Gln Gln Lys Pro Gly Gln
        195                 200                 205

Pro Pro Lys Leu Leu Ile Tyr Leu Ala Ser Asn Leu Glu Ser Gly Val
    210                 215                 220

Pro Ala Arg Phe Ser Gly Ser Gly Ser Gly Thr Asp Phe Thr Leu Thr
225                 230                 235                 240

Ile Asn Pro Val Glu Ala Asn Asp Thr Ala Asn Tyr Tyr Cys Gln His
                245                 250                 255

Ser Arg Glu Leu Pro Phe Thr Phe Gly Gly Gly Thr Lys Val Glu Ile
            260                 265                 270

Lys Arg Thr Glu Pro Lys Ser Cys Asp Lys Thr His Thr Cys Pro Pro
        275                 280                 285

Cys Pro Ala Pro Glu Leu Leu Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg

```
            340                 345                 350
Glu Glu Gln Tyr Asn Ser Thr Tyr Arg Val Val Ser Val Leu Thr Val
                355                 360                 365

Leu His Gln Asp Trp Leu Asn Gly Lys Glu Tyr Lys Cys Lys Val Ser
        370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
        435                 440                 445

Asn Asn Tyr Lys Thr Thr Pro Pro Val Leu Asp Ser Asp Gly Ser Phe
    450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys
            500                 505

<210> SEQ ID NO 368
<211> LENGTH: 501
<212> TYPE: PRT
<213> ORGANISM: Artificial Sequence
<220> FEATURE:
<223> OTHER INFORMATION: pSECTag2 E6 scFV-FC

<400> SEQUENCE: 368

Met Glu Thr Asp Thr Leu Leu Leu Trp Val Leu Leu Leu Trp Val Pro
1               5                   10                  15

Gly Ser Thr Gly Asp Ala Ala Gln Pro Ala Glu Val Gln Leu Val Glu
                20                  25                  30

Ser Gly Gly Gly Leu Val Lys Pro Gly Gly Ser Leu Arg Leu Ser Cys
            35                  40                  45

Ala Ala Ser Gly Phe Thr Phe Ser Arg Tyr Gly Met Ser Trp Val Arg
        50                  55                  60

Gln Ala Pro Gly Lys Arg Leu Glu Trp Val Ser Thr Ile Ser Gly Gly
65                  70                  75                  80

Gly Thr Tyr Ile Tyr Tyr Pro Asp Ser Val Lys Gly Arg Phe Thr Ile
                85                  90                  95

Ser Arg Asp Asn Ala Lys Asn Thr Leu Tyr Leu Gln Met Asn Ser Leu
            100                 105                 110

Arg Ala Glu Asp Thr Ala Val Tyr Tyr Cys Thr Arg Asp Asn Tyr Gly
        115                 120                 125

Arg Asn Tyr Asp Tyr Gly Met Asp Tyr Trp Gly Gln Gly Thr Leu Val
    130                 135                 140

Thr Val Ser Ser Gly Gly Gly Ser Gly Gly Gly Gly Ser Gly Gly Gly
145                 150                 155                 160

Gly Gly Ser Glu Ile Val Leu Thr Gln Ser Pro Ala Thr Leu Ser Leu
                165                 170                 175

Ser Pro Gly Glu Arg Ala Thr Leu Thr Cys Ser Ala Thr Ser Ser Val
            180                 185                 190

Ser Tyr Ile His Trp Tyr Gln Gln Arg Pro Gly Gln Ser Pro Arg Leu
```

```
            195                 200                 205
Leu Ile Tyr Ser Thr Ser Asn Leu Ala Ser Gly Ile Pro Ala Arg Phe
            210                 215                 220

Ser Gly Ser Gly Ser Gly Ser Asp Tyr Thr Leu Thr Ile Ser Ser Leu
225                 230                 235                 240

Glu Pro Glu Asp Phe Ala Val Tyr Tyr Cys Gln Gln Arg Ser Ser Ser
                245                 250                 255

Pro Phe Thr Phe Gly Ser Gly Thr Lys Val Glu Ile Lys Glu Pro Lys
                260                 265                 270

Ser Cys Asp Lys Thr His Thr Cys Pro Pro Cys Pro Ala Pro Glu Leu
                275                 280                 285

Leu Gly Gly Pro Ser Val Phe Leu Phe Pro Pro Lys Pro Lys Asp Thr
            290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
                340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
            370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
                420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500

<210> SEQ ID NO 369
<211> LENGTH: 249
<212> TYPE: PRT
<213> ORGANISM: Artificial Sequence
<220> FEATURE:
<223> OTHER INFORMATION: Humanized C2 scFV (VH-VL) sequence

<400> SEQUENCE: 369

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
                20                  25                  30

Ala Met Ser Trp Val Arg Gln Ala Pro Gly Lys Gly Leu Glu Trp Val
            35                  40                  45

Ser Thr Ile Ser Ser Gly Gly Thr Tyr Ile Tyr Tyr Pro Asp Ser Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Asp Asn Tyr Tyr Glu Tyr Phe Asp Val Trp Gly
                100                 105                 110

Lys Gly Thr Thr Val Thr Val Ser Ser Gly Gly Gly Ser Gly Gly
                115                 120                 125

Gly Gly Ser Gly Gly Gly Ser Asp Ile Val Leu Thr Gln Ser Pro
        130                 135                 140

Ala Ser Leu Ala Val Ser Pro Gly Gln Arg Ala Thr Ile Thr Cys Arg
145                 150                 155                 160

Ala Ser Lys Ser Val Ser Thr Ser Gly Tyr Ser Tyr Met His Trp Tyr
                165                 170                 175

Gln Gln Lys Pro Gly Gln Pro Pro Lys Leu Leu Ile Tyr Leu Ala Ser
                180                 185                 190

Asn Leu Glu Ser Gly Val Pro Ala Arg Phe Ser Gly Ser Gly Ser Gly
                195                 200                 205

Thr Asp Phe Thr Leu Thr Ile Asn Pro Val Glu Ala Asn Asp Thr Ala
                210                 215                 220

Asn Tyr Tyr Cys Gln His Ser Arg Glu Leu Pro Phe Thr Phe Gly Gly
225                 230                 235                 240

Gly Thr Lys Val Glu Ile Lys Arg Thr
                245

<210> SEQ ID NO 370
<211> LENGTH: 249
<212> TYPE: PRT
<213> ORGANISM: Artificial Sequence
<220> FEATURE:
<223> OTHER INFORMATION: Humanized E6 scFV (VL-VH) sequence

<400> SEQUENCE: 370

Asp Ile Val Leu Thr Gln Ser Pro Ala Ser Leu Ala Val Ser Pro Gly
  1               5                  10                  15

Gln Arg Ala Thr Ile Thr Cys Arg Ala Ser Lys Ser Val Ser Thr Ser
                 20                  25                  30

Gly Tyr Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Ser Arg
                 85                  90                  95

Glu Leu Pro Phe Thr Phe Gly Gly Gly Thr Lys Val Glu Ile Lys Arg
                100                 105                 110

Thr Gly Gly Gly Gly Ser Gly Gly Gly Gly Ser Gly Gly Gly Gly Ser
                115                 120                 125

Glu Val Gln Leu Val Glu Ser Gly Gly Gly Leu Val Lys Pro Gly Gly
            130                 135                 140

Ser Leu Arg Leu Ser Cys Ala Ala Ser Gly Phe Thr Phe Ser Gly Tyr
145                 150                 155                 160

Ala Met Ser Trp Val Arg Gln Ala Pro Gly Lys Gly Leu Glu Trp Val
```

```
                    165                 170                 175
Ser Thr Ile Ser Ser Gly Gly Thr Tyr Ile Tyr Tyr Pro Asp Ser Val
                180                 185                 190

Lys Gly Arg Phe Thr Ile Ser Arg Asp Asn Ala Lys Asn Ser Leu Tyr
            195                 200                 205

Leu Gln Met Asn Ser Leu Arg Ala Glu Asp Thr Ala Val Tyr Tyr Cys
        210                 215                 220

Ala Arg Leu Gly Gly Asp Asn Tyr Tyr Glu Tyr Phe Asp Val Trp Gly
225                 230                 235                 240

Lys Gly Thr Thr Val Thr Val Ser Ser
                245

<210> SEQ ID NO 371
<211> LENGTH: 119
<212> TYPE: PRT
<213> ORGANISM: Artificial Sequence
<220> FEATURE:
<223> OTHER INFORMATION: Humanized C3 heavy chain variable region
      sequence

<400> SEQUENCE: 371

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met Asn Trp Val Arg Gln Ala Pro Gly Gln Gly Leu Glu Trp Met
        35                  40                  45

Gly Val Ile Ser Thr Phe Ser Gly Asn Thr Asn Phe Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asp Tyr Tyr Gly Pro Tyr Phe Asp Tyr Trp Gly Gln Gly
            100                 105                 110

Thr Thr Leu Thr Val Ser Ser
        115

<210> SEQ ID NO 372
<211> LENGTH: 5
<212> TYPE: PRT
<213> ORGANISM: Artificial Sequence
<220> FEATURE:
<223> OTHER INFORMATION: Humanized C3 heavy chain variable
      complementarity determining regions 1 (CDR) sequence

<400> SEQUENCE: 372

Asp Tyr Ala Met Asn
1               5

<210> SEQ ID NO 373
<211> LENGTH: 17
<212> TYPE: PRT
<213> ORGANISM: Artificial Sequence
<220> FEATURE:
<223> OTHER INFORMATION: Humanized C3 heavy chain variable
      complementarity determining regions 2 (CDR2) sequence

<400> SEQUENCE: 373

Val Ile Ser Thr Phe Ser Gly Asn Thr Asn Phe Asn Gln Lys Phe Lys
1               5                   10                  15
```

Gly

<210> SEQ ID NO 374
<211> LENGTH: 10
<212> TYPE: PRT
<213> ORGANISM: Artificial Sequence
<220> FEATURE:
<223> OTHER INFORMATION: Humanized C3 heavy chain variable
      complementarity determining regions 3 (CDR3) sequence

<400> SEQUENCE: 374

Ser Asp Tyr Tyr Gly Pro Tyr Phe Asp Tyr
1               5                   10

<210> SEQ ID NO 375
<211> LENGTH: 114
<212> TYPE: PRT
<213> ORGANISM: Artificial Sequence
<220> FEATURE:
<223> OTHER INFORMATION: Humanized C3 light chain variable region
      sequence

<400> SEQUENCE: 375

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

Arg Thr

<210> SEQ ID NO 376
<211> LENGTH: 16
<212> TYPE: PRT
<213> ORGANISM: Artificial Sequence
<220> FEATURE:
<223> OTHER INFORMATION: Humanized C3 light chain variable
      complementarity determining regions 1 (CDR1) sequence

<400> SEQUENCE: 376

Arg Ser Ser Gln Thr Ile Val His Ser Asn Gly Asn Thr Tyr Leu Glu
1               5                   10                  15

<210> SEQ ID NO 377
<211> LENGTH: 7
<212> TYPE: PRT
<213> ORGANISM: Artificial Sequence
<220> FEATURE:
<223> OTHER INFORMATION: Humanized C3 light chain variable
      complementarity determining regions 2 (CDR2) sequence

<400> SEQUENCE: 377

Lys Val Ser Asn Arg Phe Ser
1               5

```
<210> SEQ ID NO 378
<211> LENGTH: 9
<212> TYPE: PRT
<213> ORGANISM: Artificial Sequence
<220> FEATURE:
<223> OTHER INFORMATION: Humanized C3 light chain variable
      complementarity determining regions 3 (CDR3) sequence

<400> SEQUENCE: 378

Phe Gln Gly Ser His Val Pro Phe Thr
1               5

<210> SEQ ID NO 379
<211> LENGTH: 118
<212> TYPE: PRT
<213> ORGANISM: Artificial Sequence
<220> FEATURE:
<223> OTHER INFORMATION: Humanized C8 heavy chain variable region
      sequence

<400> SEQUENCE: 379

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Asp Asn Tyr Tyr Glu Tyr Trp Gly Lys Gly Thr
            100                 105                 110

Thr Val Thr Val Ser Ser
        115

<210> SEQ ID NO 380
<211> LENGTH: 5
<212> TYPE: PRT
<213> ORGANISM: Artificial Sequence
<220> FEATURE:
<223> OTHER INFORMATION: Humanized C8 heavy chain variable
      complementarity determining region 1 (CDR1) sequence

<400> SEQUENCE: 380

Gly Tyr Ala Met Ser
1               5

<210> SEQ ID NO 381
<211> LENGTH: 17
<212> TYPE: PRT
<213> ORGANISM: Artificial Sequence
<220> FEATURE:
<223> OTHER INFORMATION: Humanized C8 heavy chain variable
      complementarity determining region 2 (CDR2) sequence

<400> SEQUENCE: 381

Thr Ile Ser Ser Gly Gly Thr Tyr Ile Tyr Tyr Pro Asp Ser Val Lys
1               5                   10                  15

Gly
```

<210> SEQ ID NO 382
<211> LENGTH: 9
<212> TYPE: PRT
<213> ORGANISM: Artificial Sequence
<220> FEATURE:
<223> OTHER INFORMATION: Humanized C8 heavy chain variable
      complementarity determining region 3 (CDR3) sequence

<400> SEQUENCE: 382

Leu Gly Gly Asp Asn Tyr Tyr Glu Tyr
1               5

<210> SEQ ID NO 383
<211> LENGTH: 114
<212> TYPE: PRT
<213> ORGANISM: Artificial Sequence
<220> FEATURE:
<223> OTHER INFORMATION: Humanized C8 light chain variable region
      sequence

<400> SEQUENCE: 383

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Val Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ile Arg
                85                  90                  95

Glu Leu Thr Arg Ser Glu Phe Gly Gly Gly Thr Lys Val Glu Ile Lys
            100                 105                 110

Arg Thr

<210> SEQ ID NO 384
<211> LENGTH: 14
<212> TYPE: PRT
<213> ORGANISM: Artificial Sequence
<220> FEATURE:
<223> OTHER INFORMATION: Humanized C8 light chain variable
      complementarity determining region 1 (CDR1) sequence

<400> SEQUENCE: 384

Arg Ala Ser Lys Ser Val Ser Thr Ser Gly Tyr Ser Tyr Met
1               5                   10

<210> SEQ ID NO 385
<211> LENGTH: 7
<212> TYPE: PRT
<213> ORGANISM: Artificial Sequence
<220> FEATURE:
<223> OTHER INFORMATION: Humanized C8 light chain variable
      complementarity determining region 2 (CDR2) sequence

<400> SEQUENCE: 385

Leu Val Ser Asn Leu Glu Ser
1               5

<210> SEQ ID NO 386
<211> LENGTH: 10

-continued

```
<212> TYPE: PRT
<213> ORGANISM: Artificial Sequence
<220> FEATURE:
<223> OTHER INFORMATION: Humanized C8 light chain variable
      complementarity determining region 3 (CDR3) sequence

<400> SEQUENCE: 386

Gln His Ile Arg Glu Leu Thr Arg Ser Glu
1               5                   10
```